(12) United States Patent
Hampl et al.

(10) Patent No.: US 9,320,812 B2
(45) Date of Patent: Apr. 26, 2016

(54) MODULATORS AND METHODS OF USE

(75) Inventors: Johannes Hampl, Santa Clara, CA (US); Scott J. Dylla, Mountain View, CA (US); Orit Foord, Foster City, CA (US); Robert A. Stull, Alameda, CA (US)

(73) Assignee: Stemcentrx, Inc., South San Francisco, CA (US)

( * ) Notice: Subject to any disclaimer, the term of this patent is extended or adjusted under 35 U.S.C. 154(b) by 0 days.

(21) Appl. No.: 13/992,599

(22) PCT Filed: Dec. 7, 2011

(86) PCT No.: PCT/US2011/063831
§ 371 (c)(1),
(2), (4) Date: Sep. 25, 2013

(87) PCT Pub. No.: WO2012/118547
PCT Pub. Date: Sep. 7, 2012

(65) Prior Publication Data
US 2014/0093495 A1 Apr. 3, 2014

Related U.S. Application Data

(60) Provisional application No. 61/421,157, filed on Dec. 8, 2010.

(30) Foreign Application Priority Data

Sep. 2, 2011 (WO) .................. PCT/US2011/05045

(51) Int. Cl.
| | | |
|---|---|---|
| C07K 16/18 | (2006.01) |
| A61K 47/48 | (2006.01) |
| C07K 16/28 | (2006.01) |
| G01N 33/574 | (2006.01) |
| C07K 16/40 | (2006.01) |
| C07K 16/30 | (2006.01) |

(52) U.S. Cl.
CPC ..... *A61K 47/48723* (2013.01); *A61K 47/48246* (2013.01); *C07K 16/28* (2013.01); *C07K 16/2809* (2013.01); *C07K 16/2896* (2013.01); *C07K 16/30* (2013.01); *C07K 16/40* (2013.01); *G01N 33/574* (2013.01); *C07K 2317/33* (2013.01); *C07K 2317/34* (2013.01); *C07K 2317/73* (2013.01); *C07K 2317/76* (2013.01); *C07K 2317/77* (2013.01); *C07K 2317/92* (2013.01)

(58) Field of Classification Search
None
See application file for complete search history.

(56) References Cited

U.S. PATENT DOCUMENTS

| | | | |
|---|---|---|---|
| 5,112,946 A | 5/1992 | Maione | |
| 5,336,603 A | 8/1994 | Capon et al. | |
| 5,349,053 A | 9/1994 | Landolfi | |
| 5,359,046 A | 10/1994 | Capon et al. | |
| 5,447,851 A | 9/1995 | Beutler et al. | |
| 5,516,658 A | 5/1996 | Beckmann et al. | |
| 5,622,929 A | 4/1997 | Willner et al. | |
| 5,738,844 A | 4/1998 | Beckmann et al. | |
| 5,969,110 A | 10/1999 | Beckmann et al. | |
| 5,994,076 A | 11/1999 | Chenchik et al. | |
| 6,274,117 B1 | 8/2001 | Beckmann et al. | |
| 6,927,203 B1 | 8/2005 | Kinch et al. | |
| 6,949,366 B2 | 9/2005 | Beckmann et al. | |
| 7,341,997 B2 | 3/2008 | Bartlett et al. | |
| 7,422,739 B2 | 9/2008 | Anderson et al. | |
| 7,604,799 B2 | 10/2009 | Kinch et al. | |
| 7,659,374 B2 | 2/2010 | Wu et al. | |
| 7,807,459 B2 | 10/2010 | Tsang et al. | |
| 7,897,570 B2 | 3/2011 | Bartlett et al. | |
| 8,003,098 B2 | 8/2011 | Nakatsuru et al. | |
| 8,222,253 B2 | 7/2012 | Wang et al. | |
| 8,461,119 B2 | 6/2013 | Pasquale et al. | |
| 8,865,873 B2 * | 10/2014 | Liu et al. ................. | 530/388.8 |
| 2004/0043928 A1 | 3/2004 | Kekuda et al. | |
| 2005/0013819 A1 | 1/2005 | Kinch et al. | |
| 2005/0153923 A1 | 7/2005 | Kinch | |
| 2007/0292904 A1 | 12/2007 | Roifman et al. | |
| 2008/0003210 A1 | 1/2008 | Bruckheimer et al. | |
| 2009/0155255 A1 | 6/2009 | Glaser et al. | |
| 2010/0113415 A1 | 5/2010 | Rajapakse et al. | |
| 2010/0184119 A1 | 7/2010 | Bright et al. | |
| 2010/0273160 A1 | 10/2010 | Donahoe et al. | |
| 2011/0020221 A1 | 1/2011 | Berman et al. | |
| 2011/0280892 A1 | 11/2011 | Kinch et al. | |
| 2012/0083454 A1 | 4/2012 | Vescovi et al. | |
| 2013/0061340 A1 | 3/2013 | Dylla et al. | |
| 2013/0061342 A1 | 3/2013 | Dylla et al. | |
| 2013/0260385 A1 | 10/2013 | Dylla et al. | |
| 2015/0030636 A1 | 1/2015 | Dylla et al. | |

FOREIGN PATENT DOCUMENTS

| | | |
|---|---|---|
| EP | 0307434 | 3/1989 |
| EP | 0367166 | 5/1990 |
| EP | 1575509 | 9/2005 |
| EP | 1852441 | 11/2007 |
| EP | 2338898 | 6/2011 |
| EP | 2446895 | 5/2012 |
| WO | WO 88/07089 | 9/1988 |
| WO | WO 91/06570 | 5/1991 |
| WO | WO 95/06065 | 3/1995 |
| WO | WO 96/04388 | 2/1996 |

(Continued)

OTHER PUBLICATIONS

Liu et al. (Clin Cancer Res, 20(23): 6059-6070, 2014).*

(Continued)

*Primary Examiner* — Brad Duffy
*Assistant Examiner* — Nelson B Moseley, II
(74) *Attorney, Agent, or Firm* — Womble Carlyle Sandridge & Rice, LLP

(57) ABSTRACT

Novel modulators, including antibodies and derivatives thereof, and methods of such modulators to treat hyperproliferative disorders are provided.

36 Claims, 43 Drawing Sheets

(56) References Cited

FOREIGN PATENT DOCUMENTS

| WO | WO 98/01548 | | 1/1998 | | |
|---|---|---|---|---|---|
| WO | WO 99/52541 | | 10/1999 | | |
| WO | WO 01/11086 | | 2/2001 | | |
| WO | WO 03/004057 | | 1/2003 | | |
| WO | WO 03/040304 | | 5/2003 | | |
| WO | WO 03/064589 | | 8/2003 | | |
| WO | WO 03/075957 | | 9/2003 | | |
| WO | WO 2004/029218 | | 4/2004 | | |
| WO | WO 2004/048938 | | 6/2004 | | |
| WO | WO 2005/048917 A2 | | 6/2005 | | |
| WO | WO 2006/047298 | | 5/2006 | | |
| WO | WO 2007/146968 | * | 12/2007 | ........... | C07K 14/435 |
| WO | WO 2008/071447 | | 6/2008 | | |
| WO | WO 2009/052830 | | 4/2009 | | |
| WO | WO 2010/141974 | | 12/2010 | | |
| WO | WO 2012/031280 | | 3/2012 | | |
| WO | WO 2012/042021 | | 4/2012 | | |
| WO | WO 2012/118547 | | 9/2012 | | |
| WO | WO 2013/119964 | | 8/2013 | | |
| WO | WO 2015/031698 | | 3/2015 | | |

OTHER PUBLICATIONS

Stancovski et al. (PNAS, 88:8691-8695, 1991).*
Guenther et al. (Pathology—Research and Practice, 201: 649-663, 2005).*
Trinidad et al. (Blood, 114(24): 5081-5090, published online: Oct. 14, 2009).*
Abdou, AG t al "Ephrin A4 expression in osteosarcoma, impact on prognosis, and patient outcome", *Indian Journal of Cancer*, vol. 47, No. 1, Jan. 2010, pp. 46-52.
Al-Hajj, Muhammad et al "Self-renewal and solid tumor stem cells." *Oncogene*. Sep. 20, 2004;23(43):7274-82.
Alonso-C, LM et al "Expression profile of Eph receptors and ephrin ligands in healthy human B lymphocytes and chronic lymphocytic leukemia B-cells." *Leuk Res*. Mar. 2009;33(3):395-406.
Ashkenazi, A et al "Protection against endotoxic shock by a tumor necrosis factor receptor immunoadhesin." *Proc Natl Acad Sci U S A*. Dec. 1, 1991; 88(23):10535-9.
Batlle, E. et al "Beta-catenin and TCF mediate cell positioning in the intestinal epithelium by controlling the expression of EphB/ephrinB" *Cell*. Oct. 18, 2002;111(2):251-63.
Chothia, C. et al "Canonical structures for the hypervariable regions of immunoglobulins." *J. Mol. Biol.* (1987) 196, 901-917.
Chothia, C. et al "Conformations of immunoglobulin hypervariable regions." *Nature* 342, 877-883 (Dec. 28, 1989).
Dalerba, P. et al "Phenotypic characterization of human colorectal cancer stem cells." *Proc Natl Acad Sci U S A*. Jun. 12, 2007;104(24):10158-63. Epub Jun. 4, 2007.
De Nardo, GL et al "Comparison of 1,4,7,10-tetraazacyclododecane-N,N',N'',N'''-tetraacetic acid (DOTA)-peptide-ChL6, a novel immunoconjugate with catabolizable linker, to 2-iminothiolane-2-[p-(bromoacetamido)benzyl]-DOTA-ChL6 in breast cancer xenografts." *Clin Cancer Res*. Oct. 1998;4(10):2483-90.
Dylla, SJ et al "Colorectal cancer stem cells are enriched in xenogeneic tumors following chemotherapy." *PLoS One*. Jun. 18, 2008;3(6):e2428.
Eph Nomenclature Committee "Unified Nomenclature for Eph Family Receptors and Their Ligands, the Ephrins." *Cell* Aug. 8, 1997; 90(3):403-4.
Fuhrmann, S et al "Abstract 5625: In vitro and in vivo pharmacology of MEDI-565 (MT111), a novel CEA/CD3-bispecific single-chain BiTE antibody in development for the treatment of gastrointestinal adenocarcinomas" AACR Abstract No. 5625 (2010).
Garnett, MC "Targeted drug conjugates: principles and progress." *Adv Drug Deliv Rev*. Dec. 17, 2001;53(2):171-216.
GenBank NM_0044282; Homo sapiens ephrin-A1 (EFNA1), transcript variant 1, mRNA.
GenBank NM_005227; Homo sapiens ephrin-A4 (EFNA4), transcript variant 1, mRNA.
GenBank NM_182689; Homo sapiens ephrin-A4 (EFNA4), transcript variant 2, mRNA.
GenBank NM_182690; Homo sapiens ephrin-A4 (EFNA4), transcript variant 3, mRNA.
GenBank NP_001101162; ephrin-A4 precursor [Rattus norvegicus].
GenBank NP_005218; ephrin-A4 isoform a precursor [Homo sapiens.
GenBank NP_031936; ephrin-A4 precursor [Mus musculus].
GenBank NP_872631; ephrin-A4 isoform b precursor [Homo sapiens].
GenBank NP_872632; ephrin-A4 isoform c precursor [Homo sapiens].
GenBank XP_001152916; Predicted: ephrin A4 isoform 1 [Pan troglodytes].
GenBank XP_001152971; Predicted: ephrin-A4 isoform 2 [Pan troglodytes].
GenBank XP_001153095; Predicted: ephrin-A4 isoform 3 [Pan troglodytes].
GenBank XP_524893; Predicted: ephrin-A4 isoform 4 [Pan troglodytes].
Hoey, T. et al "DLL4 blockade inhibits tumor growth and reduces tumor-initiating cell frequency." *Cell Stem Cell*. Aug. 7, 2009;5(2):168-77.
Huff, Carol Ann et al "Strategies to eliminate cancer stem cells: Clinical implications" *Eur J Cancer*. Jun. 2006;42(9):1293-7. Epub Apr. 27, 2006.
Maccallum, RM et al "Antibody-antigen interactions: contact analysis and binding site topography." *J Mol Biol*. Oct. 11, 1996;262(5):732-45.
Merlos-Suárez, A et al "The intestinal stem cell signature identifies colorectal cancer stem cells and predicts disease relapse." *Cell Stem Cell*. May 6, 2011;8(5):511-24.
Mosch, Birgit et al "Eph Receptors and Ephrin Ligands: Important Players in Angiogenesis and Tumor Angiogenesis", *Journal of Oncology*, vol. 2010, Article ID 135285, 12 pages.
Orsulic, S. et al "Expression of Eph receptors and ephrins is differentially regulated by E-cadherin." J Cell Sci. May 2000;113 ( Pt 10):1793-802.
Peterson, JJ et al "Enzymatic cleavage of peptide-linked radiolabels from immunoconjugates." *Bioconjug Chem*. Jul.-Aug. 1999;10(4):553-7.
Stuehmer W. et al: "Murine EAG1 ion channel protein targeted antibody SEQ ID No:2", Database UniProt [Online] IBIS; Jun. 15, 2006, XP002672640, Database accession no. AEG89626.
Tsuchiya M. et al.: "Novel cell having fucose transporter function inhibited, useful for producing antibodies that can be used for treating diseases such as tumors.", Database UniProt [Online] IBIS; Aug. 24, 2006, XP002672641, Database accession No. AE167098.
Vié, H et al "Human fusion proteins between interleukin 2 and IgM heavy chain are cytotoxic that bind to cells expressing the interleukin 2 receptor." Proc Natl Acad Sci U S A. Dec. 1 1992;89(23):11337-41.
Yang Jun-Jie et al "[Preparation and analysis of monoclonal antibody against EphA4 peptide]." Zhong Nan Da Xue Xue Bao Yi Xue Ban. Oct. 2005;30(5):529-32.
Zantek, ND "E-cadherin regulates the function of the EphA2 receptor tyrosine kinase." *Cell Growth Differ*. Sep. 1999;10(9):629-38.
Zheng, XX et al "Administration of noncytolytic IL-10/Fc in murine models of lipopolysaccharide-induced induced septic shock and allogeneic islet transplantation." *J Immunol*. May 15, 1995;154(10):5590-600.
Zhou, BB et al "Tumour-initiating cells: challenges and opportunities for anticancer drug discovery." *Nat Rev Drug Discov*. Oct. 2009;8(10):806-23.
Zimmerman, K. et al "A triglycine linker improves tumor uptake and biodistributions of 67-Cu-labeled anti-neuroblastoma MAb chCE7 F(ab')2 fragments." *Nucl Med Biol*. Nov. 1999;26(8):943-50.
Merrill et al "Cell mixing at a neural crest-mesoderm boundary and deficient ephrin-Eph signaling in the pathogenesis of craniosynostosis." *Human molecular genetics* 15.8 (2006): 1319-1328.
Official Action dated Mar. 11, 2015 issued in Australian application (No. 2011360938).

(56) References Cited

OTHER PUBLICATIONS

Official Action dated May 16, 2014 issued in Chinese application (No. 201180065609.1).
Official Action dated Jan. 23, 2015 issued in Chinese application (No. 201180065609.1).
Official Action dated Dec. 30, 2014 Issued in Colombian application (No. 13-216.891).
Official Action dated Sep. 29, 2014 issued in European application (No. 11801934.8).
Official Action dated Nov. 13, 2013 issued in New Zeland application (No. 611428).
Official Action dated Mar. 3, 2015 issued in New Zeland application (No. 611428).
Official Action dated Mar. 3, 2015 issued in New Zealand application (No. 705008).
Official Action dated Apr. 21, 2014 issued in Saudi Arabian application (No. 111330037).
Official Action issued in Saudi Arabian application (No. 111330037) received Apr. 9, 2015.
Holen et al. "Signaling through ephrin-A ligand leads to activation of Src-family kinases, Akt phosphorylation, and inhibition of antigen receptor-induced apoptosis." *Journal of Leukocyte Biology* (2008) 84:1183-1191.
Office action dated Aug. 13, 2015 issued in Chinese patent appln. (No. 201180065609.1).
Office action dated Oct. 12, 2015 issued in European patent appln (No. 11801934.8).
Office action dated Oct. 6, 2015 issued in Mexican patent appln. (No. MX/a/2013/006569).
Office action dated Jun. 26, 2015 issued in Russian patent appln. (No. 2013128444).

\* cited by examiner gi|33359684|ref|NM_005227.2| Homo sapiens ephrin-A4 (EFNA4), transcript variant 1, mRNA (SEQ ID NO: 1)

CTTCCCTCTTCACTTTGTACCTTTCTCTCCTCGACTGTGAAGCGGGCCGGGACCTGCCAGGCCAGACCAA
ACCGGACCTCGGGGGCGATGCGGCTGCTGCCCCTGCTGCGGACTGTCCTCTGGGCCGCGTTCCTCGGCTC
CCCTCTGCGCGGGGGCTCCAGCCTCCGCCACGTAGTCTACTGGAACTCCAGTAACCCCAGGTTGCTTCGA
GGAGACGCCGTGGTGGAGCTGGGCCTCAACGATTACCTAGACATTGTCTGCCCCCACTACGAAGGCCCAG
GGCCCCCTGAGGGCCCCGAGACGTTTGCTTTGTACATGGTGGACTGGCCAGGCTATGAGTCCTGCCAGGC
AGAGGGCCCCCGGGCCTACAAGCGCTGGGTGTGCTCCCTGCCCTTTGGCCATGTTCAATTCTCAGAGAAG
ATTCAGCGCTTCACACCCTTCTCCCTCGGCTTTGAGTTCTTACCTGGAGAGACTTACTACTACATCTCGG
TGCCCACTCCAGAGAGTTCTGGCCAGTGCTTGAGGCTCCAGGTGTCTGTCTGCTGCAAGGAGAGGAAGTC
TGAGTCAGCCCATCCTGTTGGGAGCCCTGGAGAGAGTGGCACATCAGGGTGGCGAGGGGGGGACACTCCC
AGCCCCCTCTGTCTCTTGCTATTACTGCTGCTTCTGATTCTTCGTCTTCTGCGAATTCTGTGAGCCAAGC
AGACCTTCCCTCTCATCCCAAGGAGCCAGAGTCCTCCCAAGATCCCCTGGAGGAGGAGGGATCCCTGCTG
CCTGCACTGGGGGTGCCAATTCAGACCGACAAGATGGAGCATTGATGGGGGAGATCAGAGGGTCTGAGGT
GACTCTTGCAGGAGCCTGTCCCCTCATCACAGGCTAAAGAAGAGCAGTAGACAGCCCTGGACACTCTGAA
GCAGAGGCAAGACAAACACAGGCGCTTTGCAGGCTGCTCTGAGGGTCTCAGCCCATCCCCCAGGAGGACT
GGGATTTGGTATGATCAAATCCTCAAGCCAGCTGGGGGCCCAGGCTGAAGACCTGGGGACAGGTCGATTG
CTGGACCAGGGCAAAGAAGAAGCCCTGCCATCTGTGCCCTGTGGGCCTTTTCCCTGGGGCAGCACCTTGC
CCTCCCCAGGGGATCACTCACTTGTCTTCTATGAAGACGGACTCTTCATGAGGTTGAATTTCATGCCAGT
TTGTATTTTTATAAGTATCTAGACCAAACCTTCAATAAACCACTCATCTTTTGTTGCCCTCCCCAAAAA
AAAAAAAAAAAAAAAA

FIG. 1A

>gi|4885197|ref|NP_005218.1| ephrin-A4 isoform a [Homo sapiens]

(SEQ ID NO: 2)

MRLLPLLRTVLWAAFLGSPLRGGSSLRHVVYWNSSNPRLLRGDAVVELGLNDYLDIVCPHYEGPGPPEGP
ETFALYMVDWPGYESCQAEGPRAYKRWVCSLPFGHVQFSEKIQRFTPFSLGFEFLPGETYYYISVPTPES
SGQCLRLQVSVCCKERKSESAHPVGSPGESGTSGWRGGDTPSPLCLLLLLLLILRLLRIL

FIG. 1B

```
hEFNA4 iso b NP_872631.1    (1)   MRLLPLLRTVLWAAFLGSPLRGGSSLRHVVYWNSSNPRLLRGDAVVELGL   50
hEFNA4 iso c NP_872632.2    (1)   MRLLPLLRTVLWAAFLGSPLRGGSSLRHVVYWNSSNPRLLRGDAVVELGL
hEFNA4 iso a NP_005218.1    (1)   MRLLPLLRTVLWAAFLGSPLRGGSSLRHVVYWNSSNPRLLRGDAVVELGL hEFNA4 iso b NP_872631.1    (51)  NDYLDIVCPHYEGPGPPEGPETFALYMVDWPGYESCQAEGPRAYKRWVCS   100
hEFNA4 iso c NP_872632.2    (51)  NDYLDIVCPHYEGPGPPEGPETFALYMVDWPGYESCQAEGPRAYKRWVCS
hEFNA4 iso a NP_005218.1    (51)  NDYLDIVCPHYEGPGPPEGPETFALYMVDWPGYESCQAEGPRAYKRWVCS hEFNA4 iso b NP_872631.1    (101) LPFGHVQFSEKIQRFTPFSLGEEFLPGETYYISVPTPESSGQCLRLQVS   150
hEFNA4 iso c NP_872632.2    (101) LPFGHVQFSEKIQRFTPFSLGEEFLPGETYYISVPTPESSGQCLRLQVS
hEFNA4 iso a NP_005218.1    (101) LPFGHVQFSEKIQRFTPFSLGEEFLPGETYYISVPTPESSGQCLRLQVS hEFNA4 iso b NP_872631.1    (151) VCCKERR-ARVLPRSPGGGIPAACTGGANSDRQDGALMGEIRGSEVTLA   200
hEFNA4 iso c NP_872632.2    (151) VCCKERN-LPSHPKEP----E-----SSQDPLEEEGSLLPALGVPIQTDK
hEFNA4 iso a NP_005218.1    (151) VCCKERKSESAHPVGSPGESG----TSGWRGGDTPSPLCLLLLLLILR hEFNA4 iso b NP_872631.1    (200) GACPLITG   (SEQ ID NO: 3)
hEFNA4 iso c NP_872632.2    (191) MEH-----   (SEQ ID NO: 4)
hEFNA4 iso a NP_005218.1    (197) LLRIL---   (SEQ ID NO: 2)
```

FIG. 1C gi:33359681 / NM_004428.2
Homo sapiens ephrin-A1 (EFNA1), transcript variant 1, mRNA (Seq ID NO: 5)

```
gccagatctg tgagcccagc gctgactgcg ccgcggagaa agccagtggg aacccagacc
cataggagac ccgcgtcccc gctcggcctg gccaggcccc gcgctatgga gttcctctgg
gcccctctct tgggtctgtg ctgcagtctg gccgctgctg atcgccacac cgtcttctgg
aacagttcaa atcccaagtt ccggaatgag gactacacca tacatgtgca gctgaatgac
tacgtggaca tcatctgtcc gcactatgaa gatcactctg tggcagacgc tgccatggag
cagtacatac tgtacctggt ggagcatgag gagtaccagc tgtgccagcc ccagtccaag
gaccaagtcc gctggcagtg caaccggccc agtgccaagc atgcccgga gaagctgtct
gagaagttcc agcgcttcac acctttcacc ctgggcaagg agttcaaaga aggacacagc
tactactaca tctccaaacc catccaccag catgaagacc gctgcttgag gttgaaggtg
actgtcagtg gcaaaatcac tcacagtcct caggcccatg acaatccaca ggagaagaga
cttgcagcag atgacccaga ggtgcgggtt ctacatagca tcggtcacag tgctgcccca
cgcctcttcc cacttgcctg gactgtgctg ctccttccac ttctgctgct gcaaaccccg
tgaaggtgta tgccacacct ggccttaaag agggacaggc tgaagagagg gacaggcact
ccaaacctgt cttggggcca ctttcagagc ccccagccct gggaaccact cccaccacag
gcataagcta tcacctagca gcctcaaaac gggtcagtat taaggttttc aaccggaagg
aggccaacca gcccgacagt gccatcccca ccttcacctc ggagggatgg agaaagaagt
ggagacagtc ctttcccacc attcctgcct ttaagccaaa gaaacaagct gtgcaggcat
ggtcccttaa ggcacagtgg gagctgagct ggaaggggcc acgtggatgg gcaaagcttg
tcaaagatgc cccctccagg agagagccag gatgcccaga tgaactgact gaaggaaaag
caagaaacag tttcttgctt ggaagccagg tacaggagag gcagcatgct tgggctgacc
cagcatctcc cagcaagacc tcatctgtgg agctgccaca gagaagtttg tagccaggta
ctgcattctc tcccatcctg gggcagcact ccccagagct gtgccagcag gggggctgtg
ccaacctgtt cttagagtgt agctgtaagg gcagtgccca tgtgtacatt ctgcctagag
tgtagcctaa agggcagggc ccacgtgtat agtatctgta tataagttgc tgtgtgtctg
tcctgatttc tacaactgga gttttttat acaatgttct ttgtctcaaa ataaagcaat
gtgttttttc ggacatgctt ttctgccact ccatattaaa acatatgacc attgagtccc
tgctaaaaaa aaaaaaaaa aaaaaaaaa
```

FIG. 1D gi:33359682 / NP_004419
Homo sapiens ephrin-A1 (EFNA1), isoform a (Seq ID No: 6)

```
meflwapllg lccslaaadr htvfwnssnp kfrnedytih vqlndyvdii cphyedhsva
vqlndyvdii cphyedhsva qpqskdqvrw qcnrpsakhg peklsekfqr ftpftlgkef
keghsyyyis kpihqhedrc lrlkvtvsgk ithspqahdn pqekrlaadd pevrvlhsig
hsaaprlfpl awtvlllpll hsaaprlfpl awtvlllpll
```

FIG. 1E

Alignment of Homo sapiens ephrin-A1 (EFNA1), isoforms a and b

```
hEFNA1 iso a NP_004419 (1): meflwapllg lccslaaadr htvfwnssnp kfrnedytih
hEFNA1 iso b NP_872626 (2): meflwapllg lccslaaadr htvfwnssnp kfrnedytih hEFNA1 iso a NP_004419 (1): vqlndyvdii cphyedhsva vqlndyvdii cphyedhsva
hEFNA1 iso b NP_872626 (2): vqlndyvdii cphyedhsva daameqyily lveheeyqlc hEFNA1 iso a NP_004419 (1): qpqskdqvrw qcnrpsakhg peklsekfqr ftpftlgkef
hEFNA1 iso b NP_872626 (2): qpqskdqvrw qcnrpsakhg peklsekfqr ftpftlgkef hEFNA1 iso a NP_004419 (1): keghsyyyis kpihqhedrc lrlkvtvsgk ithspqahdn
hEFNA1 iso b NP_872626 (2): keghsyyyis                            hspqahdn hEFNA1 iso a NP_004419 (1): pqekrlaadd pevrvlhsig hsaaprlfpl awtvlllpll
hEFNA1 iso b NP_872626 (2): pqekrlaadd pevrvlhsig hsaaprlfpl awtvlllpll hEFNA1 iso a NP_004419 (1): hsaaprlfpl awtvlllpll  (SEQ ID No: 6)
hEFNA1 iso b NP_872626 (2): llqtp                  (SEQ ID No: 7)
```

FIG. 1F

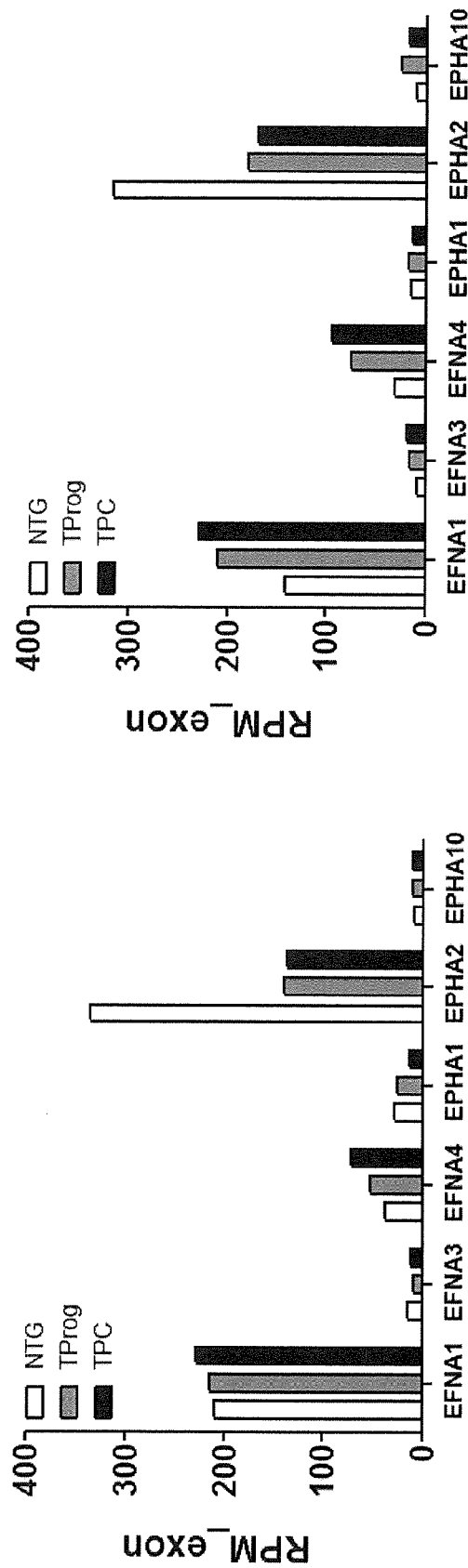

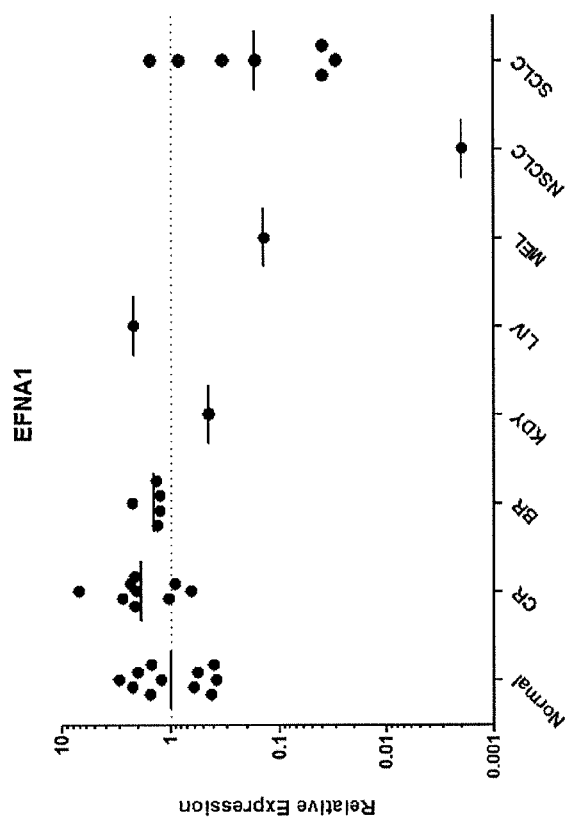
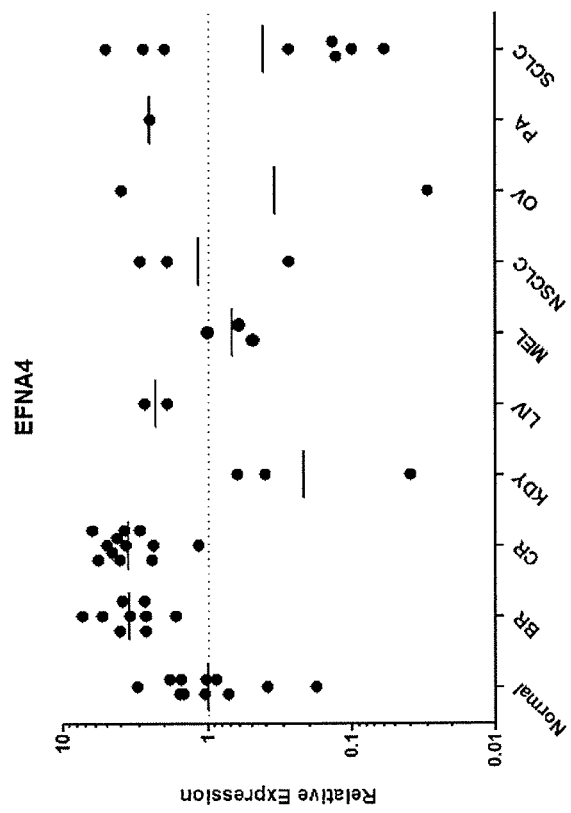
EFNA4 is Expressed in Various NTX Cell Lines
FIG. 6C
FIG. 6D

Complementarity Determining Regions and
Genetic Arrangements of Distinct Anti-EFNA Antibodies

| Clone | Isotype | VH | DH | JH | CDRH1 (SEQ ID NOS: 8-20) | CDRH2 (SEQ ID NOS: 21-33) | CDRH3 (SEQ ID NOS: 34-46) | VL | JL | CDRL1 (SEQ ID NOS: 47-59) | CDRL2 (SEQ ID NOS: 70-82) | CDRL3 (SEQ ID NOS: 83-95) |
|---|---|---|---|---|---|---|---|---|---|---|---|---|
| SC4.2 | IgG1/K | VHJ558 | P1 | JH3 | GYTFTDYE | FDPETGNT | ARGYPAWFGY | IGKV1-110 | JK1 | QSLAHTNGNTY | KVSNMRFS | SQDTHVPPT |
| SC4.5 | IgG1/K | IGHV2-6 | none | JH3 | GFSLTTYG | IWGGGST | ASDWAY | IGKV6-15 | JK2 | QNVGTN | SASYRYS | QQYKRYPYT |
| SC4.8 | not done | VHJ558 | IGHD6-1 | JH4 | GYTFTNYW | IDPSDSYI | ARERLSHAMDY | IGVK9-128 | JK2 | QDIKSY | YATSLAD | LQHGESPYT |
| SC4.15 | IgG1/K | IGHV5-6 | DSP2.9 | JH3 | GFFSTYG | ISSGGTYT | TRHDPNDGYYFLFAY | IGKV6-b | JK5 | QSVGNN | YASNRYT | QQHYSSPLT |
| SC4.22 | IgG2b/K | VHJ558 | DFL16.1e | JH4 | GYTFTGYY | IYPGNFNT | AREDGSPYYAMDY | IGKV1-110 | JK1 | QSLVHSNGNTF | RVSNRFS | FQATHVPWT |
| SC4.31 | IgG1/K | VHJ558 | DFL16.1 | JH4 | GYTFTRDW | IHPYDSET | VTFIKTMVDTYYYAMDY | IGKV1-135 | JK1 | QSLLHSDGKTY | LVSNLDS | WQGTHFPCT |
| SC4.47 | IgG1/K | IGHV1-26 | P1inv | JH2 | GYTFTYFY | INPNNGGT | ARWVGTHYFDY | IGKV21-7 | JK1 | QSVSSSYTY | FASNLES | QHSWEIPPT |
| SC4.60 | IgG2a/K | IGHV1-39 | DQ52a.2 | JH4 | GYSFTVYN | INPYYGGT | ARGGKTGTYYVMDY | IGKV12-44 | JK5 | ENIDSY | AATLAD | QHYSTLT |
| SC4.73 | IgG1/K | IGHV3-6 | DSP2.13 | JH2 | GYSITSGYY | ISYDGRN | AREGYGDYPFDY | IGKV21-7 | JK1 | QSVSSSYSY | YASNLES | QHSWEIPRT |
| SC4.76 | IgG2b/K | J558.87.193 | DFL16.1e | JH4 | GYTFTGYY | IYPGNFNT | AREDGSPYYAMDY | IGKV1-110 | JK1 | QSLVHSNGNTF | RVSNRFS | FQATHVPWT |
| SC4.91 | IgG2b/K | IGHV1-64 | P8inv | JH4 | GYTFSYW | IHPNSDTI | ATPERRAMDY | IGKV4-74 | JK4 | SSLSSSY | STSFLAS | QQYDSSPFT |
| SC4.105 | IgG1/K | VH3660 | DSP2.2 | JH3 | GASITSGY | INYSGNT | ARSTMITGAWFAY | IGKV6-32 | JK5 | QSVSKD | YASNRYT | QQDYSSPLT |
| SC9.65 | not done | IGHV1S113 | DFL16.1 | JH3 | GYTFTEYT | INPKNVGS | ARGGNYYASSPFDY | IGKV8-21 | JK2 | QSLLNSRTRKNY | WASTRES | KQSYNLYT |

FIG. 7A

SC4.2    Heavy chain - nucleotide sequence  (SEQ ID NO: 96)
CAGGTTCAACTGCAGCAGTCTGGAGCTGAGCTGGTGAGGCCTGGGACTTCAGTGACGCTGTCCTGCAAGGCTTCG
GGCTACACATTTACTGACTATGAAATGCACTGGGTGAAGCAGACACCTGTGCTTGGCCTGGAATGGATTGGAGCT
TTTGATCCTGAAACTGGAAATACTGTCTACAATCAGAAGTTCAAGGGCAAGGCCACACTGACTGCAGACAAATCC
CCCAACACAGCCTACATGGAGCTCATCAGCCTGACATCTGAGGACTCTGCCGTCTATTACTGTGCAAGGGGGTACC
CGGCCTGGTTTGGTTACTGGGGCCAAGGGACTCTGGTCACTGTCTCTGCA SC4.2    Heavy chain - protein sequence  (SEQ ID NO: 97)
QVQLQQSGAELVRPGTSVTLSCKASGYTFTDYEMHWVKQTPVLGLEWIGAFDPETGNTVY
NQKFKGKATLTADKSPNTAYMELISLTSEDSAVYYCARGYPAWFGYWGQGTLVTVSA

FIG. 7B

SC4.2    Light chain - nucleotide sequence (SEQ ID NO: 98)
GATGTTGTGATGACCCAAATTCCACTCTCCCTGCCTGTCACTCTTGGAGATCAAGCCTCCATCTCTTGCAGATCTAG
TCAGAGCCTTGCACACACTAATGGAAACACCTATTTACATTGGTACCTGCAGAAGCCAGGCCAGTCTCCAAAGCTC
CTGATCTACAAAGTTTCCAACCGATTTTCTGGGGTCCCAGACAGGTTCAGTGGCAGTGGATCAGGGACAGATTTCA
CTCTCAAGATCAGCAGAGTGGAGGCTGAGGATCTGGGAGTTTATTTCTGCTCTCAAGATACACATGTTCCTCCGAC
GTTCGGTGGAGGCACCAAGCTGGAAATGAAAC SC4.2    Light chain - protein sequence (SEQ ID NO: 99)
DVVMTQIPLSLPVTLGDQASISCRSSQSLAHTNGNTYLHWYLQKPGQSPKLLIYKV
SNRFSGVPDRFSGSGSGTDFTLKISRVEAEDLGVYFCSQDTHVPPTFGGGTKLEMK SC4.5    Heavy chain - nucleotide sequence  (SEQ ID NO: 100)
CAGGTGCAGCTGAAGCAGTCAGGACCTGGCCTGGTGGCGCCCTCACAGAGCCTGTCCATCACATGCACTGTCTCTG
GTTTCTCATTAACCACTTATGGTGTAGACTGGGTTCGCCAGTCTCCAGGAAAGGGTCTGGAGTGGCTGGGAGTGA
TATGGGGTGGTGGAAGCACAAATTATAATTCAGCTCTCAAATCCAGACTGAGCATCAGCAAGGACAACTCCAAGA
GCCAAGTTTTCTTAAAAATGAACAGTCTGCAAACTGATGACACAGCCATGTATTACTGTGCCAGTGATTGGGCTTA
CTGGGGCCAAGGGACTCTGGTCACTGTCTCTGCA SC4.5    Heavy chain - protein sequence  (SEQ ID NO: 101)
QVQLKQSGPGLVAPSQSLSITCTVSGFSLTTYGVDWVRQSPGKGLEWLGVIWGGGST
NYNSALKSRLSISKDNSKSQVFLKMNSLQTDDTAMYYCASDWAYWGQGTLVTVSA

FIG. 7C

SC4.5    Light chain - nucleotide sequence (SEQ ID NO: 102)
GACATTGTGATGACCCAGTCTCAAAAATTCATGTCCACATCAGTAGGAGACAGGGTCACCGTCACCTGCAAGGCC
AGTCAGAATGTGGGTACAAATGTAGCCTGGTTTCAACAGAAATCAGGGCAATCTCCTAAACCACTGATTCACTCG
GCATCCTACCGTTACAGTGGAGTCCCTGATCGCTTCACAGGCAGTGGATCTGGGACAGATTTCACTCTCACCATCA
CCAATGTGCAGTCTGAAGACTTGGTAGCGTATTTCTGTCAGCAATATAAGAGGTATCCGTACACGTTCGGAGGGG
GGACCAAGCTGGAAATAAAACG SC4.5    Light chain - protein sequence (SEQ ID NO: 103)
DIVMTQSQKFMSTSVGDRVTVTCKASQNVGTNVAWFQQKSGQSPKPLIHSASYRYS
GVPDRFTGSGSGTDFTLTITNVQSEDLVAYFCQQYKRYPYTFGGGTKLEIKR SC4.8    Heavy chain - nucleotide sequence (SEQ ID NO: 104)
    CAGGTCCAGCTGCAGCAGCCTGGGGCTGAACTGGTGAAGCCTGGGGCTTCAGTGAAGCTGTCCTGTAAGGCTTCT
    GGATACACCTTCACTAACTACTGGATACACTGGGTGAAGCAGAGGCCTGGACAAGGCCTTGAGTGGATCGGAGA
    GATTGATCCTTCTGATAGTTATATTTATTACAATCAAAAGTTCAAGGGCAAGGCCACATTGACTGTAGACAAATCT
    TCCAGCACAGCCCACATGCAACTCAGCAGCCTGACATCTGAGGACTCTGCGGTCTATTACTGTGCAAGAGAGAGG
    TTATCTCATGCTATGGACTACTGGGGTCAAGGAACCTCAGTCACCGTCTCCTCA SC4.8    Heavy chain - protein sequence (SEQ ID NO: 105)
    QVQLQQPGAELVKPGASVKLSCKASGYTFTNYWIHWVKQRPGQGLEWIGEIDPSDSYIYY
    NQKFKGKATLTVDKSSTAHMQLSSLTSEDSAVYYCARERLSHAMDYWGQGTSVTVSS

FIG. 7D

SC4.8    Light chain - nucleotide sequence (SEQ ID NO: 106)
    GACATCAAGATGACCCAGTCTCCATCCTCCATGTATGCATCGCTGGGAGAGAGAGTCACTATACACTTGCAAGGCG
    AGTCAGGACATTAAAAGCTATTTAAGCTGGTACCAGCAGAAACCTTGGAAATCTCCTAAGACCCTGATCTATTATG
    CAACAAGCTTGGCAGATGGGGTCCCATCAAGATTCAGTGGCAGTGGATCTGGGGAAGATTATTCTCTAACCATCA
    GCAGCCTGGAGTCTGACGATACAGCAACTTATTACTGTCTACAGCATGGTGAGAGCCCGTATACGTTCGGATCGG
    GGACCAAGCTGGAAATAAAACG SC4.8    Light chain - protein sequence (SEQ ID NO: 107)
    DIKMTQSPSSMYASLGERVTITCKASQDIKSYLSWYQQKPWKSPKTLIYYATSLADGVPSR
    FSGSGSGEDYSLTISSLESDDTATYYCLQHGESPYTFGSGTKLEIKR SC4.15    Heavy chain - nucleotide sequence (SEQ ID NO: 108)
    GAGGTGCAGGTGGTGGAGTCTGGGGGAGACTTAGTGAAGCCTGGAGGGTCCCTGAAACTCTCCTGTGCAGCCTC
    TGGATTCACTTTCAGTACCTATGGCATGTCTTGGGTTCGCCAGACTCCAGACAAGAGGCTGGAATGGGTCGCAACC
    ATTAGTAGTGGTGGTACTTACACCTACTATCCAGACAGTGTGAAGGGGCGATTCAAAATCTCCAGAGACAATGCC
    AAGGACACCCTGTACCTGCAAATGAGCAGTCTGAAGTCTGAGGACACAGCCATGTATTACTGTACAAGACATGAC
    CCCAATGATGGTTACTACTTCCTGTTTGCTTACTGGGGCCAGGGGACTCTGGTCATTGTCTCTGCA SC4.15    Heavy chain - protein sequence (SEQ ID NO: 109)
    EVQVVESGGDLVKPGGSLKLSCAASGFTFSTYGMSWVRQTPDKRLEWVATISSGGTYTYYP
    DSVKGRFKISRDNAKDTLYLQMSSLKSEDTAMYYCTRHDPNDGYYFLFAYWGQGTLVIVSA

FIG. 7E

SC4.15    Light chain - nucleotide sequence (SEQ ID NO: 110)
    AGTATAGGGAGGACCCAGATTCCCAAATTCCTGCCTGTATCAGCAGGAGACAGGGTTACCATGACCTGCAAGGCC
    AGTCAGAGTGTGGGTAATAATGTAGCCTGGTACCAACAGAAGGCAGGACAGTCTCCTAAACTGCTGATATACTAT
    GCATCCAATCGCTACACTGGAGTCCCTGATCGCTTCACTGGCAGTGGATCTGGGACAGATTTCACTTTCACCATCA
    GCAGTGTGCAGGTTGAAGACCTGGCAGTTTATTTCTGTCAGCAGCATTATAGCTCTCCGCTCACGTTCGGTGCTGG
    GACCAAGCTGGAGCTGAAAC SC4.15    Light chain - protein sequence (SEQ ID NO: 111)
    SIGRTQIPKFLPVSAGDRVTMTCKASQSVGNNVAWYQQKAGQSPKLLIYYASN
    RYTGVPDRFTGSGSGTDFTFTISSVQVEDLAVYFCQQHYSSPLTFGAGTKLELK SC4.22  Heavy chain - nucleotide sequence (SEQ ID NO: 112)
CAGATCCAGCTGCAGCAGTCTGGACCTGAGCTGGTGAAGCCTGGGGCTTCAGTGAAGATATCCTGCAAGGCTTCT
GGCTACACCTTCACTGGCTACTATATACACTGGGTGAAGCAGAGGCCTGGACAGGGACTTGAGTGGATTGGATGG
ATTTATCCTGGAAACTTTAATACTAAGTACAATGAGCGGTTCAAGGGCATGGCCACTTTGACTGTAGACACATCCT
CCAGCACAGCCTACATGCAGCTCAGCAGCCTGACCTCTGAGGACTCTGCGGTCTATCTCTGTGCAAGAGAGGATG
GTAGCCCCTACTATGCTATGGACTACTGGGGTCAAGGAACCTCAGTCACCGTCTCCTCA SC4.22  Heavy chain - protein sequence (SEQ ID NO: 113)
QIQLQQSGPELVKPGASVKISCKASGYTFTGYYIHWVKQRPGQGLEWIGWIYPGNFNTKY
NERFKGMATLTVDTSSSTAYMQLSSLTSEDSAVYLCAREDGSPYYAMDYWGQGTSVTVSS

FIG. 7F

SC4.22  Light chain - nucleotide sequence (SEQ ID NO: 114)
GATGTTGTGATGACCCAAACTCCACTCTCCCTGCCTGTCAGTCTTGGAGATCAAGCTTCCATCTCTTGCAGATCTAG
TCAGAGCCTTGTCCACAGCAATGGAAACACCTTTTTATATTGGTACCTGCAGAAGCCAGGCCAGTCTCCAAAACTC
CTGATCTACAGGGTTTCCAACCGATTTTCTGGGGTCCCAGACAGGTTCAGTGGCAGTGGATCAGGGACAGATTTC
ACACTCAAGATCAGCAGAGTGGAGGCTGAGGATCTGGGTGTTTATTTCTGCTTTCAAGCTACACATGTTCCGTGGA
CGTTCGGTGGAGGCACCAAACTGGAAATCAAAC SC4.22  Light chain - protein sequence (SEQ ID NO: 115)
DVVMTQTPLSLPVSLGDQASISCRSSQSLVHSNGNTFLYWYLQKPGQSPKLLIYRVSNRFS
GVPDRFSGSGSGTDFTLKISRVEAEDLGVYFCFQATHVPWTFGGGTKLEIK

---

SC4.31  Heavy chain - nucleotide sequence (SEQ ID NO: 116)
CAGGTCCAACTGCAGCAGCCTGGGGCTGAACTGGTGAGGCCTGGGGCGTCAGTGAAGCTGTCCTGCAAGGCTTCT
GGCTACACATTCACCAGGGACTGGATGCACTGGATTAAGCAGAGGCCTGGACAAGGTCTTGACTGGATTGGAAC
GATTCATCCTTACGATAGTGAAACACATTACAATCAAAACTTCAAGGACAAGGCCACATTGACTGTAGACAAATCC
TCCAGCACAGCCTACATGCAACTCAGCAGCCTGACATCTGAGGACTCTGCGGTCTATTACTGTGTAACATTTATTAA
GACGATGGTAGACACATATTACTATGCTATGGACTACTGGGGTCAAGGAACCTCAGTCACCGTCTCCTCA SC4.31  Heavy chain - protein sequence (SEQ ID NO: 117)
QVQLQQPGAELVRPGASVKLSCKASGYTFTRDWMHWIKQRPGQGLDWIGTIHPYDSETH
YNQNFKDKATLTVDKSSSTAYMQLSSLTSEDSAVYYCVTFIKTMVDTYYYAMDYWGQGTSVTVSS

FIG. 7G

SC4.31  Light chain - nucleotide sequence (SEQ ID NO: 118)
GATGTTGTGATGACCCAGACTCCACTCACTTTGTCGGTTACCATTGGACAACCAGCCTCCATCTCTTGCAAGTCAAG
TCAGAGCCTCTTACATAGTGATGGAAAGACATATTTGAATTGGTTGTTACAGAGGCCAGGCCAGTCTCCAAAGCG
CCTAATCTATCTGGTGTCTAACCTGGACTCTGGAGTCCCTGACAGGTTCACTGGCAGTGGATCAGGGACAGATTTC
ACACTGAAATTCAGCAGGTTGGAGGCTGAGGATTTGGGAGTTTATTATTGCTGGCAAGGTACACATTTTCCTCAG
ACGTTCGGTGGAGGCACCAAACTGGAAATCAAAC SC4.31  Light chain - protein sequence (SEQ ID NO: 119)
DVVMTQTPLTLSVTIGQPASISCKSSQSLLHSDGKTYLNWLLQRPGQSPKRLIYLVSN
LDSGVPDRFTGSGSGTDFTLKFSRLEAEDLGVYYCWQGTHFPQTFGGGTKLEIK SC4.47  Heavy chain - nucleotide sequence (SEQ ID NO: 120)
CAGGTCCAGCTGCAACAATCTGGACCTGAGCTGGTGAAGCCTGGGGCTTCAGTGAAGATATCCTGTACGGCTTCT
GGATACACGTTCACTTATTTCTACATGAACTGGGTGAAGCAGAGCCAAGGAAAGAGCCTTGAGTGGGTTGGACA
GATTAATCCTAACAATGGTGGGACTGCCTACAACCACAAGTTCAGGGGCAAGACCACATTGACTGTGGACAAGTC
CTCCAACACAGCCTTCATGGAGCTCCGCAGCCTGACATCTGAGGACTCTGCAGTCTATTTCTGTGCAAGATGGGTC
GGGACTCACTACTTTGACTACTGGGGCCAAGGCACCACTCTCACAGTCTCCTC SC4.47  Heavy chain - protein sequence (SEQ ID NO: 121)
EVQLQQSGPELVKPGASVKISCTASGYTFTYFYMNWVKQSQGKSLEWVGQINPNNGGT
AYNHKFRGKTTLTVDKSSNTAFMELRSLTSEDSAVYFCARWVGTHYFDYWGQGTTLTVSS

FIG. 7H

SC4.47  Light chain - nucleotide sequence (SEQ ID NO: 122)
GACATTGTGCTGACACAGTCTCCTGCTTCCTTACCTGTTTCTCTGGGGCAGAGGGCCACCATCTCATGCAGGGCCA
GCCAAAGTGTCAGTTCATCTAGCTATACTTATATACACTGGTACCAACAGAAACCAGGACAGCCACCCAAACTCCT
CATCAACTTTGCATCCAACCTAGAATCTGGGGTCCCTGCCAGGTTCAGTGTCAGTGGGTCTGGGACAGACTTCACC
CTCAACATCCATCCTGTGGAGGGGGAGGATACTGCAACATATTACTGTCAGCACAGTTGGGAGATTCCTCCGACG
TTCGGTGGAGGCACCAAGCTGGAAATCAAAC SC4.47  Light chain - protein sequence (SEQ ID NO: 123)
DIVLTQSPASLPVSLGQRATISCRASQSVSSSSYTYIHWYQQKPGQPPKLLINFASN
LESGVPARFSVSGSGTDFTLNIHPVEGEDTATYYCQHSWEIPPTFGGGTKLEIK

---

SC4.60  Heavy chain - nucleotide sequence (SEQ ID NO: 124)
GAGATCCAGCTGCAGCAGTCTGGAGCTGACCTGGTGAAGCCTGGGGCTTCAGTGAAGATATCCTGCAAGGCTTCT
GGTTACTCATTCACTGTCTACAACATGAACTGGGTGAAGCAGAGCCATGGAAAGAGCCTTGAGTGGATTGGAATT
ATTAATCCTTACTATGGTGGTACTACCTACAATCAGAAATTCAAGGTCAAGGCCACATTGACTGTAGACAAATCTT
CCAGCACAGCCTACATGCAGCTCAACAGCCTGACATCTGAGGACTCTGCAGTCTATTACTGTGCAAGAGGGGGAA
AGACTGGGACCTATTACTATGTTATGGACTACTGGGGTCAGGGAACCCTCAGTCACCGTCTCCTCA SC4.60  Heavy chain - protein sequence (SEQ ID NO: 125)
EIQLQQSGADLVKPGASVKISCKASGYSFTVYNMNWVKQSHGKSLEWIGIINPYYGGTT
YNQKFKVKATLTVDKSSSTAYMQLNSLTSEDSAVYYCARGGKTGTYYYVMDYWGQGTSVTVSS

FIG. 7I

SC4.60  Light chain - nucleotide sequence (SEQ ID NO: 126)
GACATCCAGATGACTCAGTCTCCAGCTTCCCTGTCTGCATCTGTGGGAGAAACTGTCAGCATCACATGTCGAGCAA
GTGAGAATATTGACAGTTATTTAGCATGGTATCAGCAGAAACAGGGAAAATCTCCTCAGCTCCTGGTCCATGCTGC
AACACTCTTAGCAGATGGTGTGCCATCAAGGTTCAGTGGCAGTGGATCAGGCACACAGTTTTCTCTCAAGATCAAC
AGCCTGCAGTCTGAAGATGTTGCGACATATTTCTGTCAACATTATTATAGTACTCTCACGTTCGGTGGTGGGACCA
AGCTGGAGCTGAAAC SC4.60  Light chain - protein sequence (SEQ ID NO: 127)
DIQMTQSPASLSASVGETVSITCRASENIDSYLAWYQQKQGKSPQLLVHAATLL
ADGVPSRFSGSGSGTQFSLKINSLQSEDVATYFCQHYYSTLTFGGGTKLELK SC4.73  Heavy chain - nucleotide sequence (SEQ ID NO: 128)
TCTGATGTACAGCTTCAGGAGTCAGGACCTGGCCTCGTGAAACCTTCTCAGTCTCTGTCTCTCACCTGCTCTGTCACT
GGCTACTCCATCACCAGTGGTTATTATTGGAACTGGATCCGGCAGTTTCCAGGAAACAAACTGGAATGGATGGGC
TACATAAGCTACGACGGTAGGAATAACTACAACCCTTCTCTCAAAAATCGAATCTCCATCACTCGTGACACATCTA
AGACCCAGTTTTTCCTGAAGTTGAATTCTGTGACTACTGGGGACACAGCTACATATTACTGTGCAAGAGAGGGGT
ATGGTGACTACCCCTTTGACTACTGGGGCCAAGGCACCACTCTCACAGTCTCCTCA SC4.73  Heavy chain - protein sequence (SEQ ID NO: 129)
SDVQLQESGPGLVKPSQSLSLTCSVTGYSITSGYYWNWIRQFPGNKLEWMGYISYDGRN
NYNPSLKNRISITRDTSKTQFFLKLNSVTTGDTATYYCAREGYGDYPFDYWGQGTTLTVSS

FIG. 7J

SC4.73  Light chain - nucleotide sequence (SEQ ID NO: 130)
GACATTGTGCTGACACAGTCTCCTGCTTCCTTAGCTGTATCTCTGGGGCAGAGGGCCACCATCTCATGCAGGGCCA
GCCAAAGTGTCAGTTCATCTAGCTATAGTTATGTGCACTGGTACCAACAGAAACCAGGACAGCCACCCAAACTCCT
CATCAAGTATGCATCCAACCTAGAATCTGGGGTCCCTGCCAGGTTCAGTGGCAGTGGGTCTGGGACAGACTTCAC
CCTCAACATCCATCCTGTGGAGGAGGAGGATTCTGCAACATATTTCTGTCAGCACAGTTGGGAGATTCCTCGGACG
TTCGGTGGAGGCACCAAGCTGGAAATCAAAC SC4.73  Light chain - protein sequence (SEQ ID NO: 131)
DIVLTQSPASLAVSLGQRATISCRASQSVSSSSYSYVHWYQQKPGQPPKLL
IKYASNLESGVPARFSGSGSGTDFTLNIHPVEEEDSATYFCQHSWEIPRTFGGGTKLEIK

---

SC4.76  Heavy chain - nucleotide sequence (SEQ ID NO: 132)
CAGATCCAGCTGCAGCAGTCTGGACCTGAGCTGGTGAAGCCTGGGGCTTCAGTGAAGATATCCTGCAAGGCTTCT
GGCTACACCTTCACTGGCTACTATATACACTGGGTGAAGCAGAGGCCTGGACAGGGACTTGAGTGGATTGGATGG
ATTTATCCTGGAAACTTTAATACTAAGTACAATGAGCGGTTCAAGGGCATGGCCACTTTGACTGTAGACACATCCT
CCAGCACAGCCTACATGCAGCTCAGCAGCCTGACCTCTGAGGACTCTGCGGTCTATCTCTGTGCAAGAGAGGATG
GTAGCCCCTACTATGCTATGGACTACTGGGGTCAAGGAACCTCAGTCACCGTCTCCTCA SC4.76  Heavy chain - protein sequence (SEQ ID NO: 133)
QIQLQQSGPELVKPGASVKISCKASGYTFTGYYIHWVKQRPGQGLEWIGWIYPGNFN
TKYNERFKGMATLTVDTSSSTAYMQLSSLTSEDSAVYLCAREDGSPYYAMDYWGQGTSVTVSS

FIG. 7K

SC4.76  Light chain - nucleotide sequence (SEQ ID NO: 134)
GATGTTGTGATGACCCAAACTCCACTCTCCCTGCCTGTCAGTCTTGGAGATCAAGCTTCCATCTCTTGCAGATCTAG
TCAGAGCCTTGTCCACAGCAATGGAAACACCTTTTTATATTGGTACCTGCAGAAGCCAGGCCAGTCTCCAAAACTC
CTGATCTACAGGGTTTCCAACCGATTTTCTGGGGTCCCAGACAGGTTCAGTGGCAGTGGATCAGGGACAGATTTC
ACACTCAAGATCAGCAGAGTGGAGGCTGAGGATCTGGGTGTTTATTTCTGCTTTCAAGCTACACATGTTCCGTGGA
CGTTCGGTGGAGGCACCAAACTGGAAATCAAAC SC4.76  Light chain - protein sequence (SEQ ID NO: 135)
DVVMTQTPLSLPVSLGDQASISCRSSQSLVHSNGNTFLYWYLQKPGQSPKLLIYRVS
NRFSGVPDRFSGSGSGTDFTLKISRVEAEDLGVYFCFQATHVPWTFGGGTKLEIK SC4.91    Heavy chain - nucleotide sequence (SEQ ID NO: 136)
CAGGTCCAACTACAGCAGCCTGGGGCTGAGCTGGTAAAGCCTGGGGCTTCAGTGAAGTTGTCCTGCAAGGCTTCT
GGCTACACTTTCACCAGCTACTGGATGCACTGGATGAAGCAGAGGCCTGGACAAGGCCTTGAGTGGATTGGAATG
ATTCATCCTAATAGTGATACTATCAACTACAATGCGAAGTTCAAGAGCAAGGCCACACTGTCTGTAGACAAATCCT
CCAGCACAGCCTACATGCAACTCAGCAGCCTGACATCTGAGGACTCTGCGGTCTATTACTGTGCAACCCCGGAACG
GCGGAGGGCTATGGACTACTGGGGTCAAGGAACCTCAGTCACCGTCTCCTCA SC4.91    Heavy chain - protein sequence (SEQ ID NO: 137)
QVQLQQPGAELVKPGASVKLSCKASGYTFTSYWMHWMKQRPGQGLEWIGMIHPNSD
TINYNAKFKSKATLSVDKSSSTAYMQLSSLTSEDSAVYYCATPERRRAMDYWGQGTSVTVSS

FIG. 7L

SC4.91    Light chain - nucleotide sequence (SEQ ID NO: 138)
CAGATTGTTCTCACCCAGTCTCCAGCAATCATGTCTGCATCTCCAGGGGAGAAGGTCACCATGACCTGCAGGGCCA
GCTCAAGTTTAAGTTCCAGTTACTTGCACTGGTACCAGCAGAAGCCAGGATCTTCCCCCAAACTCTGGATTTATAGC
ACATCCTTCCTGGCTTCAGGAGTCCCAGCTCGCTTCAGTGGCAGTGGGTCTGGGACCTCTTACTCTCTCACAATCAG
CAGTGTGGAGGCTGAGGATGCTGCCACTTATTACTGCCAGCAGTATGATAGTTCCCCGTTTACGTTCGGCTCGGGG
ACCAAGCTGGAAATAAAAC SC4.91    Light chain - protein sequence (SEQ ID NO: 139)
QIVLTQSPAIMSASPGEKVTMTCRASSSLSSSYLHWYQQKPGSSPKLWIYSTSFLAS
GVPARFSGSGSGTSYSLTISSVEAEDAATYYCQQYDSSPFTFGSGTKLEIK

---

SC4.105   Heavy chain - nucleotide sequence (SEQ ID NO: 140)
GAGGTGCAGCTTCAGGAGTCAGGACCTAGCCTCGTGAAACCTTCTCAGACTCTGTCCCTCACCTGTTCTGTCACTGG
CGCCTCCATCACCAGTGGTTACTGGAACTGGATCCGGAAATTCCCAGGGAATAATCTTGAGTACATGGGATTCATA
AACTACAGTGGTAACACTTACTACAATCCATCTCTCAAAAGTCGAATCTCCATCACTCGAGACACATCCAAGCACC
AGTACTACCTGCAGTTGAATTCTGTGACTCCTGAGGACACAGCCACATATTACTGTGCAAGATCTACTATGATTAC
GACGGGGGCCTGGTTTGCTTACTGGGGCCAAGGGTCTCTGGTCACTGTCTCTGCA SC4.105   Heavy chain - protein sequence (SEQ ID NO: 141)
EVQLQESGPSLVKPSQTLSLTCSVTGASITSGYWNWIRKFPGNNLEYMGFINYSGN
TYYNPSLKSRISITRDTSKHQYYLQLNSVTPEDTATYYCARSTMITTGAWFAYWGQGSLVTVSA

FIG. 7M

SC4.105   Light chain - nucleotide sequence (SEQ ID NO: 142)
AGTATTGTGATGACCCAGACTCCCAAATTCCTCCTTGTATCAGCTGGAGCCAGGATTACCCTAACCTGCAAGGCCA
GTCAGAGTGTGAGTAAAGATGTAGCTTGGTACCAACAGAAGCCAGGGCAGTCTCCTAAACTGCTAATATACTATG
CATCCAATCGCTACACTGGAGTCCCTGATCGCTTCACTGGCAGTGGATATGGGACGGATTTCACTTTCACCATCAG
CTCTGTGCAGGCTGAAGACCTGGCAGTTTATTTCTGTCAGCAGGATTATAGCTCGCCGCTCACGTTCGGTGCTGGG
ACCAAGCTGGAGCTGAAAC SC4.105   Light chain - protein sequence (SEQ ID NO: 143)
SIVMTQTPKFLLVSAGARITLTCKASQSVSKDVAWYQQKPGQSPKLLIYYAS
NRYTGVPDRFTGSGYGTDFTFTISSVQAEDLAVYFCQQDYSSPLTFGAGTKLELK SC9.65  Heavy chain - nucleotide sequence (SEQ ID NO: 144)
GAGGTCCAGCTGCAACAGTCTGGACCTGAGCTGGTGAAGCCTGGGGCTTCAGTGAAGATATCCTGCAAGACTTCT
GGATACACATTCACTGAATACACCATGCACTGGGTGAGGCAGAGCCATGGAAAGAGCCTTGAGTGGATTGTAGG
TATTAATCCTAAAAATGTTGGTTCTGCCTACAACCAGAAGTTCAAGGGCAAGGCCACATTGACTGTAGACAAGTCC
TCCAGCACAGCCTACATGGAGCTCCGCAGCCTGACATCTGAGGATTCTGCAGTCTATTACTGTGCAAGAGGAGGG
AATTACTACGCTAGTAGCCCCTTTGATTATTGGGGCCAAGGGACTCTGGTCACTGTCTCTGCA SC9.65  Heavy chain - protein sequence (SEQ ID NO: 145)
EVQLQQSGPELVKPGASVKISCKTSGYTFTEYTMHWVRQSHGKSLEWIVGINPKNVGSA
YNQKFKGKATLTVDKSSSTAYMELRSLTSEDSAVYYCARGGNYYASSPFDYWGQGTLVTVSA

FIG. 7N

SC9.65  Light chain - nucleotide sequence (SEQ ID NO: 146)
GACATTGTGATGTCACAGTCTCCATCCTCCCTGGCTGTGTCAGCAGGAGAGAAGGTCACTATGAGCTGCAAGTCCA
GTCAGAGTCTGCTCAACAGTAGAACCCGAAAGAACTACTTGGCTTGGTACCAGCAGCAACCAGGGCAGTCTCCTA
AACTGCTGATCTACTGGGCATCCACTAGGGAATCTGGGGTCCCTGATCGCTTCACAGGCAGTGGATCTGGGACAG
ATTTCACTCTCACCATCAGCAGTGTGCAGGCTGAAGACCTGGCAGTTTATTACTGCAAGCAATCTTATAATCTTTAC
ACGTTCGGTGGGGGGACCAAGCTGGAAATAAAACG SC9.65  Light chain - protein sequence (SEQ ID NO: 147)
DIVMSQSPSSLAVSAGEKVTMSCKSSQSLLNSRTRKNYLAWYQQQPGQSPKLLIYW
ASTRESGVPDRFTGSGSGTDFTLTISSVQAEDLAVYYCKQSYNLYTFGGGTKLEIKR

--- hSC4.5  Heavy chain - nucleotide sequence (SEQ ID NO: 148)
GAGGTGCAGCTGGTGGAGTCTGGGGGAGGCTTGGTCCAGCCTGGGGGGTCCCTGAGACTCTCCTGTGCAGCCTCT
GGATTCACCGTCACTACTTATGGTGTGGACTGGGTCCGCCAAGCTCCAGGGAAGGGGCTGGAGTGGTTAGGTGTA
ATATGGGGTGGTGGAAGCACAAATTATAATAGCGCTTTGAAGAGCCGATTCACCATCTCCAGAGACAACTCCAAG
AACACCCTGTATCTGCAAATGAACAGTCTGAGAGCCGAGGACACGGCCGTGTATTACTGTGCCAGTGATTGGGCT
TACTGGGGCCAAGGGACTCTGGTCACTGTCTCTTC hSC4.5  Heavy chain - protein sequence (SEQ ID NO: 149)
EVQLVESGGGLVQPGGSLRLSCAASGFTVTTYGVDWVRQAPGKGLEWLGVIWGG
GSTNYNSALKSRFTISRDNSKNTLYLQMNSLRAEDTAVYYCASDWAYWGQGTLVTVSS

FIG. 7O hSC4.5  Light chain - nucleotide sequence (SEQ ID NO: 150)
GACATCCAGATGACCCAGTCTCCATCTTCCCTGTCTGCATCTGTAGGAGACAGAGTCACCATCACTTGTCGGGCGA
GTCAGAATGTGGGTACAAATGTAGCCTGGTTTCAGCAGAAACCAGGGAAAGCCCCTAAGTCCCTGATCCATTCGG
CATCCTACCGTTACAGTGGGGTCCCATCAAGGTTCAGCGGCAGTGGATCTGGGACAGATTTCACTCTCACCATCAG
CAGCCTGCAGCCTGAAGATTTTGCAACTTACTATTGTCAGCAATATAAGAGGTATCCGTACACGTTCGGAGGGGG
GACCAAGCTGGAAATAAAAC hSC4.5  Light chain - protein sequence (SEQ ID NO: 151)
DIQMTQSPSSLSASVGDRVTITCRASQNVGTNVAWFQQKPGKAPKSLIH
SASYRYSGVPSRFSGSGSGTDFTLTISSLQPEDFATYYCQQYKRYPYTFGGGTKLEIK hSC4.15 Heavy chain - nucleotide sequence (SEQ ID NO: 152)
GAGGTGCAACTGGTGGAGTCTGGGGGAGGCCTGGTCAAGCCTGGGGGGTCCCTGAGACTCTCCTGTGCAGCCTCT
GGATTCACCTTCAGTACCTATGGCATGAGCTGGGTCCGCCAGGCTCCAGGGAAGGGGCTGGAGTGGGTCGCAAC
CATTAGTAGTGGTGGTACTTACACATACTACCCAGACTCAGTGAAGGGCCGATTCAAAATCTCCAGAGACAACGC
CAAGAACTCACTGTATCTGCAAATGAACAGCCTGAGAGCCGAGGACACGGCTGTGTATTACTGTACAAGACATGA
CCCCAATGATGGTTACTACTTCCTGTTTGCTTACTGGGGCCAGGGGACTCTGGTCACTGTCTCTTC hSC4.15 Heavy chain - protein sequence (SEQ ID NO: 153)
EVQLVESGGGLVKPGGSLRLSCAASGFTFSTYGMSWVRQAPGKGLEWVATISSGGTYTYYP
DSVKGRFKISRDNAKNSLYLQMNSLRAEDTAVYYCTRHDPNDGYYFLFAYWGQGTLVTVSS

FIG. 7P hSC4.15 Light chain - nucleotide sequence (SEQ ID NO: 154)
GAAATTGTGTTGACGCAGTCTCCAGGCACCCTGTCTTTGTCTCCAGGGGAAAGAGCCACCCTCTCCTGCAAGGCCA
GTCAGAGTGTTGGCAACAATGTAGCTTGGTACCAGCAGAAACCTGGCCAGGCTCCCAGGCTCCTCATCTACTATGC
ATCCAATAGGTATACAGGCATCCCAGACAGGTTCAGTGGCAGTGGGTCTGGGACAGACTTCACTCTCACCATCAG
CAGACTGGAGCCTGAAGATTTTGCAGTGTATTACTGTCAACAGCATTATAGCTCTCCGCTCACGTTCGGTGCTGGG
ACCAAGCTGGAGATCAAAC hSC4.15 Light chain - protein sequence (SEQ ID NO: 155)
EIVLTQSPGTLSLSPGERATLSCKASQSVGNNVAWYQQKPGQAPRLLIY
YASNRYTGIPDRFSGSGSGTDFTLTISRLEPEDFAVYYCQQHYSSPLTFGAGTKLEIK

--- hSC4.22 Heavy chain - nucleotide sequence (SEQ ID NO: 156)
CAGGTTCAGCTGGTGCAGTCTGGAGCTGAGGTGAAGAAGCCTGGGGCCTCAGTGAAGGTCTCCTGCAAGGCTTCT
GGTTACACCTTTACCGGCTATTACATCCACTGGGTGCGACAGGCCCCTGGACAAGGGCTTGAGTGGATGGGATGG
ATCTACCCTGGCAATTTTAACACAAAATATAACGAGCGGTTCAAGGGCAGAGTCACCATGACCACAGACACATCC
ACGAGCACAGCCTACATGGAGCTGAGGAGCCTGAGATCTGACGACACGGCCGTGTATTACTGTGCGAGAGAGGA
TGGTAGCCCCTACTATGCTATGGACTACTGGGGTCAAGGAACCTCAGTCACCGTCTCCTCA hSC4.22 Heavy chain - protein sequence (SEQ ID NO: 157)
QVQLVQSGAEVKKPGASVKVSCKASGYTFTGYYIHWVRQAPGQGLEWMGWIYPGNFNTKYNE
RFKGRVTMTTDTSTSTAYMELRSLRSDDTAVYYCAREDGSPYYAMDYWGQGTSVTVSS

FIG. 7Q hSC4.22 Light chain - nucleotide sequence (SEQ ID NO: 158)
GATATTGTGATGACCCAGACTCCACTCTCTCTGTCCGTCACCCCTGGACAGCCGGCCTCCATCTCCTGCCGGTCTAG
TCAGAGCCTCGTGCATAGTAATGGAAACACCTTTTTGTATTGGTACCTGCAGAAGCCAGGCCAGTCTCCACAGCTC
CTAATCTATAGAGTTTCCAACCGGTTCTCTGGAGTGCCAGATAGGTTCAGTGGCAGCGGGTCAGGGACAGATTTC
ACACTGAAAATCAGCCGGGTGGAGGCTGAGGATGTTGGGGTTTATTACTGCTTTCAAGCTACACATGTTCCGTGG
ACGTTCGGTGGAGGCACCAAAGTGGAAATCAAA hSC4.22 Light chain - protein sequence (SEQ ID NO: 159)
DIVMTQTPLSLSVTPGQPASISCRSSQSLVHSNGNTFLYWYLQKPGQSPQLLIY
RVSNRFSGVPDRFSGSGSGTDFTLKISRVEAEDVGVYYCFQATHVPWTFGGGTKVEIK hSC4.47 Heavy chain - nucleotide sequence (SEQ ID NO: 160)
CAGGTGCAGCTGGTGCAGTCTGGGGCTGAGGTGAAGAAGCCTGGGGCCTCAGTGAAGGTTTCCTGCAAGGCATC
TGGATACACCTTCACTTACTTCTATATGAACTGGGTGCGACAGGCCCCTGGACAAGGGCTTGAGTGGGTGGGACA
AATCAACCCTAATAATGGTGGCACAGCCTACGCACAGAAGTTCCAGGGCAGAGTCACCATGACCAGGGACACGTC
CACGAGCACAGTCTACATGGAGCTGAGCAGCCTGAGATCTGAGGACACGGCCGTGTATTACTGTGCGAGATGGG
TCGGGACTCACTACTTTGACTACTGGGGCCAAGGCACCACTCTCACAGTCTCCTC N

FIG. 7R hSC4.47 Heavy chain - protein sequence (SEQ ID NO: 161)
QVQLVQSGAEVKKPGASVKVSCKASGYTFTYFYMNWVRQAPGQGLEWVGQINPNNG
GTAYAQKFQGRVTMTRDTSTSTVYMELSSLRSEDTAVYYCARWVGTHYFDYWGQGTTLTVSS hSC4.47 Light chain - nucleotide sequence (SEQ ID NO: 162)
GAAATTGTGTTGACACAGTCTCCAGCCACCCTGTCTTTGTCTCCAGGGGAAAGAGCCACCCTCTCCTGCAGGGCCA
GTCAGAGTGTTAGCAGCTCTAGCTATACTTACATTCACTGGTACCAACAGAAACCTGGCCAGGCTCCCAGGCTCCT
CATCAATTTTGCATCCAACTTGGAAAGTGGCATCCCAGCCAGGTTCAGTGGCAGTGGGTCTGGGACAGACTTCACT
CTCACCATCAGCAGCCTAGAGCCTGAAGATTTTGCAGTTTATTACTGTCAGCACAGTTGGGAGATTCCTCCGACGT
TCGGTGGAGGCACCAAGCTGGAAATCAAA hSC4.47 Light chain - protein sequence (SEQ ID NO: 163)
EIVLTQSPATLSLSPGERATLSCRASQSVSSSSYTYIHWYQQKPGQAPRLLINFASNLES
GIPARFSGSGSGTDFTLTISSLEPEDFAVYYCQHSWEIPPTFGGGTKLEIK

Properties of Selected Ephrin-A Ligand Modulators

| Clone | Bin | Affinity (nM) | Western Reactivity | Ms XR | Cyno XR | Neutralizing | Internalizing | Killing |
|---|---|---|---|---|---|---|---|---|
| SC4.2 | A | 20$^{F}$ | NR | No | ND | No | Yes | Yes |
| SC4.5 | B | 0.3$^{B}$ | NR | Yes | Yes | No | Yes | Yes |
| SC4.15 | B | 4.8$^{B}$ | NR | Yes | Yes | ND | Yes | Yes |
| SC4.22 | A | 3.1$^{B}$ | NR/R | No | Yes | No | Yes | Yes |
| SC4.31 | A | 11$^{B}$ | NR | ND | ND | Yes | Yes | Yes |
| SC4.47 | C | <0.1$^{B}$ | NR | No | Yes | Yes | Yes | Yes |
| SC4.76 | A | 0.4$^{F}$ | NR | ND | ND | No | Yes | ND |
| SC4.91 | B | 0.2$^{B}$ | NR/R | Yes | Yes | No | Yes | Yes |
| SC4.105 | B | 16$^{F}$ | ND | Yes | Yes | ND | Yes | Yes |
| SC9.65 | ND | 20$^{F}$ | ND | ND | ND | ND | Yes | Yes |

$^{B}$ Biacore affinity; $^{F}$ ForteBIO in-house comparison

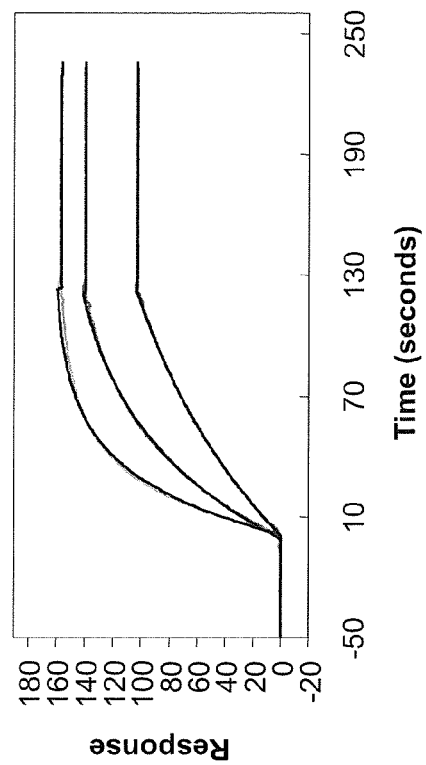
FIG. 8C
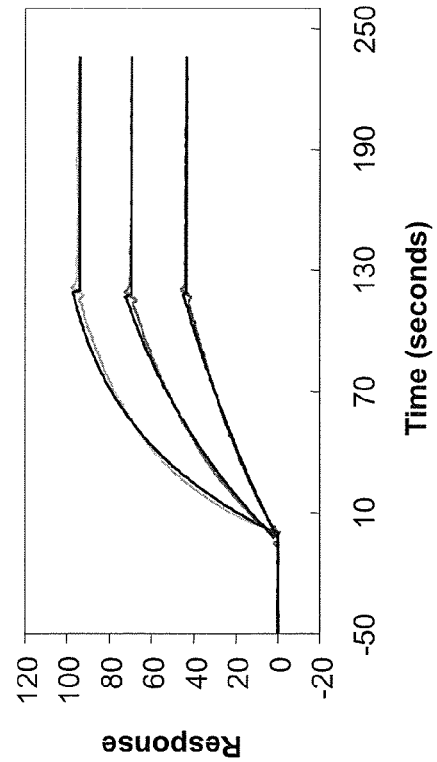
FIG. 8B
| hClone | Bin | MAb Isotype | Mouse Ag Affinity | Cyno Ag Binding | Hu Ag Affinity (Murine mAb) | Hu Ag Affinity (Human mAb) |
|---|---|---|---|---|---|---|
| SC4.15 | B | HuIgG$_1$ | 3.4 nM | + | 2.7 nM | 4.8 nM |
| SC4.22 | A | IgG$_{2b}$ | >100 nM | + | 3.1 nM | 3.8 nM |
| SC4.47 | C | IgG$_1$ | >100 nM | + | <0.1 nM | <0.1 nM |
FIG. 8D

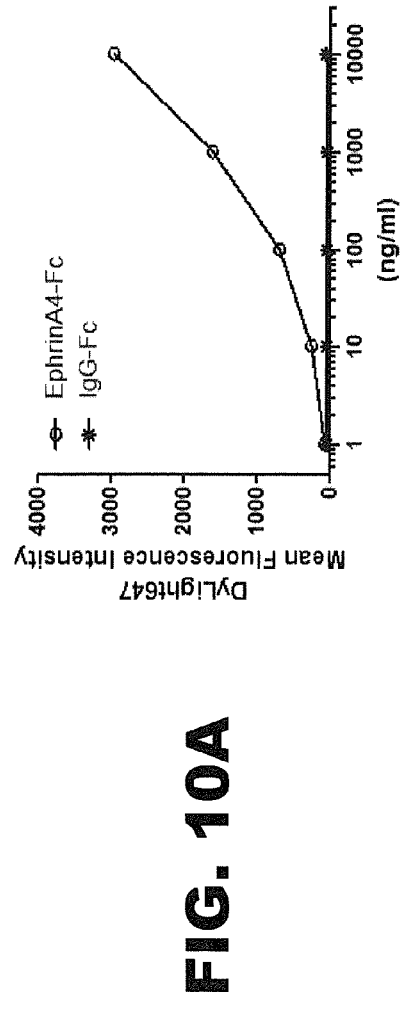
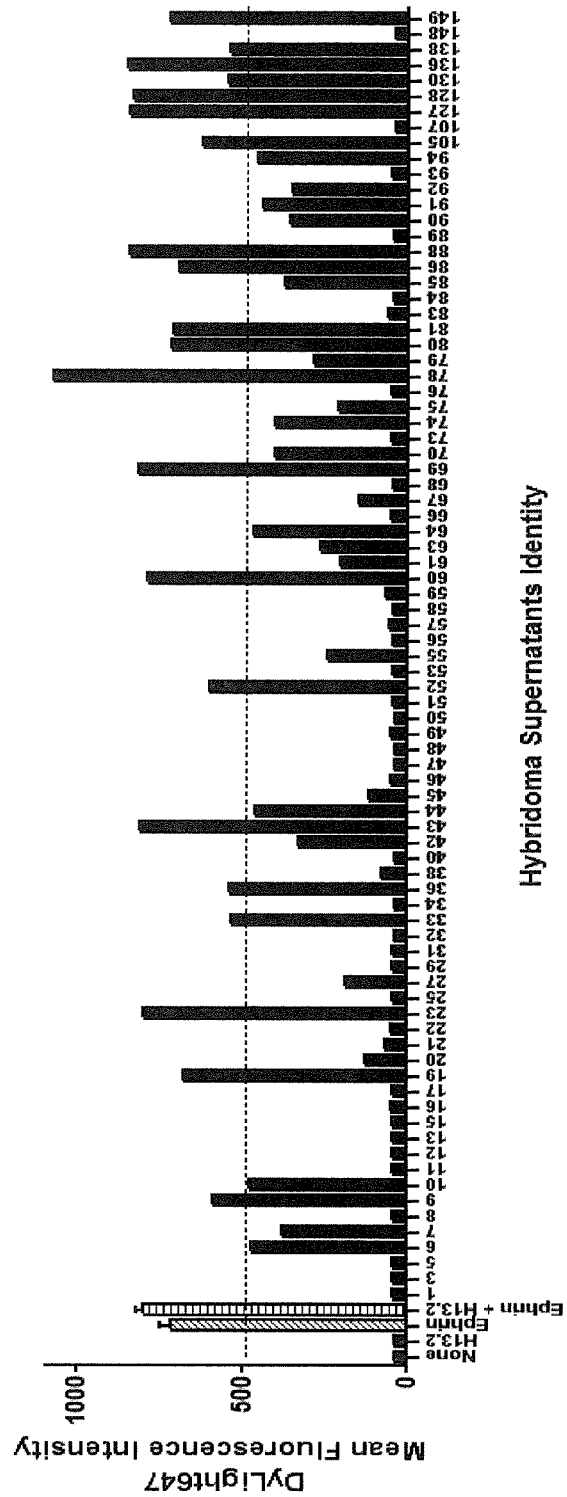
FIG. 10A
FIG. 10B

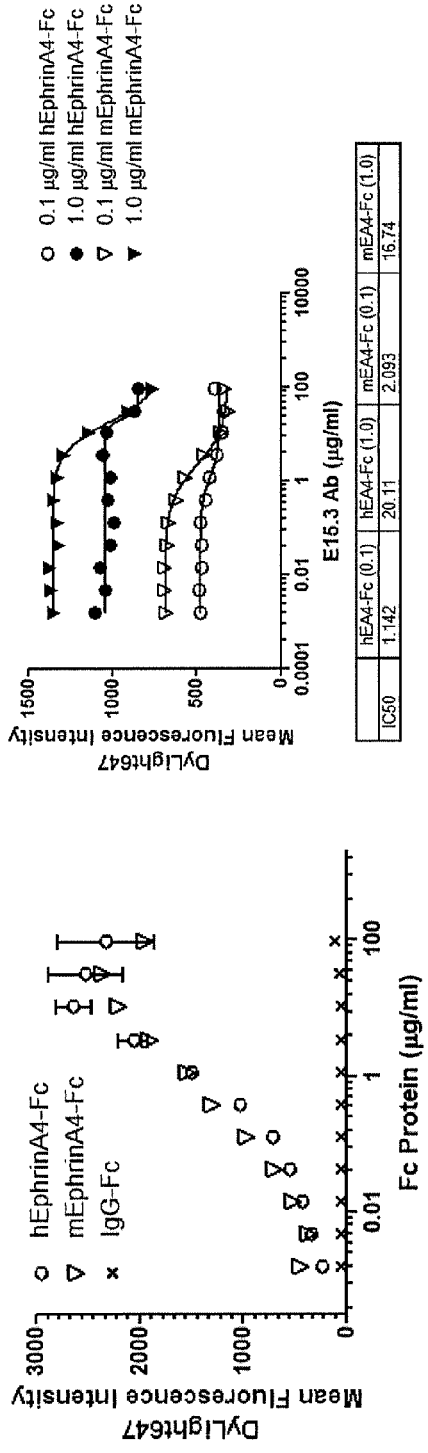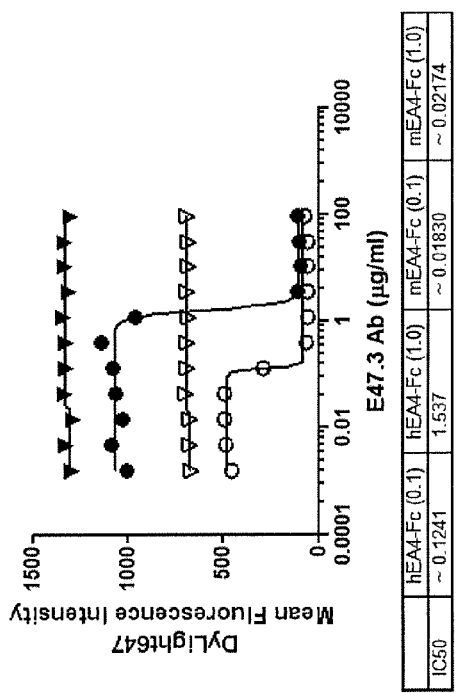

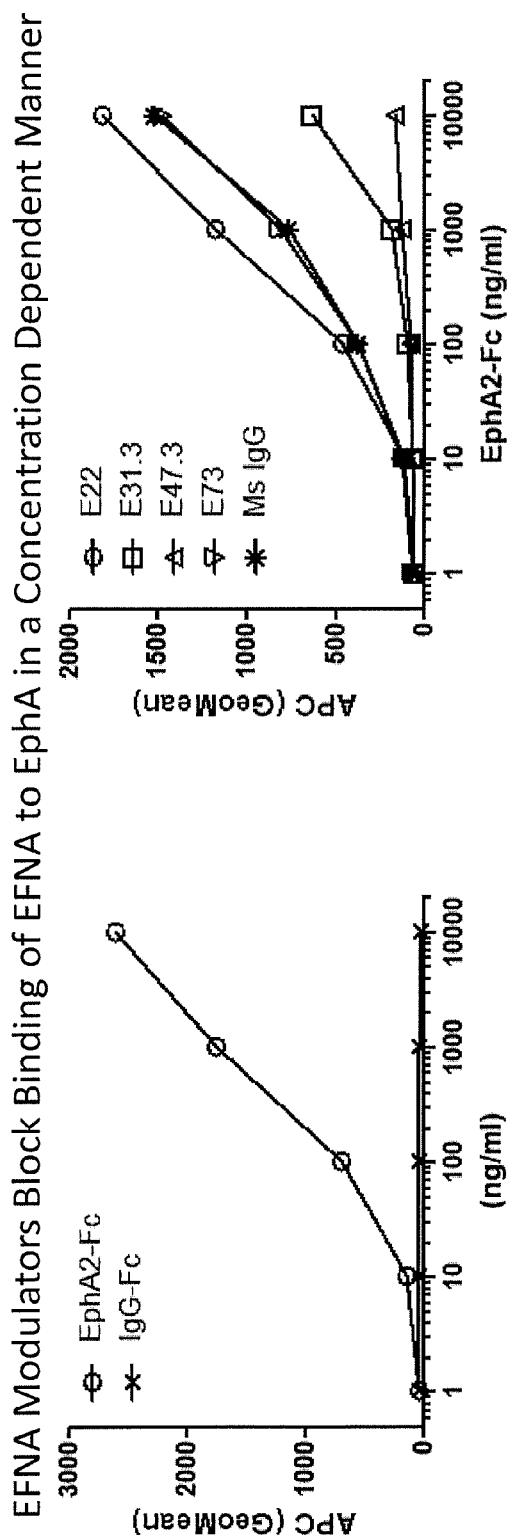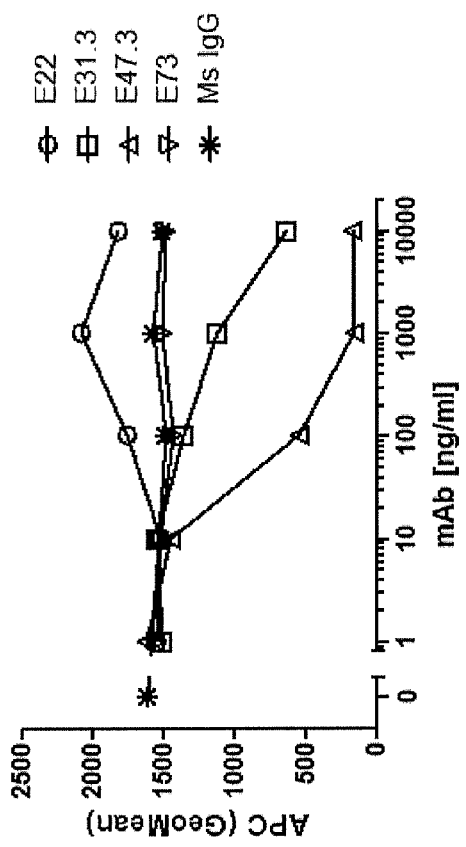
FIG. 12A
FIG. 12B
FIG. 12C
EFNA Modulators Block Binding of EFNA to EphA in a Concentration Dependent Manner Selected Modulators to EFNA4 Cross-React With the Mouse Ortholog EFNA4 Protein Expression is Elevated in both Stage 4 Colorectal Cancer Tumor Lysates and on the Tumorigenic Subpopulation of Tumor Cells EFNA Modulators Mediate the Delivery of Cytotoxic Agents

FIG. 16A

EFNA Modulator Mediation of Cytotoxic Agents is Related to EFNA Expression

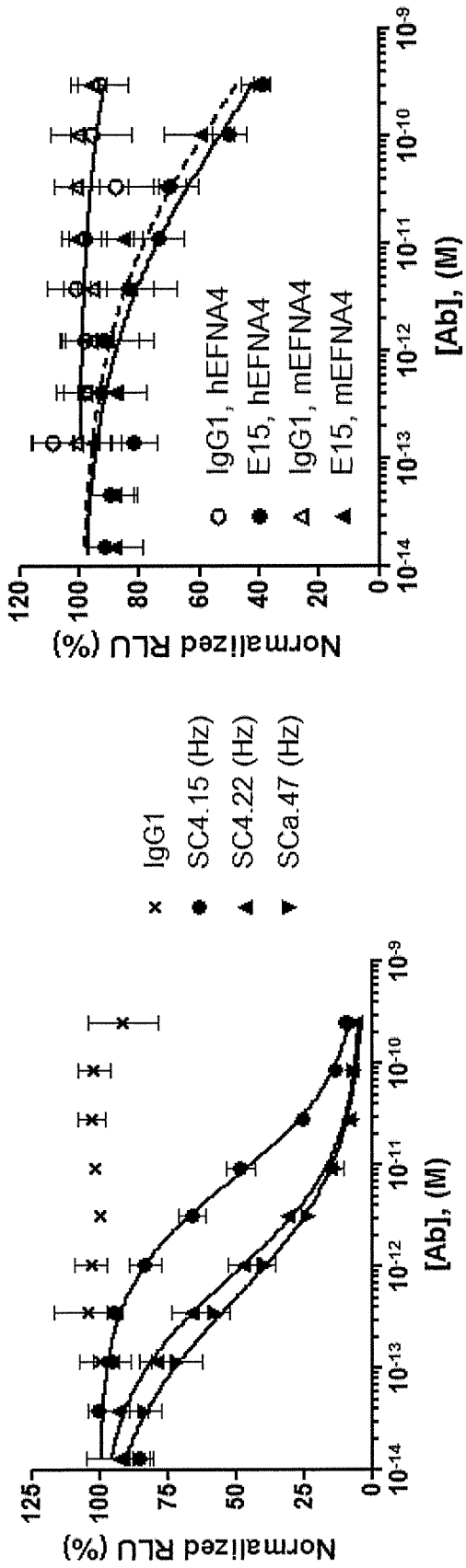

EFNA Modulators Detect
Secreted Ephrin-A Ligand

EFNA Modulators Interact With EFNA1, EFNA3 and EFNA4

EFNA Ligands React With Selected EPHA Receptors

SEQUENCE LISTING

```
<160> NUMBER OF SEQ ID NOS: 166

<210> SEQ ID NO 1
<211> LENGTH: 1276
<212> TYPE: DNA
<213> ORGANISM: Homo sapiens

<400> SEQUENCE: 1
cttccctctt cactttgtac ctttctctcc tcgactgtga agcgggccgg gacctgccag     60
gccagaccaa accggacctc gggggcgatg cggctgctgc ccctgctgcg gactgtcctc    120
tgggccgcgt tcctcggctc ccctctgcgc gggggctcca gcctccgcca cgtagtctac    180
tggaactcca gtaacccccag gttgcttcga ggagacgccg tggtggagct gggcctcaac    240
gattacctag acattgtctg cccccactac gaaggcccag ggcccctga gggccccgag    300 acgtttgctt tgtacatggt ggactggcca ggctatgagt cctgccaggc agagggcccc    360
cgggcctaca agcgctgggt gtgctccctg ccctttggcc atgttcaatt ctcagagaag    420
attcagcgct tcacaccctt ctccctcggc tttgagttct tacctggaga gacttactac    480
tacatctcgg tgcccactcc agagagttct ggccagtgct tgaggctcca ggtgtctgtc    540
tgctgcaagg agaggaagtc tgagtcagcc catcctgttg ggagccctgg agagagtggc    600
acatcagggt ggcgaggggg ggacactccc agcccctct gtctcttgct attactgctg    660
cttctgattc ttcgtcttct gcgaattctg tgagccaagc agaccttccc tctcatccca    720
aggagccaga gtcctcccaa gatcccctgg aggaggaggg atccctgctg cctgcactgg    780
gggtgccaat tcagaccgac aagatggagc attgatgggg gagatcagag ggtctgaggt    840
gactcttgca ggagcctgtc ccctcatcac aggctaaaga agagcagtag acagccctgg    900
acactctgaa gcagaggcaa gacaaacaca ggcgctttgc aggctgctct gagggtctca    960
gcccatcccc caggaggact gggatttggt atgatcaaat cctcaagcca gctgggggcc   1020
caggctgaag acctggggac aggtcgattg ctggaccagg gcaaagaaga agccctgcca   1080
tctgtgccct gtgggccttt tccctgggggc agcaccttgc cctccccagg ggatcactca   1140
cttgtcttct atgaagacgg actcttcatg aggttgaatt tcatgccagt ttgtattttt   1200
ataagtatct agaccaaacc ttcaataaac cactcatctt tttgttgccc tccccaaaaa   1260
aaaaaaaaaa aaaaaa                                                   1276

<210> SEQ ID NO 2
<211> LENGTH: 201
<212> TYPE: PRT
<213> ORGANISM: Homo sapiens

<400> SEQUENCE: 2

Met Arg Leu Leu Pro Leu Leu Arg Thr Val Leu Trp Ala Ala Phe Leu
1               5                   10                  15

Gly Ser Pro Leu Arg Gly Gly Ser Ser Leu Arg His Val Val Tyr Trp
            20                  25                  30
```

-continued

```
Asn Ser Ser Asn Pro Arg Leu Leu Arg Gly Asp Ala Val Val Glu Leu
         35                  40                  45

Gly Leu Asn Asp Tyr Leu Asp Ile Val Cys Pro His Tyr Glu Gly Pro
 50                  55                  60

Gly Pro Pro Glu Gly Pro Glu Thr Phe Ala Leu Tyr Met Val Asp Trp
 65                  70                  75                  80

Pro Gly Tyr Glu Ser Cys Gln Ala Glu Gly Pro Arg Ala Tyr Lys Arg
                 85                  90                  95

Trp Val Cys Ser Leu Pro Phe Gly His Val Gln Phe Ser Glu Lys Ile
                100                 105                 110

Gln Arg Phe Thr Pro Phe Ser Leu Gly Phe Glu Phe Leu Pro Gly Glu
            115                 120                 125

Thr Tyr Tyr Tyr Ile Ser Val Pro Thr Pro Glu Ser Ser Gly Gln Cys
        130                 135                 140

Leu Arg Leu Gln Val Ser Val Cys Cys Lys Glu Arg Lys Ser Glu Ser
145                 150                 155                 160

Ala His Pro Val Gly Ser Pro Gly Glu Ser Thr Ser Gly Trp Arg
                165                 170                 175

Gly Gly Asp Thr Pro Ser Pro Leu Cys Leu Leu Leu Leu Leu Leu
            180                 185                 190

Leu Ile Leu Arg Leu Leu Arg Ile Leu
        195                 200

<210> SEQ ID NO 3
<211> LENGTH: 207
<212> TYPE: PRT
<213> ORGANISM: Homo sapiens

<400> SEQUENCE: 3

Met Arg Leu Leu Pro Leu Leu Arg Thr Val Leu Trp Ala Ala Phe Leu
 1               5                  10                  15

Gly Ser Pro Leu Arg Gly Gly Ser Ser Leu Arg His Val Val Tyr Trp
                 20                  25                  30

Asn Ser Ser Asn Pro Arg Leu Leu Arg Gly Asp Ala Val Val Glu Leu
         35                  40                  45

Gly Leu Asn Asp Tyr Leu Asp Ile Val Cys Pro His Tyr Glu Gly Pro
 50                  55                  60

Gly Pro Pro Glu Gly Pro Glu Thr Phe Ala Leu Tyr Met Val Asp Trp
 65                  70                  75                  80

Pro Gly Tyr Glu Ser Cys Gln Ala Glu Gly Pro Arg Ala Tyr Lys Arg
                 85                  90                  95

Trp Val Cys Ser Leu Pro Phe Gly His Val Gln Phe Ser Glu Lys Ile
                100                 105                 110

Gln Arg Phe Thr Pro Phe Ser Leu Gly Phe Glu Phe Leu Pro Gly Glu
            115                 120                 125

Thr Tyr Tyr Tyr Ile Ser Val Pro Thr Pro Glu Ser Ser Gly Gln Cys
        130                 135                 140

Leu Arg Leu Gln Val Ser Val Cys Cys Lys Glu Arg Arg Ala Arg Val
145                 150                 155                 160

Leu Pro Arg Ser Pro Gly Gly Gly Ile Pro Ala Ala Cys Thr Gly
                165                 170                 175

Gly Ala Asn Ser Asp Arg Gln Asp Gly Ala Leu Met Gly Glu Ile Arg
            180                 185                 190

Gly Ser Glu Val Thr Leu Ala Gly Ala Cys Pro Leu Ile Thr Gly
        195                 200                 205
```

<210> SEQ ID NO 4
<211> LENGTH: 193
<212> TYPE: PRT
<213> ORGANISM: Homo sapiens

<400> SEQUENCE: 4

Met Arg Leu Leu Pro Leu Leu Arg Thr Val Leu Trp Ala Ala Phe Leu
1               5                   10                  15

Gly Ser Pro Leu Arg Gly Gly Ser Ser Leu Arg His Val Val Tyr Trp
            20                  25                  30

Asn Ser Ser Asn Pro Arg Leu Leu Arg Gly Asp Ala Val Val Glu Leu
        35                  40                  45

Gly Leu Asn Asp Tyr Leu Asp Ile Val Cys Pro His Tyr Glu Gly Pro
    50                  55                  60

Gly Pro Pro Glu Gly Pro Glu Thr Phe Ala Leu Tyr Met Val Asp Trp
65                  70                  75                  80

Pro Gly Tyr Glu Ser Cys Gln Ala Glu Gly Pro Arg Ala Tyr Lys Arg
                85                  90                  95

Trp Val Cys Ser Leu Pro Phe Gly His Val Gln Phe Ser Glu Lys Ile
            100                 105                 110

Gln Arg Phe Thr Pro Phe Ser Leu Gly Phe Glu Phe Leu Pro Gly Glu
        115                 120                 125

Thr Tyr Tyr Tyr Ile Ser Val Pro Thr Pro Glu Ser Ser Gly Gln Cys
    130                 135                 140

Leu Arg Leu Gln Val Ser Val Cys Cys Lys Glu Arg Asn Leu Pro Ser
145                 150                 155                 160

His Pro Lys Glu Pro Glu Ser Ser Gln Asp Pro Leu Glu Glu Glu Gly
                165                 170                 175

Ser Leu Leu Pro Ala Leu Gly Val Pro Ile Gln Thr Asp Lys Met Glu
            180                 185                 190

His

<210> SEQ ID NO 5
<211> LENGTH: 1590
<212> TYPE: DNA
<213> ORGANISM: Homo sapiens

<400> SEQUENCE: 5
gccagatctg tgagcccagc gctgactgcg ccgcggagaa agccagtggg aacccagacc      60
cataggagac ccgcgtcccc gctcggcctg gccaggcccc gcgctatgga gttcctctgg     120 gccctctct tgggtctgtg ctgcagtctg gccgctgctg atcgccacac cgtcttctgg      180
aacagttcaa atcccaagtt ccggaatgag gactacacca tacatgtgca gctgaatgac     240
tacgtggaca tcatctgtcc gcactatgaa gatcactctg tggcagacgc tgccatggag     300
cagtacatac tgtacctggt ggagcatgag gagtaccagc tgtgccagcc ccagtccaag     360
gaccaagtcc gctggcagtg caaccggccc agtgccaagc atggcccgga gaagctgtct     420
gagaagttcc agcgcttcac acctttcacc ctgggcaagg agttcaaaga aggacacagc     480
tactactaca tctccaaacc catccaccag catgaagacc gctgcttgag gttgaaggtg     540
actgtcagtg gcaaaatcac tcacagtcct caggcccatg acaatccaca ggagaagaga     600
cttgcagcag atgacccaga ggtgcgggtt ctacatagca tcggtcacag tgctgcccca     660
cgcctcttcc cacttgcctg gactgtgctg ctccttccac ttctgctgct gcaaaccccg     720

```
tgaaggtgta tgccacacct ggccttaaag agggacaggc tgaagagagg gacaggcact    780
ccaaacctgt cttggggcca ctttcagagc ccccagccct gggaaccact cccaccacag    840
gcataagcta tcacctagca gcctcaaaac gggtcagtat taaggttttc aaccggaagg    900
aggccaacca gcccgacagt gccatcccca ccttcacctc ggagggatgg agaaagaagt    960
ggagacagtc ctttcccacc attcctgcct ttaagccaaa gaaacaagct gtgcaggcat   1020
ggtcccttaa ggcacagtgg gagctgagct ggaaggggcc acgtggatgg caaagcttg    1080 tcaaagatgc cccctccagg agagagccag gatgcccaga tgaactgact gaaggaaaag   1140
caagaaacag tttcttgctt ggaagccagg tacaggagag gcagcatgct tgggctgacc   1200
cagcatctcc cagcaagacc tcatctgtgg agctgccaca gagaagtttg tagccaggta   1260
ctgcattctc tcccatcctg ggcagcact ccccagagct gtgccagcag gggggctgtg   1320
ccaacctgtt cttagagtgt agctgtaagg gcagtgccca tgtgtacatt ctgcctagag   1380
tgtagcctaa agggcagggc ccacgtgtat agtatctgta tataagttgc tgtgtgtctg   1440
tcctgatttc tacaactgga gttttttat acaatgttct ttgtctcaaa ataaagcaat   1500
gtgttttttc ggacatgctt ttctgccact ccatattaaa acatatgacc attgagtccc   1560
tgctaaaaaa aaaaaaaaa aaaaaaaaa                                      1590
```

<210> SEQ ID NO 6
<211> LENGTH: 220
<212> TYPE: PRT
<213> ORGANISM: Homo sapiens

<400> SEQUENCE: 6

```
Met Glu Phe Leu Trp Ala Pro Leu Leu Gly Leu Cys Cys Ser Leu Ala
1               5                   10                  15

Ala Ala Asp Arg His Thr Val Phe Trp Asn Ser Ser Asn Pro Lys Phe
            20                  25                  30

Arg Asn Glu Asp Tyr Thr Ile His Val Gln Leu Asn Asp Tyr Val Asp
        35                  40                  45

Ile Ile Cys Pro His Tyr Glu Asp His Ser Val Ala Val Gln Leu Asn
    50                  55                  60

Asp Tyr Val Asp Ile Ile Cys Pro His Tyr Glu Asp His Ser Val Ala
65                  70                  75                  80

Gln Pro Gln Ser Lys Asp Gln Val Arg Trp Gln Cys Asn Arg Pro Ser
                85                  90                  95

Ala Lys His Gly Pro Glu Lys Leu Ser Glu Lys Phe Gln Arg Phe Thr
            100                 105                 110

Pro Phe Thr Leu Gly Lys Glu Phe Lys Glu Gly His Ser Tyr Tyr Tyr
        115                 120                 125

Ile Ser Lys Pro Ile His Gln His Glu Asp Arg Cys Leu Arg Leu Lys
    130                 135                 140

Val Thr Val Ser Gly Lys Ile Thr His Ser Pro Gln Ala His Asp Asn
145                 150                 155                 160

Pro Gln Glu Lys Arg Leu Ala Ala Asp Asp Pro Glu Val Arg Val Leu
                165                 170                 175

His Ser Ile Gly His Ser Ala Ala Pro Arg Leu Phe Pro Leu Ala Trp
            180                 185                 190

Thr Val Leu Leu Leu Pro Leu Leu His Ser Ala Ala Pro Arg Leu Phe
        195                 200                 205

Pro Leu Ala Trp Thr Val Leu Leu Pro Leu Leu
    210                 215                 220
```

<210> SEQ ID NO 7
<211> LENGTH: 183
<212> TYPE: PRT
<213> ORGANISM: Homo sapiens

<400> SEQUENCE: 7

```
Met Glu Phe Leu Trp Ala Pro Leu Leu Gly Leu Cys Cys Ser Leu Ala
1               5                   10                  15

Ala Ala Asp Arg His Thr Val Phe Trp Asn Ser Ser Asn Pro Lys Phe
            20                  25                  30

Arg Asn Glu Asp Tyr Thr Ile His Val Gln Leu Asn Asp Tyr Val Asp
        35                  40                  45

Ile Ile Cys Pro His Tyr Glu Asp His Ser Val Ala Asp Ala Ala Met
50                  55                  60

Glu Gln Tyr Ile Leu Tyr Leu Val Glu His Glu Glu Tyr Gln Leu Cys
65                  70                  75                  80

Gln Pro Gln Ser Lys Asp Gln Val Arg Trp Gln Cys Asn Arg Pro Ser
                85                  90                  95

Ala Lys His Gly Pro Glu Lys Leu Ser Glu Lys Phe Gln Arg Phe Thr
            100                 105                 110

Pro Phe Thr Leu Gly Lys Glu Phe Lys Glu Gly His Ser Tyr Tyr Tyr
        115                 120                 125

Ile Ser His Ser Pro Gln Ala His Asp Asn Pro Gln Glu Lys Arg Leu
130                 135                 140

Ala Ala Asp Asp Pro Glu Val Arg Val Leu His Ser Ile Gly His Ser
145                 150                 155                 160

Ala Ala Pro Arg Leu Phe Pro Leu Ala Trp Thr Val Leu Leu Leu Pro
                165                 170                 175

Leu Leu Leu Leu Gln Thr Pro
            180
```

<210> SEQ ID NO 8
<211> LENGTH: 8
<212> TYPE: PRT
<213> ORGANISM: Mus sp.

<400> SEQUENCE: 8

```
Gly Tyr Thr Phe Thr Asp Tyr Glu
1               5
```

<210> SEQ ID NO 9
<211> LENGTH: 8
<212> TYPE: PRT
<213> ORGANISM: Mus sp.

<400> SEQUENCE: 9

```
Gly Phe Ser Leu Thr Thr Tyr Gly
1               5
```

<210> SEQ ID NO 10
<211> LENGTH: 8
<212> TYPE: PRT
<213> ORGANISM: Mus sp.

<400> SEQUENCE: 10

```
Gly Tyr Thr Phe Thr Asn Tyr Trp
1               5
```

<210> SEQ ID NO 11
<211> LENGTH: 8
<212> TYPE: PRT
<213> ORGANISM: Mus sp.

<400> SEQUENCE: 11

Gly Phe Thr Phe Ser Thr Tyr Gly
1               5

<210> SEQ ID NO 12
<211> LENGTH: 8
<212> TYPE: PRT
<213> ORGANISM: Mus sp.

<400> SEQUENCE: 12

Gly Tyr Thr Phe Thr Gly Tyr Tyr
1               5

<210> SEQ ID NO 13
<211> LENGTH: 8
<212> TYPE: PRT
<213> ORGANISM: Mus sp.

<400> SEQUENCE: 13

Gly Tyr Thr Phe Thr Arg Asp Trp
1               5

<210> SEQ ID NO 14
<211> LENGTH: 8
<212> TYPE: PRT
<213> ORGANISM: Mus sp.

<400> SEQUENCE: 14

Gly Tyr Thr Phe Thr Tyr Phe Tyr
1               5

<210> SEQ ID NO 15
<211> LENGTH: 8
<212> TYPE: PRT
<213> ORGANISM: Mus sp.

<400> SEQUENCE: 15

Gly Tyr Ser Phe Thr Val Tyr Asn
1               5

<210> SEQ ID NO 16
<211> LENGTH: 9
<212> TYPE: PRT
<213> ORGANISM: Mus sp.

<400> SEQUENCE: 16

Gly Tyr Ser Ile Thr Ser Gly Tyr Tyr
1               5

<210> SEQ ID NO 17
<211> LENGTH: 8
<212> TYPE: PRT
<213> ORGANISM: Mus sp.

<400> SEQUENCE: 17

Gly Tyr Thr Phe Thr Gly Tyr Tyr
1               5

<210> SEQ ID NO 18
<211> LENGTH: 8

```
<212> TYPE: PRT
<213> ORGANISM: Mus sp.

<400> SEQUENCE: 18

Gly Tyr Thr Phe Thr Ser Tyr Trp
1               5

<210> SEQ ID NO 19
<211> LENGTH: 8
<212> TYPE: PRT
<213> ORGANISM: Mus sp.

<400> SEQUENCE: 19

Gly Ala Ser Ile Thr Ser Gly Tyr
1               5

<210> SEQ ID NO 20
<211> LENGTH: 8
<212> TYPE: PRT
<213> ORGANISM: Mus sp.

<400> SEQUENCE: 20

Gly Tyr Thr Phe Thr Glu Tyr Thr
1               5

<210> SEQ ID NO 21
<211> LENGTH: 8
<212> TYPE: PRT
<213> ORGANISM: Mus sp.

<400> SEQUENCE: 21

Phe Asp Pro Glu Thr Gly Asn Thr
1               5

<210> SEQ ID NO 22
<211> LENGTH: 7
<212> TYPE: PRT
<213> ORGANISM: Mus sp.

<400> SEQUENCE: 22

Ile Trp Gly Gly Gly Ser Thr
1               5

<210> SEQ ID NO 23
<211> LENGTH: 8
<212> TYPE: PRT
<213> ORGANISM: Mus sp.

<400> SEQUENCE: 23

Ile Asp Pro Ser Asp Ser Tyr Ile
1               5

<210> SEQ ID NO 24
<211> LENGTH: 8
<212> TYPE: PRT
<213> ORGANISM: Mus sp.

<400> SEQUENCE: 24

Ile Ser Ser Gly Gly Thr Tyr Thr
1               5

<210> SEQ ID NO 25
<211> LENGTH: 8
<212> TYPE: PRT
<213> ORGANISM: Mus sp.
```

<400> SEQUENCE: 25

Ile Tyr Pro Gly Asn Phe Asn Thr
1               5

<210> SEQ ID NO 26
<211> LENGTH: 8
<212> TYPE: PRT
<213> ORGANISM: Mus sp.

<400> SEQUENCE: 26

Ile His Pro Tyr Asp Ser Glu Thr
1               5

<210> SEQ ID NO 27
<211> LENGTH: 8
<212> TYPE: PRT
<213> ORGANISM: Mus sp.

<400> SEQUENCE: 27

Ile Asn Pro Asn Asn Gly Gly Thr
1               5

<210> SEQ ID NO 28
<211> LENGTH: 8
<212> TYPE: PRT
<213> ORGANISM: Mus sp.

<400> SEQUENCE: 28

Ile Asn Pro Tyr Tyr Gly Gly Thr
1               5

<210> SEQ ID NO 29
<211> LENGTH: 7
<212> TYPE: PRT
<213> ORGANISM: Mus sp.

<400> SEQUENCE: 29

Ile Ser Tyr Asp Gly Arg Asn
1               5

<210> SEQ ID NO 30
<211> LENGTH: 8
<212> TYPE: PRT
<213> ORGANISM: Mus sp.

<400> SEQUENCE: 30

Ile Tyr Pro Gly Asn Phe Asn Thr
1               5

<210> SEQ ID NO 31
<211> LENGTH: 8
<212> TYPE: PRT
<213> ORGANISM: Mus sp.

<400> SEQUENCE: 31

Ile His Pro Asn Ser Asp Thr Ile
1               5

<210> SEQ ID NO 32
<211> LENGTH: 7
<212> TYPE: PRT
<213> ORGANISM: Mus sp.

<400> SEQUENCE: 32

Ile Asn Tyr Ser Gly Asn Thr
1               5

<210> SEQ ID NO 33
<211> LENGTH: 8
<212> TYPE: PRT
<213> ORGANISM: Mus sp.

<400> SEQUENCE: 33

Ile Asn Pro Lys Asn Val Gly Ser
1               5

<210> SEQ ID NO 34
<211> LENGTH: 10
<212> TYPE: PRT
<213> ORGANISM: Mus sp.

<400> SEQUENCE: 34

Ala Arg Gly Tyr Pro Ala Trp Phe Gly Tyr
1               5                   10

<210> SEQ ID NO 35
<211> LENGTH: 6
<212> TYPE: PRT
<213> ORGANISM: Mus sp.

<400> SEQUENCE: 35

Ala Ser Asp Trp Ala Tyr
1               5

<210> SEQ ID NO 36
<211> LENGTH: 11
<212> TYPE: PRT
<213> ORGANISM: Mus sp.

<400> SEQUENCE: 36

Ala Arg Glu Arg Leu Ser His Ala Met Asp Tyr
1               5                   10

<210> SEQ ID NO 37
<211> LENGTH: 15
<212> TYPE: PRT
<213> ORGANISM: Mus sp.

<400> SEQUENCE: 37

Thr Arg His Asp Pro Asn Asp Gly Tyr Tyr Phe Leu Phe Ala Tyr
1               5                   10                  15

<210> SEQ ID NO 38
<211> LENGTH: 13
<212> TYPE: PRT
<213> ORGANISM: Mus sp.

<400> SEQUENCE: 38

Ala Arg Glu Asp Gly Ser Pro Tyr Tyr Ala Met Asp Tyr
1               5                   10

<210> SEQ ID NO 39
<211> LENGTH: 17
<212> TYPE: PRT
<213> ORGANISM: Mus sp.

<400> SEQUENCE: 39

Val Thr Phe Ile Lys Thr Met Val Asp Thr Tyr Tyr Tyr Ala Met Asp

```
1               5                  10                  15

Tyr

<210> SEQ ID NO 40
<211> LENGTH: 11
<212> TYPE: PRT
<213> ORGANISM: Mus sp.

<400> SEQUENCE: 40

Ala Arg Trp Val Gly Thr His Tyr Phe Asp Tyr
1               5                  10

<210> SEQ ID NO 41
<211> LENGTH: 15
<212> TYPE: PRT
<213> ORGANISM: Mus sp.

<400> SEQUENCE: 41

Ala Arg Gly Gly Lys Thr Gly Thr Tyr Tyr Tyr Val Met Asp Tyr
1               5                  10                  15

<210> SEQ ID NO 42
<211> LENGTH: 12
<212> TYPE: PRT
<213> ORGANISM: Mus sp.

<400> SEQUENCE: 42

Ala Arg Glu Gly Tyr Gly Asp Tyr Pro Phe Asp Tyr
1               5                  10

<210> SEQ ID NO 43
<211> LENGTH: 13
<212> TYPE: PRT
<213> ORGANISM: Mus sp.

<400> SEQUENCE: 43

Ala Arg Glu Asp Gly Ser Pro Tyr Tyr Ala Met Asp Tyr
1               5                  10

<210> SEQ ID NO 44
<211> LENGTH: 11
<212> TYPE: PRT
<213> ORGANISM: Mus sp.

<400> SEQUENCE: 44

Ala Thr Pro Glu Arg Arg Ala Met Asp Tyr
1               5                  10

<210> SEQ ID NO 45
<211> LENGTH: 14
<212> TYPE: PRT
<213> ORGANISM: Mus sp.

<400> SEQUENCE: 45

Ala Arg Ser Thr Met Ile Thr Thr Gly Ala Trp Phe Ala Tyr
1               5                  10

<210> SEQ ID NO 46
<211> LENGTH: 14
<212> TYPE: PRT
<213> ORGANISM: Mus sp.

<400> SEQUENCE: 46

Ala Arg Gly Gly Asn Tyr Tyr Ala Ser Ser Pro Phe Asp Tyr
```

```
<210> SEQ ID NO 47
<211> LENGTH: 11
<212> TYPE: PRT
<213> ORGANISM: Mus sp.

<400> SEQUENCE: 47

Gln Ser Leu Ala His Thr Asn Gly Asn Thr Tyr
1               5                   10

<210> SEQ ID NO 48
<211> LENGTH: 6
<212> TYPE: PRT
<213> ORGANISM: Mus sp.

<400> SEQUENCE: 48

Gln Asn Val Gly Thr Asn
1               5

<210> SEQ ID NO 49
<211> LENGTH: 6
<212> TYPE: PRT
<213> ORGANISM: Mus sp.

<400> SEQUENCE: 49

Gln Asp Ile Lys Ser Tyr
1               5

<210> SEQ ID NO 50
<211> LENGTH: 6
<212> TYPE: PRT
<213> ORGANISM: Mus sp.

<400> SEQUENCE: 50

Gln Ser Val Gly Asn Asn
1               5

<210> SEQ ID NO 51
<211> LENGTH: 11
<212> TYPE: PRT
<213> ORGANISM: Mus sp.

<400> SEQUENCE: 51

Gln Ser Leu Val His Ser Asn Gly Asn Thr Phe
1               5                   10

<210> SEQ ID NO 52
<211> LENGTH: 11
<212> TYPE: PRT
<213> ORGANISM: Mus sp.

<400> SEQUENCE: 52

Gln Ser Leu Leu His Ser Asp Gly Lys Thr Tyr
1               5                   10

<210> SEQ ID NO 53
<211> LENGTH: 10
<212> TYPE: PRT
<213> ORGANISM: Mus sp.

<400> SEQUENCE: 53

Gln Ser Val Ser Ser Ser Tyr Thr Tyr
1               5                   10
```

```
<210> SEQ ID NO 54
<211> LENGTH: 6
<212> TYPE: PRT
<213> ORGANISM: Mus sp.

<400> SEQUENCE: 54

Glu Asn Ile Asp Ser Tyr
1               5

<210> SEQ ID NO 55
<211> LENGTH: 10
<212> TYPE: PRT
<213> ORGANISM: Mus sp.

<400> SEQUENCE: 55

Gln Ser Val Ser Ser Ser Tyr Ser Tyr
1               5                   10

<210> SEQ ID NO 56
<211> LENGTH: 11
<212> TYPE: PRT
<213> ORGANISM: Mus sp.

<400> SEQUENCE: 56

Gln Ser Leu Val His Ser Asn Gly Asn Thr Phe
1               5                   10

<210> SEQ ID NO 57
<211> LENGTH: 7
<212> TYPE: PRT
<213> ORGANISM: Mus sp.

<400> SEQUENCE: 57

Ser Ser Leu Ser Ser Ser Tyr
1               5

<210> SEQ ID NO 58
<211> LENGTH: 6
<212> TYPE: PRT
<213> ORGANISM: Mus sp.

<400> SEQUENCE: 58

Gln Ser Val Ser Lys Asp
1               5

<210> SEQ ID NO 59
<211> LENGTH: 12
<212> TYPE: PRT
<213> ORGANISM: Mus sp.

<400> SEQUENCE: 59

Gln Ser Leu Leu Asn Ser Arg Thr Arg Lys Asn Tyr
1               5                   10

<210> SEQ ID NO 60

<400> SEQUENCE: 60

000

<210> SEQ ID NO 61

<400> SEQUENCE: 61

000
```

<210> SEQ ID NO 62

<400> SEQUENCE: 62

000

<210> SEQ ID NO 63

<400> SEQUENCE: 63

000

<210> SEQ ID NO 64

<400> SEQUENCE: 64

000

<210> SEQ ID NO 65

<400> SEQUENCE: 65

000

<210> SEQ ID NO 66

<400> SEQUENCE: 66

000

<210> SEQ ID NO 67

<400> SEQUENCE: 67

000

<210> SEQ ID NO 68

<400> SEQUENCE: 68

000

<210> SEQ ID NO 69

<400> SEQUENCE: 69

000

<210> SEQ ID NO 70
<211> LENGTH: 8
<212> TYPE: PRT
<213> ORGANISM: Mus sp.

<400> SEQUENCE: 70

Lys Val Ser Asn Met Arg Phe Ser
1               5

<210> SEQ ID NO 71
<211> LENGTH: 7
<212> TYPE: PRT
<213> ORGANISM: Mus sp.

<400> SEQUENCE: 71

Ser Ala Ser Tyr Arg Tyr Ser
1               5

```
<210> SEQ ID NO 72
<211> LENGTH: 7
<212> TYPE: PRT
<213> ORGANISM: Mus sp.

<400> SEQUENCE: 72

Tyr Ala Thr Ser Leu Ala Asp
1               5

<210> SEQ ID NO 73
<211> LENGTH: 7
<212> TYPE: PRT
<213> ORGANISM: Mus sp.

<400> SEQUENCE: 73

Tyr Ala Ser Asn Arg Tyr Thr
1               5

<210> SEQ ID NO 74
<211> LENGTH: 7
<212> TYPE: PRT
<213> ORGANISM: Mus sp.

<400> SEQUENCE: 74

Arg Val Ser Asn Arg Phe Ser
1               5

<210> SEQ ID NO 75
<211> LENGTH: 7
<212> TYPE: PRT
<213> ORGANISM: Mus sp.

<400> SEQUENCE: 75

Leu Val Ser Asn Leu Asp Ser
1               5

<210> SEQ ID NO 76
<211> LENGTH: 7
<212> TYPE: PRT
<213> ORGANISM: Mus sp.

<400> SEQUENCE: 76

Phe Ala Ser Asn Leu Glu Ser
1               5

<210> SEQ ID NO 77
<211> LENGTH: 7
<212> TYPE: PRT
<213> ORGANISM: Mus sp.

<400> SEQUENCE: 77

Ala Ala Thr Leu Leu Ala Asp
1               5

<210> SEQ ID NO 78
<211> LENGTH: 7
<212> TYPE: PRT
<213> ORGANISM: Mus sp.

<400> SEQUENCE: 78

Tyr Ala Ser Asn Leu Glu Ser
1               5

<210> SEQ ID NO 79
```

<211> LENGTH: 7
<212> TYPE: PRT
<213> ORGANISM: Mus sp.

<400> SEQUENCE: 79

Arg Val Ser Asn Arg Phe Ser
1               5

<210> SEQ ID NO 80
<211> LENGTH: 7
<212> TYPE: PRT
<213> ORGANISM: Mus sp.

<400> SEQUENCE: 80

Ser Thr Ser Phe Leu Ala Ser
1               5

<210> SEQ ID NO 81
<211> LENGTH: 7
<212> TYPE: PRT
<213> ORGANISM: Mus sp.

<400> SEQUENCE: 81

Tyr Ala Ser Asn Arg Tyr Thr
1               5

<210> SEQ ID NO 82
<211> LENGTH: 7
<212> TYPE: PRT
<213> ORGANISM: Mus sp.

<400> SEQUENCE: 82

Trp Ala Ser Thr Arg Glu Ser
1               5

<210> SEQ ID NO 83
<211> LENGTH: 9
<212> TYPE: PRT
<213> ORGANISM: Mus sp.

<400> SEQUENCE: 83

Ser Gln Asp Thr His Val Pro Pro Thr
1               5

<210> SEQ ID NO 84
<211> LENGTH: 9
<212> TYPE: PRT
<213> ORGANISM: Mus sp.

<400> SEQUENCE: 84

Gln Gln Tyr Lys Arg Tyr Pro Tyr Thr
1               5

<210> SEQ ID NO 85
<211> LENGTH: 9
<212> TYPE: PRT
<213> ORGANISM: Mus sp.

<400> SEQUENCE: 85

Leu Gln His Gly Glu Ser Pro Tyr Thr
1               5

<210> SEQ ID NO 86
<211> LENGTH: 9
<212> TYPE: PRT

<213> ORGANISM: Mus sp.

<400> SEQUENCE: 86

Gln Gln His Tyr Ser Ser Pro Leu Thr
1               5

<210> SEQ ID NO 87
<211> LENGTH: 9
<212> TYPE: PRT
<213> ORGANISM: Mus sp.

<400> SEQUENCE: 87

Phe Gln Ala Thr His Val Pro Trp Thr
1               5

<210> SEQ ID NO 88
<211> LENGTH: 9
<212> TYPE: PRT
<213> ORGANISM: Mus sp.

<400> SEQUENCE: 88

Trp Gln Gly Thr His Phe Pro Gln Thr
1               5

<210> SEQ ID NO 89
<211> LENGTH: 9
<212> TYPE: PRT
<213> ORGANISM: Mus sp.

<400> SEQUENCE: 89

Gln His Ser Trp Glu Ile Pro Pro Thr
1               5

<210> SEQ ID NO 90
<211> LENGTH: 8
<212> TYPE: PRT
<213> ORGANISM: Mus sp.

<400> SEQUENCE: 90

Gln His Tyr Tyr Ser Thr Leu Thr
1               5

<210> SEQ ID NO 91
<211> LENGTH: 9
<212> TYPE: PRT
<213> ORGANISM: Mus sp.

<400> SEQUENCE: 91

Gln His Ser Trp Glu Ile Pro Arg Thr
1               5

<210> SEQ ID NO 92
<211> LENGTH: 9
<212> TYPE: PRT
<213> ORGANISM: Mus sp.

<400> SEQUENCE: 92

Phe Gln Ala Thr His Val Pro Trp Thr
1               5

<210> SEQ ID NO 93
<211> LENGTH: 9
<212> TYPE: PRT
<213> ORGANISM: Mus sp.

<400> SEQUENCE: 93

Gln Gln Tyr Asp Ser Ser Pro Phe Thr
1               5

<210> SEQ ID NO 94
<211> LENGTH: 9
<212> TYPE: PRT
<213> ORGANISM: Mus sp.

<400> SEQUENCE: 94

Gln Gln Asp Tyr Ser Ser Pro Leu Thr
1               5

<210> SEQ ID NO 95
<211> LENGTH: 8
<212> TYPE: PRT
<213> ORGANISM: Mus sp.

<400> SEQUENCE: 95

Lys Gln Ser Tyr Asn Leu Tyr Thr
1               5

<210> SEQ ID NO 96
<211> LENGTH: 351
<212> TYPE: DNA
<213> ORGANISM: Mus sp.

<400> SEQUENCE: 96
caggttcaac tgcagcagtc tggagctgag ctggtgaggc ctgggacttc agtgacgctg      60
tcctgcaagg cttcgggcta cacatttact gactatgaaa tgcactgggt gaagcagaca     120
cctgtgcttg gcctggaatg gattggagct tttgatcctg aaactggaaa tactgtctac     180
aatcagaagt tcaagggcaa ggccacactg actgcagaca atccccccaa cacagcctac     240
atggagctca tcagcctgac atctgaggac tctgccgtct attactgtgc aaggggggtac     300 ccggcctggt ttggttactg gggccaaggg actctggtca ctgtctctgc a              351

<210> SEQ ID NO 97
<211> LENGTH: 117
<212> TYPE: PRT
<213> ORGANISM: Mus sp.

<400> SEQUENCE: 97

Gln Val Gln Leu Gln Gln Ser Gly Ala Glu Leu Val Arg Pro Gly Thr
1               5                   10                  15

Ser Val Thr Leu Ser Cys Lys Ala Ser Gly Tyr Thr Phe Thr Asp Tyr
                20                  25                  30

Glu Met His Trp Val Lys Gln Thr Pro Val Leu Gly Leu Glu Trp Ile
            35                  40                  45

Gly Ala Phe Asp Pro Glu Thr Gly Asn Thr Val Tyr Asn Gln Lys Phe
        50                  55                  60

Lys Gly Lys Ala Thr Leu Thr Ala Asp Lys Ser Pro Asn Thr Ala Tyr
65                  70                  75                  80

Met Glu Leu Ile Ser Leu Thr Ser Glu Asp Ser Ala Val Tyr Tyr Cys
                85                  90                  95

Ala Arg Gly Tyr Pro Ala Trp Phe Gly Tyr Trp Gly Gln Gly Thr Leu
                100                 105                 110

Val Thr Val Ser Ala
            115

<210> SEQ ID NO 98
<211> LENGTH: 337
<212> TYPE: DNA
<213> ORGANISM: Mus sp.

<400> SEQUENCE: 98
gatgttgtga tgacccaaat tccactctcc ctgcctgtca ctcttggaga tcaagcctcc       60
atctcttgca gatctagtca gagccttgca cacactaatg aaacaccta tttacattgg      120 tacctgcaga agccaggcca gtctccaaag ctcctgatct acaaagtttc caaccgattt      180
tctggggtcc cagacaggtt cagtggcagt ggatcaggga cagatttcac tctcaagatc      240
agcagagtgg aggctgagga tctgggagtt tatttctgct ctcaagatac acatgttcct      300
ccgacgttcg gtggaggcac caagctggaa atgaaac                               337

<210> SEQ ID NO 99
<211> LENGTH: 112
<212> TYPE: PRT
<213> ORGANISM: Mus sp.

<400> SEQUENCE: 99

Asp Val Val Met Thr Gln Ile Pro Leu Ser Leu Pro Val Thr Leu Gly
1               5                   10                  15

Asp Gln Ala Ser Ile Ser Cys Arg Ser Ser Gln Ser Leu Ala His Thr
            20                  25                  30

Asn Gly Asn Thr Tyr Leu His Trp Tyr Leu Gln Lys Pro Gly Gln Ser
        35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Phe Cys Ser Gln Asp
                85                  90                  95

Thr His Val Pro Pro Thr Phe Gly Gly Gly Thr Lys Leu Glu Met Lys
            100                 105                 110

<210> SEQ ID NO 100
<211> LENGTH: 336
<212> TYPE: DNA
<213> ORGANISM: Mus sp.

<400> SEQUENCE: 100
caggtgcagc tgaagcagtc aggacctggc ctggtggcgc cctcacagag cctgtccatc       60
acatgcactg tctctggttt ctcattaacc acttatggtg tagactgggt tcgccagtct      120
ccaggaaagg gtctggagtg gctgggagtg atatggggtg gtggaagcac aaattataat      180
tcagctctca aatccagact gagcatcagc aaggacaact ccaagagcca gttttctta       240 aaaatgaaca gtctgcaaac tgatgacaca gccatgtatt actgtgccag tgattgggct      300
tactggggcc aagggactct ggtcactgtc tctgca                                336

<210> SEQ ID NO 101
<211> LENGTH: 112
<212> TYPE: PRT
<213> ORGANISM: Mus sp.

<400> SEQUENCE: 101

Gln Val Gln Leu Lys Gln Ser Gly Pro Gly Leu Val Ala Pro Ser Gln
1               5                   10                  15

```
Ser Leu Ser Ile Thr Cys Thr Val Ser Gly Phe Ser Leu Thr Thr Tyr
        20                  25                  30

Gly Val Asp Trp Val Arg Gln Ser Pro Gly Lys Gly Leu Glu Trp Leu
    35                  40                  45

Gly Val Ile Trp Gly Gly Gly Ser Thr Asn Tyr Asn Ser Ala Leu Lys
50                  55                  60

Ser Arg Leu Ser Ile Ser Lys Asp Asn Ser Lys Ser Gln Val Phe Leu
65                  70                  75                  80

Lys Met Asn Ser Leu Gln Thr Asp Asp Thr Ala Met Tyr Tyr Cys Ala
                85                  90                  95

Ser Asp Trp Ala Tyr Trp Gly Gln Gly Thr Leu Val Thr Val Ser Ala
            100                 105                 110

<210> SEQ ID NO 102
<211> LENGTH: 323
<212> TYPE: DNA
<213> ORGANISM: Mus sp.

<400> SEQUENCE: 102
gacattgtga tgacccagtc tcaaaaattc atgtccacat cagtaggaga cagggtcacc      60
gtcacctgca aggccagtca gaatgtgggt acaaatgtag cctggtttca acagaaatca    120
gggcaatctc ctaaaccact gattcactcg gcatcctacc gttacagtgg agtccctgat    180
cgcttcacag gcagtggatc tgggacagat ttcactctca ccatcaccaa tgtgcagtct    240
gaagacttgg tagcgtattt ctgtcagcaa tataagaggt atccgtacac gttcggaggg    300
gggaccaagc tggaaataaa acg                                             323

<210> SEQ ID NO 103
<211> LENGTH: 108
<212> TYPE: PRT
<213> ORGANISM: Mus sp.

<400> SEQUENCE: 103

Asp Ile Val Met Thr Gln Ser Gln Lys Phe Met Ser Thr Ser Val Gly
1               5                   10                  15

Asp Arg Val Thr Val Thr Cys Lys Ala Ser Gln Asn Val Gly Thr Asn
            20                  25                  30

Val Ala Trp Phe Gln Gln Lys Ser Gly Gln Ser Pro Lys Pro Leu Ile
        35                  40                  45

His Ser Ala Ser Tyr Arg Tyr Ser Gly Val Pro Asp Arg Phe Thr Gly
    50                  55                  60

Ser Gly Ser Gly Thr Asp Phe Thr Leu Thr Ile Thr Asn Val Gln Ser
65                  70                  75                  80

Glu Asp Leu Val Ala Tyr Phe Cys Gln Gln Tyr Lys Arg Tyr Pro Tyr
                85                  90                  95

Thr Phe Gly Gly Gly Thr Lys Leu Glu Ile Lys Arg
            100                 105

<210> SEQ ID NO 104
<211> LENGTH: 354
<212> TYPE: DNA
<213> ORGANISM: Mus sp.

<400> SEQUENCE: 104
caggtccagc tgcagcagcc tggggctgaa ctggtgaagc ctggggcttc agtgaagctg      60
tcctgtaagg cttctggata caccttcact aactactgga tacactgggt gaagcagagg    120
```

```
cctggacaag gccttgagtg gatcggagag attgatcctt ctgatagtta tatttattac    180
aatcaaaagt tcaagggcaa ggccacattg actgtagaca atcttccag cacagcccac    240 atgcaactca gcagcctgac atctgaggac tctgcggtct attactgtgc aagagagagg    300
ttatctcatg ctatggacta ctggggtcaa ggaacctcag tcaccgtctc ctca          354
```

<210> SEQ ID NO 105
<211> LENGTH: 118
<212> TYPE: PRT
<213> ORGANISM: Mus sp.

<400> SEQUENCE: 105

```
Gln Val Gln Leu Gln Gln Pro Gly Ala Glu Leu Val Lys Pro Gly Ala
1               5                   10                  15

Ser Val Lys Leu Ser Cys Lys Ala Ser Gly Tyr Thr Phe Thr Asn Tyr
            20                  25                  30

Trp Ile His Trp Val Lys Gln Arg Pro Gly Gln Gly Leu Glu Trp Ile
        35                  40                  45

Gly Glu Ile Asp Pro Ser Asp Ser Tyr Ile Tyr Tyr Asn Gln Lys Phe
    50                  55                  60

Lys Gly Lys Ala Thr Leu Thr Val Asp Lys Ser Ser Thr Ala His
65                  70                  75                  80

Met Gln Leu Ser Ser Leu Thr Ser Glu Asp Ser Ala Val Tyr Tyr Cys
                85                  90                  95

Ala Arg Glu Arg Leu Ser His Ala Met Asp Tyr Trp Gly Gln Gly Thr
            100                 105                 110

Ser Val Thr Val Ser Ser
        115
```

<210> SEQ ID NO 106
<211> LENGTH: 323
<212> TYPE: DNA
<213> ORGANISM: Mus sp.

<400> SEQUENCE: 106

```
gacatcaaga tgacccagtc tccatcctcc atgtatgcat cgctgggaga gagagtcact    60
atcacttgca aggcgagtca ggacattaaa agctatttaa gctggtacca gcagaaacct    120
tggaaatctc ctaagaccct gatctattat gcaacaagct ggcagatgg ggtcccatca    180 agattcagtg gcagtggatc tgggaagat tattctctaa ccatcagcag cctggagtct    240
gacgatacag caacttatta ctgtctacag catggtgaga gcccgtatac gttcggatcg    300
gggaccaagc tggaaataaa acg                                           323
```

<210> SEQ ID NO 107
<211> LENGTH: 108
<212> TYPE: PRT
<213> ORGANISM: Mus sp.

<400> SEQUENCE: 107

```
Asp Ile Lys Met Thr Gln Ser Pro Ser Ser Met Tyr Ala Ser Leu Gly
1               5                   10                  15

Glu Arg Val Thr Ile Thr Cys Lys Ala Ser Gln Asp Ile Lys Ser Tyr
            20                  25                  30

Leu Ser Trp Tyr Gln Gln Lys Pro Trp Lys Ser Pro Lys Thr Leu Ile
        35                  40                  45

Tyr Tyr Ala Thr Ser Leu Ala Asp Gly Val Pro Ser Arg Phe Ser Gly
```

```
                    50                  55                  60
Ser Gly Ser Gly Glu Asp Tyr Ser Leu Thr Ile Ser Ser Leu Glu Ser
 65                  70                  75                  80

Asp Asp Thr Ala Thr Tyr Tyr Cys Leu Gln His Gly Glu Ser Pro Tyr
                 85                  90                  95

Thr Phe Gly Ser Gly Thr Lys Leu Glu Ile Lys Arg
            100                 105

<210> SEQ ID NO 108
<211> LENGTH: 366
<212> TYPE: DNA
<213> ORGANISM: Mus sp.

<400> SEQUENCE: 108
gaggtgcagg tggtggagtc tgggggagac ttagtgaagc ctggagggtc cctgaaactc      60
tcctgtgcag cctctggatt cactttcagt acctatggca tgtcttgggt tcgccagact     120
ccagacaaga ggctggaatg ggtcgcaacc attagtagtg gtggtactta cacctactat     180
ccagacagtg tgaaggggcg attcaaaatc tccagagaca atgccaagga caccctgtac     240
ctgcaaatga gcagtctgaa gtctgaggac acagccatgt attactgtac aagacatgac     300
cccaatgatg gttactactt cctgtttgct tactggggcc aggggactct ggtcattgtc     360
tctgca                                                                366

<210> SEQ ID NO 109
<211> LENGTH: 122
<212> TYPE: PRT
<213> ORGANISM: Mus sp.

<400> SEQUENCE: 109

Glu Val Gln Val Val Glu Ser Gly Gly Asp Leu Val Lys Pro Gly Gly
  1               5                  10                  15

Ser Leu Lys Leu Ser Cys Ala Ala Ser Gly Phe Thr Phe Ser Thr Tyr
                 20                  25                  30

Gly Met Ser Trp Val Arg Gln Thr Pro Asp Lys Arg Leu Glu Trp Val
             35                  40                  45

Ala Thr Ile Ser Ser Gly Gly Thr Tyr Thr Tyr Tyr Pro Asp Ser Val
         50                  55                  60

Lys Gly Arg Phe Lys Ile Ser Arg Asp Asn Ala Lys Asp Thr Leu Tyr
 65                  70                  75                  80

Leu Gln Met Ser Ser Leu Lys Ser Glu Asp Thr Ala Met Tyr Tyr Cys
                 85                  90                  95

Thr Arg His Asp Pro Asn Asp Gly Tyr Tyr Phe Leu Phe Ala Tyr Trp
            100                 105                 110

Gly Gln Gly Thr Leu Val Ile Val Ser Ala
        115                 120

<210> SEQ ID NO 110
<211> LENGTH: 322
<212> TYPE: DNA
<213> ORGANISM: Mus sp.

<400> SEQUENCE: 110
agtataggga ggacccagat tcccaaattc ctgcctgtat cagcaggaga cagggttacc      60
atgacctgca aggccagtca gagtgtgggt aataatgtag cctggtacca acagaaggca     120
ggacagtctc ctaaactgct gatatactat gcatccaatc gctacactgg agtccctgat     180
```

```
cgcttcactg gcagtggatc tgggacagat ttcactttca ccatcagcag tgtgcaggtt      240
gaagacctgg cagtttattt ctgtcagcag cattatagct ctccgctcac gttcggtgct      300
gggaccaagc tggagctgaa ac                                               322
```

```
<210> SEQ ID NO 111
<211> LENGTH: 107
<212> TYPE: PRT
<213> ORGANISM: Mus sp.

<400> SEQUENCE: 111
```

Ser Ile Gly Arg Thr Gln Ile Pro Lys Phe Leu Pro Val Ser Ala Gly
1               5                   10                  15

Asp Arg Val Thr Met Thr Cys Lys Ala Ser Gln Ser Val Gly Asn Asn
            20                  25                  30

Val Ala Trp Tyr Gln Gln Lys Ala Gly Gln Ser Pro Lys Leu Leu Ile
        35                  40                  45

Tyr Tyr Ala Ser Asn Arg Tyr Thr Gly Val Pro Asp Arg Phe Thr Gly
    50                  55                  60

Ser Gly Ser Gly Thr Asp Phe Thr Phe Thr Ile Ser Ser Val Gln Val
65                  70                  75                  80

Glu Asp Leu Ala Val Tyr Phe Cys Gln Gln His Tyr Ser Ser Pro Leu
                85                  90                  95

Thr Phe Gly Ala Gly Thr Lys Leu Glu Leu Lys
            100                 105

```
<210> SEQ ID NO 112
<211> LENGTH: 360
<212> TYPE: DNA
<213> ORGANISM: Mus sp.

<400> SEQUENCE: 112
cagatccagc tgcagcagtc tggacctgag ctggtgaagc ctggggcttc agtgaagata      60
tcctgcaagg cttctggcta caccttcact ggctactata tacactgggt gaagcagagg      120
cctggacagg gacttgagtg gattggatgg atttatcctg gaaactttaa tactaagtac      180
aatgagcggt tcaagggcat ggccactttg actgtagaca catcctccag cacagcctac      240
atgcagctca gcagcctgac ctctgaggac tctgcggtct atctctgtgc aagagaggat      300
ggtagcccct actatgctat ggactactgg ggtcaaggaa cctcagtcac cgtctcctca      360
```

```
<210> SEQ ID NO 113
<211> LENGTH: 120
<212> TYPE: PRT
<213> ORGANISM: Mus sp.

<400> SEQUENCE: 113
```

Gln Ile Gln Leu Gln Gln Ser Gly Pro Glu Leu Val Lys Pro Gly Ala
1               5                   10                  15

Ser Val Lys Ile Ser Cys Lys Ala Ser Gly Tyr Thr Phe Thr Gly Tyr
            20                  25                  30

Tyr Ile His Trp Val Lys Gln Arg Pro Gly Gln Gly Leu Glu Trp Ile
        35                  40                  45

Gly Trp Ile Tyr Pro Gly Asn Phe Asn Thr Lys Tyr Asn Glu Arg Phe
    50                  55                  60

Lys Gly Met Ala Thr Leu Thr Val Asp Thr Ser Ser Ser Thr Ala Tyr
65                  70                  75                  80

Met Gln Leu Ser Ser Leu Thr Ser Glu Asp Ser Ala Val Tyr Leu Cys

```
                    85                  90                  95
Ala Arg Glu Asp Gly Ser Pro Tyr Tyr Ala Met Asp Tyr Trp Gly Gln
            100                 105                 110

Gly Thr Ser Val Thr Val Ser Ser
            115                 120
```

<210> SEQ ID NO 114
<211> LENGTH: 337
<212> TYPE: DNA
<213> ORGANISM: Mus sp.

<400> SEQUENCE: 114

```
gatgttgtga tgacccaaac tccactctcc ctgcctgtca gtcttggaga tcaagcttcc      60
atctcttgca gatctagtca gagccttgtc cacagcaatg aaacacctt tttatattgg     120
tacctgcaga agccaggcca gtctccaaaa ctcctgatct acagggtttc caaccgattt     180
tctggggtcc cagacaggtt cagtggcagt ggatcaggga cagatttcac actcaagatc     240
agcagagtgg aggctgagga tctgggtgtt tatttctgct ttcaagctac acatgttccg     300
tggacgttcg gtggaggcac caaactggaa atcaaac                              337
```

<210> SEQ ID NO 115
<211> LENGTH: 112
<212> TYPE: PRT
<213> ORGANISM: Mus sp.

<400> SEQUENCE: 115

```
Asp Val Val Met Thr Gln Thr Pro Leu Ser Leu Pro Val Ser Leu Gly
1               5                   10                  15

Asp Gln Ala Ser Ile Ser Cys Arg Ser Ser Gln Ser Leu Val His Ser
            20                  25                  30

Asn Gly Asn Thr Phe Leu Tyr Trp Tyr Leu Gln Lys Pro Gly Gln Ser
        35                  40                  45

Pro Lys Leu Leu Ile Tyr Arg Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Phe Cys Phe Gln Ala
                85                  90                  95

Thr His Val Pro Trp Thr Phe Gly Gly Gly Thr Lys Leu Glu Ile Lys
            100                 105                 110
```

<210> SEQ ID NO 116
<211> LENGTH: 372
<212> TYPE: DNA
<213> ORGANISM: Mus sp.

<400> SEQUENCE: 116

```
caggtccaac tgcagcagcc tggggctgaa ctggtgaggc ctggggcgtc agtgaagctg      60
tcctgcaagg cttctggcta cacattcacc agggactgga tgcactggat taagcagagg     120
cctggacaag tccttgactg gattggaacg attcatcctt acgatagtga aacacattac     180
aatcaaaact tcaaggacaa ggccacattg actgtagaca atcctccag cacagcctac      240
atgcaactca gcagcctgac atctgaggac tctgcggtct attactgtgt aacatttatt     300
aagacgatgg tagacacata ttactatgct atggactact ggggtcaagg aacctcagtc     360
accgtctcct ca                                                         372
```

<210> SEQ ID NO 117
<211> LENGTH: 124
<212> TYPE: PRT
<213> ORGANISM: Mus sp.

<400> SEQUENCE: 117

```
Gln Val Gln Leu Gln Gln Pro Gly Ala Glu Leu Val Arg Pro Gly Ala
1               5                   10                  15

Ser Val Lys Leu Ser Cys Lys Ala Ser Gly Tyr Thr Phe Thr Arg Asp
            20                  25                  30

Trp Met His Trp Ile Lys Gln Arg Pro Gly Gln Gly Leu Asp Trp Ile
        35                  40                  45

Gly Tyr Ile His Pro Tyr Asp Ser Glu Thr His Tyr Asn Gln Asn Phe
    50                  55                  60

Lys Asp Lys Ala Thr Leu Thr Val Asp Lys Ser Ser Thr Ala Tyr
65                  70                  75                  80

Met Gln Leu Ser Ser Leu Thr Ser Glu Asp Ser Ala Val Tyr Tyr Cys
                85                  90                  95

Val Thr Phe Ile Lys Thr Met Val Asp Thr Tyr Tyr Tyr Ala Met Asp
            100                 105                 110

Tyr Trp Gly Gln Gly Thr Ser Val Thr Val Ser Ser
        115                 120
```

<210> SEQ ID NO 118
<211> LENGTH: 337
<212> TYPE: DNA
<213> ORGANISM: Mus sp.

<400> SEQUENCE: 118

```
gatgttgtga tgacccagac tccactcact ttgtcggtta ccattggaca accagcctcc    60
atctcttgca agtcaagtca gagcctctta catagtgatg aaagacata tttgaattgg   120
ttgttacaga ggccaggcca gtctccaaag cgcctaatct atctggtgtc taacctggac   180
tctggagtcc ctgacaggtt cactggcagt ggatcaggga cagatttcac actgaaattc   240
agcaggttgg aggctgagga tttgggagtt tattattgct ggcaaggtac acattttcct   300
cagacgttcg gtggaggcac caaactggaa atcaaac                            337
```

<210> SEQ ID NO 119
<211> LENGTH: 112
<212> TYPE: PRT
<213> ORGANISM: Mus sp.

<400> SEQUENCE: 119

```
Asp Val Val Met Thr Gln Thr Pro Leu Thr Leu Ser Val Thr Ile Gly
1               5                   10                  15

Gln Pro Ala Ser Ile Ser Cys Lys Ser Ser Gln Ser Leu Leu His Ser
            20                  25                  30

Asp Gly Lys Thr Tyr Leu Asn Trp Leu Leu Gln Arg Pro Gly Gln Ser
        35                  40                  45

Pro Lys Arg Leu Ile Tyr Leu Val Ser Asn Leu Asp Ser Gly Val Pro
    50                  55                  60

Asp Arg Phe Thr Gly Ser Gly Ser Gly Thr Asp Phe Thr Leu Lys Phe
65                  70                  75                  80

Ser Arg Leu Glu Ala Glu Asp Leu Gly Val Tyr Tyr Cys Trp Gln Gly
                85                  90                  95

Thr His Phe Pro Gln Thr Phe Gly Gly Gly Thr Lys Leu Glu Ile Lys
```

<210> SEQ ID NO 120
<211> LENGTH: 353
<212> TYPE: DNA
<213> ORGANISM: Mus sp.

<400> SEQUENCE: 120
caggtccagc tgcaacaatc tggacctgag ctggtgaagc ctggggcttc agtgaagata    60
tcctgtacgg cttctggata cacgttcact tatttctaca tgaactgggt gaagcagagc   120
caaggaaaga gccttgagtg ggttggacag attaatccta acaatggtgg gactgcctac   180
aaccacaagt tcaggggcaa gaccacattg actgtggaca gtcctccaa cacagccttc    240 atggagctcc gcagcctgac atctgaggac tctgcagtct atttctgtgc aagatgggtc   300
gggactcact actttgacta ctggggccaa ggcaccactc tcacagtctc ctc          353

<210> SEQ ID NO 121
<211> LENGTH: 118
<212> TYPE: PRT
<213> ORGANISM: Mus sp.

<400> SEQUENCE: 121

Glu Val Gln Leu Gln Gln Ser Gly Pro Glu Leu Val Lys Pro Gly Ala
1               5                   10                  15

Ser Val Lys Ile Ser Cys Thr Ala Ser Gly Tyr Thr Phe Thr Tyr Phe
            20                  25                  30

Tyr Met Asn Trp Val Lys Gln Ser Gln Gly Lys Ser Leu Glu Trp Val
        35                  40                  45

Gly Gln Ile Asn Pro Asn Asn Gly Gly Thr Ala Tyr Asn His Lys Phe
    50                  55                  60

Arg Gly Lys Thr Thr Leu Thr Val Asp Lys Ser Ser Asn Thr Ala Phe
65                  70                  75                  80

Met Glu Leu Arg Ser Leu Thr Ser Glu Asp Ser Ala Val Tyr Phe Cys
                85                  90                  95

Ala Arg Trp Val Gly Thr His Tyr Phe Asp Tyr Trp Gly Gln Gly Thr
            100                 105                 110

Thr Leu Thr Val Ser Ser
        115

<210> SEQ ID NO 122
<211> LENGTH: 334
<212> TYPE: DNA
<213> ORGANISM: Mus sp.

<400> SEQUENCE: 122
gacattgtgc tgacacagtc tcctgcttcc ttacctgttt ctctggggca gagggccacc    60
atctcatgca gggccagcca aagtgtcagt tcatctagct atacttatat acactggtac   120
caacagaaac caggacagcc acccaaactc ctcatcaact ttgcatccaa cctagaatct   180
ggggtccctg ccaggttcag tgtcagtggg tctgggacag acttcaccct caacatccat   240
cctgtggagg gggaggatac tgcaacatat tactgtcagc acagttggga gattcctccg   300
acgttcggtg gaggcaccaa gctggaaatc aaac                               334

<210> SEQ ID NO 123
<211> LENGTH: 111
<212> TYPE: PRT
<213> ORGANISM: Mus sp.

<400> SEQUENCE: 123

Asp Ile Val Leu Thr Gln Ser Pro Ala Ser Leu Pro Val Ser Leu Gly
1               5                   10                  15

Gln Arg Ala Thr Ile Ser Cys Arg Ala Ser Gln Ser Val Ser Ser Ser
            20                  25                  30

Ser Tyr Thr Tyr Ile His Trp Tyr Gln Gln Lys Pro Gly Gln Pro Pro
        35                  40                  45

Lys Leu Leu Ile Asn Phe Ala Ser Asn Leu Glu Ser Gly Val Pro Ala
50                  55                  60

Arg Phe Ser Val Ser Gly Ser Gly Thr Asp Phe Thr Leu Asn Ile His
65                  70                  75                  80

Pro Val Glu Gly Glu Asp Thr Ala Thr Tyr Tyr Cys Gln His Ser Trp
                85                  90                  95

Glu Ile Pro Pro Thr Phe Gly Gly Gly Thr Lys Leu Glu Ile Lys
            100                 105                 110

<210> SEQ ID NO 124
<211> LENGTH: 366
<212> TYPE: DNA
<213> ORGANISM: Mus sp.

<400> SEQUENCE: 124
gagatccagc tgcagcagtc tggagctgac ctggtgaagc ctggggcttc agtgaagata     60
tcctgcaagg cttctggtta ctcattcact gtctacaaca tgaactgggt gaagcagagc    120
catggaaaga gccttgagtg gattggaatt attaatcctt actatggtgg tactacctac    180
aatcagaaat tcaaggtcaa ggccacattg actgtagaca atcttccag cacagcctac     240 atgcagctca acagcctgac atctgaggac tctgcagtct attactgtgc aagagggga     300 aagactggga cctattacta tgttatggac tactggggtc agggaacctc agtcaccgtc    360
tcctca                                                                366

<210> SEQ ID NO 125
<211> LENGTH: 122
<212> TYPE: PRT
<213> ORGANISM: Mus sp.

<400> SEQUENCE: 125

Glu Ile Gln Leu Gln Gln Ser Gly Ala Asp Leu Val Lys Pro Gly Ala
1               5                   10                  15

Ser Val Lys Ile Ser Cys Lys Ala Ser Gly Tyr Ser Phe Thr Val Tyr
            20                  25                  30

Asn Met Asn Trp Val Lys Gln Ser His Gly Lys Ser Leu Glu Trp Ile
        35                  40                  45

Gly Ile Ile Asn Pro Tyr Tyr Gly Gly Thr Thr Tyr Asn Gln Lys Phe
50                  55                  60

Lys Val Lys Ala Thr Leu Thr Val Asp Lys Ser Ser Thr Ala Tyr
65                  70                  75                  80

Met Gln Leu Asn Ser Leu Thr Ser Glu Asp Ser Ala Val Tyr Tyr Cys
                85                  90                  95

Ala Arg Gly Gly Lys Thr Gly Thr Tyr Tyr Tyr Val Met Asp Tyr Trp
            100                 105                 110

Gly Gln Gly Thr Ser Val Thr Val Ser Ser
            115                 120

<210> SEQ ID NO 126
<211> LENGTH: 319
<212> TYPE: DNA
<213> ORGANISM: Mus sp.

<400> SEQUENCE: 126

```
gacatccaga tgactcagtc tccagcttcc ctgtctgcat ctgtgggaga aactgtcagc    60
atcacatgtc gagcaagtga gaatattgac agttatttag catggtatca gcagaaacag   120
ggaaaatctc ctcagctcct ggtccatgct gcaacactct tagcagatgg tgtgccatca   180
aggttcagtg gcagtggatc aggcacacag ttttctctca agatcaacag cctgcagtct   240
gaagatgttg cgacatattt ctgtcaacat tattatagta ctctcacgtt cggtggtggg   300
accaagctgg agctgaaac                                                319
```

<210> SEQ ID NO 127
<211> LENGTH: 106
<212> TYPE: PRT
<213> ORGANISM: Mus sp.

<400> SEQUENCE: 127

```
Asp Ile Gln Met Thr Gln Ser Pro Ala Ser Leu Ser Ala Ser Val Gly
1               5                   10                  15

Glu Thr Val Ser Ile Thr Cys Arg Ala Ser Glu Asn Ile Asp Ser Tyr
            20                  25                  30

Leu Ala Trp Tyr Gln Gln Lys Gln Gly Lys Ser Pro Gln Leu Leu Val
        35                  40                  45

His Ala Ala Thr Leu Leu Ala Asp Gly Val Pro Ser Arg Phe Ser Gly
    50                  55                  60

Ser Gly Ser Gly Thr Gln Phe Ser Leu Lys Ile Asn Ser Leu Gln Ser
65                  70                  75                  80

Glu Asp Val Ala Thr Tyr Phe Cys Gln His Tyr Tyr Ser Thr Leu Thr
                85                  90                  95

Phe Gly Gly Gly Thr Lys Leu Glu Leu Lys
            100                 105
```

<210> SEQ ID NO 128
<211> LENGTH: 360
<212> TYPE: DNA
<213> ORGANISM: Mus sp.

<400> SEQUENCE: 128

```
tctgatgtac agcttcagga gtcaggacct ggcctcgtga aaccttctca gtctctgtct    60
ctcacctgct ctgtcactgg ctactccatc accagtggtt attattggaa ctggatccgg   120
cagtttccag gaaacaaact ggaatggatg ggctacataa gctacgacgg taggaataac   180
tacaacccct tctctcaaaaa tcgaatctcc atcactcgtg acacatctaa gacccagttt   240
ttcctgaagt tgaattctgt gactactggg acacagcta catattactg tgcaagagag   300
gggtatggtg actacccctt tgactactgg ggccaaggca ccactctcac agtctcctca   360
```

<210> SEQ ID NO 129
<211> LENGTH: 120
<212> TYPE: PRT
<213> ORGANISM: Mus sp.

<400> SEQUENCE: 129

```
Ser Asp Val Gln Leu Gln Glu Ser Gly Pro Gly Leu Val Lys Pro Ser
1               5                   10                  15
```

Gln Ser Leu Ser Leu Thr Cys Ser Val Thr Gly Tyr Ser Ile Thr Ser
            20                  25                  30

Gly Tyr Tyr Trp Asn Trp Ile Arg Gln Phe Pro Gly Asn Lys Leu Glu
        35                  40                  45

Trp Met Gly Tyr Ile Ser Tyr Asp Gly Arg Asn Asn Tyr Asn Pro Ser
 50                  55                  60

Leu Lys Asn Arg Ile Ser Ile Thr Arg Asp Thr Ser Lys Thr Gln Phe
 65                  70                  75                  80

Phe Leu Lys Leu Asn Ser Val Thr Thr Gly Asp Thr Ala Thr Tyr Tyr
                85                  90                  95

Cys Ala Arg Glu Gly Tyr Gly Asp Tyr Pro Phe Asp Tyr Trp Gly Gln
            100                 105                 110

Gly Thr Thr Leu Thr Val Ser Ser
            115                 120

<210> SEQ ID NO 130
<211> LENGTH: 334
<212> TYPE: DNA
<213> ORGANISM: Mus sp.

<400> SEQUENCE: 130
gacattgtgc tgacacagtc tcctgcttcc ttagctgtat ctctggggca gagggccacc      60
atctcatgca gggccagcca aagtgtcagt tcatctagct atagttatgt gcactggtac     120
caacagaaac aggacagcc acccaaactc ctcatcaagt atgcatccaa cctagaatct     180
ggggtccctg ccaggttcag tggcagtggg tctgggacag acttcaccct caacatccat     240
cctgtggagg aggaggattc tgcaacatat ttctgtcagc acagttggga gattcctcgg     300
acgttcggtg gaggcaccaa gctggaaatc aaac                                 334

<210> SEQ ID NO 131
<211> LENGTH: 111
<212> TYPE: PRT
<213> ORGANISM: Mus sp.

<400> SEQUENCE: 131

Asp Ile Val Leu Thr Gln Ser Pro Ala Ser Leu Ala Val Ser Leu Gly
 1               5                  10                  15

Gln Arg Ala Thr Ile Ser Cys Arg Ala Ser Gln Ser Val Ser Ser Ser
            20                  25                  30

Ser Tyr Ser Tyr Val His Trp Tyr Gln Gln Lys Pro Gly Gln Pro Pro
        35                  40                  45

Lys Leu Leu Ile Lys Tyr Ala Ser Asn Leu Glu Ser Gly Val Pro Ala
 50                  55                  60

Arg Phe Ser Gly Ser Gly Ser Gly Thr Asp Phe Thr Leu Asn Ile His
 65                  70                  75                  80

Pro Val Glu Glu Glu Asp Ser Ala Thr Tyr Phe Cys Gln His Ser Trp
                85                  90                  95

Glu Ile Pro Arg Thr Phe Gly Gly Gly Thr Lys Leu Glu Ile Lys
            100                 105                 110

<210> SEQ ID NO 132
<211> LENGTH: 360
<212> TYPE: DNA
<213> ORGANISM: Mus sp.

<400> SEQUENCE: 132
cagatccagc tgcagcagtc tggacctgag ctggtgaagc ctggggcttc agtgaagata      60

```
tcctgcaagg cttctggcta caccttcact ggctactata tacactgggt gaagcagagg    120
cctggacagg gacttgagtg gattggatgg atttatcctg gaaactttaa tactaagtac    180
aatgagcggt tcaagggcat ggccactttg actgtagaca catcctccag cacagcctac    240
atgcagctca gcagcctgac ctctgaggac tctgcggtct atctctgtgc aagagaggat    300
ggtagcccct actatgctat ggactactgg ggtcaaggaa cctcagtcac cgtctcctca    360
```

<210> SEQ ID NO 133
<211> LENGTH: 120
<212> TYPE: PRT
<213> ORGANISM: Mus sp.

<400> SEQUENCE: 133

```
Gln Ile Gln Leu Gln Gln Ser Gly Pro Glu Leu Val Lys Pro Gly Ala
1               5                   10                  15

Ser Val Lys Ile Ser Cys Lys Ala Ser Gly Tyr Thr Phe Thr Gly Tyr
            20                  25                  30

Tyr Ile His Trp Val Lys Gln Arg Pro Gly Gln Gly Leu Glu Trp Ile
        35                  40                  45

Gly Trp Ile Tyr Pro Gly Asn Phe Asn Thr Lys Tyr Asn Glu Arg Phe
    50                  55                  60

Lys Gly Met Ala Thr Leu Thr Val Asp Thr Ser Ser Ser Thr Ala Tyr
65                  70                  75                  80

Met Gln Leu Ser Ser Leu Thr Ser Glu Asp Ser Ala Val Tyr Leu Cys
                85                  90                  95

Ala Arg Glu Asp Gly Ser Pro Tyr Tyr Ala Met Asp Tyr Trp Gly Gln
            100                 105                 110

Gly Thr Ser Val Thr Val Ser Ser
        115                 120
```

<210> SEQ ID NO 134
<211> LENGTH: 337
<212> TYPE: DNA
<213> ORGANISM: Mus sp.

<400> SEQUENCE: 134

```
gatgttgtga tgacccaaac tccactctcc ctgcctgtca gtcttggaga tcaagcttcc     60
atctcttgca gatctagtca gagccttgtc cacagcaatg gaaacacctt tttatattgg    120
tacctgcaga agccaggcca gtctccaaaa ctcctgatct acagggtttc caaccgattt    180
tctggggtcc cagacaggtt cagtggcagt ggatcaggga cagatttcac actcaagatc    240
agcagagtgg aggctgagga tctgggtgtt tatttctgct ttcaagctac acatgttccg    300
tggacgttcg gtggaggcac caaactggaa atcaaac                             337
```

<210> SEQ ID NO 135
<211> LENGTH: 112
<212> TYPE: PRT
<213> ORGANISM: Mus sp.

<400> SEQUENCE: 135

```
Asp Val Val Met Thr Gln Thr Pro Leu Ser Leu Pro Val Ser Leu Gly
1               5                   10                  15

Asp Gln Ala Ser Ile Ser Cys Arg Ser Ser Gln Ser Leu Val His Ser
            20                  25                  30

Asn Gly Asn Thr Phe Leu Tyr Trp Tyr Leu Gln Lys Pro Gly Gln Ser
        35                  40                  45
```

```
Pro Lys Leu Leu Ile Tyr Arg Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Phe Cys Phe Gln Ala
                85                  90                  95

Thr His Val Pro Trp Thr Phe Gly Gly Gly Thr Lys Leu Glu Ile Lys
            100                 105                 110
```

<210> SEQ ID NO 136
<211> LENGTH: 354
<212> TYPE: DNA
<213> ORGANISM: Mus sp.

<400> SEQUENCE: 136

```
caggtccaac tacagcagcc tgggctgag ctggtaaagc ctggggcttc agtgaagttg      60
tcctgcaagg cttctggcta cactttcacc agctactgga tgcactggat gaagcagagg    120
cctggacaag gccttgagtg gattggaatg attcatccta atagtgatac tatcaactac    180
aatgcgaagt tcaagagcaa ggccacactg tctgtagaca atcctccag cacagcctac    240
atgcaactca gcagcctgac atctgaggac tctgcggtct attactgtgc aaccccggaa    300
cggcggaggg ctatggacta ctggggtcaa ggaacctcag tcaccgtctc ctca          354
```

<210> SEQ ID NO 137
<211> LENGTH: 118
<212> TYPE: PRT
<213> ORGANISM: Mus sp.

<400> SEQUENCE: 137

```
Gln Val Gln Leu Gln Gln Pro Gly Ala Glu Leu Val Lys Pro Gly Ala
1               5                   10                  15

Ser Val Lys Leu Ser Cys Lys Ala Ser Gly Tyr Thr Phe Thr Ser Tyr
                20                  25                  30

Trp Met His Trp Met Lys Gln Arg Pro Gly Gln Gly Leu Glu Trp Ile
            35                  40                  45

Gly Met Ile His Pro Asn Ser Asp Thr Ile Asn Tyr Asn Ala Lys Phe
    50                  55                  60

Lys Ser Lys Ala Thr Leu Ser Val Asp Lys Ser Ser Ser Thr Ala Tyr
65                  70                  75                  80

Met Gln Leu Ser Ser Leu Thr Ser Glu Asp Ser Ala Val Tyr Tyr Cys
                85                  90                  95

Ala Thr Pro Glu Arg Arg Arg Ala Met Asp Tyr Trp Gly Gln Gly Thr
            100                 105                 110

Ser Val Thr Val Ser Ser
            115
```

<210> SEQ ID NO 138
<211> LENGTH: 325
<212> TYPE: DNA
<213> ORGANISM: Mus sp.

<400> SEQUENCE: 138

```
cagattgttc tcacccagtc tccagcaatc atgtctgcat ctccagggga gaaggtcacc      60
atgacctgca gggccagctc aagtttaagt tccagttact tgcactggta ccagcagaag    120
ccaggatctt cccccaaact ctggatttat agcacatcct tcctggcttc aggagtccca    180
```

```
gctcgcttca gtggcagtgg gtctgggacc tcttactctc tcacaatcag cagtgtggag      240
gctgaggatg ctgccactta ttactgccag cagtatgata gttccccgtt tacgttcggc      300
tcggggacca agctggaaat aaaac                                             325
```

<210> SEQ ID NO 139
<211> LENGTH: 108
<212> TYPE: PRT
<213> ORGANISM: Mus sp.

<400> SEQUENCE: 139

```
Gln Ile Val Leu Thr Gln Ser Pro Ala Ile Met Ser Ala Ser Pro Gly
1               5                   10                  15

Glu Lys Val Thr Met Thr Cys Arg Ala Ser Ser Ser Leu Ser Ser Ser
            20                  25                  30

Tyr Leu His Trp Tyr Gln Lys Pro Gly Ser Ser Pro Lys Leu Trp
        35                  40                  45

Ile Tyr Ser Thr Ser Phe Leu Ala Ser Gly Val Pro Ala Arg Phe Ser
    50                  55                  60

Gly Ser Gly Ser Gly Thr Ser Tyr Ser Leu Thr Ile Ser Ser Val Glu
65                  70                  75                  80

Ala Glu Asp Ala Ala Thr Tyr Tyr Cys Gln Gln Tyr Asp Ser Ser Pro
                85                  90                  95

Phe Thr Phe Gly Ser Gly Thr Lys Leu Glu Ile Lys
            100                 105
```

<210> SEQ ID NO 140
<211> LENGTH: 360
<212> TYPE: DNA
<213> ORGANISM: Mus sp.

<400> SEQUENCE: 140

```
gaggtgcagc ttcaggagtc aggacctagc ctcgtgaaac cttctcagac tctgtccctc      60
acctgttctg tcactggcgc ctccatcacc agtggttact ggaactggat ccggaaattc      120
ccagggaata tcttgagta catgggattc ataaactaca gtggtaacac ttactacaat      180
ccatctctca aaagtcgaat ctccatcact cgagacacat ccaagcacca gtactacctg      240
cagttgaatt ctgtgactcc tgaggacaca gccacatatt actgtgcaag atctactatg      300
attacgacgg gggcctggtt tgcttactgg ggccaagggt ctctggtcac tgtctctgca      360
```

<210> SEQ ID NO 141
<211> LENGTH: 120
<212> TYPE: PRT
<213> ORGANISM: Mus sp.

<400> SEQUENCE: 141

```
Glu Val Gln Leu Gln Glu Ser Gly Pro Ser Leu Val Lys Pro Ser Gln
1               5                   10                  15

Thr Leu Ser Leu Thr Cys Ser Val Thr Gly Ala Ser Ile Thr Ser Gly
            20                  25                  30

Tyr Trp Asn Trp Ile Arg Lys Phe Pro Gly Asn Asn Leu Glu Tyr Met
        35                  40                  45

Gly Phe Ile Asn Tyr Ser Gly Asn Thr Tyr Tyr Asn Pro Ser Leu Lys
    50                  55                  60

Ser Arg Ile Ser Ile Thr Arg Asp Thr Ser Lys His Gln Tyr Tyr Leu
65                  70                  75                  80

Gln Leu Asn Ser Val Thr Pro Glu Asp Thr Ala Thr Tyr Tyr Cys Ala
```

```
                    85                  90                  95
Arg Ser Thr Met Ile Thr Thr Gly Ala Trp Phe Ala Tyr Trp Gly Gln
                100                 105                 110

Gly Ser Leu Val Thr Val Ser Ala
        115                 120

<210> SEQ ID NO 142
<211> LENGTH: 322
<212> TYPE: DNA
<213> ORGANISM: Mus sp.

<400> SEQUENCE: 142
agtattgtga tgacccagac tcccaaattc ctccttgtat cagctggagc caggattacc      60
ctaacctgca aggccagtca gagtgtgagt aaagatgtag cttggtacca acagaagcca     120
gggcagtctc ctaaactgct aatatactat gcatccaatc gctacactgg agtccctgat     180
cgcttcactg gcagtggata tgggacggat ttcactttca ccatcagctc tgtgcaggct     240
gaagacctgg cagtttattt ctgtcagcag gattatagct cgccgctcac gttcggtgct     300
gggaccaagc tggagctgaa ac                                              322

<210> SEQ ID NO 143
<211> LENGTH: 107
<212> TYPE: PRT
<213> ORGANISM: Mus sp.

<400> SEQUENCE: 143

Ser Ile Val Met Thr Gln Thr Pro Lys Phe Leu Leu Val Ser Ala Gly
1               5                   10                  15

Ala Arg Ile Thr Leu Thr Cys Lys Ala Ser Gln Ser Val Ser Lys Asp
            20                  25                  30

Val Ala Trp Tyr Gln Gln Lys Pro Gly Gln Ser Pro Lys Leu Leu Ile
        35                  40                  45

Tyr Tyr Ala Ser Asn Arg Tyr Thr Gly Val Pro Asp Arg Phe Thr Gly
    50                  55                  60

Ser Gly Tyr Gly Thr Asp Phe Thr Phe Thr Ile Ser Ser Val Gln Ala
65                  70                  75                  80

Glu Asp Leu Ala Val Tyr Phe Cys Gln Gln Asp Tyr Ser Ser Pro Leu
                85                  90                  95

Thr Phe Gly Ala Gly Thr Lys Leu Glu Leu Lys
                100                 105

<210> SEQ ID NO 144
<211> LENGTH: 363
<212> TYPE: DNA
<213> ORGANISM: Mus sp.

<400> SEQUENCE: 144
gaggtccagc tgcaacagtc tggacctgag ctggtgaagc ctggggcttc agtgaagata      60
tcctgcaaga cttctggata cacattcact gaatacacca tgcactgggt gaggcagagc     120
catggaaaga gccttgagtg gattgtaggt attaatccta aaaatgttgg ttctgcctac     180
aaccagaagt tcaagggcaa ggccacattg actgtagaca gtcctccag cacagcctac      240 atggagctcc gcagcctgac atctgaggat tctgcagtct attactgtgc aagaggaggg     300
aattactacg ctagtagccc ctttgattat tggggccaag gactctggt cactgtctct      360 gca                                                                   363
```

<210> SEQ ID NO 145
<211> LENGTH: 121
<212> TYPE: PRT
<213> ORGANISM: Mus sp.

<400> SEQUENCE: 145

Glu Val Gln Leu Gln Gln Ser Gly Pro Glu Leu Val Lys Pro Gly Ala
1               5                   10                  15

Ser Val Lys Ile Ser Cys Lys Thr Ser Gly Tyr Thr Phe Thr Glu Tyr
            20                  25                  30

Thr Met His Trp Val Arg Gln Ser His Gly Lys Ser Leu Glu Trp Ile
        35                  40                  45

Val Gly Ile Asn Pro Lys Asn Val Gly Ser Ala Tyr Asn Gln Lys Phe
    50                  55                  60

Lys Gly Lys Ala Thr Leu Thr Val Asp Lys Ser Ser Thr Ala Tyr
65                  70                  75                  80

Met Glu Leu Arg Ser Leu Thr Ser Glu Asp Ser Ala Val Tyr Tyr Cys
                85                  90                  95

Ala Arg Gly Gly Asn Tyr Tyr Ala Ser Ser Pro Phe Asp Tyr Trp Gly
            100                 105                 110

Gln Gly Thr Leu Val Thr Val Ser Ala
        115                 120

<210> SEQ ID NO 146
<211> LENGTH: 338
<212> TYPE: DNA
<213> ORGANISM: Mus sp.

<400> SEQUENCE: 146
gacattgtga tgtcacagtc tccatcctcc ctggctgtgt cagcaggaga gaaggtcact      60
atgagctgca agtccagtca gagtctgctc aacagtagaa cccgaaagaa ctacttggct     120
tggtaccagc agcaaccagg gcagtctcct aaactgctga tctactgggc atccactagg     180
gaatctgggg tccctgatcg cttcacaggc agtggatctg ggacagattt cactctcacc     240
atcagcagtg tgcaggctga agacctggca gtttattact gcaagcaatc ttataatctt     300
tacacgttcg gtgggggga caagctggaa ataaaacg                              338

<210> SEQ ID NO 147
<211> LENGTH: 113
<212> TYPE: PRT
<213> ORGANISM: Mus sp.

<400> SEQUENCE: 147

Asp Ile Val Met Ser Gln Ser Pro Ser Leu Ala Val Ser Ala Gly
1               5                   10                  15

Glu Lys Val Thr Met Ser Cys Lys Ser Ser Gln Ser Leu Leu Asn Ser
            20                  25                  30

Arg Thr Arg Lys Asn Tyr Leu Ala Trp Tyr Gln Gln Pro Gly Gln
        35                  40                  45

Ser Pro Lys Leu Leu Ile Tyr Trp Ala Ser Thr Arg Glu Ser Gly Val
    50                  55                  60

Pro Asp Arg Phe Thr Gly Ser Gly Ser Gly Thr Asp Phe Thr Leu Thr
65                  70                  75                  80

Ile Ser Ser Val Gln Ala Glu Asp Leu Ala Val Tyr Tyr Cys Lys Gln
                85                  90                  95

Ser Tyr Asn Leu Tyr Thr Phe Gly Gly Gly Thr Lys Leu Glu Ile Lys

Arg

<210> SEQ ID NO 148
<211> LENGTH: 335
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 148
gaggtgcagc tggtggagtc tgggggaggc ttggtccagc ctggggggtc cctgagactc    60
tcctgtgcag cctctggatt caccgtcact acttatggtg tggactgggt ccgccaagct   120
ccagggaagg ggctggagtg gttaggtgta atatggggtg gtggaagcac aaattataat   180
agcgctttga agagccgatt caccatctcc agagacaact ccaagaacac cctgtatctg   240
caaatgaaca gtctgagagc cgaggacacg gccgtgtatt actgtgccag tgattgggct   300
tactggggcc aagggactct ggtcactgtc tcttc                              335

<210> SEQ ID NO 149
<211> LENGTH: 112
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 149

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Val Thr Thr Tyr
            20                  25                  30

Gly Val Asp Trp Val Arg Gln Ala Pro Gly Lys Gly Leu Glu Trp Leu
        35                  40                  45

Gly Val Ile Trp Gly Gly Gly Ser Thr Asn Tyr Asn Ser Ala Leu Lys
    50                  55                  60

Ser Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95

Ser Asp Trp Ala Tyr Trp Gly Gln Gly Thr Leu Val Thr Val Ser Ser
            100                 105                 110

<210> SEQ ID NO 150
<211> LENGTH: 322
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 150
gacatccaga tgacccagtc tccatcttcc ctgtctgcat ctgtaggaga cagagtcacc    60
atcacttgtc gggcgagtca gaatgtgggt acaaatgtag cctggtttca gcagaaacca   120
gggaaagccc ctaagtccct gatccattcg gcatcctacc gttacagtgg ggtcccatca   180

```
aggttcagcg gcagtggatc tgggacagat tcactctca ccatcagcag cctgcagcct    240
gaagattttg caacttacta ttgtcagcaa tataagaggt atccgtacac gttcggaggg    300
gggaccaagc tggaaataaa ac                                             322
```

<210> SEQ ID NO 151
<211> LENGTH: 107
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 151

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asn Val Gly Thr Asn
            20                  25                  30

Val Ala Trp Phe Gln Gln Lys Pro Gly Lys Ala Pro Lys Ser Leu Ile
        35                  40                  45

His Ser Ala Ser Tyr Arg Tyr Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Lys Arg Tyr Pro Tyr
                85                  90                  95

Thr Phe Gly Gly Gly Thr Lys Leu Glu Ile Lys
            100                 105
```

<210> SEQ ID NO 152
<211> LENGTH: 365
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 152

```
gaggtgcaac tggtggagtc tgggggaggc ctggtcaagc ctgggggtc cctgagactc     60 tcctgtgcag cctctggatt caccttcagt acctatggca tgagctgggt ccgccaggct    120
ccagggaagg gctggagtg gtcgcaacc attagtagtg gtggtactta cacatactac      180
ccagactcag tgaagggccg attcaaaatc tccagagaca cgccaagaa ctcactgtat     240 ctgcaaatga acagcctgag agccgaggac acggctgtgt attactgtac aagacatgac    300
cccaatgatg gttactactt cctgtttgct tactggggcc aggggactct ggtcactgtc    360
tcttc                                                                365
```

<210> SEQ ID NO 153
<211> LENGTH: 122
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 153

```
Glu Val Gln Leu Val Glu Ser Gly Gly Gly Leu Val Lys Pro Gly Gly
1               5                   10                  15
```

| Ser | Leu | Arg | Leu | Ser | Cys | Ala | Ala | Ser | Gly | Phe | Thr | Phe | Ser | Thr | Tyr |
|---|---|---|---|---|---|---|---|---|---|---|---|---|---|---|---|
| | | | 20 | | | | 25 | | | | | 30 | | | |

| Gly | Met | Ser | Trp | Val | Arg | Gln | Ala | Pro | Gly | Lys | Gly | Leu | Glu | Trp | Val |
|---|---|---|---|---|---|---|---|---|---|---|---|---|---|---|---|
| | | 35 | | | | | 40 | | | | 45 | | | | |

| Ala | Thr | Ile | Ser | Ser | Gly | Gly | Thr | Tyr | Thr | Tyr | Tyr | Pro | Asp | Ser | Val |
|---|---|---|---|---|---|---|---|---|---|---|---|---|---|---|---|
| 50 | | | | | | 55 | | | | | 60 | | | | |

| Lys | Gly | Arg | Phe | Lys | Ile | Ser | Arg | Asp | Asn | Ala | Lys | Asn | Ser | Leu | Tyr |
|---|---|---|---|---|---|---|---|---|---|---|---|---|---|---|---|
| 65 | | | | | 70 | | | | 75 | | | | | | 80 |

| Leu | Gln | Met | Asn | Ser | Leu | Arg | Ala | Glu | Asp | Thr | Ala | Val | Tyr | Tyr | Cys |
|---|---|---|---|---|---|---|---|---|---|---|---|---|---|---|---|
| | | | | 85 | | | | | 90 | | | | | 95 | |

| Thr | Arg | His | Asp | Pro | Asn | Asp | Gly | Tyr | Tyr | Phe | Leu | Phe | Ala | Tyr | Trp |
|---|---|---|---|---|---|---|---|---|---|---|---|---|---|---|---|
| | | | 100 | | | | | 105 | | | | | 110 | | |

| Gly | Gln | Gly | Thr | Leu | Val | Thr | Val | Ser | Ser |
|---|---|---|---|---|---|---|---|---|---|
| | | | 115 | | | | 120 | | |

<210> SEQ ID NO 154
<211> LENGTH: 322
<212> TYPE: DNA
<213> ORGANISM: Artificial Sequence
<220> FEATURE:
<221> NAME/KEY: source
<223> OTHER INFORMATION: /note="Description of Artificial Sequence:
     Synthetic polynucleotide"

<400> SEQUENCE: 154

```
gaaattgtgt tgacgcagtc tccaggcacc ctgtctttgt ctccagggga aagagccacc      60
ctctcctgca aggccagtca gagtgttggc aacaatgtag cttggtacca gcagaaacct     120
ggccaggctc ccaggctcct catctactat gcatccaata ggtatacagg catcccagac     180
aggttcagtg gcagtgggtc tgggacagac ttcactctca ccatcagcag actggagcct     240
gaagattttg cagtgtatta ctgtcaacag cattatagct ctccgctcac gttcggtgct     300
gggaccaagc tggagatcaa ac                                              322
```

<210> SEQ ID NO 155
<211> LENGTH: 107
<212> TYPE: PRT
<213> ORGANISM: Artificial Sequence
<220> FEATURE:
<221> NAME/KEY: source
<223> OTHER INFORMATION: /note="Description of Artificial Sequence:
     Synthetic polypeptide"

<400> SEQUENCE: 155

| Glu | Ile | Val | Leu | Thr | Gln | Ser | Pro | Gly | Thr | Leu | Ser | Leu | Ser | Pro | Gly |
|---|---|---|---|---|---|---|---|---|---|---|---|---|---|---|---|
| 1 | | | | 5 | | | | | 10 | | | | | 15 | |

| Glu | Arg | Ala | Thr | Leu | Ser | Cys | Lys | Ala | Ser | Gln | Ser | Val | Gly | Asn | Asn |
|---|---|---|---|---|---|---|---|---|---|---|---|---|---|---|---|
| | | | 20 | | | | 25 | | | | | 30 | | | |

| Val | Ala | Trp | Tyr | Gln | Gln | Lys | Pro | Gly | Gln | Ala | Pro | Arg | Leu | Leu | Ile |
|---|---|---|---|---|---|---|---|---|---|---|---|---|---|---|---|
| | | 35 | | | | | 40 | | | | 45 | | | | |

| Tyr | Tyr | Ala | Ser | Asn | Arg | Tyr | Thr | Gly | Ile | Pro | Asp | Arg | Phe | Ser | Gly |
|---|---|---|---|---|---|---|---|---|---|---|---|---|---|---|---|
| | 50 | | | | | 55 | | | | | 60 | | | | |

| Ser | Gly | Ser | Gly | Thr | Asp | Phe | Thr | Leu | Thr | Ile | Ser | Arg | Leu | Glu | Pro |
|---|---|---|---|---|---|---|---|---|---|---|---|---|---|---|---|
| 65 | | | | | 70 | | | | | 75 | | | | | 80 |

| Glu | Asp | Phe | Ala | Val | Tyr | Tyr | Cys | Gln | Gln | His | Tyr | Ser | Ser | Pro | Leu |
|---|---|---|---|---|---|---|---|---|---|---|---|---|---|---|---|
| | | | | 85 | | | | | 90 | | | | | 95 | |

| Thr | Phe | Gly | Ala | Gly | Thr | Lys | Leu | Glu | Ile | Lys |
|---|---|---|---|---|---|---|---|---|---|---|
| | | | 100 | | | | | 105 | | |

<210> SEQ ID NO 156
<211> LENGTH: 361
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 156

```
caggttcagc tggtgcagtc tggagctgag gtgaagaagc ctggggcctc agtgaaggtc    60
tcctgcaagg cttctggtta ccctttacc ggctattaca tccactgggt gcgacaggcc   120
cctggacaag gcttgagtg gatgggatgg atctaccctg caattttaa cacaaaatat   180
aacgagcggt tcaagggcag agtcaccatg accacagaca catccacgag cacagcctac   240
atggagctga ggagcctgag atctgacgac acggccgtgt attactgtgc gagagaggat   300
ggtagcccct actatgctat ggactactgg ggtcaaggaa cctcagtcac cgtctcctca   360
g                                                                    361
```

<210> SEQ ID NO 157
<211> LENGTH: 120
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 157

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Tyr Ile His Trp Val Arg Gln Ala Pro Gly Gln Gly Leu Glu Trp Met
        35                  40                  45

Gly Trp Ile Tyr Pro Gly Asn Phe Asn Thr Lys Tyr Asn Glu Arg Phe
    50                  55                  60

Lys Gly Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Glu Asp Gly Ser Pro Tyr Tyr Ala Met Asp Tyr Trp Gly Gln
            100                 105                 110

Gly Thr Ser Val Thr Val Ser Ser
        115                 120

<210> SEQ ID NO 158
<211> LENGTH: 337
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 158

```
gatattgtga tgacccagac tccactctct ctgtccgtca cccctggaca gccggcctcc    60
atctcctgcc ggtctagtca gagcctcgtg catagtaatg aaacacctt tttgtattgg   120
tacctgcaga agccaggcca gtctccacag ctcctaatct atagagtttc caaccggttc   180
```

-continued

```
tctggagtgc cagataggtt cagtggcagc gggtcaggga cagatttcac actgaaaatc    240
agccgggtgg aggctgagga tgttgggggtt tattactgct ttcaagctac acatgttccg    300
tggacgttcg gtggaggcac caaagtggaa atcaaac                             337
```

<210> SEQ ID NO 159
<211> LENGTH: 112
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 159

```
Asp Ile Val Met Thr Gln Thr Pro Leu Ser Leu Ser Val Thr Pro Gly
1               5                   10                  15

Gln Pro Ala Ser Ile Ser Cys Arg Ser Ser Gln Ser Leu Val His Ser
            20                  25                  30

Asn Gly Asn Thr Phe Leu Tyr Trp Tyr Leu Gln Lys Pro Gly Gln Ser
        35                  40                  45

Pro Gln Leu Leu Ile Tyr Arg Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Phe Gln Ala
                85                  90                  95

Thr His Val Pro Trp Thr Phe Gly Gly Gly Thr Lys Val Glu Ile Lys
            100                 105                 110
```

<210> SEQ ID NO 160
<211> LENGTH: 353
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 160

```
caggtgcagc tggtgcagtc tggggctgag gtgaagaagc ctggggcctc agtgaaggtt    60
tcctgcaagg catctggata caccttcact tacttctata tgaactgggt gcgacaggcc    120
cctggacaag gcttgagtg gtgggacaa atcaaccctaataatggtgg cacagcctac    180 gcacagaagt tccagggcag agtcaccatg accagggaca cgtccacgag cacagtctac    240
atggagctga gcagcctgag atctgaggac acggccgtgt attactgtgc gagatgggtc    300
gggactcact actttgacta ctggggccaa ggcaccactc tcacagtctc ctc          353
```

<210> SEQ ID NO 161
<211> LENGTH: 118
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 161

```
Gln Val Gln Leu Val Gln Ser Gly Ala Glu Val Lys Lys Pro Gly Ala
1               5                   10                  15
```

```
Ser Val Lys Val Ser Cys Lys Ala Ser Gly Tyr Thr Phe Thr Tyr Phe
            20                  25                  30

Tyr Met Asn Trp Val Arg Gln Ala Pro Gly Gln Gly Leu Glu Trp Val
        35                  40                  45

Gly Gln Ile Asn Pro Asn Asn Gly Gly Thr Ala Tyr Ala Gln Lys Phe
    50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Trp Val Gly Thr His Tyr Phe Asp Tyr Trp Gly Gln Gly Thr
            100                 105                 110

Thr Leu Thr Val Ser Ser
            115

<210> SEQ ID NO 162
<211> LENGTH: 334
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 162
gaaattgtgt tgacacagtc tccagccacc ctgtctttgt ctccagggga aagagccacc     60
ctctcctgca gggccagtca gagtgttagc agctctagct atacttacat tcactggtac    120
caacagaaac ctggccaggc tcccaggctc ctcatcaatt ttgcatccaa cttggaaagt    180
ggcatcccag ccaggttcag tggcagtggg tctgggacag acttcactct caccatcagc    240
agcctagagc ctgaagattt tgcagtttat tactgtcagc acagtgggga gattcctccg    300
acgttcggtg aggcaccaa gctggaaatc aaac                                 334

<210> SEQ ID NO 163
<211> LENGTH: 111
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 163

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Ser Tyr Thr Tyr Ile His Trp Tyr Gln Gln Lys Pro Gly Gln Ala Pro
        35                  40                  45

Arg Leu Leu Ile Asn Phe Ala Ser Asn Leu Glu Ser Gly Ile Pro Ala
    50                  55                  60

Arg Phe Ser Gly Ser Gly Ser Gly Thr Asp Phe Thr Leu Thr Ile Ser
65                  70                  75                  80

Ser Leu Glu Pro Glu Asp Phe Ala Val Tyr Tyr Cys Gln His Ser Trp
                85                  90                  95

Glu Ile Pro Pro Thr Phe Gly Gly Gly Thr Lys Leu Glu Ile Lys
            100                 105                 110
```

```
<210> SEQ ID NO 164
<211> LENGTH: 11
<212> TYPE: PRT
<213> ORGANISM: Homo sapiens

<400> SEQUENCE: 164

Gln Arg Phe Thr Pro Phe Ser Leu Gly Phe Glu
1               5                   10

<210> SEQ ID NO 165
<211> LENGTH: 10
<212> TYPE: PRT
<213> ORGANISM: Homo sapiens

<400> SEQUENCE: 165

Arg Leu Leu Arg Gly Asp Ala Val Val Glu
1               5                   10

<210> SEQ ID NO 166
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic 6xHis tag"

<400> SEQUENCE: 166

His His His His His His
1               5
```

MODULATORS AND METHODS OF USE

CROSS REFERENCED APPLICATIONS

This is a national stage application of PCT/US2011/063831 filed Dec. 7, 2011, which claims priority to U.S. Provisional Application Ser. No. 61/421,157 filed Dec. 8, 2010 and Patent Cooperation Treaty (PCT) No. PCT/US2011/050451, filed Sep. 2, 2011, each of which is incorporated herein by reference in its entirety.

SEQUENCE LISTING

The instant application contains a Sequence Listing which has been submitted in ASCII format via EFS-Web and is hereby incorporated by reference in its entirety. Said ASCII copy, created on Nov. 22, 2011, is named 11200PCT.txt and is 80,102 bytes in size.

FIELD OF THE INVENTION

This application generally relates to novel compositions and methods of their use in preventing, treating or ameliorating hyperproliferative disorders and any expansion, recurrence, relapse or metastasis thereof. In a broad aspect, the present invention relates to the use of ephrin-A ligand (EFNA) modulators, including anti-EFNA antibodies and fusion constructs, for the treatment or prophylaxis of neoplastic disorders. Particularly preferred embodiments of the present invention provide for the use of such EFNA modulators for the immunotherapeutic treatment of malignancies comprising a reduction in tumor initiating cell frequency.

BACKGROUND OF THE INVENTION

Stem and progenitor cell differentiation and cell proliferation are normal ongoing processes that act in concert to support tissue growth during organogenesis and cell replacement and repair of most tissues during the lifetime of all living organisms. Differentiation and proliferation decisions are often controlled by numerous factors and signals that are balanced to maintain cell fate decisions and tissue architecture. Normal tissue architecture is largely maintained by cells responding to microenvironmental cues that regulate cell division and tissue maturation. Accordingly, cell proliferation and differentiation normally occurs only as necessary for the replacement of damaged or dying cells or for growth. Unfortunately, disruption of cell proliferation and/or differentiation can result from a myriad of factors including, for example, the under- or overabundance of various signaling chemicals, the presence of altered microenvironments, genetic mutations or some combination thereof. When normal cellular proliferation and/or differentiation is disturbed or somehow disrupted it can lead to various diseases or disorders including hyperproliferative disorders such as cancer.

Conventional treatments for cancer include chemotherapy, radiotherapy, surgery, immunotherapy (e.g., biological response modifiers, vaccines or targeted therapeutics) or combinations thereof. Sadly, far too many cancers are non-responsive or minimally responsive to such conventional treatments leaving few options for patients. For example, in some patients certain cancers exhibit gene mutations that render them non-responsive despite the general effectiveness of selected therapies. Moreover, depending on the type of cancer some available treatments, such as surgery, may not be viable alternatives. Limitations inherent in current standard of care therapeutics are particularly evident when attempting to care for patients who have undergone previous treatments and have subsequently relapsed. In such cases the failed therapeutic regimens and resulting patient deterioration may contribute to refractory tumors which often manifest themselves as a more aggressive disease that ultimately proves to be incurable. Although there have been great improvements in the diagnosis and treatment of cancer over the years, overall survival rates for many solid tumors have remained largely unchanged due to the failure of existing therapies to prevent relapse, tumor recurrence and metastases. Thus, it remains a challenge to develop more targeted and potent therapies.

One promising area of research involves the use of targeted therapeutics to go after the tumorigenic "seed" cells that appear to underlie many cancers. To that end most solid tissues are now known to contain adult, tissue-resident stem cell populations generating the differentiated cell types that comprise the majority of that tissue. Tumors arising in these tissues similarly consist of heterogeneous populations of cells that also arise from stem cells, but differ markedly in their overall proliferation and organization. While it is increasingly recognized that the majority of tumor cells have a limited ability to proliferate, a minority population of cancer cells (commonly known as cancer stem cells or CSC) have the exclusive ability to extensively self-renew thereby enabling an inherent tumor reinitiating capacity. More specifically, the cancer stem cell hypothesis proposes that there is a distinct subset of cells (i.e. CSC) within each tumor (approximately 0.1-10%) that is capable of indefinite self-renewal and of generating tumor cells progressively limited in their replication capacity as a result of differentiation to tumor progenitor cells and, subsequently, to terminally differentiated tumor cells.

In recent years it has become more evident these CSC (also known as tumor perpetuating cells or TPC) might be more resistant to traditional chemotherapeutic agents or radiation and thus persist after standard of care clinical therapies to later fuel the growth of refractory tumors, secondary tumors and promote metastases. Moreover, growing evidence suggests that pathways that regulate organogenesis and/or the self-renewal of normal tissue-resident stem cells are deregulated or altered in CSC, resulting in the continuous expansion of self-renewing cancer cells and tumor formation. See generally Al-Hajj et al., 2004, PMID: 15378087; and Dalerba et al., 2007, PMID: 17548814; each of which is incorporated herein in its entirety by reference. Thus, the effectiveness of traditional, as well as more recent targeted treatment methods, has apparently been limited by the existence and/or emergence of resistant cancer cells that are capable of perpetuating the cancer even in face of these diverse treatment methods. Huff et al., European Journal of Cancer 42: 1293-1297 (2006) and Zhou et al., Nature Reviews Drug Discovery 8: 806-823 (2009) each of which is incorporated herein in its entirety by reference. Such observations are confirmed by the consistent inability of traditional debulking agents to substantially increase patient survival when suffering from solid tumors, and through the development of an increasingly sophisticated understanding as to how tumors grow, recur and metastasize. Accordingly, recent strategies for treating neoplastic disorders have recognized the importance of eliminating, depleting, silencing or promoting the differentiation of tumor perpetuating cells so as to diminish the possibility of tumor recurrence, metastasis or patient relapse.

Efforts to develop such strategies have incorporated recent work involving non-traditional xenograft (NTX) models, wherein primary human solid tumor specimens are implanted and passaged exclusively in immunocompromised mice. In numerous cancers such techniques confirm the existence of a subpopulation of cells with the unique ability to generate heterogeneous tumors and fuel their growth indefinitely. As previously hypothesized, work in NTX models has confirmed that identified CSC subpopulations of tumor cells appear more resistant to debulking regimens such as chemotherapy and radiation, potentially explaining the disparity between clinical response rates and overall survival. Further, employment of NTX models in CSC research has sparked a fundamental change in drug discovery and preclinical evaluation of drug candidates that may lead to CSC-targeted therapies having a major impact on tumor recurrence and metastasis thereby improving patient survival rates. While progress has been made, inherent technical difficulties associated with handling primary and/or xenograft tumor tissue, along with a lack of experimental platforms to characterize CSC identity and differentiation potential, pose major challenges. As such, there remains a substantial need to selectively target cancer stem cells and develop diagnostic, prophylactic or therapeutic compounds or methods that may be used in the treatment, prevention and/or management of hyperproliferative disorders.

SUMMARY OF THE INVENTION

These and other objectives are provided for by the present invention which, in a broad sense, is directed to methods, compounds, compositions and articles of manufacture that may be used in the treatment of EFNA associated disorders (e.g., hyperproliferative disorders or neoplastic disorders). To that end, the present invention provides novel EFNA (or ephrin-A ligand) modulators that effectively target tumor cells or cancer stem cells and may be used to treat patients suffering from a wide variety of malignancies. As will be discussed in more detail herein, there are presently six known ephrin-A ligands (i.e., EFNAs 1-6) and the disclosed modulators may comprise or associate with any one, or more than one, ephrin-A ligand. Moreover, in certain embodiments the disclosed EFNA modulators may comprise any compound that recognizes, competes, agonizes, antagonizes, interacts, binds or associates with an EFNA polypeptide, its receptor or its gene and modulates, adjusts, alters, changes or modifies the impact of the EFNA protein on one or more physiological pathways. Thus, in a broad sense the present invention is directed to isolated EFNA modulators. In preferred embodiments the invention is more particularly directed to isolated EFNA1 modulators or isolated EFNA4 modulators (i.e., modulators that comprise or associate with at least EFNA1 or EFNA4). Moreover, as discussed extensively below such modulators may be used to provide pharmaceutical compositions.

In selected embodiments of the invention, EFNA modulators may comprise an ephrin-A ligand itself or fragments thereof, either in an isolated form or fused or associated with other moieties (e.g., Fc-EFNA, PEG-EFNA or EFNA associated with a targeting moiety). In other selected embodiments EFNA modulators may comprise EFNA antagonists which, for the purposes of the instant application, shall be held to mean any construct or compound that recognizes, competes, interacts, binds or associates with EFNA and neutralizes, eliminates, reduces, sensitizes, reprograms, inhibits or controls the growth of neoplastic cells including tumor initiating cells. In preferred embodiments the EFNA modulators of the instant invention comprise anti-EFNA antibodies, or fragments or derivatives thereof, that have unexpectedly been found to silence, neutralize, reduce, decrease, deplete, moderate, diminish, reprogram, eliminate, or otherwise inhibit the ability of tumor initiating cells to propagate, maintain, expand, proliferate or otherwise facilitate the survival, recurrence, regeneration and/or metastasis of neoplastic cells. In particularly preferred embodiments the antibodies or immunoreactive fragments may be associated with or conjugated to one or more anti-cancer agents.

In one embodiment the EFNA modulator may comprise a humanized antibody wherein said antibody comprises a heavy chain variable region amino acid sequence selected from the group consisting of SEQ ID NO: 149, SEQ ID NO: 153, SEQ ID NO: 157 and SEQ ID NO: 161 and a light chain variable region amino acid sequence selected from the group consisting of SEQ ID NO: 151, SEQ ID NO: 155, SEQ ID NO: 159 and SEQ ID NO: 163. In other preferred embodiments the invention will be in the form of a composition comprising a humanized antibody selected from the group consisting of hSC4.5, hSC4.15, hSC4.22 and hSC4.47 and a pharmaceutically acceptable carrier. In another preferred embodiment the EFNA modulator may comprise an antibody that comprises one or more CDRs from FIG. 7A (SEQ ID NOS: 8-59 and 70-95). Preferably the antibody comprising at least one CDR from FIG. 7A will comprise a humanized antibody.

In certain other embodiments the invention will comprise an EFNA modulator that reduces the frequency of tumor initiating cells upon administration to a subject. Preferably the reduction in frequency will be determined using in vitro or in vivo limiting dilution analysis. In particularly preferred embodiments such analysis may be conducted using in vivo limiting dilution analysis comprising transplant of live human tumor cells into immunocompromised mice. Alternatively, the limiting dilution analysis may be conducted using in vitro limiting dilution analysis comprising limiting dilution deposition of live human tumor cells into in vitro colony supporting conditions. In either case, the analysis, calculation or quantification of the reduction in frequency will preferably comprise the use of Poisson distribution statistics to provide an accurate accounting. It will be appreciated that, while such quantification methods are preferred, other, less labor intensive methodology such as flow cytometry or immunohistochemistry may also be used to provide the desired values and, accordingly, are expressly contemplated as being within the scope of the instant invention. In such cases the reduction in frequency may be determined using flow cytometric analysis or immunohistochemical detection of tumor cell surface markers known to enrich for tumor initiating cells.

As such, in another preferred embodiment of the instant invention comprises a method of treating an EFNA associated disorder comprising administering a therapeutically effective amount of an EFNA modulator to a subject in need thereof whereby the frequency of tumor initiating cells is reduced. Again, the reduction in the tumor initiating cell frequency will preferably be determined using in vitro or in vivo limiting dilution analysis.

In this regard it will be appreciated that the present invention is based, at least in part, upon the discovery that EFNA polypeptides (and particularly EFNA4 as discussed below) are associated with tumor perpetuating cells (i.e., cancer stem cells) that are involved in the etiology of various neoplasia. More specifically, the instant application unexpectedly demonstrates that the administration of various exemplary EFNA modulators can mediate, reduce, inhibit or eliminate tumorigenic signaling by tumor initiating cells (i.e., reduce the frequency of tumor initiating cells). This reduced signaling, whether by reduction, elimination, reprogramming or silencing of the tumor initiating cells or by modifying tumor cell morphology (e.g., induced differentiation, niche disruption), in turn allows for the more effective treatment of EFNA associated disorders by inhibiting tumorigenesis, tumor maintenance, expansion and/or metastasis and recurrence. In other embodiments the disclosed modulators may promote, support or otherwise enhance EFNA mediated signaling that may limit or restrain tumor growth. In other embodiments the disclosed modulators may interfere, suppress or otherwise retard EFNA mediated signaling that may fuel tumor growth. Further, as will be discussed in more detail below, EFNA polypeptides are involved in generating adhesive and repulsive forces between cells through integrin and cytoskeleton rearrangements. Intervention in such intercellular interactions, using the novel EFNA modulators described herein, may thereby ameliorate a disorder by more than one mechanism (i.e., tumor initiating cell reduction and disruption of cellular adhesion) to provide additive or synergistic effects. Still other preferred embodiments may take advantage of the cellular internalization of ephrin-A ligands to deliver a modulator mediated anti-cancer agent. In this regard it will be appreciated that the present invention is not limited by any particular mechanism of action but rather encompasses the broad use of the disclosed modulators to treat EFNA associated disorders (including various neoplasia).

Thus, another preferred embodiment of the invention comprises a method of treating an EFNA associated disorder in a subject in need thereof comprising the step of administering an EFNA modulator to said subject. In particularly preferred embodiments the EFNA modulator will be associated (e.g., conjugated) with an anti-cancer agent. Moreover the beneficial aspects of the instant invention, including any cellular adhesion disruption and collateral benefits, may be achieved whether the subject tumor tissue exhibits elevated levels of EFNA or reduced or depressed levels of EFNA as compared with normal adjacent tissue.

As alluded to above and discussed in more detail below there are currently six known ephrin-A ligands (i.e., EFNAs 1-6). In accordance with the instant invention it will be appreciated that the disclosed modulators may be generated, fabricated and/or selected to react with a single ephrin-A ligand (e.g., EFNA4), a subset of ephrin-A ligands (e.g., EFNA4 and EFNA1) or all six ephrin-A ligands. More particularly, as described herein and set forth in the Examples below, preferred modulators such as antibodies may be generated and selected so that they react or bind with domains or epitopes that are expressed on a single ephrin-A ligand or with epitopes that are conserved (at least to some extent) and presented across multiple or all EFNA polypeptides (e.g., EFNAs 1 and 4 or EFNAs 3 and 4). This is significant with respect to the instant invention in that, as shown in Example 18 below, certain ephrin-A ligands have been found to be preferably expressed on TIC and, in combination, may serve as particularly effective therapeutic targets that provide for the selective reduction in tumorigenic cell frequency and/or depletion of cancer stem cell populations.

Therefore, in a selected embodiment the invention comprises a pan-EFNA modulator that immunospecifically associates with two or more ephrin-A ligands. In such embodiments the selected modulator may have been generated through immunization with a particular ligand (e.g., EFNA4) and associate or cross-react with the various subject ligands to a greater or lesser degree. Accordingly, in yet other embodiments the present invention comprises a method of treating a subject in need thereof comprising administering a therapeutically effective amount of a pan-EFNA modulator. Still other embodiments comprise a method of treating a subject in need thereof comprising administering a therapeutically effective amount of an EFNA modulator that immunospecifically associates with one or more ephrin-A ligands.

Accordingly, in yet other embodiments the present invention will comprise a pan-EFNA modulator. In still other embodiments the present invention will comprise a method of treating an EFNA associated disorder in a subject in need thereof comprising the step of administering a pan-EFNA modulator to said subject.

Of course it will be appreciated that the disclosed EFNA modulators may be generated, fabricated and/or selected to preferentially react or associate with a single ephrin-A ligand (e.g., EFNA4) and exhibit minimal or no association with any other ephrin-A ligand. Accordingly, other embodiments of the invention are directed to EFNA modulators that immunospecifically associate with a selected ephrin-A ligand and exhibit little or no association with any other ephrin-A ligand. In this regard preferred embodiments disclosed herein will comprise methods of treating an EFNA associated disorder in a subject in need thereof comprising the step of administering an EFNA modulator wherein the EFNA modulator immunospecifically associates with a selected ephrin-A ligand and is substantially non-reactive with any other ephrin-A ligand. Further, methods of generating, fabricating and selecting such modulators are within the scope of the instant invention.

Other facets of the instant invention exploit the ability of the disclosed modulators to potentially disrupt cell adhesion interactions while simultaneously silencing tumor initiating cells. Such multi-active EFNA modulators (e.g., EFNA antagonists) may prove to be particularly effective when used in combination with standard of care anti-cancer agents or debulking agents. In addition, two or more EFNA antagonists (e.g. antibodies that specifically bind to two discrete epitopes on an ephrin-A ligand or that associate with discrete ligands) may be used in combination in accordance with the present teachings. Moreover, as discussed in some detail below, the EFNA modulators of the present invention may be used in a conjugated or unconjugated state and, optionally, as a sensitizing agent in combination with a variety chemical or biological anti-cancer agents.

Thus, another preferred embodiment of the instant invention comprises a method of sensitizing a tumor in a subject for treatment with an anti-cancer agent comprising the step of administering an EFNA modulator to said subject. In a particularly preferred aspect of the invention the EFNA modulator will specifically result in a reduction of tumor initiating cell frequency as is determined using in vitro or in vivo limiting dilution analysis thereby sensitizing the tumor for concomitant or subsequent debulking.

Similarly, as the compounds of the instant invention may exert therapeutic benefits through various physiological mechanisms, the present invention is also directed to selected effectors or modulators that are specifically fabricated to exploit certain cellular processes. For example, in certain embodiments the preferred modulator may be engineered to associate with EFNA on or near the surface of the tumor initiating cell and stimulate the subject's immune response. In other embodiments the modulator may comprise an antibody directed to an epitope that neutralizes ephrin-A ligand activity and interactions with ephrin receptors which may impact adhesive and repulsive forces between cells through integrin and cytoskeleton rearrangements. In yet other embodiments the disclosed modulators may act by depleting or eliminating the EFNA associated cells. As such, it is important to appreciate that the present invention is not limited to any particular mode of action but rather encompasses any method or EFNA modulator that achieves the desired outcome.

Within such a framework preferred embodiments of the disclosed embodiments are directed to a method of treating a subject suffering from neoplastic disorder comprising the step of administering a therapeutically effective amount of at least one neutralizing EFNA modulator.

Other embodiments are directed to a method of treating a subject suffering from an EFNA associated disorder comprising the step of administering a therapeutically effective amount of at least one depleting EFNA modulator. A related method is directed to depleting EFNA associated cells in a subject in need thereof comprising the step of administering an EFNA modulator.

In yet another embodiment the present invention provides methods of maintenance therapy wherein the disclosed effectors or modulators are administered over a period of time following an initial procedure (e.g., chemotherapeutic, radiation or surgery) designed to remove at least a portion of the tumor mass. Such therapeutic regimens may be administered over a period of weeks, a period of months or even a period of years wherein the EFNA modulators may act prophylactically to inhibit metastasis and/or tumor recurrence. In yet other embodiments the disclosed modulators may be administrated in concert with known debulking regimens to prevent or retard metastasis.

Beyond the therapeutic uses discussed above it will also be appreciated that the modulators of the instant invention may be used to diagnose EFNA related disorders and, in particular, hyperproliferative disorders. In some embodiments the modulator may be administered to the subject and detected or monitored in vivo. Those of skill in the art will appreciate that such modulators may be labeled or associated with markers or reporters as disclosed below and detected using any one of a number of standard techniques (e.g., MRI or CAT scan). In other instances the modulators may be used in an in vitro diagnostic setting using art-recognized procedures. As such, a preferred embodiment comprises a method of diagnosing a hyperproliferative disorder in a subject in need thereof comprising the steps of:
 a. obtaining a tissue sample from said subject;
 b. contacting the tissue sample with at least one EFNA modulator; and
 c. detecting or quantifying the EFNA modulator associated with the sample.

Such methods may be easily discerned in conjunction with the instant application and may be readily performed using generally available commercial technology such as automatic plate readers, dedicated reporter systems, etc. In selected embodiments the EFNA modulator will be associated with tumor perpetuating cells present in the sample. In other preferred embodiments the detecting or quantifying step will comprise a reduction of tumor initiating cell frequency and detection thereof. Moreover, limiting dilution analysis may be conducted as previously alluded to above and will preferably employ the use of Poisson distribution statistics to provide an accurate accounting as to the reduction of frequency.

In a similar vein the present invention also provides kits that are useful in the diagnosis and monitoring of EFNA associated disorders such as cancer. To this end the present invention preferably provides an article of manufacture useful for diagnosing or treating EFNA associated disorders comprising a receptacle comprising an EFNA modulator and instructional materials for using said EFNA modulator to treat or diagnose the EFNA associated disorder.

Other preferred embodiments of the invention also exploit the properties of the disclosed modulators as an instrument useful for identifying, isolating, sectioning or enriching populations or subpopulations of tumor initiating cells through methods such as fluorescence activated cell sorting (FACS) or laser mediated sectioning.

As such, another preferred embodiment of the instant invention is directed to a method of identifying, isolating, sectioning or enriching a population of tumor initiating cells comprising the step of contacting said tumor initiating cells with an EFNA modulator.

The foregoing is a summary and thus contains, by necessity, simplifications, generalizations, and omissions of detail; consequently, those skilled in the art will appreciate that the summary is illustrative only and is not intended to be in any way limiting. Other aspects, features, and advantages of the methods, compositions and/or devices and/or other subject matter described herein will become apparent in the teachings set forth herein. The summary is provided to introduce a selection of concepts in a simplified form that are further described below in the Detailed Description. This summary is not intended to identify key features or essential features of the claimed subject matter, nor is it intended to be used as an aid in determining the scope of the claimed subject matter.

BRIEF DESCRIPTION OF THE FIGURES

Figures 6A, 6B:
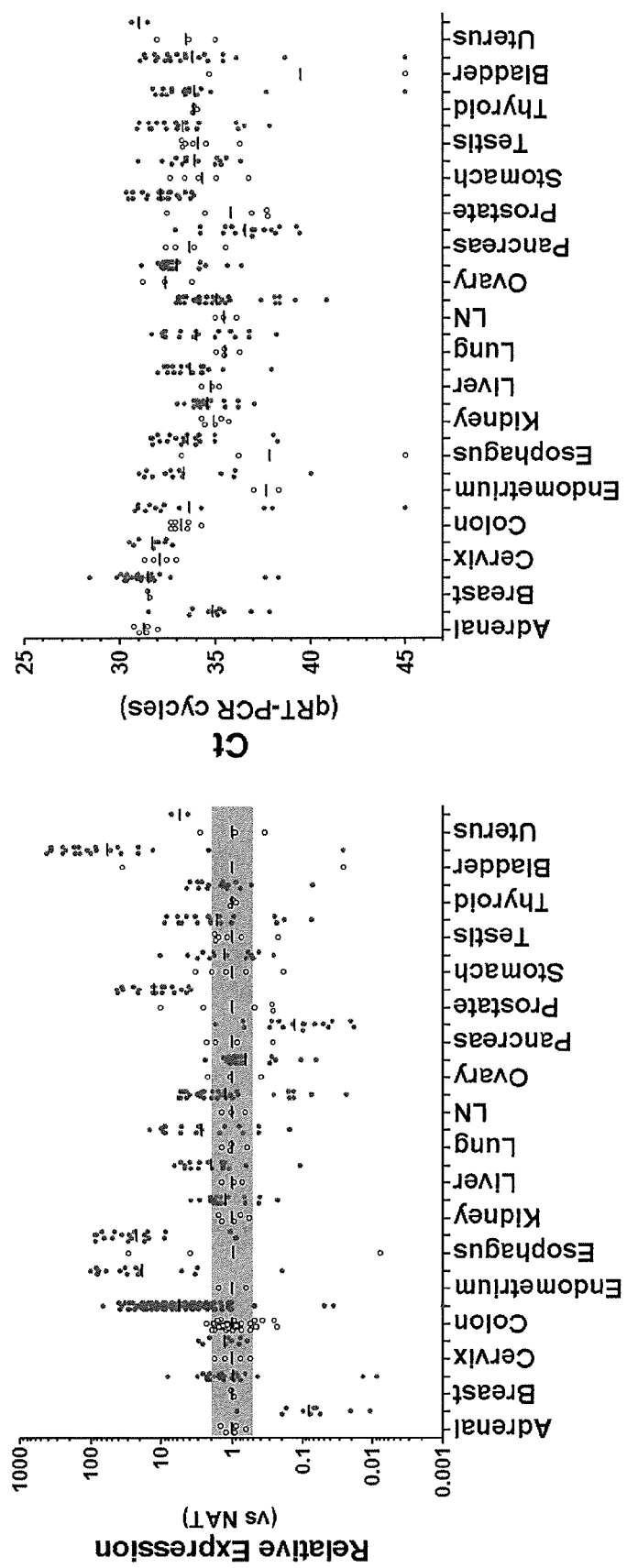
Figure 6E:
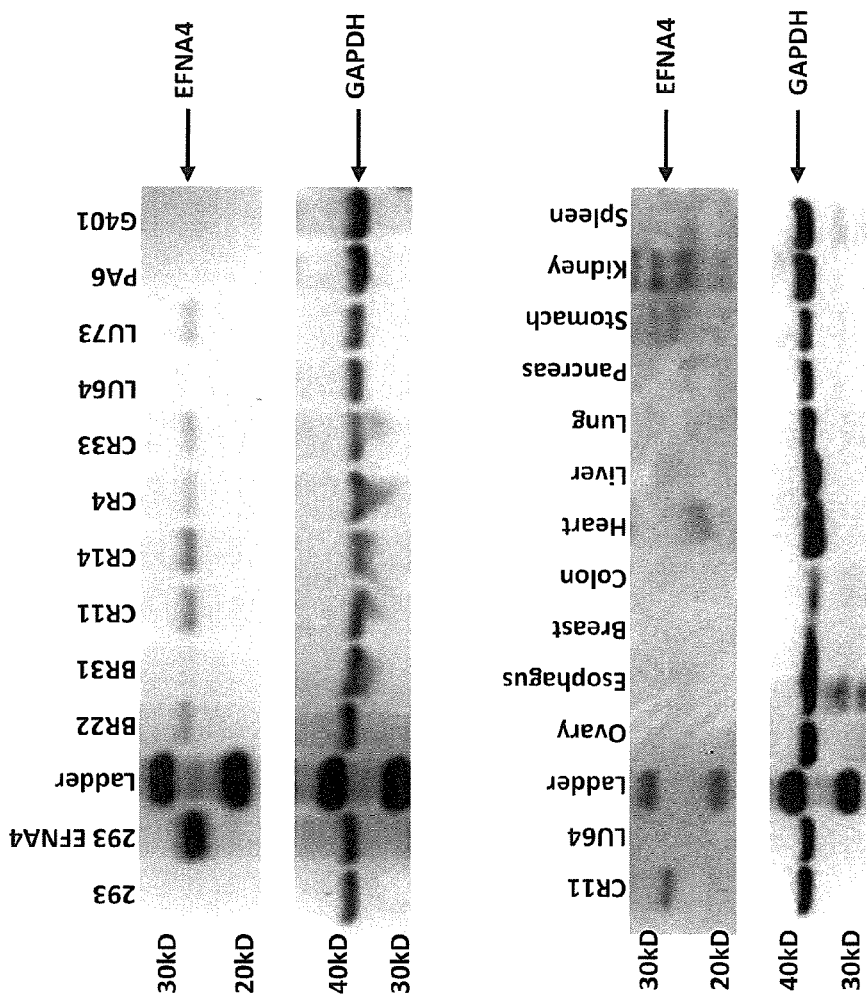

FIGS. 1A-C depict, respectively, the nucleic acid sequence encoding human EFNA4 (SEQ ID NO: 1), the corresponding amino acid sequence of human EFNA4 isoform a (SEQ ID NO: 2) and an alignment of human EFNA4 a, b and c isoform sequences showing amino acid differences (SEQ ID NOS: 2-4) whereas FIGS. 1 D-F depict, respectively, the nucleic acid sequence encoding human EFNA1 (SEQ ID NO: 5), the corresponding amino acid sequence of human EFNA1 isoform a (SEQ ID NO: 6) and an alignment of human EFNA1 a and b isoforms sequences showing amino acid differences (SEQ ID NOS: 6 and 7);

FIGS. 2A and 2B are graphical representations depicting the gene expression levels of selected human ephrin-A ligands and ephrin-A receptors in untreated (FIG. 2A) and in irinotecan treated (FIG. 2B) mice as measured using whole transcriptome sequencing of highly enriched tumor progenitor cell (TProg) and tumor perpetuating cell (TPC) and non-tumorigenic cell (NTG) populations obtained from a subset of whole colorectal tumor specimens;

FIGS. 6A-6E represent gene expression levels of human EFNA genes as measured for EFNA4 in FIGS. 6A and 6B by RT-PCR in whole tumor specimens (grey dot) or matched NAT (white dots) from patients with one of eighteen different solid tumor types, in FIGS. 6C and 6D by RT-PCR for EFNA4 and EFNA1 in selected NTX tumor cell lines and by Western blot analysis in FIG. 6E for EFNA4 in normal tissue and selected NTX tumor cell lines;

Figure 9:
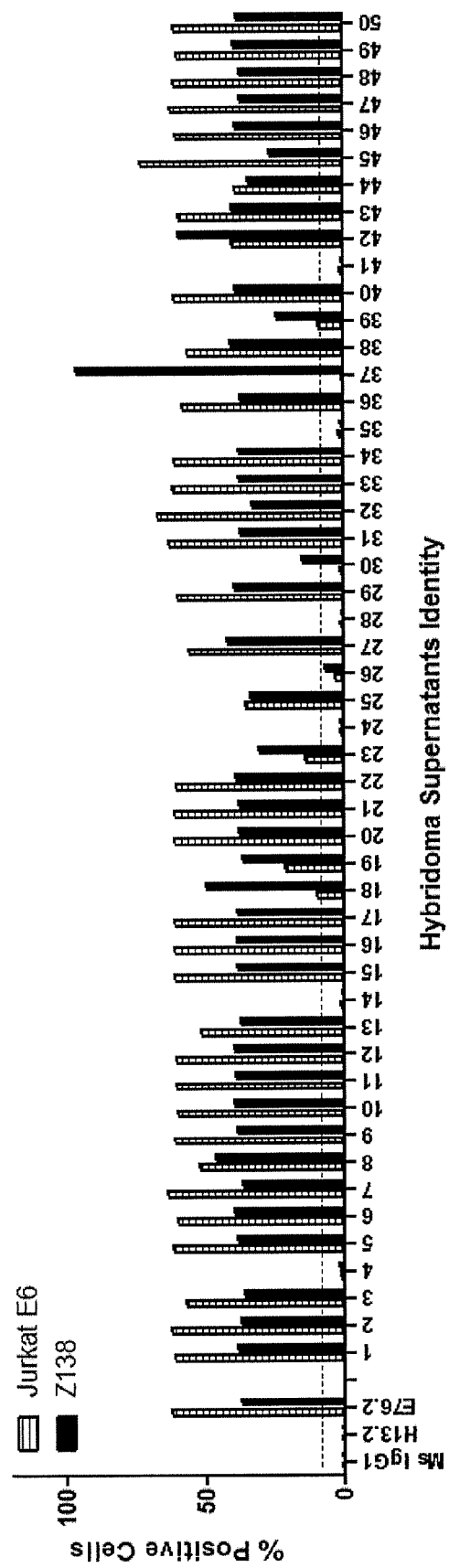
Figures 12D, 12E:
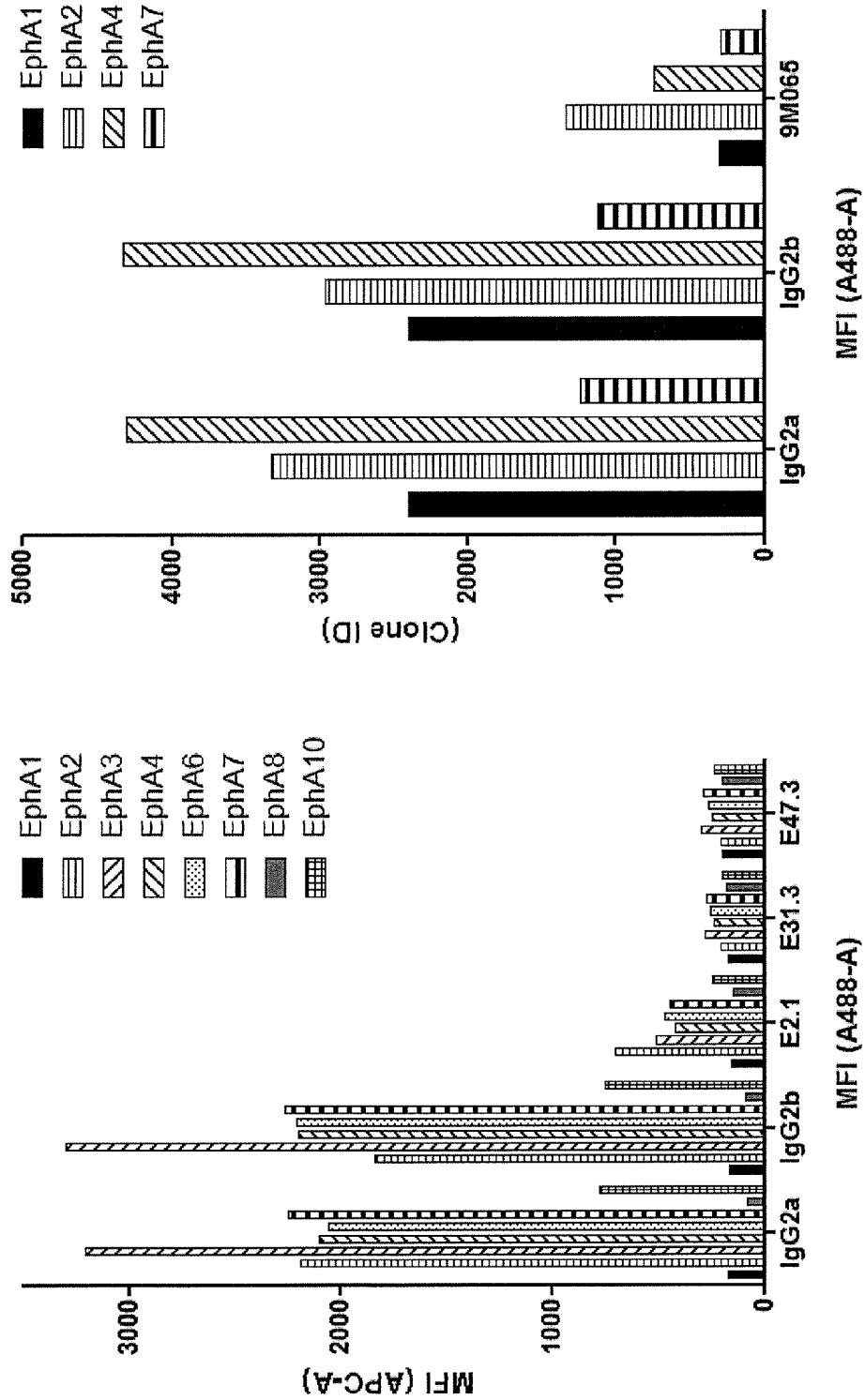
Figures 13A, 13B:
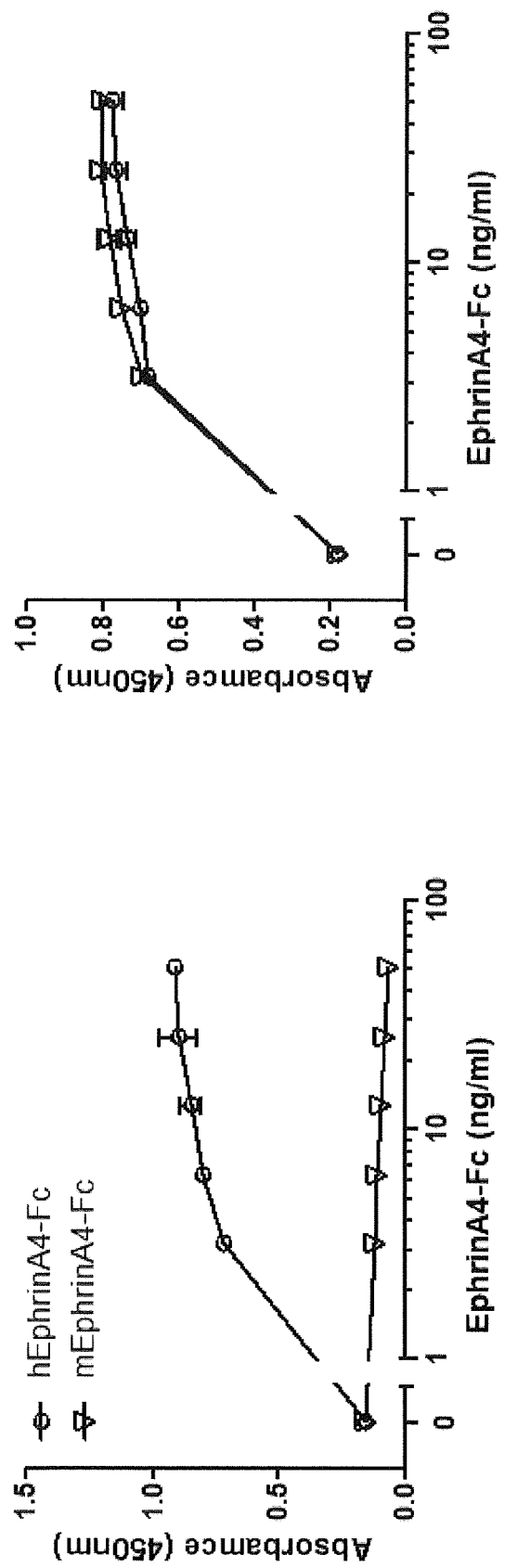
Figure 13C:
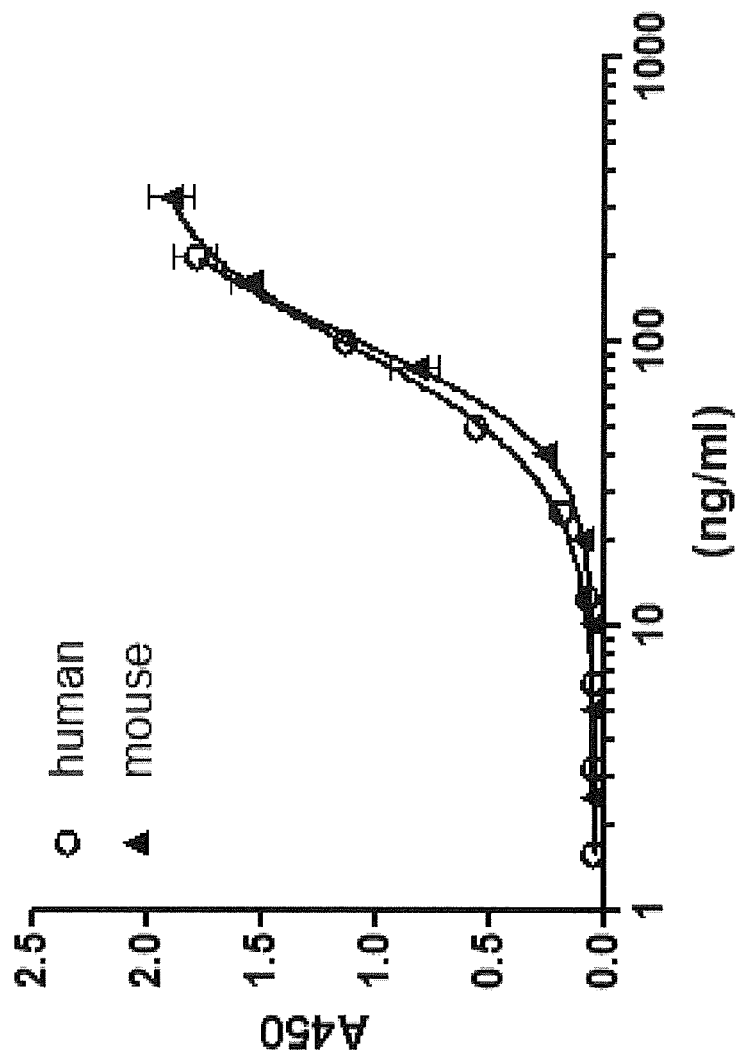
Figure 14A:
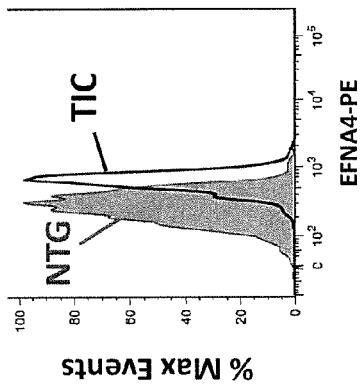
Figure 14B:
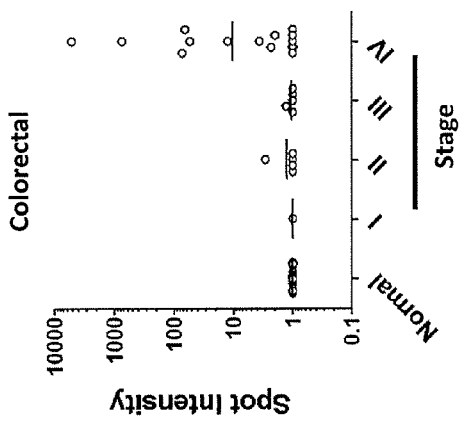
Figure 14C:
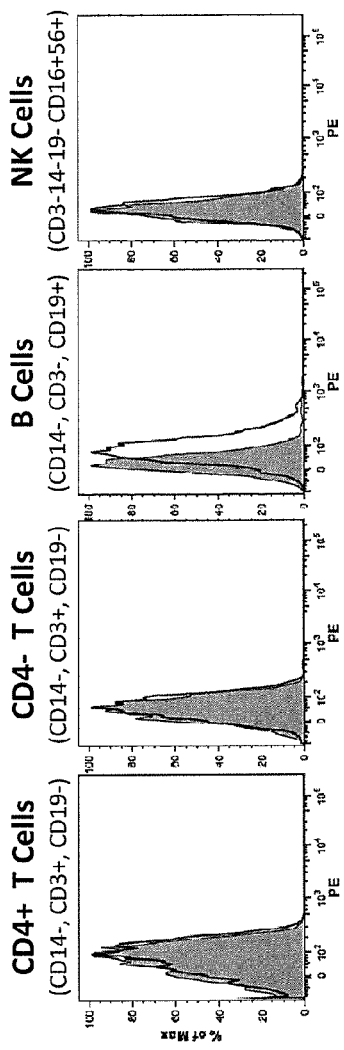
Figures 15A, 15B:
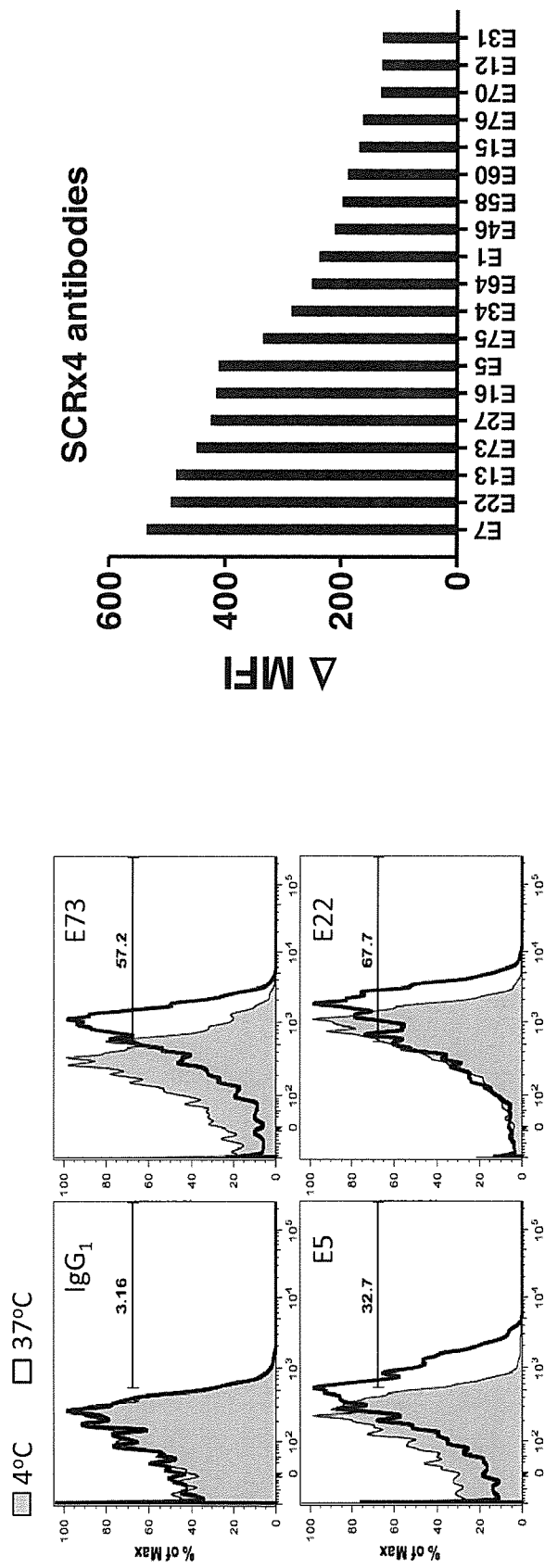
Figures 15C, 15D:
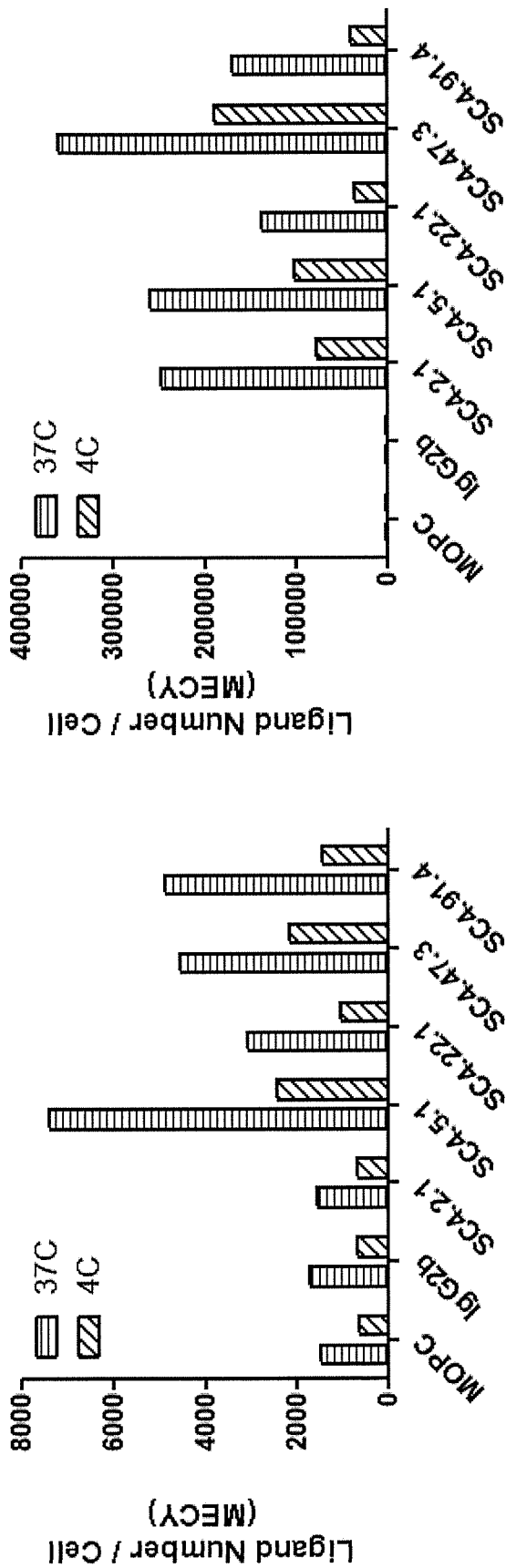
Figure 16B:
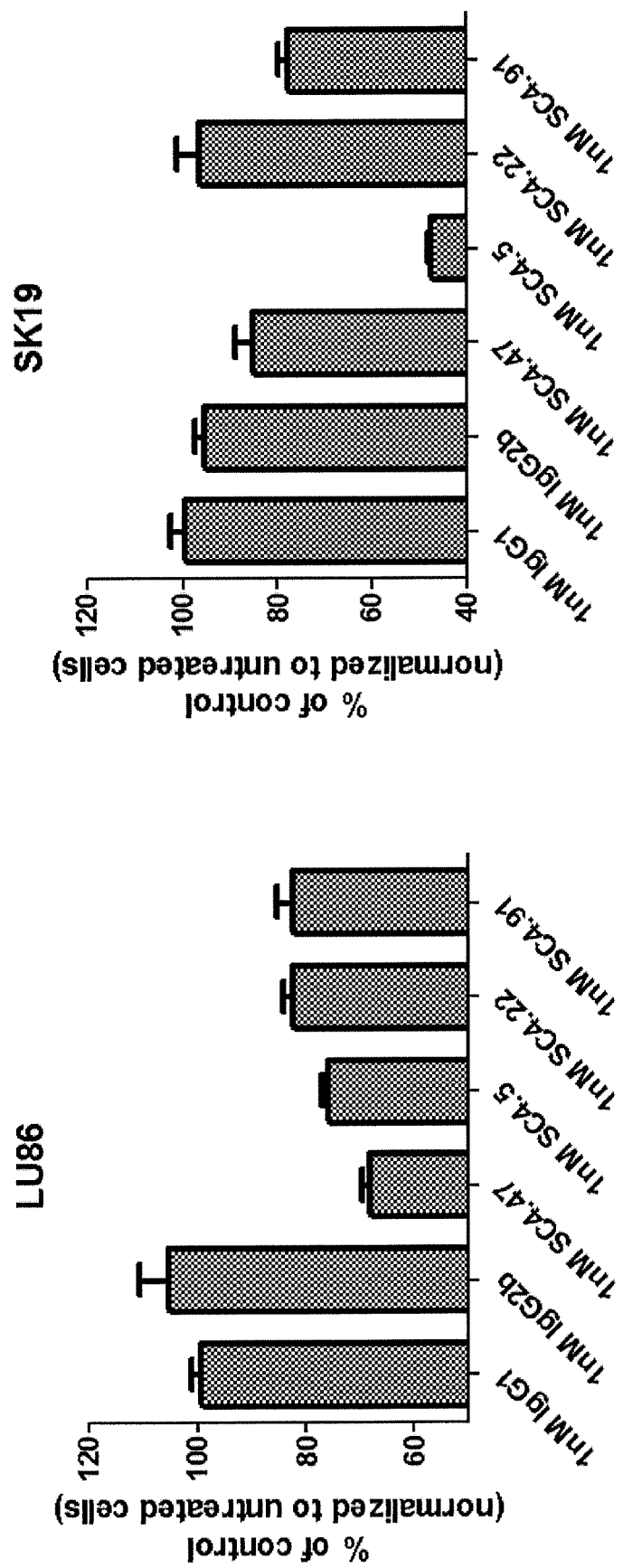
Figures 16C, 16D:
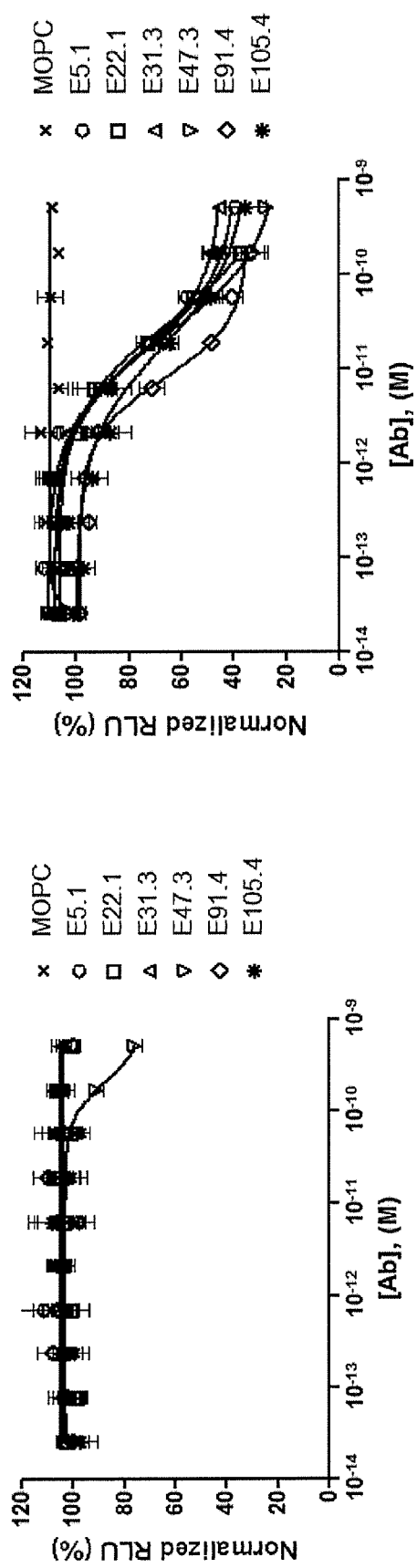
Figure 17A:
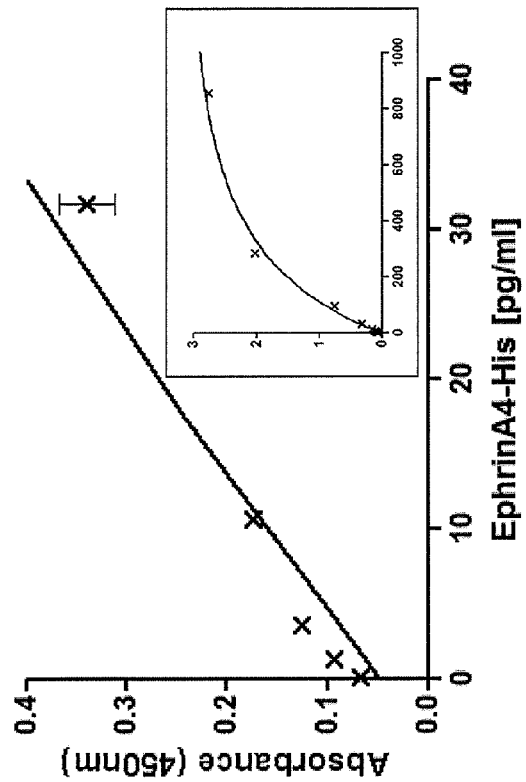
Figure 17C:
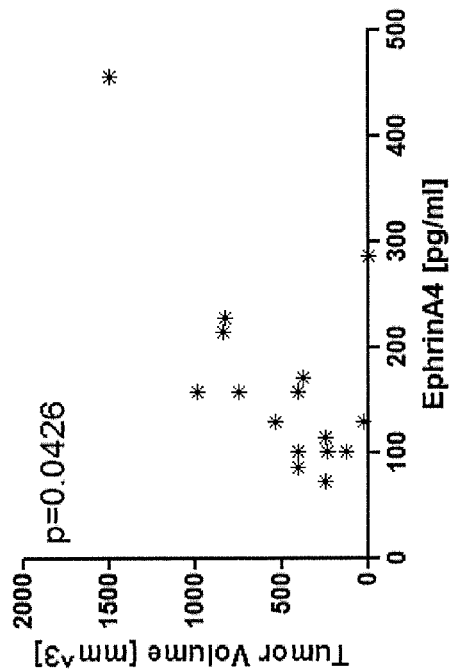
Figure 17B:
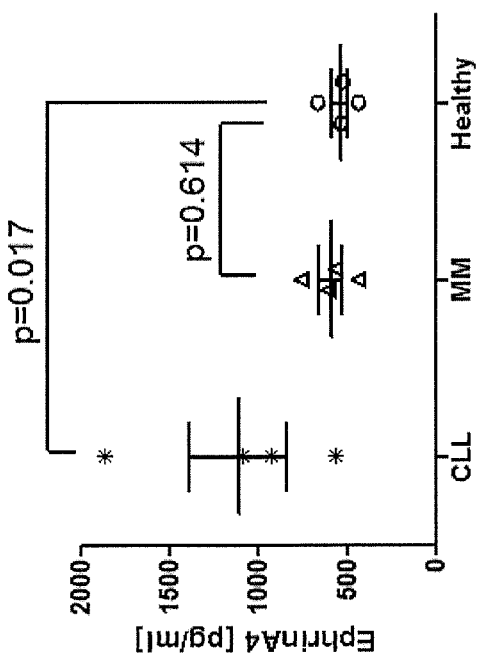
Figures 17D, 17E:
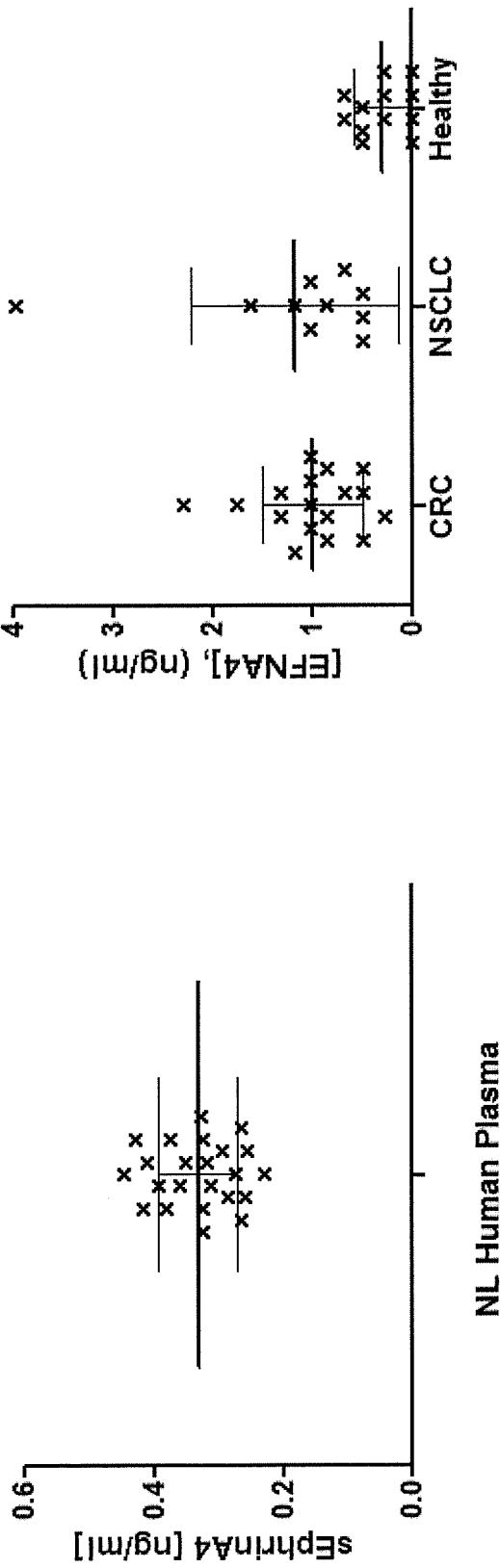
Figure 18A:
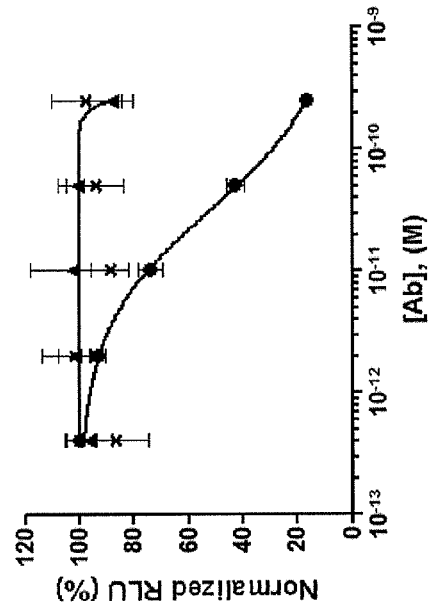
Figure 18B:
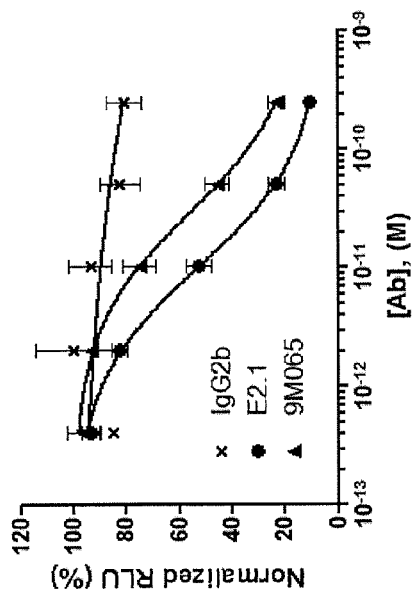
Figure 18C:
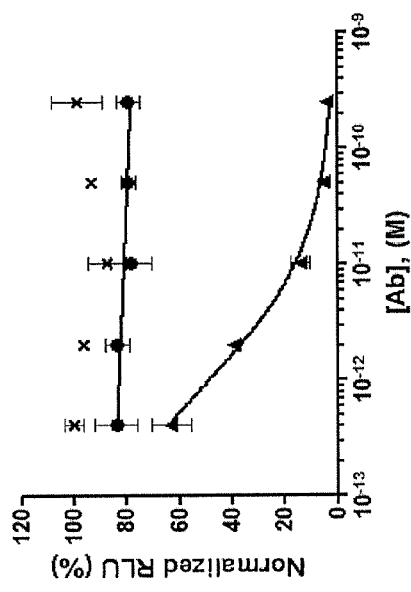
Figures 19A, 19B:
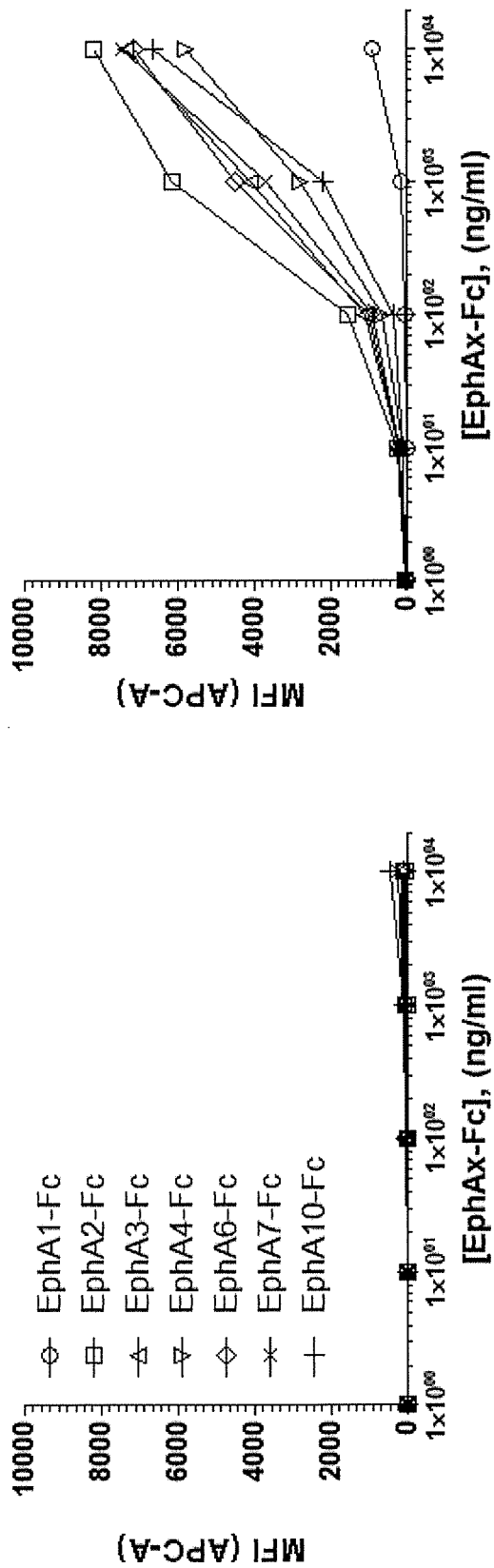
Figures 20A, 20B:
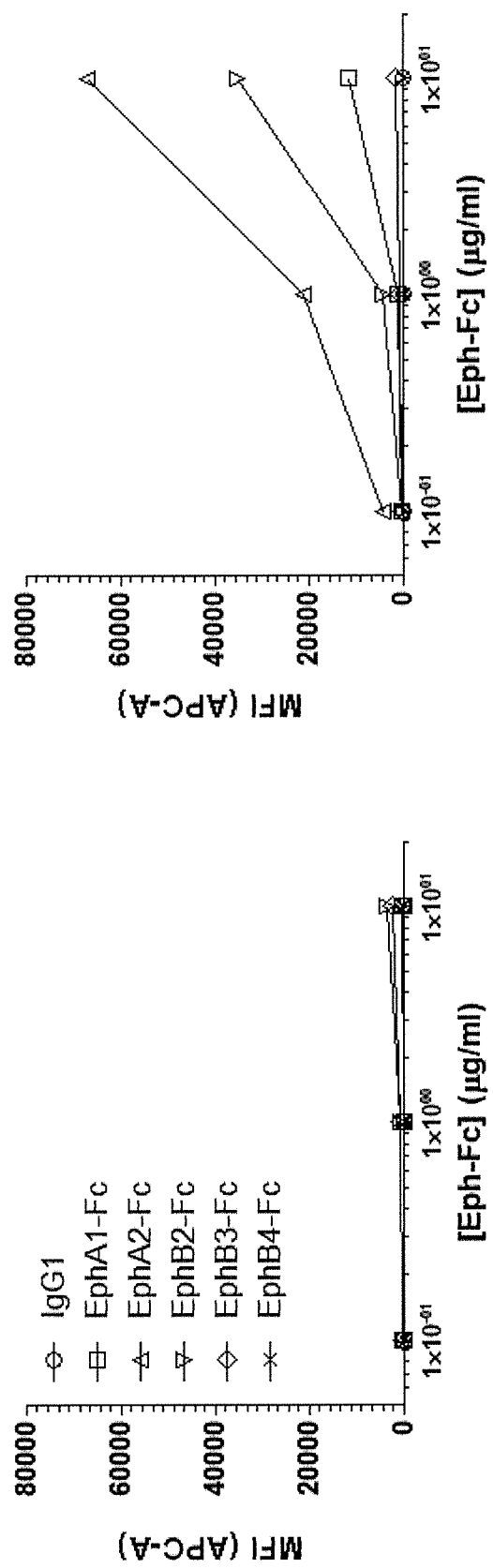

FIGS. 7A-7R depict the sequences of several EFNA modulators wherein FIG. 7A is a tabular representation showing the genetic arrangement and the heavy and light chain CDR sequences (derived from VBASE2 analysis) of discrete EFNA modulators isolated and cloned as described herein, FIGS. 7B-7N provide murine heavy and light chain variable region nucleic acid and amino acid sequences for the same modulators set forth in FIG. 7A and FIGS. 7O-7R provide heavy and light chain variable region nucleic acid and amino acid sequences of exemplary humanized versions of disclosed EFNA modulators;

FIGS. 8A-8D set forth biochemical and immunological properties of exemplary modulators as represented in a tabular format in FIG. 8A, a comparison of the affinity of murine SC4.47 and humanized SC4.47 respectively as determined using label free interaction analysis with a fixed amount of antibody and serial dilutions of antigen in FIGS. 8B and 8C and a tabular comparison of the properties of selected humanized and murine modulators in FIG. 8D;

FIG. 9 illustrates cell surface binding properties of fifty exemplary ephrin-A ligand modulators of the instant invention with regard to Jurkat E6 cells and Z138 cells respectively;

FIGS. 10A and 10B depict the binding of an ephrin-A ligand to cells expressing ephrin-A receptors in a dose dependent manner (FIG. 10A) and inhibition of ephrin-A ligand cell surface binding through exposure to exemplary disclosed modulators (FIG. 10B);

FIGS. 11A-11D are graphical representations illustrating the ability the disclosed modulators to inhibit the cell surface binding of human and murine ephrin-A ligand wherein FIG. 11A shows positive control curves and FIGS. 11B-11D demonstrate the ability of three exemplary EFNA modulators to reduce ligand binding;

FIGS. 12A-12E are graphical representations showing the ability of the modulators of the instant invention to inhibit the cell surface binding of soluble ephrin-A receptor wherein FIG. 12A provides a standard curve of receptor binding, FIG. 12B illustrates the properties of exemplary modulators as the concentration of the soluble receptor is varied, FIG. 12C demonstrates the consequences of varying the concentration of modulator while holding the amount of receptor steady and FIGS. 12D and 12E show the ability of the modulators to inhibit ephrin-A receptor binding to ephrin-A4 and ephrin-A1 ligand, respectively;

FIGS. 13A-13C illustrate the ability of selected modulators of the instant invention to cross-react with the mouse ortholog of ephrin-A4 ligand wherein FIG. 13A illustrates a non-reactive modulator and FIG. 13B and FIG. 13C illustrate murine and humanized modulators respectively that do cross-react;

FIGS. 14A-14D demonstrate the expression of ephrin-A ligand is upregulated in whole colorectal tumor samples (FIG. 14A) and in the tumorigenic subpopulation of colorectal NTX tumor cells (FIG. 14B) and in the tumorigenic subpopulation of a lung NTX cell line (FIG. 14D) but not on normal peripheral blood mononuclear cells (FIG. 14C);

FIGS. 15A-15D illustrate the ability of selected modulators of the instant invention to internalize upon binding with ephrin-A ligands where FIG. 15A shows the fluorescent shift associated with three exemplary modulators, FIG. 15B demonstrates that nineteen disclosed modulators exhibit a delta mean fluorescent intensity indicative of internalization, FIG. 15C shows relatively little internalization in low EFNA expressing cells and FIG. 15D shows substantial internalization with respect to cells expressing high levels of EFNA;

FIGS. 16A-16F provide evidence that the disclosed modulators may effectively be used as targeting moieties to direct cytotoxic payloads to cells expressing ephrin-A ligands in which the downward sloping curve is indicative of cell killing through internalized and wherein FIG. 16A shows the killing effects of modulator SC4.5, FIG. 16B illustrates the ability of selected modulators to internalize and kill lung and skin NTX tumor cell lines, FIGS. 16C and 16D show that modulators carry an associated cytotoxin into HEK293T cells (FIG. 16C) and HEK-.hEFNA4 cells (FIG. 16D), FIG. 16E illustrates that humanized modulators react similarly and FIG. 16F demonstrates killing of target cells expressing mouse or human ephrin-A ligand (note that throughout FIG. 16 the modulators may be termed E rather than SC4);

FIGS. 17A-17E are graphical representations of various aspects of a biochemical assay demonstrating the ability of the disclosed modulators to detect secreted ephrin-A ligand wherein FIG. 17A provides a standard curve, FIG. 17B quantifies the level of secreted EFNA from select hematologic tumors, FIG. 17C presents a correlation between tumor volume and secreted EFNA, FIG. 17D establishes a range of circulating ephrin-A ligand in healthy adults and FIG. 17E demonstrates that patients with selected solid tumors have significantly higher levels of circulating ephrin-A ligand;

FIGS. 18A-18C are graphical representations illustrating that various ephrin-A ligand modulators can be used as targeting moieties to associate cytotoxic payloads with selected cells in which the downward sloping curve is indicative of cell killing through internalized toxin and wherein FIGS. 18A-18C specifically demonstrate the ability of the modulators SC4.2.1 (or E2.1) and SC9.65 (or 9M065) to mediate killing of HEK293T cells overexpressing ephrin-A4 ligand (FIG. 18A), ephrin-A3 ligand (FIG. 18B) and ephrin-A1 ligand (FIG. 18C) in the presence of bound Saporin;

FIGS. 19A and 19B illustrate the ability of ephrin-A ligands to interact selectively with numerous EPHA receptors wherein HEK293T cells only bind EPHA-ECD-Fc receptor constructs via endogenously expressed ephrin-A ligands to a limited degree (FIG. 19A) while HEK293T.hEFNA4 cells bind all tested EPHA receptor constructs to various degrees, except for EPHA1 which does not bind (FIG. 19B); and FIGS. 20A and 20B illustrate the ability of ephrin-A ligands to interact selectively with EPHB receptors wherein HEK293T cells only bind EPHB-ECD-Fc receptor constructs via endogenously expressed ephrin-A ligands to a limited degree (FIG. 20A) while HEK293T.hEFNA4 cells bind EphB2 but not EphB3 and EphB4 receptors (FIG. 20B).

DETAILED DESCRIPTION OF THE INVENTION

I. Introduction

While the present invention may be embodied in many different forms, disclosed herein are specific illustrative embodiments thereof that exemplify the principles of the invention. It should be emphasized that the present invention is not limited to the specific embodiments illustrated. Moreover, any section headings used herein are for organizational purposes only and are not to be construed as limiting the subject matter described.

As previously alluded to, it has surprisingly been found that the expression of ephrin-A ligands (or EFNA) are associated with neoplastic growth and hyperproliferative disorders and that such ligands provide useful tumor markers which may be exploited in the treatment of related diseases.

More specifically, it has been discovered that EFNA modulators such as those disclosed herein may advantageously be used in the diagnosis, theragnosis, treatment or prevention of neoplastic disorders in subjects in need thereof. Accordingly, while preferred embodiments of the invention will be discussed extensively below, particularly in the context of cancer stem cells and their interactions with the disclosed modulators, those skilled in the art will appreciate that the scope of the instant invention is not limited by such exemplary embodiments. Rather, the present invention and the appended claims are broadly and expressly directed to EFNA modulators and their use in the diagnosis, theragnosis, treatment or prevention of a variety of EFNA associated or mediated disorders, including neoplastic or hyperproliferative disorders, regardless of any particular mechanism of action or specifically targeted tumor component.

It will further be appreciated that, in contrast to many prior art disclosures, the present invention is largely directed to ephrin ligand modulators (i.e. EFN) rather than ephrin receptor (i.e. EPH) modulators. That is, while ephrin receptors have been widely implicated in several types of disorders and generally targeted for therapeutic intervention, ephrin ligands have heretofore attracted much less attention. In part this may be as a result of the promiscuous behavior attributed to the ligands and the misplaced belief that such varied interactions made them untenable therapeutic targets as pathway redundancy would likely compensate for any ligand antagonism. However, as demonstrated herein the disclosed ephrin-A ligand modulators can effectively be used to target and eliminate or otherwise incapacitate tumorigenic cells. Moreover, in selected embodiments the present invention comprises pan-EFNA modulators that associate or react with more than one ephrin-A ligand thereby providing an unexpected additive or synergistic effect that may allow for quiescence of more than one ephrin ligand mediated pathway.

Besides the general association discussed immediately above, the inventors have further discovered a heretofore unknown phenotypical association between selected "tumor initiating cells" (TIC) and ephrin-A ligands. In this regard, it has been found that selected TICs express elevated levels of ephrin-A ligands when compared to normal tissue and non-tumorigenic cells (NTG), which together comprise much of a solid tumor. Thus, the ephrin-A ligands comprise tumor associated markers (or antigens) and have been found to provide effective agents for the detection and suppression of TIC and associated neoplasia due to elevated levels of the proteins on cell surfaces or in the tumor microenvironment. More specifically, it has further been discovered that EFNA modulators, including immunoreactive antagonists and antibodies that associate or react with the proteins, effectively reduce the frequency of tumor initiating cells and are therefore useful in eliminating, incapacitating, reducing, promoting the differentiation of, or otherwise precluding or limiting the ability of these tumor-initiating cells to lie dormant and/or continue to fuel tumor growth, metastasis or recurrence in a patient. As discussed in more detail below, the TIC tumor cell subpopulation is composed of both tumor perpetuating cells (TPC) and highly proliferative tumor progenitor cells (TProg).

In view of these discoveries, those skilled in the art will appreciate that the present invention further provides EFNA modulators and their use in reducing the frequency of tumor initiating cells. As will be discussed extensively below, EFNA modulators of the invention broadly comprise any compound that recognizes, reacts, competes, antagonizes, interacts, binds, agonizes, or associates with an ephrin-A ligand or its gene. By these interactions, the EFNA modulators thereby reduce or moderate the frequency of tumor initiating cells.

Exemplary modulators disclosed herein comprise nucleotides, oligonucleotides, polynucleotides, peptides or polypeptides. In certain preferred embodiments the selected modulators will comprise antibodies to an EFNA or immunoreactive fragments or derivatives thereof. Such antibodies may be antagonistic or agonistic in nature and may optionally be conjugated or associated with a cytotoxic agent. In other embodiments, modulators within the instant invention will comprise an EFNA construct comprising an ephrin-A ligand or a reactive fragment thereof. It will be appreciated that such constructs may comprise fusion proteins and can include reactive domains from other polypeptides such as immunoglobulins or biological response modifiers. In still other aspects, the EFNA modulator will comprise a nucleic acid assembly that exerts the desired effects at a genomic level. Still other modulators compatible with the instant teachings will be discussed in detail below.

Whichever form of modulator is ultimately selected it will preferably be in an isolated and purified state prior to introduction into a subject. In this regard the term "isolated EFNA modulator" shall be construed in a broad sense and in accordance with standard pharmaceutical practice to mean any preparation or composition comprising the modulator in a state substantially free of unwanted contaminants (biological or otherwise). As will be discussed in some detail below these preparations may be purified and formulated as desired using various art recognized techniques. Of course, it will be appreciated that such "isolated" preparations may be intentionally formulated or combined with inert or active ingredients as desired to improve the commercial, manufacturing or therapeutic aspects of the finished product and provide pharmaceutical compositions.

II. EFNA Physiology

Ephrin receptor tyrosine kinases (EPH), type-I transmembrane proteins, comprise the largest family of receptor tyrosine kinases within animal genomes and interact with ephrin ligands (EFN), which are also cell surface associated. Receptors in the EPH subfamily typically have a single kinase domain and an extracellular region containing a Cys-rich domain and 2 fibronectin type III repeats. Convention holds that ephrin receptors are divided into two groups based on the similarity of their extracellular domain sequences and their affinities for binding ephrin-A and ephrin-B ligands. Previous research has shown that EPH mediated signaling events control multiple aspects of embryonic development, particularly in the nervous system and are important mediators of cell-cell communication regulating cell attachment, shape, and mobility. Moreover, many members of the ephrin receptor family, as opposed to ephrin ligands, have been identified as important markers and/or regulators of the development and progression of cancer. To date nine ephrin-A receptors and six ephrin-B receptors are known For the purposes of the instant application the terms "ephrin receptor," "ephrin-A receptor," "ephrin-B receptor," "EPHA," or "EPHB" (or EphA or EphB) may be used interchangeably and held to mean the specified family, subfamily or individual receptor (i.e., EPHA1, EPHA2, EPHA3, EPHA4, EPHA5, EPHA6, EPHA7, EPHA8, EPHA9, EPHB1, EPHB2, EPHB3, EPHB4, EPHB5, EPHB6) as dictated by context.

Based upon sequence analyses, ephrin ligands can be divided into two groups: six ephrin-A ligands (or EFNA), typically anchored to the cell surface via glycosylphosphatidylinositol linkages (although some non-GPI-anchored proteins are produced through alternative splicing of ephrin mRNAs; e.g. EFNA4) and three ephrin-B ligands (or EFNB) containing a transmembrane domain and a short cytoplasmic region with conserved tyrosine residues and a PDZ-binding motif. EFNA ligands interact preferentially with any of the nine different EPHA receptors, whereas EFNB ligands interact preferentially with any of six different EPHB receptors, although some specific EFNA-EPHB and EFNB-EPHA cross-interactions have been reported.

For the purposes of the instant application the terms "ephrin ligand," "ephrin-A ligand," "ephrin-B ligand," "EFNA," or "EFNB" may be used interchangeably and held to mean the specified family, subfamily or individual receptor (i.e., EFNA1, EFNA2, EFNA3, EFNA4, EFNA5, EFNA6, EFNB 1, EFNB2, EFNB3) as dictated by context. For example, the terms "ephrin-A4," ephrin-A4 ligand" or "EFNA4" shall all be held to designate the same family of protein isoforms (e.g., as set forth in FIG. 1C) while the terms "ephrin-A ligand" and "ENFA" shall be held to mean the ephrin subfamily (i.e. A as opposed to B) comprising all six A type ligands and any isoforms thereof. In this regard an "ephrin-A modulator," "ephrin-A ligand modulator" or "EFNA modulator" means any modulator (as defined herein) that associates, binds or reacts with one or more A type ligand or isoform, or fragment or derivative thereof.

A more detailed summary of ephrin receptor and ligand nomenclature may be found in Table 1 immediately below.

reflect cell sorting and cell positioning processes that EPH and EFN have evolved to co-ordinate in animal embryonic development.

EPH-EFN signaling frequently activates cell-signaling pathways that regulate cytoskeletal dynamics and lead to modulation of the adhesive and repulsive interactions between different types of cells. As a generalization, EPH and EFN proteins are found at much higher levels during embryogenesis versus those observed in adult tissues, although continued low-level expression in the adult may reflect roles for these molecules in the normal function of tissues such as the adult gut, which has a well defined architecture arising from the migration of differentiating cells from their source at the tissue stem cell in the crypt to their final location at the surface of the villi facing the intestinal lumen. Since ephrin receptors were first identified in hepatocellular carcinomas, and EPH and EFN expression is typically limited in adults, reactivation of the expression of ephrin ligands and/or ephrin receptors in human cancers may be linked to the dedifferentiation of the cancer cells and/or the ability of these cancer cells to invade surrounding normal tissue and to migrate from the site of the primary tumor to distant locations. Other studies have suggested that EPH-EFN interactions also have a role in neoangiogenesis.

Consistent with findings that EPH-EFN interactions in non-lymphoid tissues regulate cellular interactions by generating adhesive or repulsive forces between cells through inte-

TABLE 1

| Receptors | | Ligands | |
|---|---|---|---|
| new name | previous names | new name | previous names |
| EphA1 | Eph, Esk | ephrin-A1 | B61; LERK-1, EFL-1 |
| EphA2 | Eck, Myk2, Sek2 | ephrin-A2 | ELF-1; Cek7-L, LERK-6 |
| EphA3 | Cek4, Mek4, Hek, Tyro4; Hek4 | ephrin-A3 | Ehk1-L, EFL-2, LERK-3 |
| EphA4 | Sek, Sek1, Cek8, Hek8, Tyro1 | ephrin-A4 | LERK-4; EFL-4 |
| EphA5 | Ehk1, Bsk, Cek7, Hek7; Rek7 | ephrin-A5 | AL-1, RAGS; LERK-7, EFL-5 |
| EphA6 | Ehk2; Hek12 | ephrin-A6 | |
| EphA7 | Mdk1, Hek11, Ehk3, Ebk, Cek11 | | |
| EphA8 | Eek; Hek3 | | |
| EphA9 | | | |
| EphB1 | Elk, Cek6, Net; Hek6 | ephrin-B1 | LERK-2, Elk-L, EFL-3, Cek5-L; STRA1 |
| EphB2 | Cek5, Nuk, Erk, Qek5, Tyro5, Sek3; Hek5, Drt | ephrin-B2 | Htk-L, ELF-2; LERK-5, NLERK-1 |
| EphB3 | Cek10, Hek2, Mdk5, Tyro6, Sek4 | ephrin-B3 | NLERK-2, Elk-L3, EFL-6, ELF-3; LERK-8 |
| EphB4 | Htk, Myk1, Tyro11; Mdk2 | | |
| EphB5 | Cek9; Hek9 | | |
| EphB6 | Mep | | |

Eph Nomenclature Committee, *Cell*. 1997; 90 (3):403-4, which is incorporated herein in its entirety by reference.

As with all cell surface receptor-ligand interactions, engagement of the ephrin receptor by an ephrin ligand ultimately results in the activation of intracellular signaling cascades. Although receptor-ligand interactions may take place between molecules on the surface of the same cell (cis interactions), it is generally thought that cis interactions do not lead to the triggering of signaling cascades, or that cis interactions may actually antagonize signaling cascades initiated by trans interactions (e.g., between receptors and ligands on separate cells). One unique aspect of EPH-EFN trans interactions is the capacity for the triggering of two signaling cascades upon receptor-ligand engagement—a forward signaling cascade in the cell expressing the ephrin receptor, and a reverse signaling cascade in the cell expressing the ephrin ligand. The activation of two separate signaling cascades may grin and cytoskeleton rearrangements, EPH and EFN molecules found on lymphoid cells have been shown to mediate cell adhesion to extracellular matrix components, chemotaxis and cell migration. For example, EFNA1, (which binds to the EphA2 receptor and comprises, for example, an amino sequence as in Genbank accession NM_004428) engagement on primary CD4 and CD8 T cells has been found to stimulate cell migration and enhance chemotaxis. Like EFNA1, EFNA4 is expressed on primary CD4 T cells but, due to the promiscuity of the EPH-EFN interaction, it is unclear if EFNA4 engagement has similar effects on these cells. However, it has been demonstrated that mature human B-lymphocytes express EFNA4 and secrete it upon activation. Further EFNA4, unlike any other EFN or EPH molecule, is also consistently expressed on or by B cells of chronic lymphocytic leukemia (CLL) patients. Interestingly, the expression of EFNA4 isoforms as measured by Q-PCR may be correlated with the clinical manifestation of the disease. Also, B cells from CLL patients known to have increased expression of EFNA4 showed impairment in transendothelial migration potential compared to B cells from healthy individuals. Apparently engagement of EFNA4 reduced the ability of CLL cells to adhere to extracellular matrix molecules and reduced their chemotactic response to CCL1. Together these reports suggest a role for EFNA4 in B and T cell trafficking and, when viewed in combination with the intracellular signaling data discussed above, make ephrin-A ligands, and EFNA4 in particular, very intriguing targets for the development of anti-cancer therapeutics.

In addition to the aforementioned characteristics the present disclosure demonstrates that the expression of EFNA4 is elevated in various cancer stem cell populations. Along with concomitant upregulation of several EPHA receptors in the bulk tumor, this raises the possibility that EFNA4 mediated ligand receptor interactions may be triggering cell signaling cascades linked to tumor proliferation, neoangiogenesis and/or tumor metastasis. While not wishing to be bound by any particular theory it is believed that EFNA4 modulators of the present invention (particularly antagonistic or neutralizing embodiments) act, at least in part, by either reducing or eliminating tumor initiating cell frequency thereby interfering with tumor propagation or survival in a different manner than traditional standard of care therapeutic regimens (e.g. irinotecan), or through immunotherapeutic signaling or delivering a payload able to kill EFNA4 expressing cells. For example, elimination of TPC by antagonizing EFNA4 may include simply promoting cell proliferation in the face of chemotherapeutic regimens that eliminate proliferating cells, or promote differentiation of TPC such that their self-renewal (i.e. unlimited proliferation and maintenance of multipotency) capacity is lost. Alternatively, in preferred embodiments the recruitment of cytotoxic T-cells to attack EFNA4 expressing cells, or delivery of a potent toxin conjugated to an anti-EFNA4 antibody that is able to internalize, may selectively kill or otherwise incapacitate TPC.

As used herein the term EFNA4 (also known as ligand of eph-related kinase 4, LERK4; or eph-related receptor tyrosine kinase ligand 4, EFL-4) refers to naturally occurring human EFNA4 unless contextually dictated otherwise. Representative EFNA4 protein orthologs include, but are not limited to, human (i.e. hEFNA4, NP_005218, NP_872631 or NP_872632), mouse (NP_031936), chimpanzee (XP_001153095, XP_001152971, XP_524893, and XP_001152916) and rat (NP_001101162). The transcribed human EFNA4 gene comprises at minimum 5817 bp from chromosome 1. Three mRNA transcript variants have been described, each of which arises from alternative splicing of the transcribed RNA: (1) a 1276 bp variant (NM_005227; EFNA4 transcript variant 1; SEQ ID NO: 1) which encodes a 201 amino acid proprotein (NP_005218; EFNA4 variant a; SEQ ID NO: 2); (2) a 1110 bp variant (NM_182689; EFNA4 transcript variant 2) which encodes a 207 amino acid proprotein (NM_872631; EFNA4 variant b; SEQ ID NO: 3); and (3) a 1111 bp variant (NM_182690; EFNA4 transcript variant 3) which encodes a 193 amino acid proprotein (NP_872632; EFNA4 variant c; SEQ ID NO: 4). It will be appreciated that each of the human EFNA4 proteins include a predicted signal or leader sequence comprising amino acids 1-25 of SEQ ID NO: 2 which is clipped off to provide the mature form of the protein (i.e. 168-182 aa). This signal peptide targets the polypeptide to the cell surface/secretory pathway. Due to the alternative splicing of the mRNA with consequent effects upon the protein coding sequences, the protein isoforms are processed differently by the cell—isoform a is membrane localized and anchored to the cell surface by a glycosylphosphatidylinositol (GPI) linkage, whereas isoforms b and c lack the GPI-anchor signal sequence and therefore are expected to be secreted by the cell. An alignment of the three protein isoforms of human EFNA4 is shown in FIG. 1C. As previously indicated, unless otherwise indicated by direct reference or contextual necessity the term EFNA4 shall be directed to isoform a of human EFNA4 and immunoreactive equivalents. It will further be appreciated that the term may also refer to a derivative or fragment of a native or variant form of EFNA4 that contains an epitope to which an antibody or immunoreactive fragment can specifically bind.

III. Tumor Perpetuating Cells

In contrast to teachings of the prior art, the present invention provides EFNA modulators that are particularly useful for targeting tumor initiating cells, and especially tumor perpetuating cells, thereby facilitating the treatment, management or prevention of neoplastic disorders. More specifically, as previously indicated it has surprisingly been found that specific tumor cell subpopulations express EFNA and likely modify localized coordination of morphogen signaling important to cancer stem cell self-renewal and cell survival. Thus, in preferred embodiments modulators of EFNA may be used to reduce tumor initiating cell frequency in accordance with the present teachings and thereby facilitate the treatment or management of hyperproliferative diseases.

As used herein, the term tumor initiating cell (TIC) encompasses both tumor perpetuating cells (TPC; i.e., cancer stem cells or CSC) and highly proliferative tumor progenitor cells (termed TProg), which together generally comprise a unique subpopulation (i.e. 0.1-40%) of a bulk tumor or mass. For the purposes of the instant disclosure the terms tumor perpetuating cells and cancer stem cells are equivalent and may be used interchangeably herein. Conversely, TPC differ from TProg in that they can completely recapitulate the composition of tumor cells existing within a tumor and have unlimited self-renewal capacity as demonstrated by serial transplantation (two or more passages through mice) of low numbers of isolated cells. As will be discussed in more detail below fluorescence-activated cell sorting (FACS) using appropriate cell surface markers is a reliable method to isolate highly enriched cell subpopulations (>99.5% purity) due, at least in part, to its ability to discriminate between single cells and clumps of cells (i.e. doublets, etc.). Using such techniques it has been shown that when low cell numbers of highly purified TProg cells are transplanted into immunocompromised mice they can fuel tumor growth in a primary transplant. However, unlike purified TPC subpopulations the TProg generated tumors do not completely reflect the parental tumor in phenotypic cell heterogeneity and are demonstrably inefficient at reinitiating serial tumorigenesis in subsequent transplants. In contrast, TPC subpopulations completely reconstitute the cellular heterogeneity of parental tumors and can efficiently initiate tumors when serially isolated and transplanted. Thus, those skilled in the art will recognize that a definitive difference between TPC and TProg, though both may be tumor generating in primary transplants, is the unique ability of TPC to perpetually fuel heterogeneous tumor growth upon serial transplantation at low cell numbers. Other common approaches to characterize TPC involve morphology and examination of cell surface markers, transcriptional profile, and drug response although marker expression may change with culture conditions and with cell line passage in vitro.

Accordingly, for the purposes of the instant invention tumor perpetuating cells, like normal stem cells that support cellular hierarchies in normal tissue, are preferably defined by their ability to self-renew indefinitely while maintaining the capacity for multilineage differentiation. Tumor perpetuating cells are thus capable of generating both tumorigenic progeny (i.e., tumor initiating cells: TPC and TProg) and non-tumorigenic (NTG) progeny. As used herein a non-tumorigenic cell (NTG) refers to a tumor cell that arises from tumor initiating cells, but does not itself have the capacity to self-renew or generate the heterogeneous lineages of tumor cells that comprise a tumor. Experimentally, NTG cells are incapable of reproducibly forming tumors in mice, even when transplanted in excess cell numbers.

As indicated, TProg are also categorized as tumor initiating cells (or TIC) due to their limited ability to generate tumors in mice. TProg are progeny of TPC and are typically capable of a finite number of non-self-renewing cell divisions. Moreover, TProg cells may further be divided into early tumor progenitor cells (ETP) and late tumor progenitor cells (LTP), each of which may be distinguished by phenotype (e.g., cell surface markers) and different capacities to recapitulate tumor cell architecture. In spite of such technical differences, both ETP and LTP differ functionally from TPC in that they are generally less capable of serially reconstituting tumors when transplanted at low cell numbers and typically do not reflect the heterogeneity of the parental tumor. Notwithstanding the foregoing distinctions, it has also been shown that various TProg populations can, on rare occasion, gain self-renewal capabilities normally attributed to stem cells and themselves become TPC (or CSC). In any event both types of tumor-initiating cells are likely represented in the typical tumor mass of a single patient and are subject to treatment with the modulators as disclosed herein. That is, the disclosed compositions are generally effective in reducing the frequency or altering the chemosensitivity of such EFNA positive tumor initiating cells regardless of the particular embodiment or mix represented in a tumor.

In the context of the instant invention, TPC are more tumorigenic, relatively more quiescent and often more chemoresistant than the TProg (both ETP and LTP), NTG cells and the tumor-infiltrating non-TPC derived cells (e.g., fibroblasts/stroma, endothelial & hematopoietic cells) that comprise the bulk of a tumor. Given that conventional therapies and regimens have, in large part, been designed to both debulk tumors and attack rapidly proliferating cells, TPC are likely to be more resistant to conventional therapies and regimens than the faster proliferating TProg and other bulk tumor cell populations. Further, TPC often express other characteristics that make them relatively chemoresistant to conventional therapies, such as increased expression of multi-drug resistance transporters, enhanced DNA repair mechanisms and anti-apoptotic proteins. These properties, each of which contribute to drug tolerance by TPC, constitute a key reason for the failure of standard oncology treatment regimens to ensure long-term benefit for most patients with advanced stage neoplasia; i.e. the failure to adequately target and eradicate those cells that fuel continued tumor growth and recurrence (i.e. TPC or CSC).

Unlike many of the aforementioned prior art treatments, the novel compositions of the present invention preferably reduce the frequency of tumor initiating cells upon administration to a subject regardless of the form or specific target (e.g., genetic material, EFNA antibody or ligand fusion construct) of the selected modulator. As noted above, the reduction in tumor initiating cell frequency may occur as a result of a) elimination, depletion, sensitization, silencing or inhibition of tumor initiating cells; b) controlling the growth, expansion or recurrence of tumor initiating cells; c) interrupting the initiation, propagation, maintenance, or proliferation of tumor initiating cells; or d) by otherwise hindering the survival, regeneration and/or metastasis of the tumorigenic cells. In some embodiments, the reduction in the frequency of tumor initiating cells occurs as a result of a change in one or more physiological pathways. The change in the pathway, whether by reduction or elimination of the tumor initiating cells or by modifying their potential (e.g., induced differentiation, niche disruption) or otherwise interfering with their ability to exert affects on the tumor environment or other cells, in turn allows for the more effective treatment of EFNA-associated disorders by inhibiting tumorigenesis, tumor maintenance and/or metastasis and recurrence.

Among the methods that can be used to assess such a reduction in the frequency of tumor initiating cells is limiting dilution analysis either in vitro or in vivo, preferably followed by enumeration using Poisson distribution statistics or assessing the frequency of predefined definitive events such as the ability to generate tumors in vivo or not. While such limiting dilution analysis are the preferred methods of calculating reduction of tumor initiating cell frequency, other, less demanding methods, may also be used to effectively determine the desired values, albeit slightly less accurately, and are entirely compatible with the teachings herein. Thus, as will be appreciated by those skilled in the art, it is also possible to determine reduction of frequency values through well-known flow cytometric or immunohistochemical means. As to all the aforementioned methods see, for example, Dylla et al. 2008, PMCID: PMC2413402 & Hoey et al. 2009, PMID: 19664991; each of which is incorporated herein by reference in its entirety.

With respect to limiting dilution analysis, in vitro enumeration of tumor initiating cell frequency may be accomplished by depositing either fractionated or unfractionated human tumor cells (e.g. from treated and untreated tumors, respectively) into in vitro growth conditions that foster colony formation. In this manner, colony forming cells might be enumerated by simple counting and characterization of colonies, or by analysis consisting of, for example, the deposition of human tumor cells into plates in serial dilutions and scoring each well as either positive or negative for colony formation at least 10 days after plating. In vivo limiting dilution experiments or analyses, which are generally more accurate in their ability to determine tumor initiating cell frequency encompass the transplantation of human tumor cells, from either untreated control or treated conditions, for example, into immunocompromised mice in serial dilutions and subsequently scoring each mouse as either positive or negative for tumor formation at least 60 days after transplant. The derivation of cell frequency values by limiting dilution analysis in vitro or in vivo is preferably done by applying Poisson distribution statistics to the known frequency of positive and negative events, thereby providing a frequency for events fulfilling the definition of a positive event; in this case, colony or tumor formation, respectively.

As to other methods compatible with the instant invention that may be used to calculate tumor initiating cell frequency, the most common comprise quantifiable flow cytometric techniques and immunohistochemical staining procedures. Though not as precise as the limiting dilution analysis techniques described immediately above, these procedures are much less labor intensive and provide reasonable values in a relatively short time frame. Thus, it will be appreciated that a skilled artisan may use flow cytometric cell surface marker profile determination employing one or more antibodies or reagents that bind art recognized cell surface proteins known to enrich for tumor initiating cells (e.g., potentially compatible markers as are set forth in Example 1 below) and thereby measure TIC levels from various samples. In still another compatible method one skilled in the art might enumerate TIC frequency in situ (e.g., in a tissue section) by immunohistochemistry using one or more antibodies or reagents that are able to bind cell surface proteins thought to demarcate these cells.

Using any of the above-referenced methods it is then possible to quantify the reduction in frequency of TIC (or the TPC therein) provided by the disclosed EFNA modulators (including those conjugated to cytotoxic agents) in accordance with the teachings herein. In some instances, the compounds of the instant invention may reduce the frequency of TIC (by a variety of mechanisms noted above, including elimination, induced differentiation, niche disruption, silencing, etc.) by 10%, 15%, 20%, 25%, 30% or even by 35%. In other embodiments, the reduction in frequency of TIC may be on the order of 40%, 45%, 50%, 55%, 60% or 65%. In certain embodiments, the disclosed compounds my reduce the frequency of TIC by 70%, 75%, 80%, 85%, 90% or even 95%. Of course it will be appreciated that any reduction of the frequency of the TIC likely results in a corresponding reduction in the tumorigenicity, persistence, recurrence and aggressiveness of the neoplasia.

IV. EFNA Modulators

In any event, the present invention is directed to the use of EFNA modulators, including EFNA antagonists, for the diagnosis, treatment and/or prophylaxis of any one of a number of EFNA associated malignancies. The disclosed modulators may be used alone or in conjunction with a wide variety of anti-cancer compounds such as chemotherapeutic or immunotherapeutic agents or biological response modifiers. In other selected embodiments, two or more discrete EFNA modulators may be used in combination to provide enhanced anti-neoplastic effects or may be used to fabricate multispecific constructs.

In certain embodiments, the EFNA modulators of the present invention will comprise nucleotides, oligonucleotides, polynucleotides, peptides or polypeptides. Even more preferably the modulators will comprise soluble EFNA (sEFNA) or a form, variant, derivative or fragment thereof including, for example, EFNA fusion constructs (e.g., EFNA-Fc, EFNA-targeting moiety, etc.) or EFNA-conjugates (e.g., EFNA-PEG, EFNA-cytotoxic agent, EFNA-brm, etc.). It will also be appreciated that, in other embodiments, the EFNA modulators comprise antibodies (e.g., anti-EFNA1 or anti-EFNA4 mAbs) or immunoreactive fragments or derivatives thereof. In particularly preferred embodiments the modulators of the instant invention will comprise neutralizing antibodies or derivatives or fragments thereof. In other embodiments the EFNA modulators may comprise internalizing antibodies or fragments thereof. In still other embodiments the EFNA modulators may comprise depleting antibodies or fragments thereof. Moreover, as with the aforementioned fusion constructs, these antibody modulators may be conjugated, linked or otherwise associated with selected cytotoxic agents, polymers, biological response modifiers (BRMs) or the like to provide directed immunotherapies with various (and optionally multiple) mechanisms of action. As alluded to above such antibodies may be pan-EFNA antibodies and associate with two or more ephrin-A ligands or immunospecific antibodies that selectively react with one of the six ephrin-A ligands. In yet other embodiments the modulators may operate on the genetic level and may comprise compounds as antisense constructs, siRNA, micro RNA and the like.

Based on the teachings herein, those skilled in the art will appreciate that particularly preferred embodiments of the invention may comprise sEFNA4 or sEFNA1 or antibody modulators that associate with either, or both, of EFNA4 or EFNA1.

It will further be appreciated that the disclosed EFNA modulators may deplete, silence, neutralize, eliminate or inhibit growth, propagation or survival of tumor cells, particularly TPC, and/or associated neoplasia through a variety of mechanisms, including agonizing or antagonizing selected pathways or eliminating specific cells depending, for example, on the form of EFNA modulator, any associated payload or dosing and method of delivery. Accordingly, while preferred embodiments disclosed herein are directed to the depletion, inhibition or silencing of specific tumor cell subpopulations such as tumor perpetuating cells, it must be emphasized that such embodiments are merely illustrative and not limiting in any sense. Rather, as set forth in the appended claims, the present invention is broadly directed to EFNA modulators and their use in the treatment, management or prophylaxis of various EFNA associated hyperproliferative disorders irrespective of any particular mechanism or target tumor cell population.

In the same sense disclosed embodiments of the instant invention may comprise one or more EFNA antagonists. To that end it will be appreciated that EFNA antagonists of the instant invention may comprise any ligand, polypeptide, peptide, fusion protein, antibody or immunologically active fragment or derivative thereof that recognizes, reacts, binds, combines, competes, associates or otherwise interacts with the EFNA protein or fragment thereof and eliminates, silences, reduces, inhibits, hinders, restrains or controls the growth of tumor initiating cells or other neoplastic cells including bulk tumor or NTG cells. In selected embodiments the EFNA modulator comprises an EFNA antagonist.

As used herein an antagonist refers to a molecule capable of neutralizing, blocking, inhibiting, abrogating, reducing or interfering with the activities of a particular or specified protein, including the binding of receptors to ligands or the interactions of enzymes with substrates. More generally antagonists of the invention may comprise antibodies and antigen-binding fragments or derivatives thereof, proteins, peptides, glycoproteins, glycopeptides, glycolipids, polysaccharides, oligosaccharides, nucleic acids, antisense constructs, siRNA, miRNA, bioorganic molecules, peptidomimetics, pharmacological agents and their metabolites, transcriptional and translation control sequences, and the like. Antagonists may also include small molecule inhibitors, fusion proteins, receptor molecules and derivatives which bind specifically to the protein thereby sequestering its binding to its substrate target, antagonist variants of the protein, antisense molecules directed to the protein, RNA aptamers, and ribozymes against the protein.

As used herein and applied to two or more molecules or compounds, the terms recognizes or associates shall be held to mean the reaction, binding, specific binding, combination, interaction, connection, linkage, uniting, coalescence, merger or joining, covalently or non-covalently, of the molecules whereby one molecule exerts an effect on the other molecule.

Moreover, as demonstrated in the examples herein, some modulators of human EFNA may, in certain cases, cross-react with EFNA from a species other than human (e.g., murine). In other cases exemplary modulators may be specific for one or more isoforms of human EFNA and will not exhibit cross-reactivity with EFNA orthologs from other species. Of course, in conjunction with the teachings herein such embodiments may comprise pan-EFNA antibodies that associate with two or more ephrin-A ligands from a single species or antibodies that exclusively associate with a single ephrin-A ligand.

In any event, and as will be discussed in more detail below, those skilled in the art will appreciate that the disclosed modulators may be used in a conjugated or unconjugated form. That is, the modulator may be associated with or conjugated to (e.g. covalently or non-covalently) pharmaceutically active compounds, biological response modifiers, anti-cancer agents, cytotoxic or cytostatic agents, diagnostic moieties or biocompatible modifiers. In this respect it will be understood that such conjugates may comprise peptides, polypeptides, proteins, fusion proteins, nucleic acid molecules, small molecules, mimetic agents, synthetic drugs, inorganic molecules, organic molecules and radioisotopes. Moreover, as indicated herein the selected conjugate may be covalently or non-covalently linked to the EFNA modulator in various molar ratios depending, at least in part, on the method used to effect the conjugation.

V. Antibodies a. Overview

As previously alluded to particularly preferred embodiments of the instant invention comprise EFNA modulators in the form of antibodies. The term antibody is used in the broadest sense and specifically covers synthetic antibodies, monoclonal antibodies, oligoclonal or polyclonal antibodies, multiclonal antibodies, recombinantly produced antibodies, intrabodies, multispecific antibodies, bispecific antibodies, monovalent antibodies, multivalent antibodies, human antibodies, humanized antibodies, chimeric antibodies, CDR-grafted antibodies, primatized antibodies, Fab fragments, F(ab') fragments, single-chain FvFcs (scFvFc), single-chain Fvs (scFv), anti-idiotypic (anti-Id) antibodies and any other immunologically active antibody fragments so long as they exhibit the desired biological activity (i.e., EFNA association or binding). In a broader sense, the antibodies of the present invention include immunoglobulin molecules and immunologically active fragments of immunoglobulin molecules, i.e., molecules that contain an antigen binding site, where these fragments may or may not be fused to another immunoglobulin domain including, but not limited to, an Fc region or fragment thereof. Further, as outlined in more detail herein, the terms antibody and antibodies specifically include Fc variants as described below, including full length antibodies and variant Fc-Fusions comprising Fc regions, or fragments thereof, optionally comprising at least one amino acid residue modification and fused to an immunologically active fragment of an immunoglobulin.

As discussed in more detail below, the generic terms antibody or immunoglobulin comprises five distinct classes of antibody that can be distinguished biochemically and, depending on the amino acid sequence of the constant domain of their heavy chains, can readily be assigned to the appropriate class. For historical reasons, the major classes of intact antibodies are termed IgA, IgD, IgE, IgG, and IgM. In humans, the IgG and IgA classes may be further divided into recognized subclasses (isotypes), i.e., IgG1, IgG2, IgG3, IgG4, IgA1, and IgA2 depending on structure and certain biochemical properties. It will be appreciated that the IgG isotypes in humans are named in order of their abundance in serum with IgG1 being the most abundant.

While all five classes of antibodies (i.e. IgA, IgD, IgE, IgG, and IgM) and all isotypes (i.e., IgG1, IgG2, IgG3, IgG4, IgA1, and IgA2), as well as variations thereof, are within the scope of the present invention, preferred embodiments comprising the IgG class of immunoglobulin will be discussed in some detail solely for the purposes of illustration. It will be understood that such disclosure is, however, merely demonstrative of exemplary compositions and methods of practicing the present invention and not in any way limiting of the scope of the invention or the claims appended hereto.

In this respect, human IgG immunoglobulins comprise two identical light polypeptide chains of molecular weight approximately 23,000 Daltons, and two identical heavy chains of molecular weight 53,000-70,000 depending on the isotype. Heavy-chain constant domains that correspond to the different classes of antibodies are denoted by the corresponding lower case Greek letter $\alpha$, $\delta$, $\epsilon$, $\gamma$, and $\mu$, respectively. The light chains of the antibodies from any vertebrate species can be assigned to one of two clearly distinct types, called kappa ($\kappa$) and lambda ($\lambda$), based on the amino acid sequences of their constant domains. Those skilled in the art will appreciate that the subunit structures and three-dimensional configurations of different classes of immunoglobulins are well known.

The four chains are joined by disulfide bonds in a Y configuration wherein the light chains bracket the heavy chains starting at the mouth of the Y and continuing through the variable region to the dual ends of the Y. Each light chain is linked to a heavy chain by one covalent disulfide bond while two disulfide linkages in the hinge region join the heavy chains. The respective heavy and light chains also have regularly spaced intrachain disulfide bridges the number of which may vary based on the isotype of IgG.

Each heavy chain has at one end a variable domain ($V_H$) followed by a number of constant domains. Each light chain has a variable domain at one end ($V_L$) and a constant domain at its other end; the constant domain of the light chain is aligned with the first constant domain of the heavy chain, and the light chain variable domain is aligned with the variable domain of the heavy chain. In this regard, it will be appreciated that the variable domains of both the light ($V_L$) and heavy ($V_H$) chain portions determine antigen recognition and specificity. Conversely, the constant domains of the light chain ($C_L$) and the heavy chain ($C_H1$, $C_H2$ or $C_H3$) confer and regulate important biological properties such as secretion, transplacental mobility, circulation half-life, complement binding, and the like. By convention the numbering of the constant region domains increases as they become more distal from the antigen binding site or amino-terminus of the antibody. Thus, the amino or N-terminus of the antibody comprises the variable region and the carboxy or C-terminus comprises the constant region. Thus, the $C_H3$ and $C_L$ domains actually comprise the carboxy-terminus of the heavy and light chain, respectively.

The term variable refers to the fact that certain portions of the variable domains differ extensively in sequence among immunoglobulins and these hot spots largely define the binding and specificity characteristics of a particular antibody. These hypervariable sites manifest themselves in three segments, known as complementarity determining regions (CDRs), in both the light-chain and the heavy-chain variable domains respectively. The more highly conserved portions of variable domains flanking the CDRs are termed framework regions (FRs). More specifically, in naturally occurring monomeric IgG antibodies, the six CDRs present on each arm of the antibody are short, non-contiguous sequences of amino acids that are specifically positioned to form the antigen binding site as the antibody assumes its three dimensional configuration in an aqueous environment.

The framework regions comprising the remainder of the heavy and light variable domains show less inter-molecular variability in amino acid sequence. Rather, the framework regions largely adopt a β-sheet conformation and the CDRs form loops which connect, and in some cases form part of, the β-sheet structure. Thus, these framework regions act to form a scaffold that provides for positioning the six CDRs in correct orientation by inter-chain, non-covalent interactions. The antigen-binding site formed by the positioned CDRs defines a surface complementary to the epitope on the immunoreactive antigen (i.e. EFNA4). This complementary surface promotes the non-covalent binding of the antibody to the immunoreactive antigen epitope. It will be appreciated that the position of CDRs can be readily identified by one of ordinary skill in the art.

As discussed in more detail below and shown in the appended Examples, all or part of the heavy and light chain variable regions may be recombined or engineered using standard recombinant and expression techniques to provide effective antibodies. That is, the heavy or light chain variable region from a first antibody (or any portion thereof) may be mixed and matched with any selected portion of the heavy or light chain variable region from a second antibody. For example, in one embodiment, the entire light chain variable region comprising the three light chain CDRs of a first antibody may be paired with the entire heavy chain variable region comprising the three heavy chain CDRs of a second antibody to provide an operative antibody. Moreover, in other embodiments, individual heavy and light chain CDRs derived from various antibodies may be mixed and matched to provide the desired antibody having optimized characteristics. Thus, an exemplary antibody may comprise three light chain CDRs from a first antibody, two heavy chain CDRs derived from a second antibody and a third heavy chain CDR from a third antibody.

More specifically, in the context of the instant invention it will be appreciated that any of the disclosed heavy and light chain CDRs in FIG. 7A may be rearranged in this manner to provide optimized anti-EFNA (e.g. anti-hEFNA4) antibodies in accordance with the instant teachings. That is, one or more of the CDRs disclosed in FIG. 7A may be incorporated in an EFNA modulator and, in particularly preferred embodiments, in a CDR grafted or humanized antibody that immunospecifically associates with one or more ephrin-A ligands.

In any event, the complementarity determining regions residue numbers may be defined as those of Kabat et al. (1991, NIH Publication 91-3242, National Technical Information Service, Springfield, Va.), specifically, residues 24-34 (CDR1), 50-56 (CDR2) and 89-97 (CDR3) in the light chain variable domain and 31-35 (CDR1), 50-65 (CDR2) and 95-102 (CDR3) in the heavy chain variable domain. Note that CDRs vary considerably from antibody to antibody (and by definition will not exhibit homology with the Kabat consensus sequences). Maximal alignment of framework residues frequently requires the insertion of spacer residues in the numbering system, to be used for the Fv region. In addition, the identity of certain individual residues at any given Kabat site number may vary from antibody chain to antibody chain due to interspecies or allelic divergence. See also Chothia et al., J. Mol. Biol. 196:901-917 (1987); Chothia et al., Nature 342, pp. 877-883 (1989) and by MacCallum et al., J. Mol. Biol. 262:732-745 (1996) where the definitions include overlapping or subsets of amino acid residues when compared against each other. Each of the aforementioned references is incorporated herein by reference in its entirety and the amino acid residues which encompass CDRs as defined by each of the above cited references are set forth for comparison.

| CDR Definitions | | | |
|---|---|---|---|
| | Kabat[1] | Chothia[2] | MacCallum[3] |
| $V_H$ CDR1 | 31-35 | 26-32 | 30-35 |
| $V_H$ CDR2 | 50-65 | 53-55 | 47-58 |
| $V_H$ CDR3 | 95-102 | 96-101 | 93-101 |
| $V_L$ CDR1 | 24-34 | 26-32 | 30-36 |
| $V_L$ CDR2 | 50-56 | 50-52 | 46-55 |
| $V_L$ CDR3 | 89-97 | 91-96 | 89-96 |

[1]Residue numbering follows the nomenclature of Kabat et al., supra
[2]Residue numbering follows the nomenclature of Chothia et al., supra
[3]Residue numbering follows the nomenclature of MacCallum et al., supra For purposes of convenience the CDRs set forth in FIG. 7A (SEQ ID NOS: 8-59 and 70-95) were derived from VBASE2 analysis though given the content of the instant application one skilled in the art could readily identify and enumerate the CDRs as defined by Kabat et al. or MacCallum et al. for each respective heavy and light chain sequence. In this regard CDRs as defined by Kabat et al. were used for the humanization analysis set forth in Example 7(b) and are underlined in FIGS. 7O-7R (SEQ ID NOS: 148-163) which depict humanized antibody sequences in accordance with the instant invention. Accordingly, antibodies comprising CDRs defined by all such nomenclature are expressly included within the scope of the instant invention. More broadly the term variable region CDR amino acid residue includes amino acids in a CDR as identified using any sequence or structure based method as set forth above.

As used herein the term variable region framework (FR) amino acid residues refers to those amino acids in the framework region of an Ig chain. The term framework region or FR region as used herein, includes the amino acid residues that are part of the variable region, but are not part of the CDRs (e.g., using the Kabat definition of CDRs). Therefore, a variable region framework is a non-contiguous sequence between about 100-120 amino acids in length but includes only those amino acids outside of the CDRs.

For the specific example of a heavy chain variable region and for the CDRs as defined by Kabat et al., framework region 1 corresponds to the domain of the variable region encompassing amino acids 1-30; framework region 2 corresponds to the domain of the variable region encompassing amino acids 36-49; framework region 3 corresponds to the domain of the variable region encompassing amino acids 66-94, and framework region 4 corresponds to the domain of the variable region from amino acids 103 to the end of the variable region. The framework regions for the light chain are similarly separated by each of the light claim variable region CDRs. Similarly, using the definition of CDRs by Chothia et al. or McCallum et al. the framework region boundaries are separated by the respective CDR termini as described above.

With the aforementioned structural considerations in mind, those skilled in the art will appreciate that the antibodies of the present invention may comprise any one of a number of functional embodiments. In this respect, compatible antibodies may comprise any immunoreactive antibody (as the term is defined herein) that provides the desired physiological response in a subject. While any of the disclosed antibodies may be used in conjunction with the present teachings, certain embodiments of the invention will comprise chimeric, humanized or human monoclonal antibodies or immunoreactive fragments thereof. Yet other embodiments may, for example, comprise homogeneous or heterogeneous multimeric constructs, Fc variants and conjugated or glycosylationally altered antibodies. Moreover, it will be understood that such configurations are not mutually exclusive and that compatible individual antibodies may comprise one or more of the functional aspects disclosed herein. For example, a compatible antibody may comprise a single chain diabody with humanized variable regions or a fully human full length IgG3 antibody with Fc modifications that alter the glycosylation pattern to modulate serum half-life. Other exemplary embodiments are readily apparent to those skilled in the art and may easily be discernable as being within the scope of the invention.

b. Antibody Generation

As is well known various host animals, including rabbits, mice, rats, etc. may be inoculated and used to provide antibodies in accordance with the teachings herein. Art known adjuvants that may be used to increase the immunological response, depending on the inoculated species include, but are not limited to, Freund's (complete and incomplete), mineral gels such as aluminum hydroxide, surface active substances such as lysolecithin, pluronic polyols, polyanions, peptides, oil emulsions, keyhole limpet hemocyanins, dinitrophenol, and potentially useful human adjuvants such as BCG (bacille Calmette-Guerin) and *corynebacterium parvum*. Such adjuvants may protect the antigen from rapid dispersal by sequestering it in a local deposit, or they may contain substances that stimulate the host to secrete factors that are chemotactic for macrophages and other components of the immune system. Preferably, if a polypeptide is being administered, the immunization schedule will involve two or more administrations of the polypeptide, spread out over several weeks.

After immunization of an animal with an EFNA immunogen (e.g., soluble EFNA4 or EFNA1) which may comprise selected isoforms and/or peptides, or live cells or cell preparations expressing the desired protein, antibodies and/or antibody-producing cells can be obtained from the animal using art recognized techniques. In some embodiments, polyclonal anti-EFNA antibody-containing serum is obtained by bleeding or sacrificing the animal. The serum may be used for research purposes in the form obtained from the animal or, in the alternative, the anti-EFNA antibodies may be partially or fully purified to provide immunoglobulin fractions or homogeneous antibody preparations.

c. Monoclonal Antibodies

While polyclonal antibodies may be used in conjunction with certain aspects of the present invention, preferred embodiments comprise the use of EFNA reactive monoclonal antibodies. As used herein, the term monoclonal antibody or mAb refers to an antibody obtained from a population of substantially homogeneous antibodies, i.e., the individual antibodies comprising the population are identical except for possible mutations, e.g., naturally occurring mutations, that may be present in minor amounts. Thus, the modifier monoclonal indicates the character of the antibody as not being a mixture of discrete antibodies and may be used in conjunction with any type of antibody. In certain embodiments, such a monoclonal antibody includes an antibody comprising a polypeptide sequence that binds or associates with EFNA, wherein the EFNA-binding polypeptide sequence was obtained by a process that includes the selection of a single target binding polypeptide sequence from a plurality of polypeptide sequences.

In preferred embodiments, antibody-producing cell lines are prepared from cells isolated from the immunized animal. After immunization, the animal is sacrificed and lymph node and/or splenic B cells are immortalized by means well known in the art as shown in the appended Examples). Methods of immortalizing cells include, but are not limited to, transfecting them with oncogenes, infecting them with an oncogenic virus and cultivating them under conditions that select for immortalized cells, subjecting them to carcinogenic or mutating compounds, fusing them with an immortalized cell, e.g., a myeloma cell, and inactivating a tumor suppressor gene. If fusion with myeloma cells is used, the myeloma cells preferably do not secrete immunoglobulin polypeptides (a non-secretory cell line). Immortalized cells are screened using an ephrin-A ligand (including selected isoforms), or an immunoreactive portion thereof. In a preferred embodiment, the initial screening is performed using an enzyme-linked immunoassay (ELISA) or a radioimmunoassay.

More generally, discrete monoclonal antibodies consistent with the present invention can be prepared using a wide variety of techniques known in the art including hybridoma, recombinant techniques, phage display technologies, yeast libraries, transgenic animals (e.g. a XenoMouse® or HuMAb Mouse®) or some combination thereof. For example, monoclonal antibodies can be produced using hybridoma techniques such as broadly described above and taught in more detail in Harlow et al., Antibodies: A Laboratory Manual, (Cold Spring Harbor Laboratory Press, 2nd ed. 1988); Hammerling, et al., in: Monoclonal Antibodies and T-Cell Hybridomas 563-681 (Elsevier, N.Y., 1981) each of which is incorporated herein. Using the disclosed protocols, antibodies are preferably raised in mammals by multiple subcutaneous or intraperitoneal injections of the relevant antigen and an adjuvant. As previously discussed, this immunization generally elicits an immune response that comprises production of antigen-reactive antibodies (that may be fully human if the immunized animal is transgenic) from activated splenocytes or lymphocytes. While the resulting antibodies may be harvested from the serum of the animal to provide polyclonal preparations, it is generally more desirable to isolate individual lymphocytes from the spleen, lymph nodes or peripheral blood to provide homogenous preparations of monoclonal antibodies. Most typically, the lymphocytes are obtained from the spleen and immortalized to provide hybridomas.

For example, as described above, the selection process can be the selection of a unique clone from a plurality of clones, such as a pool of hybridoma clones, phage clones, or recombinant DNA clones. It should be understood that a selected EFNA binding sequence can be further altered, for example, to improve affinity for the target, to humanize the target binding sequence, to improve its production in cell culture, to reduce its immunogenicity in vivo, to create a multispecific antibody, etc., and that an antibody comprising the altered target binding sequence is also a monoclonal antibody of this invention. In contrast to polyclonal antibody preparations, which typically include discrete antibodies directed against different determinants (epitopes), each monoclonal antibody of a monoclonal antibody preparation is directed against a single determinant on an antigen. In addition to their specificity, monoclonal antibody preparations are advantageous in that they are typically uncontaminated by other immunoglobulins that may be cross-reactive.

d. Chimeric Antibodies

In another embodiment, the antibody of the invention may comprise chimeric antibodies derived from covalently joined protein segments from at least two different species or types of antibodies. It will be appreciated that, as used herein, the term chimeric antibodies is directed to constructs in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity (U.S. Pat. No. 4,816,567; Morrison et al., Proc. Natl. Acad. Sci. USA, 81:6851-6855 (1984)). In one exemplary embodiment, a chimeric antibody in accordance with the teachings herein may comprise murine $V_H$ and $V_L$ amino acid sequences and constant regions derived from human sources. In other compatible embodiments a chimeric antibody of the present invention may comprise a CDR grafted or humanized antibody as described below.

Generally, a goal of making a chimeric antibody is to create a chimera in which the number of amino acids from the intended subject species is maximized. One example is the CDR-grafted antibody, in which the antibody comprises one or more complementarity determining regions (CDRs) from a particular species or belonging to a particular antibody class or subclass, while the remainder of the antibody chain(s) is/are identical with or homologous to a corresponding sequence in antibodies derived from another species or belonging to another antibody class or subclass. For use in humans, the variable region or selected CDRs from a rodent antibody often are grafted into a human antibody, replacing the naturally occurring variable regions or CDRs of the human antibody. These constructs generally have the advantages of providing full strength modulator functions (e.g., CDC, ADCC, etc.) while reducing unwanted immune responses to the antibody by the subject.

e. Humanized Antibodies

Similar to the CDR grafted antibody is a humanized antibody. Generally, a humanized antibody is produced from a monoclonal antibody raised initially in a non-human animal. As used herein humanized forms of non-human (e.g., murine) antibodies are chimeric antibodies that contain a minimal sequence derived from a non-human immunoglobulin. In one embodiment, a humanized antibody is a human immunoglobulin (recipient or acceptor antibody) in which residues from a CDR of the recipient antibody are replaced by residues from a CDR of a non-human species (donor antibody) such as mouse, rat, rabbit, or nonhuman primate having the desired specificity, affinity, and/or capacity.

Generally humanization of an antibody comprises an analysis of the sequence homology and canonical structures of both the donor and recipient antibodies. In selected embodiments, the recipient antibody may comprise consensus sequences. To create consensus human frameworks, frameworks from several human heavy chain or light chain amino acid sequences may be aligned to identify a consensus amino acid sequence. Moreover, in many instances, one or more framework residues in the variable domain of the human immunoglobulin are replaced by corresponding non-human residues from the donor antibody. These framework substitutions are identified by methods well known in the art, e.g., by modeling of the interactions of the CDR and framework residues to identify framework residues important for antigen binding and sequence comparison to identify unusual framework residues at particular positions. Such substitutions help maintain the appropriate three-dimensional configuration of the grafted CDR(s) and often improve affinity over similar constructs with no framework substitutions. Furthermore, humanized antibodies may comprise residues that are not found in the recipient antibody or in the donor antibody. These modifications may be made to further refine antibody performance using well-known techniques.

CDR grafting and humanized antibodies are described, for example, in U.S. Pat. Nos. 6,180,370, 5,693,762, 5,693,761, 5,585,089, and 5,530,101. In general, a humanized antibody will comprise substantially all of at least one, and typically two, variable domains, in which all or substantially all of the CDRs correspond to those of a non-human immunoglobulin, and all or substantially all of the framework regions are those of a human immunoglobulin sequence. The humanized antibody optionally will also comprise at least a portion of an immunoglobulin constant region (Fc), typically that of a human immunoglobulin. For further details, see, e.g., Jones et al., Nature 321:522-525 (1986); Riechmann et al., Nature 332:323-329 (1988); and Presta, Curr. Op. Struct. Biol. 2:593-596 (1992). See also, e.g., Vaswani and Hamilton, Ann. Allergy, Asthma & Immunol. 1: 105-115 (1998); Harris, Biochem. Soc. Transactions 23:1035-1038 (1995); Hurle and Gross, Curr. Op. Biotech. 5:428-433 (1994); and U.S. Pat. Nos. 6,982,321 and 7,087,409. Still another method is termed humaneering and is described, for example, in U.S. 2005/0008625. For the purposes of the present application the term humanized antibodies will be held to expressly include CDR grafted antibodies (i.e. human antibodies comprising one or more grafted non-human CDRs) with no or minimal framework substitutions.

Additionally, a non-human anti-EFNA antibody may also be modified by specific deletion of human T cell epitopes or deimmunization by the methods disclosed in WO 98/52976 and WO 00/34317. Briefly, the heavy and light chain variable regions of an antibody can be analyzed for peptides that bind to MHC Class II; these peptides represent potential T-cell epitopes (as defined in WO 98/52976 and WO 00/34317). For detection of potential T-cell epitopes, a computer modeling approach termed peptide threading can be applied, and in addition a database of human MHC class II binding peptides can be searched for motifs present in the $V_H$ and $V_L$ sequences, as described in WO 98/52976 and WO 00/34317. These motifs bind to any of the 18 major MHC class II DR allotypes, and thus constitute potential T cell epitopes. Potential T-cell epitopes detected can be eliminated by substituting small numbers of amino acid residues in the variable regions, or by single amino acid substitutions. As far as possible, conservative substitutions are made. Often, but not exclusively, an amino acid common to a position in human germline antibody sequences may be used. After the deimmunizing changes are identified, nucleic acids encoding $V_H$ and $V_L$ can be constructed by mutagenesis or other synthetic methods (e.g., de novo synthesis, cassette replacement, and so forth). A mutagenized variable sequence can, optionally, be fused to a human constant region.

In selected embodiments, at least 60%, 65%, 70%, 75%, or 80% of the humanized antibody variable region residues will correspond to those of the parental framework region (FR) and CDR sequences. In other embodiments at least 85% or 90% of the humanized antibody residues will correspond to those of the parental framework region (FR) and CDR sequences. In a further preferred embodiment, greater than 95% of the humanized antibody residues will correspond to those of the parental framework region (FR) and CDR sequences.

Humanized antibodies may be fabricated using common molecular biology and biomolecular engineering techniques as described herein. These methods include isolating, manipulating, and expressing nucleic acid sequences that encode all or part of immunoglobulin Fv variable regions from at least one of a heavy or light chain. Sources of such nucleic acid are well known to those skilled in the art and, for example, may be obtained from a hybridoma, eukaryotic cell or phage producing an antibody or immunoreactive fragment against a predetermined target, as described above, from germline immunoglobulin genes, or from synthetic constructs.

The recombinant DNA encoding the humanized antibody can then be cloned into an appropriate expression vector.

Human germline sequences, for example, are disclosed in Tomlinson, I. A. et al. (1992) J. Mol. Biol. 227:776-798; Cook, G. P. et al. (1995) Immunol. Today 16: 237-242; Chothia, D. et al. (1992) J. Mol. Bio. 227:799-817; and Tomlinson et al. (1995) EMBO J 14:4628-4638. The V BASE directory provides a comprehensive directory of human immunoglobulin variable region sequences (See Retter et al., (2005) Nuc Acid Res 33: 671-674). These sequences can be used as a source of human sequence, e.g., for framework regions and CDRs. As set forth herein consensus human framework regions can also be used, e.g., as described in U.S. Pat. No. 6,300,064.

f. Human Antibodies

In addition to the aforementioned antibodies, those skilled in the art will appreciate that the antibodies of the present invention may comprise fully human antibodies. For the purposes of the instant application the term human antibody comprises an antibody which possesses an amino acid sequence that corresponds to that of an antibody produced by a human and/or has been made using any of the techniques for making human antibodies as disclosed herein. This definition of a human antibody specifically excludes a humanized antibody comprising non-human antigen-binding residues.

Human antibodies can be produced using various techniques known in the art. As alluded to above, phage display techniques may be used to provide immunoactive binding regions in accordance with the present teachings. Thus, certain embodiments of the invention provide methods for producing anti-EFNA antibodies or antigen-binding portions thereof comprising the steps of synthesizing a library of (preferably human) antibodies on phage, screening the library with a selected EFNA or an antibody-binding portion thereof, isolating phage that binds EFNA, and obtaining the immunoreactive fragments from the phage. By way of example, one method for preparing the library of antibodies for use in phage display techniques comprises the steps of immunizing a non-human animal comprising human or non-human immunoglobulin loci with the selected EFNA or an antigenic portion thereof to create an immune response, extracting antibody-producing cells from the immunized animal; isolating RNA encoding heavy and light chains of antibodies of the invention from the extracted cells, reverse transcribing the RNA to produce cDNA, amplifying the cDNA using primers, and inserting the cDNA into a phage display vector such that antibodies are expressed on the phage. More particularly, DNA encoding the $V_H$ and $V_L$ domains are recombined together with an scFv linker by PCR and cloned into a phagemid vector (e.g., p CANTAB 6 or pComb 3 HSS). The vector may then be electroporated in E. coli and then the E. coli is infected with helper phage. Phage used in these methods are typically filamentous phage including fd and M13 and the $V_H$ and $V_L$ domains are usually recombinantly fused to either the phage gene III or gene VIII.

Recombinant human anti-EFNA antibodies of the invention may be isolated by screening a recombinant combinatorial antibody library prepared as above. In a preferred embodiment, the library is a scFv phage display library, generated using human $V_L$ and $V_H$ cDNAs prepared from mRNA isolated from B cells. Methods for preparing and screening such libraries are well known in the art and kits for generating phage display libraries are commercially available (e.g., the Pharmacia Recombinant Phage Antibody System, catalog no. 27-9400-01; and the Stratagene SurfZAP™ phage display kit, catalog no. 240612). There also are other methods and reagents that can be used in generating and screening antibody display libraries (see, e.g., U.S. Pat. No. 5,223,409; PCT Publication Nos. WO 92/18619, WO 91/17271, WO 92/20791, WO 92/15679, WO 93/01288, WO 92/01047, WO 92/09690; Fuchs et al., Bio/Technology 9:1370-1372 (1991); Hay et al., Hum. Antibod. Hybridomas 3:81-85 (1992); Huse et al., Science 246:1275-1281 (1989); McCafferty et al., Nature 348:552-554 (1990); Griffiths et al., EMBO J. 12:725-734 (1993); Hawkins et al., J. Mol. Biol. 226:889-896 (1992); Clackson et al., Nature 352:624-628 (1991); Gram et al., Proc. Natl. Acad. Sci. USA 89:3576-3580 (1992); Garrad et al., Bio/Technology 9:1373-1377 (1991); Hoogenboom et al., Nuc. Acid Res. 19:4133-4137 (1991); and Barbas et al., Proc. Natl. Acad. Sci. USA 88:7978-7982 (1991).

The antibodies produced by naive libraries (either natural or synthetic) can be of moderate affinity ($K_a$ of about $10^6$ to $10^7$ $M^{-1}$), but affinity maturation can also be mimicked in vitro by constructing and reselecting from secondary libraries as described in the art. For example, mutation can be introduced at random in vitro by using error-prone polymerase (reported in Leung et al., Technique, 1: 11-15 (1989)) in the method of Hawkins et al., J. Mol. Biol., 226: 889-896 (1992) or in the method of Gram et al., Proc. Natl. Acad. Sci. USA, 89: 3576-3580 (1992). Additionally, affinity maturation can be performed by randomly mutating one or more CDRs, e.g. using PCR with primers carrying random sequence spanning the CDR of interest, in selected individual Fv clones and screening for higher affinity clones. WO 9607754 described a method for inducing mutagenesis in a complementarity determining region of an immunoglobulin light chain to create a library of light chain genes. Another effective approach is to recombine the $V_H$ or $V_L$ domains selected by phage display with repertoires of naturally occurring V domain variants obtained from unimmunized donors and screen for higher affinity in several rounds of chain reshuffling as described in Marks et al., Biotechnol., 10: 779-783 (1992). This technique allows the production of antibodies and antibody fragments with a dissociation constant $K_d$ ($k_{off}/k_{on}$) of about $10^{-9}$M or less.

It will further be appreciated that similar procedures may be employed using libraries comprising eukaryotic cells (e.g., yeast) that express binding pairs on their surface. As with phage display technology, the eukaryotic libraries are screened against the antigen of interest (i.e., EFNA) and cells expressing candidate-binding pairs are isolated and cloned. Steps may be taken to optimize library content and for affinity maturation of the reactive binding pairs. See, for example, U.S. Pat. No. 7,700,302 and U.S. Ser. No. 12/404,059. In one embodiment, the human antibody is selected from a phage library, where that phage library expresses human antibodies (Vaughan et al. Nature Biotechnology 14:309-314 (1996): Sheets et al. Proc. Natl. Acad. Sci. 95:6157-6162 (1998)); Hoogenboom and Winter, J. Mol. Biol, 227:381 (1991); Marks et al., J. MoI. Biol, 222:581 (1991)). In other embodiments human binding pairs may be isolated from combinatorial antibody libraries generated in eukaryotic cells such as yeast. See e.g., U.S. Pat. No. 7,700,302. Such techniques advantageously allow for the screening of large numbers of candidate modulators and provide for relatively easy manipulation of candidate sequences (e.g., by affinity maturation or recombinant shuffling).

Human antibodies can also be made by introducing human immunoglobulin loci into transgenic animals, e.g., mice in which the endogenous immunoglobulin genes have been partially or completely inactivated. Upon challenge, human antibody production is observed, which closely resembles that seen in humans in all respects, including gene rearrangement, assembly, and antibody repertoire. This approach is described, for example, in U.S. Pat. Nos. 5,545,807; 5,545, 806; 5,569,825; 5,625,126; 5,633,425; 5,661,016, and U.S. Pat. Nos. 6,075,181 and 6,150,584 regarding Xenomouse® technology along with the following scientific publications: Marks et al., Bio/Technology 10: 779-783 (1992); Lonberg et al., Nature 368: 856-859 (1994); Morrison, Nature 368:812-13 (1994); Fishwild et al., Nature Biotechnology 14: 845-51 (1996); Neuberger, Nature Biotechnology 14: 826 (1996); Lonberg and Huszar, Intern. Rev. Immunol. 13:65-93 (1995). Alternatively, the human antibody may be prepared via immortalization of human B-lymphocytes producing an antibody directed against a target antigen (such B lymphocytes may be recovered from an individual suffering from a neoplastic disorder or may have been immunized in vitro). See, e.g., Cole et al., Monoclonal Antibodies and Cancer Therapy, Alan R. Liss, p. 77 (1985); Boerner et al., J. Immunol, 147 (1):86-95 (1991); and U.S. Pat. No. 5,750,373.

VI. Antibody Characteristics

No matter how obtained or which of the aforementioned forms the antibody modulator takes (e.g., humanized, human, etc.) the preferred embodiments of the disclosed modulators may exhibit various characteristics. In this regard anti-EFNA antibody-producing cells (e.g., hybridomas or yeast colonies) may be selected, cloned and further screened for desirable characteristics including, for example, robust growth, high antibody production and, as discussed in more detail below, desirable antibody characteristics. Hybridomas can be expanded in vivo in syngeneic animals, in animals that lack an immune system, e.g., nude mice, or in cell culture in vitro. Methods of selecting, cloning and expanding hybridomas and/or colonies, each of which produces a discrete antibody species, are well known to those of ordinary skill in the art.

a. Neutralizing Antibodies

In particularly preferred embodiments the modulators of the instant invention will comprise neutralizing antibodies or derivative or fragment thereof. The term neutralizing antibody or neutralizing antagonist refers to an antibody or antagonist that binds to or interacts with an ephrin-A ligand and prevents binding or association of the ligand to its binding partner (e.g., EPHA receptor) thereby interrupting the biological response that otherwise would result from the interaction of the molecules. In assessing the binding and specificity of an antibody or immunologically functional fragment or derivative thereof, an antibody or fragment will substantially inhibit binding of the ligand to its binding partner or substrate when an excess of antibody reduces the quantity of binding partner bound to the target molecule by at least about 20%, 30%, 40%, 50%, 60%, 70%, 80%, 85%, 90%, 95%, 97%, 99% or more as measured, for example, in an in vitro competitive binding assay (see e.g., Examples 9-12 herein). In the case of antibodies to EFNA4 for example, a neutralizing antibody or antagonist will preferably diminish the ability of EFNA4 to bind to EphA4 by at least about 20%, 30%, 40%, 50%, 60%, 70%, 80%, 85%, 90%, 95%, 97%, 99% or more. It will be appreciated that this diminished activity may be measured directly using art recognized techniques or may be measured by the impact such reduction will have on EPH (e.g., EPHA4) receptor activity.

b. Internalizing Antibodies

While evidence indicates that selected ephrin-A ligands or their isoforms may be present in a soluble form, at least some EFNA (e.g., EFNA1 and EFNA4) likely remains associated with the cell surface thereby allowing for internalization of the disclosed modulators. Accordingly, the anti-EFNA antibodies of the instant invention may be internalized, at least to some extent, by cells that express an ephrin-A ligand. For example, an anti-EFNA4 antibody that binds to EFNA4 on the surface of a tumor-initiating cell may be internalized by the tumor-initiating cell. In particularly preferred embodiments such anti-EFNA antibodies may be associated with or conjugated to anti-cancer agents such as cytotoxic moieties that kill the cell upon internalization.

As used herein, an anti-EFNA antibody that internalizes is one that is taken up by the cell upon binding to an EFNA associated with a mammalian cell. The internalizing antibody includes antibody fragments, human or humanized antibody and antibody conjugates. Internalization may occur in vitro or in vivo. For therapeutic applications, internalization may occur in vivo. The number of antibody molecules internalized may be sufficient or adequate to kill an EFNA-expressing cell, especially an EFNA-expressing tumor initiating cell. Depending on the potency of the antibody or antibody conjugate, in some instances, the uptake of a single antibody molecule into the cell is sufficient to kill the target cell to which the antibody binds. For example, certain toxins are highly potent in killing such that internalization of one molecule of the toxin conjugated to the antibody is sufficient to kill the tumor cell. Whether an anti-EFNA antibody internalizes upon binding EFNA on a mammalian cell can be determined by various assays including those described in the Examples below (e.g., Examples 15 and 16). Methods of detecting whether an antibody internalizes into a cell are also described in U.S. Pat. No. 7,619,068 which is incorporated herein by reference in its entirety.

c. Depleting Antibodies

In other preferred embodiments the modulators of the instant invention will comprise depleting antibodies or derivatives or fragments thereof. The term depleting antibody refers to an antibody or fragment that binds to or associates with an EFNA on or near the cell surface and induces, promotes or causes the death or elimination of the cell (e.g., by complement-dependent cytotoxicity or antibody-dependent cellular cytotoxicity). In some embodiments discussed more fully below the selected depleting antibodies will be associated or conjugated to a cytotoxic agent. Preferably a depleting antibody will be able to remove, eliminate or kill at least 20%, 30%, 40%, 50%, 60%, 70%, 80%, 85%, 90%, 95%, 97%, or 99% of tumor perpetuating cells in a defined cell population. In some embodiments the cell population may comprise enriched, sectioned, purified or isolated tumor perpetuating cells. In other embodiments the cell population may comprise whole tumor samples or heterogeneous tumor extracts that comprise tumor perpetuating cells. Those skilled in the art will appreciate that standard biochemical techniques as described in the Examples below (e.g., Example 16) may be used to monitor and quantify the depletion of tumorigenic cells or tumor perpetuating cells in accordance with the teachings herein.

d. Epitope Binding

It will further be appreciated the disclosed anti-EFNA antibodies will associate with, or bind to, discrete epitopes or determinants presented by the selected target(s). As used herein the term epitope refers to that portion of the target antigen capable of being recognized and specifically bound by a particular antibody. When the antigen is a polypeptide such as EFNA, epitopes can be formed both from contiguous amino acids and noncontiguous amino acids juxtaposed by tertiary folding of a protein. Epitopes formed from contiguous amino acids are typically retained upon protein denaturing, whereas epitopes formed by tertiary folding are typically lost upon protein denaturing. An epitope typically includes at least 3, and more usually, at least 5 or 8-10 amino acids in a unique spatial conformation. More specifically, the skilled artisan will appreciate the term epitope includes any protein determinant capable of specific binding to an immunoglobulin or T-cell receptor or otherwise interacting with a molecule. Epitopic determinants generally consist of chemically active surface groupings of molecules such as amino acids or carbohydrate or sugar side chains and generally have specific three dimensional structural characteristics, as well as specific charge characteristics. Additionally an epitope may be linear or conformational. In a linear epitope, all of the points of interaction between the protein and the interacting molecule (such as an antibody) occur linearly along the primary amino acid sequence of the protein. In a conformational epitope, the points of interaction occur across amino acid residues on the protein that are linearly separated from one another.

Once a desired epitope on an antigen is determined, it is possible to generate antibodies to that epitope, e.g., by immunizing with a peptide comprising the epitope using techniques described in the present invention. Alternatively, during the discovery process, the generation and characterization of antibodies may elucidate information about desirable epitopes. From this information, it is then possible to competitively screen antibodies for binding to the same epitope. An approach to achieve this is to conduct competition studies to find antibodies that competitively bind with one another, i.e. the antibodies compete for binding to the antigen. A high throughput process for binning antibodies based upon their cross-competition is described in WO 03/48731.

As used herein, the term binning refers to a method to group antibodies based on their antigen binding characteristics. The assignment of bins is somewhat arbitrary, depending on how different the observed binding patterns of the antibodies tested. Thus, while the technique is a useful tool for categorizing antibodies of the instant invention, the bins do not always directly correlate with epitopes and such initial determinations should be further confirmed by other art recognized methodology.

With this caveat one can determine whether a selected primary antibody (or fragment thereof) binds to the same epitope or cross competes for binding with a second antibody by using methods known in the art and set forth in the Examples herein. In one embodiment, one allows the primary antibody of the invention to bind to EFNA under saturating conditions and then measures the ability of the secondary antibody to bind to EFNA. If the test antibody is able to bind to EFNA at the same time as the primary anti-EFNA antibody, then the secondary antibody binds to a different epitope than the primary antibody. However, if the secondary antibody is not able to bind to EFNA at the same time, then the secondary antibody binds to the same epitope, an overlapping epitope, or an epitope that is in close proximity to the epitope bound by the primary antibody. As known in the art and detailed in the Examples below, the desired data can be obtained using solid phase direct or indirect radioimmunoassay (RIA), solid phase direct or indirect enzyme immunoassay (EIA), sandwich competition assay, a Biacore™ system (i.e., surface plasmon resonance—GE Healthcare), a ForteBio® Analyzer (i.e., biolayer interferometry—ForteBio, Inc.) or flow cytometric methodology. The term surface plasmon resonance, as used herein, refers to an optical phenomenon that allows for the analysis of real-time biospecific interactions by detection of alterations in protein concentrations within a biosensor matrix. In a particularly preferred embodiment, the analysis is performed using a Biacore or ForteBio instrument as demonstrated in the Examples below.

The term compete when used in the context of antibodies that compete for the same epitope means competition between antibodies is determined by an assay in which the antibody or immunologically functional fragment under test prevents or inhibits specific binding of a reference antibody to a common antigen. Typically, such an assay involves the use of purified antigen bound to a solid surface or cells bearing either of these, an unlabeled test immunoglobulin and a labeled reference immunoglobulin. Competitive inhibition is measured by determining the amount of label bound to the solid surface or cells in the presence of the test immunoglobulin. Usually the test immunoglobulin is present in excess. Antibodies identified by competition assay (competing antibodies) include antibodies binding to the same epitope as the reference antibody and antibodies binding to an adjacent epitope sufficiently proximal to the epitope bound by the reference antibody for steric hindrance to occur. Additional details regarding methods for determining competitive binding are provided in the Examples herein. Usually, when a competing antibody is present in excess, it will inhibit specific binding of a reference antibody to a common antigen by at least 40%, 45%, 50%, 55%, 60%, 65%, 70% or 75%. In some instance, binding is inhibited by at least 80%, 85%, 90%, 95%, or 97% or more.

Besides epitope specificity the disclosed antibodies may be characterized using a number of different physical characteristics including, for example, binding affinities, melting temperature (Tm), and isoelectric points.

e. Binding Affinity

In this respect, the present invention further encompasses the use of antibodies that have a high binding affinity for a selected EFNA or, in the case of pan-antibodies, more than one type of ephrin-A ligand. An antibody of the invention is said to specifically bind its target antigen when the dissociation constant $K_d$ ($k_{off}/k_{on}$) is $\leq 10^{-8}$M. The antibody specifically binds antigen with high affinity when the $K_d$ is $\leq 5 \times 10^{-9}$M, and with very high affinity when the $K_d$ is $\leq 5 \times 10^{-10}$M. In one embodiment of the invention, the antibody has a $K_d$ of $\leq 10^{-9}$M and an off-rate of about $1 \times 10^{-4}$/sec. In one embodiment of the invention, the off-rate is $<1 \times 10^{-5}$/sec. In other embodiments of the invention, the antibodies will bind to EFNA with a $K_d$ of between about $10^{-8}$M and $10^{-10}$M, and in yet another embodiment it will bind with a $K_d \leq 2 \times 10^{-10}$M. Still other selected embodiments of the present invention comprise antibodies that have a disassociation constant or $K_d$ ($k_{off}/k_{on}$) of less than $10^{-2}$M, less than $5 \times 10^{-2}$M, less than $10^{-3}$M, less than $5 \times 10^{-3}$M, less than $10^{-4}$M, less than $5 \times 10^{-4}$M, less than $10^{-5}$M, less than $5 \times 10^{-5}$M, less than $10^{-6}$M, less than $5 \times 10^{-6}$M, less than $10^{-7}$M, less than $5 \times 10^{-7}$M, less than $10^{-8}$M, less than $5 \times 10^{-8}$M, less than $10^{-9}$M, less than $5 \times 10^{-9}$M, less than $10^{-10}$M, less than $5 \times 10^{-10}$M, less than $10^{-11}$M, less than $5 \times 10^{-11}$M, less than $10^{-12}$M, less than $5 \times 10^{-12}$M, less than $10^{-13}$M, less than $5 \times 10^{-13}$M, less than $10^{-14}$M, less than $5 \times 10^{-14}$M, less than $10^{-15}$M or less than $5 \times 10^{-15}$M.

In specific embodiments, an antibody of the invention that immunospecifically binds to EFNA has an association rate constant or $k_{on}$ rate (EFNA (Ab)+antigen (Ag)$^{k_{on}} \leftarrow$ Ab-Ag) of at least $10^5 M^{-1}s^{-1}$, at least $2 \times 10^5 M^{-1}s^{-1}$, at least $5 \times 10^5 M^{-1}s^{-1}$, at least $10^6 M^{-1}s^{-1}$, at least $5 \times 10^6 M^{-1}s^{-1}$, at least $10^7 M^{-1}s^{-1}$, at least $5 \times 10^7 M^{-1}s^{-1}$, or at least $10^8 M^{-1}s^{-1}$.

In another embodiment, an antibody of the invention that immunospecifically binds to EFNA has a $k_{off}$ rate (EFNA (Ab)+antigen (Ag)$^{k_{off}} \leftarrow$ Ab-Ag) of less than $10^{-1}s^{-1}$, less than $5 \times 10^{-1}s^{-1}$, less than $10^{-2}s^{-1}$, less than $5 \times 10^{-2}s^{-1}$, less than $10^{-3}s^{-1}$, less than $5 \times 10^{-3}s^{-1}$, less than $10^{-4}s^{-1}$, less than $5 \times 10^{-4}s^{-1}$, less than $10^{-5}s^{-1}$, less than $5 \times 10^{-5}s^{-1}$, less than $10^{-6}s^{-1}$, less than $5\times10^{-6}s^{-1}$ less than $10^{-7}s^{-1}$, less than $5\times10^{-7}s^{-1}$, less than $10^{-8}s^{-1}$, less than $5\times10^{-8}s^{-1}$, less than $10^{-9}s^{-1}$, less than $5\times10^{-9}s^{-1}$ or less than $10^{-10}s^{-1}$.

In other selected embodiments of the present invention anti-EFNA antibodies will have an affinity constant or $K_a$ ($k_{on}/k_{off}$) of at least $10^2M^{-1}$, at least $5\times10^2M^{-1}$, at least $10^3M^{-1}$, at least $5\times10^3M^{-1}$, at least $10^4M^{-1}$, at least $5\times10^4M^{-1}$, at least $10^5M^{-1}$, at least $5\times10^5M^{-1}$, at least $10^6M^{-1}$, at least $5\times10^6M^{-1}$, at least $10^7M^{-1}$, at least $5\times10^7M^{-1}$, at least $10^8M^{-1}$, at least $5\times10^8M^{-1}$, at least $10^9M^{-1}$, at least $5\times10^9M^{-1}$, at least $10^{10}M^{-1}$, at least $5\times10^{10}M^{-1}$, at least $10^{11}M^{-1}$, at least $5\times10^{11}M^{-1}$, at least $10^{12}M'$, at least $5\times10^{12}M^{-1}$, at least $10^{13}M^{-1}$, at least $5\times10^{13}M^{-1}$, at least $10^{14}M^{-1}$, at least $5\times10^{14}M^{-1}$, at least $10^{15}M^{-1}$ or at least $5\times10^{15}M^{-1}$.

f. Isoelectric Points

In addition to the aforementioned binding properties, anti-EFNA antibodies and fragments thereof, like all polypeptides, have an Isoelectric Point (pI), which is generally defined as the pH at which a polypeptide carries no net charge. It is known in the art that protein solubility is typically lowest when the pH of the solution is equal to the isoelectric point (pI) of the protein. Therefore it is possible to optimize solubility by altering the number and location of ionizable residues in the antibody to adjust the pI. For example the pI of a polypeptide can be manipulated by making the appropriate amino acid substitutions (e.g., by substituting a charged amino acid such as a lysine, for an uncharged residue such as alanine). Without wishing to be bound by any particular theory, amino acid substitutions of an antibody that result in changes of the pI of said antibody may improve solubility and/or the stability of the antibody. One skilled in the art would understand which amino acid substitutions would be most appropriate for a particular antibody to achieve a desired pI.

The pI of a protein may be determined by a variety of methods including but not limited to, isoelectric focusing and various computer algorithms (see for example Bjellqvist et al., 1993, Electrophoresis 14:1023). In one embodiment, the pI of the anti-EFNA antibodies of the invention is between is higher than about 6.5, about 7.0, about 7.5, about 8.0, about 8.5, or about 9.0. In another embodiment, the pI of the anti-EFNA antibodies of the invention is between is higher than 6.5, 7.0, 7.5, 8.0, 8.5, or 9.0. In yet another embodiment, substitutions resulting in alterations in the pI of antibodies of the invention will not significantly diminish their binding affinity for EFNA. As discussed in more detail below, it is specifically contemplated that the substitution(s) of the Fc region that result in altered binding to FcγR may also result in a change in the pI. In a preferred embodiment, substitution(s) of the Fc region are specifically chosen to effect both the desired alteration in FcγR binding and any desired change in pI. As used herein, the pI value is defined as the pI of the predominant charge form.

g. Thermal Stability

It will further be appreciated that the Tm of the Fab domain of an antibody can be a good indicator of the thermal stability of an antibody and may further provide an indication of the shelf-life. Tm is merely the temperature of 50% unfolding for a given domain or sequence. A lower Tm indicates more aggregation/less stability, whereas a higher Tm indicates less aggregation/more stability. Thus, antibodies or fragments or derivatives having higher Tm are preferable. Moreover, using art-recognized techniques it is possible to alter the composition of the anti-EFNA antibodies or domains thereof to increase or optimize molecular stability. See, for example, U.S. Pat. No. 7,960,142. Thus, in one embodiment, the Fab domain of a selected antibody has a Tm value higher than at least 50° C., 55° C., 60° C., 65° C., 70° C., 75° C., 80° C., 85° C., 90° C., 95° C., 100° C., 105° C., 110° C., 115° C. or 120° C. In another embodiment, the Fab domain of an antibody has a Tm value higher than at least about 50° C., about 55° C., about 60° C., about 65° C., about 70° C., about 75° C., about 80° C., about 85° C., about 90° C., about 95° C., about 100° C., about 105° C., about 110° C., about 115° C. or about 120° C. Thermal melting temperatures (Tm) of a protein domain (e.g., a Fab domain) can be measured using any standard method known in the art, for example, by differential scanning calorimetry (see, e.g., Vermeer et al., 2000, Biophys. J. 78:394-404; Vermeer et al., 2000, Biophys. J. 79: 2150-2154 both incorporated herein by reference).

VII. EFNA Modulator Fragments and Derivatives

Whether the agents of the present invention comprise intact fusion constructs, antibodies, fragments or derivatives, the selected modulators will react, bind, combine, complex, connect, attach, join, interact or otherwise associate with EFNA and thereby provide the desired anti-neoplastic effects. Those of skill in the art will appreciate that modulators comprising anti-EFNA antibodies interact or associate with EFNA through one or more binding sites expressed on the antibody. More specifically, as used herein the term binding site comprises a region of a polypeptide that is responsible for selectively binding to a target molecule of interest (e.g., enzyme, antigen, ligand, receptor, substrate or inhibitor). Binding domains comprise at least one binding site (e.g. an intact IgG antibody will have two binding domains and two binding sites). Exemplary binding domains include an antibody variable domain, a receptor-binding domain of a ligand, a ligand-binding domain of a receptor or an enzymatic domain. For the purpose of the instant invention the typical active region of EFNA (e.g., as part of an Fc-EFNA fusion construct) may comprise a binding site for a substrate (e.g., an Eph receptor).

a. Fragments

Regardless of which form of the modulator (e.g. chimeric, humanized, etc.) is selected to practice the invention, it will be appreciated that immunoreactive fragments of the same may be used in accordance with the teachings herein. In the broadest sense, the term antibody fragment comprises at least a portion of an intact antibody (e.g. a naturally occurring immunoglobulin). More particularly the term fragment refers to a part or portion of an antibody or antibody chain (or EFNA molecule in the case of Fc fusions) comprising fewer amino acid residues than an intact or complete antibody or antibody chain. The term antigen-binding fragment refers to a polypeptide fragment of an immunoglobulin or antibody that binds antigen or competes with intact antibody (i.e., with the intact antibody from which they were derived) for antigen binding (i.e., specific binding). As used herein, the term fragment of an antibody molecule includes antigen-binding fragments of antibodies, for example, an antibody light chain ($V_L$), an antibody heavy chain ($V_H$), a single chain antibody (scFv), a F(ab')2 fragment, a Fab fragment, an Fd fragment, an Fv fragment, single domain antibody fragments, diabodies, linear antibodies, single-chain antibody molecules and multi-specific antibodies formed from antibody fragments. Similarly, an active fragment of EFNA comprises a portion of the EFNA molecule that retains its ability to interact with EFNA substrates or receptors and modify them in a manner similar to that of an intact EFNA (though maybe with somewhat less efficiency).

Those skilled in the art will appreciate fragments can be obtained via chemical or enzymatic treatment of an intact or complete modulator (e.g., antibody or antibody chain) or by recombinant means. In this regard, while various antibody fragments are defined in terms of the digestion of an intact antibody, one of skill will appreciate that such fragments may be synthesized de novo either chemically or by using recombinant DNA methodology. Thus, the term antibody, as used herein, explicitly includes antibodies or fragments or derivatives thereof either produced by the modification of whole antibodies or synthesized de novo using recombinant DNA methodologies.

More specifically, papain digestion of antibodies produces two identical antigen-binding fragments, called Fab fragments, each with a single antigen-binding site, and a residual Fc fragment, whose name reflects its ability to crystallize readily. Pepsin treatment yields an F(ab')$_2$ fragment that has two antigen-binding sites and is still capable of cross-linking antigen. The Fab fragment also contains the constant domain of the light chain and the first constant domain ($C_H1$) of the heavy chain. Fab' fragments differ from Fab fragments by the addition of a few residues at the carboxy terminus of the heavy-chain $C_H1$ domain including one or more cysteines from the antibody hinge region. Fab'-SH is the designation herein for Fab' in which the cysteine residue(s) of the constant domains bear at least one free thiol group. F(ab')$_2$ antibody fragments originally were produced as pairs of Fab' fragments that have hinge cysteines between them. Other chemical couplings of antibody fragments are also known. See, e.g., Fundamental Immunology, W. E. Paul, ed., Raven Press, N.Y. (1999), for a more detailed description of other antibody fragments.

It will further be appreciated that an Fv fragment is an antibody fragment that contains a complete antigen recognition and binding site. This region is made up of a dimer of one heavy and one light chain variable domain in tight association, which can be covalent in nature, for example in scFv. It is in this configuration that the three CDRs of each variable domain interact to define an antigen binding site on the surface of the $V_H$-$V_L$ dimer. Collectively, the six CDRs or a subset thereof confer antigen binding specificity to the antibody. However, even a single variable domain (or half of an Fv comprising only three CDRs specific for an antigen) has the ability to recognize and bind antigen, although usually at a lower affinity than the entire binding site.

In other embodiments an antibody fragment, for example, is one that comprises the Fc region, retains at least one of the biological functions normally associated with the Fc region when present in an intact antibody, such as FcRn binding, antibody half life modulation, ADCC function and complement binding. In one embodiment, an antibody fragment is a monovalent antibody that has an in vivo half life substantially similar to an intact antibody. For example, such an antibody fragment may comprise on antigen binding arm linked to an Fc sequence capable of conferring in vivo stability to the fragment.

b. Derivatives

In another embodiment, it will further be appreciated that the modulators of the invention may be monovalent or multivalent (e.g., bivalent, trivalent, etc.). As used herein the term valency refers to the number of potential target (i.e., EFNA) binding sites associated with an antibody. Each target binding site specifically binds one target molecule or specific position or locus on a target molecule. When an antibody of the instant invention comprises more than one target binding site (multivalent), each target binding site may specifically bind the same or different molecules (e.g., may bind to different ligands or different antigens, or different epitopes or positions on the same antigen). For the purposes of the instant invention, the subject antibodies will preferably have at least one binding site specific for human EFNA. In one embodiment the antibodies of the instant invention will be monovalent in that each binding site of the molecule will specifically bind to a single EFNA position or epitope. In other embodiments, the antibodies will be multivalent in that they comprise more than one binding site and the different binding sites specifically associate with more than a single position or epitope. In such cases the multiple epitopes may be present on the selected EFNA polypeptide or spice variant or a single epitope may be present on EFNA while a second, different epitope may be present on another molecule or surface. See, for example, U.S.P.N. 2009/0130105.

As alluded to above, multivalent antibodies may immunospecifically bind to different epitopes of the desired target molecule or may immunospecifically bind to both the target molecule as well as a heterologous epitope, such as a heterologous polypeptide or solid support material. While preferred embodiments of the anti-EFNA antibodies only bind two antigens (i.e. bispecific antibodies), antibodies with additional specificities such as trispecific antibodies are also encompassed by the instant invention. Examples of bispecific antibodies include, without limitation, those with one arm directed against EFNA and the other arm directed against any other antigen (e.g., an modulator cell marker). Methods for making bispecific antibodies are known in the art. Traditional production of full-length bispecific antibodies is based on the coexpression of two immunoglobulin heavy chain-light chain pairs, where the two chains have different specificities (Millstein et al., 1983, Nature, 305:537-539). Other more sophisticated compatible multispecific constructs and methods of their fabrication are set forth in U.S.P.N. 2009/0155255.

In yet other embodiments, antibody variable domains with the desired binding specificities (antibody-antigen combining sites) are fused to immunoglobulin constant domain sequences. The fusion preferably is with an immunoglobulin heavy chain constant domain, comprising at least part of the hinge, $C_H2$, and/or $C_H3$ regions. In one example, the first heavy-chain constant region ($C_H1$) containing the site necessary for light chain binding is present in at least one of the fusions. DNAs encoding the immunoglobulin heavy chain fusions and, if desired, the immunoglobulin light chain, are inserted into separate expression vectors, and are co-transfected into a suitable host organism. This provides for great flexibility in adjusting the mutual proportions of the three polypeptide fragments in embodiments when unequal ratios of the three polypeptide chains used in the construction provide the optimum yields. It is, however, possible to insert the coding sequences for two or all three polypeptide chains in one expression vector when, the expression of at least two polypeptide chains in equal ratios results in high yields or when the ratios are of no particular significance.

In one embodiment of this approach, the bispecific antibodies are composed of a hybrid immunoglobulin heavy chain with a first binding specificity in one arm (e.g., EFNA4), and a hybrid immunoglobulin heavy chain-light chain pair (providing a second binding specificity) in the other arm. It was found that this asymmetric structure facilitates the separation of the desired bispecific compound from unwanted immunoglobulin chain combinations, as the presence of an immunoglobulin light chain in only one half of the bispecific molecule provides for a facile way of separation. This approach is disclosed in WO 94/04690. For further details of generating bispecific antibodies see, for example, Suresh et al., 1986, Methods in Enzymology, 121:210. According to another approach described in WO96/27011, a pair of antibody molecules can be engineered to maximize the percentage of heterodimers that are recovered from recombinant cell culture. The preferred interface comprises at least a part of the $C_H3$ domain of an antibody constant domain. In this method, one or more small amino acid side chains from the interface of the first antibody molecule are replaced with larger side chains (e.g. tyrosine or tryptophan). Compensatory cavities of identical or similar size to the large side chain(s) are created on the interface of the second antibody molecule by replacing large amino acid side chains with smaller ones (e.g. alanine or threonine). This provides a mechanism for increasing the yield of the heterodimer over other unwanted end-products such as homodimers.

Bispecific antibodies also include cross-linked or heteroconjugate antibodies. For example, one of the antibodies in the heteroconjugate can be coupled to avidin, the other to biotin. Such antibodies have, for example, been proposed to target immune system cells to unwanted cells (U.S. Pat. No. 4,676,980), and for treatment of HIV infection (WO 91/00360, WO 92/200373, and EP 03089). Heteroconjugate antibodies may be made using any convenient cross-linking methods. Suitable cross-linking agents are well known in the art, and are disclosed in U.S. Pat. No. 4,676,980, along with a number of cross-linking techniques.

VIII. EFNA Modulators

Constant Region Modifications a. Fc Region and Fc Receptors

In addition to the various modifications, substitutions, additions or deletions to the variable or binding region of the disclosed modulators (e.g., Fc-EFNA or anti-EFNA antibodies) set forth above, those skilled in the art will appreciate that selected embodiments of the present invention may also comprise substitutions or modifications of the constant region (i.e. the Fc region). More particularly, it is contemplated that the EFNA modulators of the invention may contain inter alia one or more additional amino acid residue substitutions, mutations and/or modifications which result in a compound with preferred characteristics including, but not limited to: altered pharmacokinetics, increased serum half life, increase binding affinity, reduced immunogenicity, increased production, altered Fc ligand binding, enhanced or reduced ADCC or CDC activity, altered glycosylation and/or disulfide bonds and modified binding specificity. In this regard it will be appreciated that these Fc variants may advantageously be used to enhance the effective anti-neoplastic properties of the disclosed modulators.

The term Fc region herein is used to define a C-terminal region of an immunoglobulin heavy chain, including native sequence Fc regions and variant Fc regions. Although the boundaries of the Fc region of an immunoglobulin heavy chain might vary, the human IgG heavy chain Fc region is usually defined to stretch from an amino acid residue at position Cys226, or from Pro230, to the carboxyl-terminus thereof. The C-terminal lysine (residue 447 according to the EU numbering system) of the Fc region may be removed, for example, during production or purification of the antibody, or by recombinantly engineering the nucleic acid encoding a heavy chain of the antibody. Accordingly, a composition of intact antibodies may comprise antibody populations with all K447 residues removed, antibody populations with no K447 residues removed, and antibody populations having a mixture of antibodies with and without the K447 residue. A functional Fc region possesses an effector function of a native sequence Fc region. Exemplary effector functions include C1q binding; CDC; Fc receptor binding; ADCC; phagocytosis; down regulation of cell surface receptors (e.g. B cell receptor; BCR), etc. Such effector functions generally require the Fc region to be combined with a binding domain (e.g., an antibody variable domain) and can be assessed using various assays as disclosed, for example, in definitions herein.

Fc receptor or FcR describes a receptor that binds to the Fc region of an antibody. In some embodiments, an FcR is a native human FcR. In some embodiments, an FcR is one that binds an IgG antibody (a gamma receptor) and includes receptors of the FcγRI, Fc.RII, and FcγRIII subclasses, including allelic variants and alternatively spliced forms of those receptors. FcγII receptors include FcγRIIA (an activating receptor) and FcγRIIB (an inhibiting receptor), which have similar amino acid sequences that differ primarily in the cytoplasmic domains thereof. Activating receptor Fcγ RIIA contains an immunoreceptor tyrosine-based activation motif (ITAM) in its cytoplasmic domain. Inhibiting receptor FγRIIB contains an immunoreceptor tyrosine-based inhibition motif (ITIM) in its cytoplasmic domain. (see, e.g., Daeron, Annu. Rev. Immunol. 15:203-234 (1997)). FcRs are reviewed, for example, in Ravetch and Kinet, Annu. Rev. Immunol 9:457-92 (1991); Capel et al., Immunomethods 4:25-34 (1994); and de Haas et al., J. Lab. Clin. Med. 126: 330-41 (1995). Other FcRs, including those to be identified in the future, are encompassed by the term FcR herein. The term Fc receptor or FcR also includes the neonatal receptor, FcRn, which, in certain instances, is responsible for the transfer of maternal IgGs to the fetus (Guyer et al., J. Immunol. 117:587 (1976) and Kim et al., J. Immunol. 24:249 (1994)) and regulation of homeostasis of immunoglobulins. Methods of measuring binding to FcRn are known (see, e.g., Ghetie and Ward., Immunol. Today 18(12):592-598 (1997); Ghetie et al., Nature Biotechnology, 15(7):637-640 (1997); Hinton et al., J. Biol. Chem. 279(8):6213-6216 (2004); WO 2004/92219 (Hinton et al.).

b. Fc Functions

As used herein complement dependent cytotoxicity and CDC refer to the lysing of a target cell in the presence of complement. The complement activation pathway is initiated by the binding of the first component of the complement system (C1q) to a molecule, an antibody for example, complexed with a cognate antigen. To assess complement activation, a CDC assay, e.g. as described in Gazzano-Santoro et al., 1996, J. Immunol. Methods, 202:163, may be performed.

Further, antibody-dependent cell-mediated cytotoxicity or ADCC refers to a form of cytotoxicity in which secreted Ig bound onto Fc receptors (FcRs) present on certain cytotoxic cells (e.g., Natural Killer (NK) cells, neutrophils, and macrophages) enables these cytotoxic effector cells to bind specifically to an antigen-bearing target cell and subsequently kill the target cell with cytotoxins. Specific high-affinity IgG antibodies directed to the target arm cytotoxic cells and are absolutely required for such killing. Lysis of the target cell is extracellular, requires direct cell-to-cell contact, and does not involve complement.

EFNA modulator variants with altered FcR binding affinity or ADCC activity is one which has either enhanced or diminished FcR binding activity and/or ADCC activity compared to a parent or unmodified antibody or to a modulator comprising a native sequence Fc region. The modulator variant which displays increased binding to an FcR binds at least one FcR with better affinity than the parent or unmodified antibody or to a modulator comprising a native sequence Fc region. A variant which displays decreased binding to an FcR, binds at least one FcR with worse affinity than the parent or unmodified antibody or to a modulator comprising a native sequence Fc region. Such variants which display decreased binding to an FcR may possess little or no appreciable binding to an FcR, e.g., 0-20% binding to the FcR compared to a native sequence IgG Fc region, e.g. as determined techniques well known in the art.

As to FcRn, the antibodies of the instant invention also comprise or encompass Fc variants with modifications to the constant region that provide half-lives (e.g., serum half-lives) in a mammal, preferably a human, of greater than 5 days, greater than 10 days, greater than 15 days, preferably greater than 20 days, greater than 25 days, greater than 30 days, greater than 35 days, greater than 40 days, greater than 45 days, greater than 2 months, greater than 3 months, greater than 4 months, or greater than 5 months. The increased half-lives of the antibodies (or Fc containing molecules) of the present invention in a mammal, preferably a human, results in a higher serum titer of said antibodies or antibody fragments in the mammal, and thus, reduces the frequency of the administration of said antibodies or antibody fragments and/or reduces the concentration of said antibodies or antibody fragments to be administered. Antibodies having increased in vivo half-lives can be generated by techniques known to those of skill in the art. For example, antibodies with increased in vivo half-lives can be generated by modifying (e.g., substituting, deleting or adding) amino acid residues identified as involved in the interaction between the Fc domain and the FcRn receptor (see, e.g., International Publication Nos. WO 97/34631; WO 04/029207; U.S. Pat. No. 6,737,056 and U.S.P.N. 2003/0190311. Binding to human FcRn in vivo and serum half life of human FcRn high affinity binding polypeptides can be assayed, e.g., in transgenic mice or transfected human cell lines expressing human FcRn, or in primates to which the polypeptides with a variant Fc region are administered. WO 2000/42072 describes antibody variants with improved or diminished binding to FcRns. See also, e.g., Shields et al. J. Biol. Chem. 9(2):6591-6604 (2001).

c. Glycosylation Modifications

In still other embodiments, glycosylation patterns or compositions of the antibodies of the invention are modified. More particularly, preferred embodiments of the present invention may comprise one or more engineered glycoforms, i.e., an altered glycosylation pattern or altered carbohydrate composition that is covalently attached to a molecule comprising an Fc region. Engineered glycoforms may be useful for a variety of purposes, including but not limited to enhancing or reducing effector function, increasing the affinity of the antibody for a target antigen or facilitating production of the antibody. In cases where reduced effector function is desired, it will be appreciated that the molecule may be engineered to express in an aglycosylated form. Such carbohydrate modifications can be accomplished by, for example, altering one or more sites of glycosylation within the antibody sequence. That is, one or more amino acid substitutions can be made that result in elimination of one or more variable region framework glycosylation sites to thereby eliminate glycosylation at that site (see e.g. U.S. Pat. Nos. 5,714,350 and 6,350,861. Conversely, enhanced effector functions or improved binding may be imparted to the Fc containing molecule by engineering in one or more additional glycosylation sites.

Additionally or alternatively, an Fc variant can be made that has an altered glycosylation composition, such as a hypo-fucosylated antibody having reduced amounts of fucosyl residues or an antibody having increased bisecting GlcNAc structures. These and similar altered glycosylation patterns have been demonstrated to increase the ADCC ability of antibodies. Engineered glycoforms may be generated by any method known to one skilled in the art, for example by using engineered or variant expression strains, by coexpression with one or more enzymes (for example N-acetylglucosaminyltransferase III (GnTI11)), by expressing a molecule comprising an Fc region in various organisms or cell lines from various organisms or by modifying carbohydrate(s) after the molecule comprising Fc region has been expressed. See, for example, Shields, R. L. et al. (2002) J. Biol. Chem. 277: 26733-26740; Umana et al. (1999) Nat. Biotech. 17:176-1, as well as, European Patent No: EP 1,176,195; PCT Publications WO 03/035835; WO 99/54342, Umana et al, 1999, Nat. Biotechnol 17:176-180; Davies et al., 20017 Biotechnol Bioeng 74:288-294; Shields et al, 2002, J Biol Chem 277: 26733-26740; Shinkawa et al., 2003, J Biol Chem 278:3466-3473) U.S. Pat. No. 6,602,684; U.S. Ser. Nos. 10/277,370; 10/113,929; PCT WO 00/61739A1; PCT WO 01/292246A1; PCT WO 02/311140A1; PCT WO 02/30954A1; Potillegent™ technology (Biowa, Inc.); GlycoMAb™ glycosylation engineering technology (GLYCART biotechnology AG); WO 00061739; EA01229125; U.S.P.N. 2003/0115614; Okazaki et al., 2004, JMB, 336: 1239-49.

IX. Modulator Expression a. Overview

DNA encoding the desired EFNA modulators may be readily isolated and sequenced using conventional procedures (e.g., by using oligonucleotide probes that are capable of binding specifically to genes encoding antibody heavy and light chains). Isolated and subcloned hybridoma cells (or phage or yeast derived colonies) may serve as a preferred source of such DNA if the modulator is an antibody. If desired, the nucleic acid can further be manipulated as described herein to create agents including fusion proteins, or chimeric, humanized or fully human antibodies. More particularly, the isolated DNA (which may be modified) can be used to clone constant and variable region sequences for the manufacture antibodies as described in U.S. Pat. No. 7,709, 611.

This exemplary method entails extraction of RNA from the selected cells, conversion to cDNA, and amplification by PCR using antibody specific primers. Suitable primers are well known in the art and, as exemplified herein, are readily available from numerous commercial sources. It will be appreciated that, to express a recombinant human or non-human antibody isolated by screening of a combinatorial library, the DNA encoding the antibody is cloned into a recombinant expression vector and introduced into host cells including mammalian cells, insect cells, plant cells, yeast, and bacteria. In yet other embodiments, the modulators are introduced into and expressed by simian COS cells, NS0 cells, Chinese Hamster Ovary (CHO) cells or myeloma cells that do not otherwise produce the desired construct. As will be discussed in more detail below, transformed cells expressing the desired modulator may be grown up in relatively large quantities to provide clinical and commercial supplies of the fusion construct or immunoglobulin.

Whether the nucleic acid encoding the desired portion of the EFNA modulator is obtained or derived from phage display technology, yeast libraries, hybridoma based technology, synthetically or from commercial sources, it is to be understood that the present invention explicitly encompasses nucleic acid molecules and sequences encoding EFNA modulators including fusion proteins and anti-EFNA antibodies or antigen-binding fragments or derivatives thereof. The invention further encompasses nucleic acids or nucleic acid molecules (e.g., polynucleotides) that hybridize under high stringency, or alternatively, under intermediate or lower stringency hybridization conditions (e.g., as defined below), to polynucleotides complementary to nucleic acids having a polynucleotide sequence that encodes a modulator of the invention or a fragment or variant thereof. The term nucleic acid molecule or isolated nucleic acid molecule, as used herein, is intended to include at least DNA molecules and RNA molecules. A nucleic acid molecule may be single-stranded or double-stranded, but preferably is double-stranded DNA. Moreover, the present invention comprises any vehicle or construct, incorporating such modulator encoding polynucleotide including, without limitation, vectors, plasmids, host cells, cosmids or viral constructs.

The term isolated nucleic acid means a that the nucleic acid was (i) amplified in vitro, for example by polymerase chain reaction (PCR), (ii) recombinantly produced by cloning, (iii) purified, for example by cleavage and gel-electrophoretic fractionation, or (iv) synthesized, for example by chemical synthesis. An isolated nucleic acid is a nucleic acid that is available for manipulation by recombinant DNA techniques.

More specifically, nucleic acids that encode a modulator, including one or both chains of an antibody of the invention, or a fragment, derivative, mutein, or variant thereof, polynucleotides sufficient for use as hybridization probes, PCR primers or sequencing primers for identifying, analyzing, mutating or amplifying a polynucleotide encoding a polypeptide, anti-sense nucleic acids for inhibiting expression of a polynucleotide, and complementary sequences of the foregoing are also provided. The nucleic acids can be any length. They can be, for example, 5, 10, 15, 20, 25, 30, 35, 40, 45, 50, 75, 100, 125, 150, 175, 200, 250, 300, 350, 400, 450, 500, 750, 1,000, 1,500, 3,000, 5,000 or more nucleotides in length, and/or can comprise one or more additional sequences, for example, regulatory sequences, and/or be part of a larger nucleic acid, for example, a vector. These nucleic acids can be single-stranded or double-stranded and can comprise RNA and/or DNA nucleotides, and artificial variants thereof (e.g., peptide nucleic acids). Nucleic acids encoding modulators of the invention, including antibodies or immunoreactive fragments or derivatives thereof, have preferably been isolated as described above.

b. Hybridization and Identity

As indicated, the invention further provides nucleic acids that hybridize to other nucleic acids under particular hybridization conditions. Methods for hybridizing nucleic acids are well known in the art. See, e.g., Current Protocols in Molecular Biology, John Wiley & Sons, N.Y. (1989), 6.3.1-6.3.6. For the purposes of the instant application, a moderately stringent hybridization condition uses a prewashing solution containing 5× sodium chloride/sodium citrate (SSC), 0.5% SDS, 1.0 mM EDTA (pH 8.0), hybridization buffer of about 50% formamide, 6×SSC, and a hybridization temperature of 55° C. (or other similar hybridization solutions, such as one containing about 50% formamide, with a hybridization temperature of 42° C.), and washing conditions of 60° C., in 0.5×SSC, 0.1% SDS. A stringent hybridization condition hybridizes in 6×SSC at 45° C., followed by one or more washes in 0.1× SSC, 0.2% SDS at 68° C. Furthermore, one of skill in the art can manipulate the hybridization and/or washing conditions to increase or decrease the stringency of hybridization such that nucleic acids comprising nucleotide sequences that are at least 65, 70, 75, 80, 85, 90, 95, 98 or 99% identical to each other typically remain hybridized to each other. More generally, for the purposes of the instant disclosure the term substantially identical with regard to a nucleic acid sequence may be construed as a sequence of nucleotides exhibiting at least about 85%, or 90%, or 95%, or 97% sequence identity to the reference nucleic acid sequence.

The basic parameters affecting the choice of hybridization conditions and guidance for devising suitable conditions are set forth by, for example, Sambrook, Fritsch, and Maniatis (1989, Molecular Cloning: A Laboratory Manual, Cold Spring Harbor Laboratory Press, Cold Spring Harbor, N.Y., chapters 9 and 11; and Current Protocols in Molecular Biology, 1995, Ausubel et al., eds., John Wiley & Sons, Inc., sections 2.10 and 6.3-6.4), and can be readily determined by those having ordinary skill in the art based on, for example, the length and/or base composition of the nucleic acid.

It will further be appreciated that nucleic acids may, according to the invention, be present alone or in combination with other nucleic acids, which may be homologous or heterologous. In preferred embodiments, a nucleic acid is functionally linked to expression control sequences that may be homologous or heterologous with respect to said nucleic acid. In this context the term homologous means that a nucleic acid is also functionally linked to the expression control sequence naturally and the term heterologous means that a nucleic acid is not functionally linked to the expression control sequence naturally.

c. Expression

A nucleic acid, such as a nucleic acid expressing RNA and/or protein or peptide, and an expression control sequence are functionally linked to one another, if they are covalently linked to one another in such a way that expression or transcription of said nucleic acid is under the control or under the influence of said expression control sequence. If the nucleic acid is to be translated into a functional protein, then, with an expression control sequence functionally linked to a coding sequence, induction of said expression control sequence results in transcription of said nucleic acid, without causing a frame shift in the coding sequence or said coding sequence not being capable of being translated into the desired protein or peptide.

The term expression control sequence comprises according to the invention promoters, ribosome binding sites, enhancers and other control elements that regulate transcription of a gene or translation of mRNA. In particular embodiments of the invention, the expression control sequences can be regulated. The exact structure of expression control sequences may vary as a function of the species or cell type, but generally comprises 5'-untranscribed and 5'- and 3'-untranslated sequences which are involved in initiation of transcription and translation, respectively, such as TATA box, capping sequence, CAAT sequence, and the like. More specifically, 5'-untranscribed expression control sequences comprise a promoter region that includes a promoter sequence for transcriptional control of the functionally linked nucleic acid. Expression control sequences may also comprise enhancer sequences or upstream activator sequences.

According to the invention the term promoter or promoter region relates to a nucleic acid sequence which is located upstream (5') to the nucleic acid sequence being expressed and controls expression of the sequence by providing a recognition and binding site for RNA-polymerase. The promoter region may include further recognition and binding sites for further factors that are involved in the regulation of transcription of a gene. A promoter may control the transcription of a prokaryotic or eukaryotic gene. Furthermore, a promoter may be inducible and may initiate transcription in response to an inducing agent or may be constitutive if transcription is not controlled by an inducing agent. A gene that is under the control of an inducible promoter is not expressed or only expressed to a small extent if an inducing agent is absent. In the presence of the inducing agent the gene is switched on or the level of transcription is increased. This is mediated, in general, by binding of a specific transcription factor.

Promoters which are preferred according to the invention include promoters for SP6, T3 and T7 polymerase, human U6 RNA promoter, CMV promoter, and artificial hybrid promoters thereof (e.g. CMV) where a part or parts are fused to a part or parts of promoters of genes of other cellular proteins such as e.g. human GAPDH (glyceraldehyde-3-phosphate dehydrogenase), and including or not including (an) additional intron(s).

According to the invention, the term expression is used in its most general meaning and comprises the production of RNA or of RNA and protein/peptide. It also comprises partial expression of nucleic acids. Furthermore, expression may be carried out transiently or stably.

In a preferred embodiment, a nucleic acid molecule is according to the invention present in a vector, where appropriate with a promoter, which controls expression of the nucleic acid. The term vector is used here in its most general meaning and comprises any intermediary vehicle for a nucleic acid which enables said nucleic acid, for example, to be introduced into prokaryotic and/or eukaryotic cells and, where appropriate, to be integrated into a genome. Vectors of this kind are preferably replicated and/or expressed in the cells. Vectors may comprise plasmids, phagemids, bacteriophages or viral genomes. The term plasmid as used herein generally relates to a construct of extrachromosomal genetic material, usually a circular DNA duplex, which can replicate independently of chromosomal DNA.

In practicing the present invention it will be appreciated that many conventional techniques in molecular biology, microbiology, and recombinant DNA technology are optionally used. Such conventional techniques relate to vectors, host cells and recombinant methods as defined herein. These techniques are well known and are explained in, for example, Berger and Kimmel, Guide to Molecular Cloning Techniques, Methods in Enzymology volume 152 Academic Press, Inc., San Diego, Calif.; Sambrook et al., Molecular Cloning-A Laboratory Manual (3rd Ed.), Vol. 1-3, Cold Spring Harbor Laboratory, Cold Spring Harbor, N.Y., 2000 and Current Protocols in Molecular Biology, F. M. Ausubel et al., eds., supra Other useful references, e.g. for cell isolation and culture (e.g., for subsequent nucleic acid or protein isolation) include Freshney (1994) Culture of Animal Cells, a Manual of Basic Technique, third edition, Wiley-Liss, New York and the references cited therein; Payne et al. (1992) Plant Cell and Tissue Culture in Liquid Systems John Wiley & Sons, Inc. New York, N.Y.; Gamborg and Phillips (Eds.) (1995) Plant Cell, Tissue and Organ Culture; Fundamental Methods Springer Lab Manual, Springer-Verlag (Berlin Heidelberg New York) and Atlas and Parks (Eds.) The Handbook of Microbiological Media (1993) CRC Press, Boca Raton, Fla. Methods of making nucleic acids (e.g., by in vitro amplification, purification from cells, or chemical synthesis), methods for manipulating nucleic acids (e.g., site-directed mutagenesis, by restriction enzyme digestion, ligation, etc.), and various vectors, cell lines and the like useful in manipulating and making nucleic acids are described in the above references. In addition, essentially any polynucleotide (including, e.g., labeled or biotinylated polynucleotides) can be custom or standard ordered from any of a variety of commercial sources.

Thus, in one aspect, the present invention provides recombinant host cells allowing recombinant expression of antibodies of the invention or portions thereof. Antibodies produced by expression in such recombinant host cells are referred to herein as recombinant antibodies. The present invention also provides progeny cells of such host cells, and antibodies produced by the same.

The term recombinant host cell (or simply host cell), as used herein, means a cell into which a recombinant expression vector has been introduced. It should be understood that recombinant host cell and host cell mean not only the particular subject cell but also the progeny of such a cell. Because certain modifications may occur in succeeding generations due to either mutation or environmental influences, such progeny may not, in fact, be identical to the parent cell, but are still included within the scope of the term host cell as used herein. Such cells may comprise a vector according to the invention as described above.

In another aspect, the present invention provides a method for making an antibody or portion thereof as described herein. According to one embodiment, said method comprises culturing a cell transfected or transformed with a vector as described above, and retrieving the antibody or portion thereof.

As indicated above, expression of an antibody of the invention (or fragment or variants thereof) preferably comprises expression vector(s) containing a polynucleotide that encodes the desired anti-EFNA antibody. Methods that are well known to those skilled in the art can be used to construct expression vectors comprising antibody coding sequences and appropriate transcriptional and translational control signals. These methods include, for example, in vitro recombinant DNA techniques, synthetic techniques, and in vivo genetic recombination. Embodiments of the invention, thus, provide replicable vectors comprising a nucleotide sequence encoding an anti-EFNA antibody of the invention (e.g., a whole antibody, a heavy or light chain of an antibody, a heavy or light chain variable domain of an antibody, or a portion thereof, or a heavy or light chain CDR, a single chain Fv, or fragments or variants thereof), operably linked to a promoter. In preferred embodiments such vectors may include a nucleotide sequence encoding the heavy chain of an antibody molecule (or fragment thereof), a nucleotide sequence encoding the light chain of an antibody (or fragment thereof) or both the heavy and light chain.

Once the nucleotides of the present invention have been isolated and modified according to the teachings herein, they may be used to produce selected modulators including anti-EFNA antibodies or fragments thereof.

X. Modulator Production and Purification

Using art recognized molecular biology techniques and current protein expression methodology, substantial quantities of the desired modulators may be produced. More specifically, nucleic acid molecules encoding modulators, such as antibodies obtained and engineered as described above, may be integrated into well known and commercially available protein production systems comprising various types of host cells to provide preclinical, clinical or commercial quantities of the desired pharmaceutical product. It will be appreciated that in preferred embodiments the nucleic acid molecules encoding the modulators are engineered into vectors or expression vectors that provide for efficient integration into the selected host cell and subsequent high expression levels of the desired EFNA modulator.

Preferably nucleic acid molecules encoding EFNA modulators and vectors comprising these nucleic acid molecules can be used for transfection of a suitable mammalian, plant, bacterial or yeast host cell though it will be appreciated that prokaryotic systems may be used for modulator production.

Transfection can be by any known method for introducing polynucleotides into a host cell. Methods for the introduction of heterologous polynucleotides into mammalian cells are well known in the art and include dextran-mediated transfection, calcium phosphate precipitation, polybrene-mediated transfection, protoplast fusion, electroporation, encapsulation of the polynucleotide(s) in liposomes, and direct microinjection of the DNA into nuclei. In addition, nucleic acid molecules may be introduced into mammalian cells by viral vectors. Methods of transforming mammalian cells are well known in the art. See, e.g., U.S. Pat. Nos. 4,399,216, 4,912,040, 4,740,461, and 4,959,455. Further, methods of transforming plant cells are well known in the art, including, e.g., *Agrobacterium*-mediated transformation, biolistic transformation, direct injection, electroporation and viral transformation. Methods of transforming bacterial and yeast cells are also well known in the art.

Moreover, the host cell may be co-transfected with two expression vectors of the invention, for example, the first vector encoding a heavy chain derived polypeptide and the second vector encoding a light chain derived polypeptide. The two vectors may contain identical selectable markers that enable substantially equal expression of heavy and light chain polypeptides. Alternatively, a single vector may be used which encodes, and is capable of expressing, both heavy and light chain polypeptides. In such situations, the light chain is preferably placed before the heavy chain to avoid an excess of toxic free heavy chain. The coding sequences for the heavy and light chains may comprise cDNA or genomic DNA.

a. Host-Expression Systems

A variety of host-expression vector systems, many commercially available, are compatible with the teachings herein and may be used to express the modulators of the invention. Such host-expression systems represent vehicles by which the coding sequences of interest may be expressed and subsequently purified, but also represent cells which may, when transformed or transfected with the appropriate nucleotide coding sequences, express a molecule of the invention in situ. Such systems include, but are not limited to, microorganisms such as bacteria (e.g., *E. coli, B. subtilis, streptomyces*) transformed with recombinant bacteriophage DNA, plasmid DNA or cosmid DNA expression vectors containing modulator coding sequences; yeast (e.g., *Saccharomyces, Pichia*) transfected with recombinant yeast expression vectors containing modulator coding sequences; insect cell systems infected with recombinant virus expression vectors (e.g., baculovirus) containing modulator coding sequences; plant cell systems (e.g., *Nicotiana, Arabidopsis*, duckweed, corn, wheat, potato, etc.) infected with recombinant virus expression vectors (e.g., cauliflower mosaic virus, CaMV; tobacco mosaic virus, TMV) or transfected with recombinant plasmid expression vectors (e.g., Ti plasmid) containing modulator coding sequences; or mammalian cell systems (e.g., COS, CHO, BHK, 293, 3T3 cells) harboring recombinant expression constructs containing promoters derived from the genome of mammalian cells (e.g., metallothionein promoter) or from mammalian viruses (e.g., the adenovirus late promoter; the vaccinia virus 7.5K promoter).

In bacterial systems, a number of expression vectors may be advantageously selected depending upon the use intended for the molecule being expressed. For example, when a large quantity of such a protein is to be produced, for the generation of pharmaceutical compositions of a modulator, vectors which direct the expression of high levels of fusion protein products that are readily purified may be desirable. Such vectors include, but are not limited to, the *E. coli* expression vector pUR278 (Ruther et al., EMBO 1. 2:1791 (1983)), in which the coding sequence may be ligated individually into the vector in frame with the lac Z coding region so that a fusion protein is produced; pIN vectors (Inouye & Inouye, Nucleic Acids Res. 13:3101-3109 (1985); Van Heeke & Schuster, J. Biol. Chem. 24:5503-5509 (1989)); and the like. pGEX vectors may also be used to express foreign polypeptides as fusion proteins with glutathione 5-transferase (GST). In general, such fusion proteins are soluble and can easily be purified from lysed cells by adsorption and binding to matrix glutathione agarose beads followed by elution in the presence of free glutathione. The pGEX vectors are designed to include thrombin or factor Xa protease cleavage sites so that the cloned target gene product can be released from the GST moiety.

In an insect system, Autographa californica nuclear polyhedrosis virus (AcNPV) may be used as a vector to express foreign genes. The virus grows in *Spodoptera frugiperda* cells. The coding sequences may be cloned individually into non-essential regions (for example, the polyhedrin gene) of the virus and placed under control of an AcNPV promoter (for example, the polyhedrin promoter).

In mammalian host cells, a number of viral-based expression systems may be used to introduce the desired nucleotide sequence. In cases where an adenovirus is used as an expression vector, the coding sequence of interest may be ligated to an adenovirus transcription/translation control complex, e.g., the late promoter and tripartite leader sequence. This chimeric gene may then be inserted in the adenovirus genome by in vitro or in vivo recombination. Insertion in a non-essential region of the viral genome (e.g., region E1 or E3) will result in a recombinant virus that is viable and capable of expressing the molecule in infected hosts (e.g., see Logan & Shenk, Proc. Natl. Acad. Sci. USA 8 1:355-359 (1984)). Specific initiation signals may also be required for efficient translation of inserted coding sequences. These signals include the ATG initiation codon and adjacent sequences. Furthermore, the initiation codon must be in phase with the reading frame of the desired coding sequence to ensure translation of the entire insert. These exogenous translational control signals and initiation codons can be of a variety of origins, both natural and synthetic. The efficiency of expression may be enhanced by the inclusion of appropriate transcription enhancer elements, transcription terminators, etc. (see, e.g., Bittner et al., Methods in Enzymol. 153:51-544 (1987)). Thus, compatible mammalian cell lines available as hosts for expression are well known in the art and include many immortalized cell lines available from the American Type Culture Collection (ATCC). These include, inter alia, Chinese hamster ovary (CHO) cells, NS0 cells, SP2 cells, HEK-293T cells, 293 Freestyle cells (Life Technologies), NIH-3T3 cells, HeLa cells, baby hamster kidney (BHK) cells, African green monkey kidney cells (COS), human hepatocellular carcinoma cells (e.g., Hep G2), A549 cells, and a number of other cell lines.

For long-term, high-yield production of recombinant proteins stable expression is preferred. Accordingly, cell lines that stably express the selected modulator may be engineered using standard art recognized techniques. Rather than using expression vectors that contain viral origins of replication, host cells can be transformed with DNA controlled by appropriate expression control elements (e.g., promoter, enhancer, sequences, transcription terminators, polyadenylation sites, etc.), and a selectable marker. Following the introduction of the foreign DNA, engineered cells may be allowed to grow for 1-2 days in an enriched media, and then are switched to a selective media. The selectable marker in the recombinant plasmid confers resistance to the selection and allows cells to stably integrate the plasmid into their chromosomes and grow to form foci which in turn can be cloned and expanded into cell lines. This method may advantageously be used to engineer cell lines which express the molecule. Such engineered cell lines may be particularly useful in screening and evaluation of compositions that interact directly or indirectly with the molecule.

A number of selection systems are well known in the art and may be used including, but not limited to, the herpes simplex virus thymidine kinase (Wigler et al., Cell 11:223 (1977)), hypoxanthineguanine phosphoribosyltransferase (Szybalska & Szybalski, Proc. Natl. Acad. Sci. USA 48:202 (1992)), and adenine phosphoribosyltransferase (Lowy et al., Cell 22:8 17 (1980)) genes can be employed in tk-, hgprt- or aprt-cells, respectively. Also, antimetabolite resistance can be used as the basis of selection for the following genes: dhfr, which confers resistance to methotrexate (Wigler et al., Natl. Acad. Sci. USA 77:357 (1980); O'Hare et al., Proc. Natl. Acad. Sci. USA 78:1527 (1981)); gpt, which confers resistance to mycophenolic acid (Mulligan & Berg, Proc. Natl. Acad. Sci. USA 78:2072 (1981)); neo, which confers resistance to the aminoglycoside G-418 (Clinical Pharmacy 12:488-505; Wu and Wu, Biotherapy 3:87-95 (1991); Tolstoshev, Ann. Rev. Pharmacol. Toxicol. 32:573-596 (1993); Mulligan, Science 260:926-932 (1993); and Morgan and Anderson, Ann. Rev. Biochem. 62: 191-217 (1993); TIB TECH 11(5):155-2 15 (May, 1993)); and hygro, which confers resistance to hygromycin (Santerre et al., Gene 30:147 (1984)). Methods commonly known in the art of recombinant DNA technology may be routinely applied to select the desired recombinant clone, and such methods are described, for example, in Ausubel et al. (eds.), Current Protocols in Molecular Biology, John Wiley & Sons, NY (1993); Kriegler, Gene Transfer and Expression, A Laboratory Manual, Stockton Press, NY (1990); and in Chapters 12 and 13, Dracopoli et al. (eds), Current Protocols in Human Genetics, John Wiley & Sons, NY (1994); Colberre-Garapin et al., J. Mol. Biol. 150:1 (1981). It will be appreciated that one particularly preferred method of establishing a stable, high yield cell line comprises the glutamine synthetase gene expression system (the GS system) which provides an efficient approach for enhancing expression under certain conditions. The GS system is discussed in whole or part in connection with EP patents 0 216 846, 0 256 055, 0 323 997 and 0 338 841 each of which is incorporated herein by reference.

In addition, a host cell strain may be chosen which modulates the expression of the inserted sequences, or modifies and processes the gene product in the specific fashion desired. Such modifications (e.g., glycosylation) and processing (e.g., cleavage) of protein products may be important for the function and/or purification of the protein. Different host cells have characteristic and specific mechanisms for the post-translational processing and modification of proteins and gene products. As known in the art appropriate cell lines or host systems can be chosen to ensure the desired modification and processing of the expressed polypeptide. To this end, eukaryotic host cells that possess the cellular machinery for proper processing of the primary transcript, glycosylation, and phosphorylation of the gene product are particularly effective for use in the instant invention. Accordingly, particularly preferred mammalian host cells include, but are not limited to, CHO, VERY, BHK, HeLa, COS, NS0, MDCK, 293, 3T3, W138, as well as breast cancer cell lines such as, for example, BT483, Hs578T, HTB2, BT2O and T47D, and normal mammary gland cell line such as, for example, CRL7O3O and HsS78Bst. Depending on the modulator and the selected production system, those of skill in the art may easily select and optimize appropriate host cells for efficient expression of the modulator.

b. Chemical Synthesis

Besides the aforementioned host cell systems, it will be appreciated that the modulators of the invention may be chemically synthesized using techniques known in the art (e.g., see Creighton, 1983, Proteins: Structures and Molecular Principles, W.H. Freeman & Co., N.Y., and Hunkapiller, M., et al., 1984, Nature 310:105-111). For example, a peptide corresponding to a polypeptide fragment of the invention can be synthesized by use of a peptide synthesizer. Furthermore, if desired, nonclassical amino acids or chemical amino acid analogs can be introduced as a substitution or addition into a polypeptide sequence. Non-classical amino acids include, but are not limited to, to the D-isomers of the common amino acids, 2,4-diaminobutyric acid, a-amino isobutyric acid, 4-aminobutyric acid, Abu, 2-amino butyric acid, g-Abu, e-Ahx, 6-amino hexanoic acid, Aib, 2-amino isobutyric acid, 3-amino propionic acid, ornithine, norleucine, norvaline, hydroxyproline, sarcosine, citrulline, homocitrulline, cysteic acid, t-butylglycine, t-butylalanine, phenylglycine, cyclohexylalanine, b-alanine, fluoro-amino acids, designer amino acids such as b-methyl amino acids, Ca-methyl amino acids, Na-methyl amino acids, and amino acid analogs in general. Furthermore, the amino acid can be D (dextrorotary) or L (levorotary).

c. Transgenic Systems

The EFNA modulators of the invention also can be produced transgenically through the generation of a mammal or plant that is transgenic for the immunoglobulin heavy and light chain sequences (or fragments or derivatives or variants thereof) of interest and production of the desired compounds in a recoverable form. In connection with the transgenic production in mammals, anti-EFNA antibodies, for example, can be produced in, and recovered from, the milk of goats, cows, or other mammals. See, e.g., U.S. Pat. Nos. 5,827,690, 5,756, 687, 5,750,172, and 5,741,957. In some embodiments, non-human transgenic animals that comprise human immunoglobulin loci are immunized with EFNA or an immunogenic portion thereof, as described above. Methods for making antibodies in plants are described, e.g., in U.S. Pat. Nos. 6,046,037 and 5,959,177.

In accordance with the teachings herein non-human transgenic animals or plants may be produced by introducing one or more nucleic acid molecules encoding an EFNA modulator of the invention into the animal or plant by standard transgenic techniques. See Hogan and U.S. Pat. No. 6,417,429. The transgenic cells used for making the transgenic animal can be embryonic stem cells or somatic cells or a fertilized egg. The transgenic non-human organisms can be chimeric, nonchimeric heterozygotes, and nonchimeric homozygotes. See, e.g., Hogan et al., Manipulating the Mouse Embryo: A Laboratory Manual 2nd ed., Cold Spring Harbor Press (1999); Jackson et al., Mouse Genetics and Transgenics: A Practical Approach, Oxford University Press (2000); and Pinkert, Transgenic Animal Technology: A Laboratory Handbook, Academic Press (1999). In some embodiments, the transgenic non-human animals have a targeted disruption and replacement by a targeting construct that encodes, for example, a heavy chain and/or a light chain of interest. In one embodiment, the transgenic animals comprise and express nucleic acid molecules encoding heavy and light chains that specifically bind to EFNA. While anti-EFNA antibodies may be made in any transgenic animal, in particularly preferred embodiments the non-human animals are mice, rats, sheep, pigs, goats, cattle or horses. In further embodiments the nonhuman transgenic animal expresses the desired pharmaceutical product in blood, milk, urine, saliva, tears, mucus and other bodily fluids from which it is readily obtainable using art recognized purification techniques.

It is likely that modulators, including antibodies, expressed by different cell lines or in transgenic animals will have different glycosylation patterns from each other. However, all modulators encoded by the nucleic acid molecules provided herein, or comprising the amino acid sequences provided herein are part of the instant invention, regardless of the glycosylation state of the molecule, and more generally, regardless of the presence or absence of post-translational modification(s). In addition the invention encompasses modulators that are differentially modified during or after translation, e.g., by glycosylation, acetylation, phosphorylation, amidation, derivatization by known protecting/blocking groups, proteolytic cleavage, linkage to an antibody molecule or other cellular ligand, etc. Any of numerous chemical modifications may be carried out by known techniques, including but not limited, to specific chemical cleavage by cyanogen bromide, trypsin, chymotrypsin, papain, V8 protease, $NaBH_4$, acetylation, formylation, oxidation, reduction, metabolic synthesis in the presence of tunicamycin, etc. Various post-translational modifications are also encompassed by the invention include, for example, e.g., N-linked or O-linked carbohydrate chains, processing of N-terminal or C-terminal ends), attachment of chemical moieties to the amino acid backbone, chemical modifications of N-linked or O-linked carbohydrate chains, and addition or deletion of an N-terminal methionine residue as a result of prokaryotic host cell expression. Moreover, as set forth in the text and Examples below the polypeptides may also be modified with a detectable label, such as an enzymatic, fluorescent, radioisotopic or affinity label to allow for detection and isolation of the modulator.

d. Purification

Once a modulator of the invention has been produced by recombinant expression or any one of the other techniques disclosed herein, it may be purified by any method known in the art for purification of immunoglobulins, or more generally by any other standard technique for the purification of proteins. In this respect the modulator may be isolated. As used herein, an isolated EFNA modulator is one that has been identified and separated and/or recovered from a component of its natural environment. Contaminant components of its natural environment are materials that would interfere with diagnostic or therapeutic uses for the polypeptide and may include enzymes, hormones, and other proteinaceous or non-proteinaceous solutes. Isolated modulators include a modulator in situ within recombinant cells because at least one component of the polypeptide's natural environment will not be present.

When using recombinant techniques, the EFNA modulator (e.g. an anti-EFNA antibody or derivative or fragment thereof) can be produced intracellularly, in the periplasmic space, or directly secreted into the medium. If the desired molecule is produced intracellularly, as a first step, the particulate debris, either host cells or lysed fragments, may be removed, for example, by centrifugation or ultrafiltration. For example, Carter, et al., Bio/Technology 10:163 (1992) describe a procedure for isolating antibodies that are secreted to the periplasmic space of E. coli. Briefly, cell paste is thawed in the presence of sodium acetate (pH 3.5), EDTA, and phenylmethylsulfonylfluoride (PMSF) over about 30 minutes. Cell debris can be removed by centrifugation. Where the antibody is secreted into the medium, supernatants from such expression systems are generally first concentrated using a commercially available protein concentration filter, for example, an Amicon or Millipore Pellicon ultrafiltration unit. A protease inhibitor such as PMSF may be included in any of the foregoing steps to inhibit proteolysis and antibiotics may be included to prevent the growth of adventitious contaminants.

The modulator (e.g., fc-EFNA or anti-EFNA antibody) composition prepared from the cells can be purified using, for example, hydroxylapatite chromatography, gel electrophoresis, dialysis, and affinity chromatography, with affinity chromatography being the preferred purification technique. The suitability of protein A as an affinity ligand depends on the species and isotype of any immunoglobulin Fc domain that is present in the selected construct. Protein A can be used to purify antibodies that are based on human IgG1, IgG2 or IgG4 heavy chains (Lindmark, et al., J Immunol Meth 62:1 (1983)). Protein G is recommended for all mouse isotypes and for human IgG3 (Guss, et al., EMBO J 5:1567 (1986)). The matrix to which the affinity ligand is attached is most often agarose, but other matrices are available. Mechanically stable matrices such as controlled pore glass or poly(styrenedivinyl)benzene allow for faster flow rates and shorter processing times than can be achieved with agarose. Where the antibody comprises a $C_H3$ domain, the Bakerbond ABX™ resin (J. T. Baker; Phillipsburg, N.J.) is useful for purification. Other techniques for protein purification such as fractionation on an ion-exchange column, ethanol precipitation, reverse phase HPLC, chromatography on silica, chromatography on heparin, sepharose chromatography on an anion or cation exchange resin (such as a polyaspartic acid column), chromatofocusing, SDS-PAGE and ammonium sulfate precipitation are also available depending on the antibody to be recovered. In particularly preferred embodiments the modulators of the instant invention will be purified, at least in part, using Protein A or Protein G affinity chromatography.

XI. Conjugated EFNA Modulators

Once the modulators of the invention have been purified according to the teachings herein they may be linked with, fused to, conjugated to (e.g., covalently or non-covalently) or otherwise associated with pharmaceutically active or diagnostic moieties or biocompatible modifiers. As used herein the term conjugate will be used broadly and held to mean any molecule associated with the disclosed modulators regardless of the method of association. In this respect it will be understood that such conjugates may comprise peptides, polypeptides, proteins, polymers, nucleic acid molecules, small molecules, mimetic agents, synthetic drugs, inorganic molecules, organic molecules and radioisotopes. Moreover, as indicated above the selected conjugate may be covalently or non-covalently linked to the modulator and exhibit various molar ratios depending, at least in part, on the method used to effect the conjugation.

In preferred embodiments it will be apparent that the modulators of the invention may be conjugated or associated with proteins, polypeptides or peptides that impart selected characteristics (e.g., biotoxins, biomarkers, purification tags, etc.). More generally, in selected embodiments the present invention encompasses the use of modulators or fragments thereof recombinantly fused or chemically conjugated (including both covalent and non-covalent conjugations) to a heterologous protein or polypeptide wherein the polypeptide comprises at least 10, at least 20, at least 30, at least 40, at least 50, at least 60, at least 70, at least 80, at least 90 or at least 100 amino acids. The construct does not necessarily need to be directly linked, but may occur through linker sequences. For example, antibodies may be used to target heterologous polypeptides to particular cell types expressing EFNA, either in vitro or in vivo, by fusing or conjugating the modulators of the present invention to antibodies specific for particular cell surface receptors. Moreover, modulators fused or conjugated to heterologous polypeptides may also be used in in vitro immunoassays and may be compatible with purification methodology known in the art. See e.g., International publication No. WO 93/21232; European Patent No. EP 439,095; Naramura et al., 1994, Immunol. Lett. 39:91-99; U.S. Pat. No. 5,474,981; Gillies et al., 1992, PNAS 89:1428-1432; and Fell et al., 1991, J. Immunol. 146:2446-2452.

a. Biocompatible Modifiers

In a preferred embodiment, the modulators of the invention may be conjugated or otherwise associated with biocompatible modifiers that may be used to adjust, alter, improve or moderate modulator characteristics as desired. For example, antibodies or fusion constructs with increased in vivo half-lives can be generated by attaching relatively high molecular weight polymer molecules such as commercially available polyethylene glycol (PEG) or similar biocompatible polymers. Those skilled in the art will appreciate that PEG may be obtained in many different molecular weight and molecular configurations that can be selected to impart specific properties to the antibody (e.g. the half-life may be tailored). PEG can be attached to modulators or antibody fragments or derivatives with or without a multifunctional linker either through site-specific conjugation of the PEG to the N- or C-terminus of said antibodies or antibody fragments or via epsilon-amino groups present on lysine residues. Linear or branched polymer derivatization that results in minimal loss of biological activity may be used. The degree of conjugation can be closely monitored by SDS-PAGE and mass spectrometry to ensure optimal conjugation of PEG molecules to antibody molecules. Unreacted PEG can be separated from antibody-PEG conjugates by, e.g., size exclusion or ion-exchange chromatography. In a similar manner, the disclosed modulators can be conjugated to albumin in order to make the antibody or antibody fragment more stable in vivo or have a longer half life in vivo. The techniques are well known in the art, see e.g., International Publication Nos. WO 93/15199, WO 93/15200, and WO 01/77137; and European Patent No. 0 413, 622. Other biocompatible conjugates are evident to those of ordinary skill and may readily be identified in accordance with the teachings herein.

b. Diagnostic or Detection Agents

In other preferred embodiments, modulators of the present invention, or fragments or derivatives thereof, are conjugated to a diagnostic or detectable agent, marker or reporter which may be a biological molecule (e.g., a peptide or nucleotide), a small molecule, flourophore, or radioisotope. Labeled modulators can be useful for monitoring the development or progression of a hyperproliferative disorder or as part of a clinical testing procedure to determine the efficacy of a particular therapy including the disclosed modulators (i.e. theragnostics). Such markers or reporters may also be useful in purifying the selected modulator, separating or isolating TIC or in preclinical procedures or toxicology studies.

Such diagnosis and detection can be accomplished by coupling the modulator to detectable substances including, but not limited to, various enzymes comprising for example horseradish peroxidase, alkaline phosphatase, beta-galactosidase, or acetylcholinesterase; prosthetic groups, such as but not limited to streptavidinlbiotin and avidin/biotin; fluorescent materials, such as but not limited to, umbelliferone, fluorescein, fluorescein isothiocynate, rhodamine, dichlorotriazinylamine fluorescein, dansyl chloride or phycoerythrin; luminescent materials, such as but not limited to, luminol; bioluminescent materials, such as but not limited to, luciferase, luciferin, and aequorin; radioactive materials, such as but not limited to iodine ($^{131}$I, $^{125}$I, $^{123}$I, $^{121}$I,), carbon ($^{14}$C), sulfur ($^{35}$S), tritium ($^{3}$H), indium ($^{115}$In, $^{113}$In, $^{112}$In, $^{111}$In), and technetium ($^{99}$Tc), thallium ($^{201}$Ti), gallium ($^{68}$Ga, $^{67}$Ga), palladium ($^{103}$Pd), molybdenum ($^{99}$Mo), xenon ($^{133}$Xe), fluorine ($^{18}$F), $^{153}$Sm, $^{177}$Lu, $^{159}$Gd, 149Pm, $^{140}$La, $^{175}$Yb, $^{166}$Ho, $^{90}$Y, $^{47}$Sc, $^{186}$Re, $^{188}$Re, $^{142}$Pr, $^{105}$Rh, $^{97}$Ru, $^{68}$Ge, $^{57}$Co, $^{65}$Zn, $^{85}$Sr, $^{32}$P, $^{153}$Gd, $^{169}$Yb, $^{51}$Cr, $^{54}$Mn, $^{75}$Se, $^{113}$Sn, and $^{117}$Tin; positron emitting metals using various positron emission tomographies, noradioactive paramagnetic metal ions, and molecules that are radiolabeled or conjugated to specific radioisotopes. In such embodiments appropriate detection methodology is well known in the art and readily available from numerous commercial sources.

As indicated above, in other embodiments the modulators or fragments thereof can be fused to marker sequences, such as a peptide or fluorophore to facilitate purification or diagnostic procedures such as immunohistochemistry or FACs. In preferred embodiments, the marker amino acid sequence is a hexa-histidine (SEQ ID NO: 166) peptide, such as the tag provided in a pQE vector (Qiagen), among others, many of which are commercially available. As described in Gentz et al., 1989, Proc. Natl. Acad. Sci. USA 86:821-824, for instance, hexa-histidine (SEQ ID NO: 166) provides for convenient purification of the fusion protein. Other peptide tags useful for purification include, but are not limited to, the hemagglutinin "HA" tag, which corresponds to an epitope derived from the influenza hemagglutinin protein (Wilson et al., 1984, Cell 37:767) and the "flag" tag (U.S. Pat. No. 4,703,004).

c. Therapeutic Moieties

As previously alluded to the modulators or fragments or derivatives thereof may also be conjugated, linked or fused to or otherwise associated with a therapeutic moiety such as anti-cancer agents, a cytotoxin or cytotoxic agent, e.g., a cytostatic or cytocidal agent, a therapeutic agent or a radioactive metal ion, e.g., alpha or beta-emitters. As used herein a cytotoxin or cytotoxic agent includes any agent or therapeutic moiety that is detrimental to cells and may inhibit cell growth or survival. Examples include paclitaxel, cytochalasin B, gramicidin D, ethidium bromide, emetine, mitomycin, etoposide, tenoposide, vincristine, vinblastine, colchicin, doxorubicin, daunorubicin, dihydroxy anthracin, maytansinoids such as DM-1 and DM-4 (Immunogen, Inc.), dione, mitoxantrone, mithramycin, actinomycin D, 1-dehydrotestosterone, glucocorticoids, procaine, tetracaine, lidocaine, propranolol, puromycin, epirubicin, and cyclophosphamide and analogs or homologs thereof. Additional cytoxins comprise auristatins, including monomethyl auristatin E (MMAE) and monomethyl auristatin F (MMAF) (Seattle Genetics, Inc.), amanitins such as alpha-amanitin, beta-amanitin, gamma-amanitin or epsilon-amanitin (Heidelberg Pharma AG), DNA minor groove binding agents such as duocarmycin derivatives (Syntarga, B.V.) and modified pyrrolobenzodiazepine dimers (PBDs, Spirogen, Ltd). Furthermore, in one embodiment the EFNA modulators of the instant invention may be associated with anti-CD3 binding molecules to recruit cytotoxic T-cells and have them target the tumor initiating cells (BiTE technology; see e.g., Fuhrmann, S. et. al. Annual Meeting of AACR Abstract No. 5625 (2010) which is incorporated herein by reference).

Additional compatible therapeutic moieties comprise cytotoxic agents including, but are not limited to, antimetabolites (e.g., methotrexate, 6-mercaptopurine, 6-thioguanine, cytarabine, 5-fluorouracil decarbazine), alkylating agents (e.g., mechlorethamine, thioepa chlorambucil, melphalan, carmustine (BCNU) and lomustine (CCNU), cyclophosphamide, busulfan, dibromomannitol, streptozotocin, mitomycin C, and cisdichlorodiamine platinum (II) (DDP) cisplatin), anthracyclines (e.g., daunorubicin (formerly daunomycin) and doxorubicin), antibiotics (e.g., dactinomycin (formerly actinomycin), bleomycin, mithramycin, and anthramycin (AMC)), and anti-mitotic agents (e.g., vincristine and vinblastine). A more extensive list of therapeutic moieties can be found in PCT publication WO 03/075957 and U.S.P.N. 2009/0155255 each of which is incorporated herein by reference.

The selected modulators can also be conjugated to therapeutic moieties such as radioactive materials or macrocyclic chelators useful for conjugating radiometal ions (see above for examples of radioactive materials). In certain embodiments, the macrocyclic chelator is 1,4,7,10-tetraazacyclododecane-N,N',N'',N'''-tetraacetic acid (DOTA) which can be attached to the antibody via a linker molecule. Such linker molecules are commonly known in the art and described in Denardo et al., 1998, Clin Cancer Res. 4:2483; Peterson et al., 1999, Bioconjug. Chem. 10:553; and Zimmerman et al., 1999, Nucl. Med. Biol. 26:943.

Exemplary radioisotopes that may be compatible with this aspect of the invention include, but are not limited to, iodine ($^{131}$I, $^{125}$I, $^{123}$I, $^{121}$I), carbon ($^{14}$C) copper ($^{62}$Cu, $^{64}$Cu, $^{67}$Cu), sulfur ($^{35}$S), tritium ($^{3}$H), indium ($^{115}$In, $^{113}$In, $^{112}$In, $^{111}$In,), bismuth ($^{212}$Bi, $^{213}$Bi), technetium ($^{99}$Tc), thallium ($^{201}$Ti), gallium ($^{68}$Ga, $^{67}$Ga), palladium ($^{103}$Pd), molybdenum ($^{99}$Mo), xenon ($^{133}$Xe), fluorine ($^{18}$F), $^{153}$Sm, $^{177}$Lu, $^{159}$Gd, $^{149}$Pm, $^{140}$La, $^{175}$Yb, $^{166}$Ho, $^{90}$Y, $^{47}$Sc, $^{186}$Re, $^{188}$Re, $^{142}$Pr, $^{105}$Rh, $^{97}$Ru, $^{68}$Ge, $^{57}$Co, $^{65}$Zn, $^{85}$Sr, $^{32}$P, $^{153}$Gd, $^{169}$Yb, $^{51}$Cr, $^{54}$Mn, $^{75}$Se, $^{113}$Sn, $^{117}$Tin, $^{225}$Ac, $^{76}$Br, and $^{211}$At. Other radionuclides are also available as diagnostic and therapeutic agents, especially those in the energy range of 60 to 4,000 keV. Depending on the condition to be treated and the desired therapeutic profile, those skilled in the art may readily select the appropriate radioisotope for use with the disclosed modulators.

EFNA modulators of the present invention may also be conjugated to a therapeutic moiety or drug that modifies a given biological response (e.g., biological response modifiers or BRMs). That is, therapeutic agents or moieties compatible with the instant invention are not to be construed as limited to classical chemical therapeutic agents. For example, in particularly preferred embodiments the drug moiety may be a protein or polypeptide or fragment thereof possessing a desired biological activity. Such proteins may include, for example, a toxin such as abrin, ricin A, Onconase (or another cytotoxic RNase), pseudomonas exotoxin, cholera toxin, or diphtheria toxin; a protein such as tumor necrosis factor, α-interferon, β-interferon, nerve growth factor, platelet derived growth factor, tissue plasminogen activator, an apoptotic agent, e.g., TNF-α, TNF-β, AIM I (see, International Publication No. WO 97/33899), AIM II (see, International Publication No. WO 97/34911), Fas Ligand (Takahashi et al., 1994, J. Immunol., 6:1567), and VEGI (see, International Publication No. WO 99/23105), a thrombotic agent or an anti-angiogenic agent, e.g., angiostatin or endostatin; or, a biological response modifier such as, for example, a lymphokine (e.g., interleukin-1 ("IL-1"), interleukin-2 ("IL-2"), interleukin-6 ("IL-6"), granulocyte macrophage colony stimulating factor ("GM-CSF"), and granulocyte colony stimulating factor ("G-CSF")), or a growth factor (e.g., growth hormone ("GH")). As set forth above, methods for fusing or conjugating modulators to polypeptide moieties are known in the art. In addition to the previously disclosed subject references see, e.g., U.S. Pat. Nos. 5,336,603; 5,622,929; 5,359,046; 5,349,053; 5,447,851, and 5,112,946; EP 307,434; EP 367,166; PCT Publications WO 96/04388 and WO 91/06570; Ashkenazi et al., 1991, PNAS USA 88:10535; Zheng et al., 1995, J Immunol 154:5590; and Vil et al., 1992, PNAS USA 89:11337 each of which is incorporated herein by reference. The association of a modulator with a moiety does not necessarily need to be direct, but may occur through linker sequences. Such linker molecules are commonly known in the art and described in Denardo et al., 1998, Clin Cancer Res 4:2483; Peterson et al., 1999, Bioconjug Chem 10:553; Zimmerman et al., 1999, Nucl Med Biol 26:943; Garnett, 2002, Adv Drug Deliv Rev 53:171 each of which is incorporated herein.

More generally, techniques for conjugating therapeutic moieties or cytotoxic agents to modulators are well known. Moieties can be conjugated to modulators by any art-recognized method, including, but not limited to aldehyde/Schiff linkage, sulphydryl linkage, acid-labile linkage, cis-aconityl linkage, hydrazone linkage, enzymatically degradable linkage (see generally Garnett, 2002, Adv Drug Deliv Rev 53:171). Also see, e.g., Amon et al., "Monoclonal Antibodies For Immunotargeting Of Drugs In Cancer Therapy", in Monoclonal Antibodies And Cancer Therapy, Reisfeld et al. (eds.), pp. 243-56 (Alan R. Liss, Inc. 1985); Hellstrom et al., "Antibodies For Drug Delivery", in Controlled Drug Delivery (2nd Ed.), Robinson et al. (eds.), pp. 623-53 (Marcel Dekker, Inc. 1987); Thorpe, "Antibody Carriers Of Cytotoxic Agents In Cancer Therapy: A Review", in Monoclonal Antibodies '84: Biological And Clinical Applications, Pinchera et al. (eds.), pp. 475-506 (1985); "Analysis, Results, And Future Prospective Of The Therapeutic Use Of Radiolabeled Antibody In Cancer Therapy", in Monoclonal Antibodies For Cancer Detection And Therapy, Baldwin et al. (eds.), pp. 303-16 (Academic Press 1985), and Thorpe et al., 1982, Immunol. Rev. 62:119. In preferred embodiments an EFNA modulator that is conjugated to a therapeutic moiety or cytotoxic agent may be internalized by a cell upon binding to an EFNA molecule associated with the cell surface thereby delivering the therapeutic payload.

XII. Diagnostics and Screening a. Diagnostics

As indicated, the present invention provides in vitro or in vivo methods for detecting, diagnosing or monitoring hyperproliferative disorders and methods of screening cells from a patient to identify tumorigenic cells including TPCs. Such methods include identifying an individual having cancer for treatment or monitoring progression of a cancer comprising contacting the patient or a sample obtained from a patient with a selected EFNA modulator as described herein and detecting presence or absence, or level of association of the modulator to bound or free ephrin-A ligand in the sample. When the modulator comprises an antibody or immunologically active fragment thereof the association with particular EFNA in the sample likely denotes that the sample may contain tumor perpetuating cells (e.g., a cancer stem cells) indicating that the individual having cancer may be effectively treated with an EFNA modulator as described herein. The methods may further comprise a step of comparing the level of binding to a control. Conversely, when the selected modulator is Fc-EFNA the binding properties of the selected ephrin-A ligand may be exploited and monitored (directly or indirectly, in vivo or in vitro) when in contact with the sample to provide the desired information. Other diagnostic or theragnostic methods compatible with the teachings herein are well known in the art and can be practiced using commercial materials such as dedicated reporting systems.

In a particularly preferred embodiment the modulators of the instant invention may be used to detect and quantify EFNA levels in a patient sample (e.g., plasma or blood) which may, in turn, be used to detect, diagnose or monitor EFNA associated disorders including hyperproliferative disorders. One such embodiment is set forth in Example 17 below which provides for the detection of EFNA in plasma samples.

Exemplary compatible assay methods include radioimmunoassays, enzyme immunoassays, competitive-binding assays, fluorescent immunoassay, immunoblot assays, Western Blot analysis, flow cytometry assays, and ELISA assays. More generally detection of EFNA in a biological sample or the measurement of EFNA enzymatic activity (or inhibition thereof) may be accomplished using any art-known assay. Compatible in vivo theragnostics or diagnostics may comprise art recognized imaging or monitoring techniques such as magnetic resonance imaging (MRI), computerized tomography (e.g. CAT scan), positron tomography (e.g., PET scan) radiography, ultrasound, etc. Those skilled in the art will readily be able to recognize and implement appropriate detection, monitoring or imaging techniques (often comprising commercially available sources) based on the etiology, pathological manifestation or clinical progression of the disorder.

In another embodiment, the invention provides a method of analyzing cancer progression and/or pathogenesis in-vivo. In another embodiment, analysis of cancer progression and/or pathogenesis in-vivo comprises determining the extent of tumor progression. In another embodiment, analysis comprises the identification of the tumor. In another embodiment, analysis of tumor progression is performed on the primary tumor. In another embodiment, analysis is performed over time depending on the type of cancer as known to one skilled in the art. In another embodiment, further analysis of secondary tumors originating from metastasizing cells of the primary tumor is analyzed in-vivo. In another embodiment, the size and shape of secondary tumors are analyzed. In some embodiments, further ex-vivo analysis is performed.

In another embodiment, the invention provides a method of analyzing cancer progression and/or pathogenesis in-vivo including determining cell metastasis. In yet another embodiment, analysis of cell metastasis comprises determination of progressive growth of cells at a site that is discontinuous from the primary tumor. In another embodiment, the site of cell metastasis analysis comprises the route of neoplastic spread. In some embodiment, cells can disperse via blood vasculature, lymphatics, within body cavities or combinations thereof. In another embodiment, cell metastasis analysis is performed in view of cell migration, dissemination, extravasation, proliferation or combinations thereof.

In certain examples, the tumorigenic cells in a subject or a sample from a subject may be assessed or characterized using the disclosed modulators prior to therapy or regimen to establish a baseline. In other examples the sample is derived from a subject that was treated. In some examples the sample is taken from the subject at least about 1, 2, 4, 6, 7, 8, 10, 12, 14, 15, 16, 18, 20, 30, 60, 90 days, 6 months, 9 months, 12 months, or >12 months after the subject begins or terminates treatment. In certain examples, the tumorigenic cells are assessed or characterized after a certain number of doses (e.g., after 2, 5, 10, 20, 30 or more doses of a therapy). In other examples, the tumorigenic cells are characterized or assessed after 1 week, 2 weeks, 1 month, 2 months, 1 year, 2 years, 3 years, 4 years or more after receiving one or more therapies.

In another aspect, and as discussed in more detail below, the present invention provides kits for detecting, monitoring or diagnosing a hyperproliferative disorder, identifying individual having such a disorder for possible treatment or monitoring progression (or regression) of the disorder in a patient, wherein the kit comprises a modulator as described herein, and reagents for detecting the impact of the modulator on a sample.

b. Screening

The EFNA modulators and cells, cultures, populations and compositions comprising the same, including progeny thereof, can also be used to screen for or identify compounds or agents (e.g., drugs) that affect a function or activity of tumor initiating cells or progeny thereof by interacting with an ephrin-A ligand (e.g., the polypeptide or genetic components thereof). The invention therefore further provides systems and methods for evaluation or identification of a compound or agent that can affect a function or activity tumor initiating cells or progeny thereof by associating with EFNA or its substrates. Such compounds and agents can be drug candidates that are screened for the treatment of a hyperproliferative disorder, for example. In one embodiment, a system or method includes tumor initiating cells exhibiting EFNA and a compound or agent (e.g., drug), wherein the cells and compound or agent (e.g., drug) are in contact with each other.

The invention further provides methods of screening and identifying EFNA modulators or agents and compounds for altering an activity or function of tumor initiating cells or progeny cells. In one embodiment, a method includes contacting tumor initiating cells or progeny thereof with a test agent or compound; and determining if the test agent or compound modulates an activity or function of the ephrin-A ligand associated tumor initiating cells.

A test agent or compound modulating an EFNA related activity or function of such tumor initiating cells or progeny thereof within the population identifies the test agent or compound as an active agent. Exemplary activity or function that can be modulated include changes in cell morphology, expression of a marker, differentiation or dedifferentiation, maturation, proliferation, viability, apoptosis or cell death neuronal progenitor cells or progeny thereof.

Contacting, when used in reference to cells or a cell culture or method step or treatment, means a direct or indirect interaction between the composition (e.g., an ephrin-A ligand associated cell or cell culture) and another referenced entity. A particular example of a direct interaction is physical interaction. A particular example of an indirect interaction is where a composition acts upon an intermediary molecule which in turn acts upon the referenced entity (e.g., cell or cell culture).

In this aspect of the invention modulates indicates influencing an activity or function of tumor initiating cells or progeny cells in a manner compatible with detecting the effects on cell activity or function that has been determined to be relevant to a particular aspect (e.g., metastasis or proliferation) of the tumor initiating cells or progeny cells of the invention. Exemplary activities and functions include, but are not limited to, measuring morphology, developmental markers, differentiation, proliferation, viability, cell respiration, mitochondrial activity, membrane integrity, or expression of markers associated with certain conditions. Accordingly, a compound or agent (e.g., a drug candidate) can be evaluated for its effect on tumor initiating cells or progeny cells, by contacting such cells or progeny cells with the compound or agent and measuring any modulation of an activity or function of tumor initiating cells or progeny cells as disclosed herein or would be known to the skilled artisan.

Methods of screening and identifying agents and compounds include those suitable for high throughput screening, which include arrays of cells (e.g., microarrays) positioned or placed, optionally at pre-determined locations or addresses. High-throughput robotic or manual handling methods can probe chemical interactions and determine levels of expression of many genes in a short period of time. Techniques have been developed that utilize molecular signals (e.g., fluorophores) and automated analyses that process information at a very rapid rate (see, e.g., Pinhasov et al., Comb. Chem. High Throughput Screen. 7:133 (2004)). For example, microarray technology has been extensively utilized to probe the interactions of thousands of genes at once, while providing information for specific genes (see, e.g., Mocellin and Rossi, Adv. Exp. Med. Biol. 593:19 (2007)).

Such screening methods (e.g., high-throughput) can identify active agents and compounds rapidly and efficiently. For example, cells can be positioned or placed (pre-seeded) on a culture dish, tube, flask, roller bottle or plate (e.g., a single multi-well plate or dish such as an 8, 16, 32, 64, 96, 384 and 1536 multi-well plate or dish), optionally at defined locations, for identification of potentially therapeutic molecules. Libraries that can be screened include, for example, small molecule libraries, phage display libraries, fully human antibody yeast display libraries (Adimab, LLC), siRNA libraries, and adenoviral transfection vectors.

XIII. Pharmaceutical Preparations and Therapeutic Uses a. Formulations and Routes of Administration Depending on the form of the modulator along with any optional conjugate, the mode of intended delivery, the disease being treated or monitored and numerous other variables, compositions of the instant invention may be formulated as desired using art recognized techniques. That is, in various embodiments of the instant invention compositions comprising EFNA modulators are formulated with a wide variety of pharmaceutically acceptable carriers (see, e.g., Gennaro, *Remington: The Science and Practice of Pharmacy with Facts and Comparisons: Drugfacts Plus,* 20th ed. (2003); Ansel et al., *Pharmaceutical Dosage Forms and Drug Delivery Systems,* 7th ed., Lippencott Williams and Wilkins (2004); Kibbe et al., *Handbook of Pharmaceutical Excipients,* $3^{rd}$ ed., Pharmaceutical Press (2000)). Various pharmaceutically acceptable carriers, which include vehicles, adjuvants, and diluents, are readily available from numerous commercial sources. Moreover, an assortment of pharmaceutically acceptable auxiliary substances, such as pH adjusting and buffering agents, tonicity adjusting agents, stabilizers, wetting agents and the like, are also available. Certain non-limiting exemplary carriers include saline, buffered saline, dextrose, water, glycerol, ethanol, and combinations thereof.

More particularly it will be appreciated that, in some embodiments, the therapeutic compositions of the invention may be administered neat or with a minimum of additional components. Conversely the EFNA modulators of the present invention may optionally be formulated to contain suitable pharmaceutically acceptable carriers comprising excipients and auxiliaries that are well known in the art and are relatively inert substances that facilitate administration of the modulator or which aid processing of the active compounds into preparations that are pharmaceutically optimized for delivery to the site of action. For example, an excipient can give form or consistency or act as a diluent to improve the pharmacokinetics of the modulator. Suitable excipients include but are not limited to stabilizing agents, wetting and emulsifying agents, salts for varying osmolarity, encapsulating agents, buffers, and skin penetration enhancers.

Disclosed modulators for systemic administration may be formulated for enteral, parenteral or topical administration. Indeed, all three types of formulation may be used simultaneously to achieve systemic administration of the active ingredient. Excipients as well as formulations for parenteral and nonparenteral drug delivery are set forth in Remington, The Science and Practice of Pharmacy 20th Ed. Mack Publishing (2000). Suitable formulations for parenteral administration include aqueous solutions of the active compounds in water-soluble form, for example, water-soluble salts. In addition, suspensions of the active compounds as appropriate for oily injection suspensions may be administered. Suitable lipophilic solvents or vehicles include fatty oils, for example, sesame oil, or synthetic fatty acid esters, for example, ethyl oleate or triglycerides. Aqueous injection suspensions may contain substances that increase the viscosity of the suspension and include, for example, sodium carboxymethyl cellulose, sorbitol, and/or dextran. Optionally, the suspension may also contain stabilizers. Liposomes can also be used to encapsulate the agent for delivery into the cell.

Suitable formulations for enteral administration include hard or soft gelatin capsules, pills, tablets, including coated tablets, elixirs, suspensions, syrups or inhalations and controlled release forms thereof.

In general the compounds and compositions of the invention, comprising EFNA modulators may be administered in vivo, to a subject in need thereof, by various routes, including, but not limited to, oral, intravenous, intra-arterial, subcutaneous, parenteral, intranasal, intramuscular, intracardiac, intraventricular, intratracheal, buccal, rectal, intraperitoneal, intradermal, topical, transdermal, and intrathecal, or otherwise by implantation or inhalation. The subject compositions may be formulated into preparations in solid, semi-solid, liquid, or gaseous forms; including, but not limited to, tablets, capsules, powders, granules, ointments, solutions, suppositories, enemas, injections, inhalants, and aerosols. The appropriate formulation and route of administration may be selected according to the intended application and therapeutic regimen.

b. Dosages

Similarly, the particular dosage regimen, i.e., dose, timing and repetition, will depend on the particular individual and that individual's medical history. Empirical considerations such as pharmacokinetics (e.g., half-life, clearance rate, etc.) will contribute to the determination of the dosage. Frequency of administration may be determined and adjusted over the course of therapy, and is based on reducing the number of hyperproliferative or neoplastic cells, including tumor initiating cells, maintaining the reduction of such neoplastic cells, reducing the proliferation of neoplastic cells, or delaying the development of metastasis. Alternatively, sustained continuous release formulations of a subject therapeutic composition may be appropriate. As alluded to above various formulations and devices for achieving sustained release are known in the art.

From a therapeutic standpoint the pharmaceutical compositions are administered in an amount effective for treatment or prophylaxis of the specific indication. The therapeutically effective amount is typically dependent on the weight of the subject being treated, his or her physical or health condition, the extensiveness of the condition to be treated, or the age of the subject being treated. In general, the EFNA modulators of the invention may be administered in an amount in the range of about 10 µg/kg body weight to about 100 mg/kg body weight per dose. In certain embodiments, the EFNA modulators of the invention may be administered in an amount in the range of about 50 µg/kg body weight to about 5 mg/kg body weight per dose. In certain other embodiments, the EFNA modulators of the invention may be administered in an amount in the range of about 100 µg/kg body weight to about 10 mg/kg body weight per dose. Optionally, the EFNA modulators of the invention may be administered in an amount in the range of about 100 µg/kg body weight to about 20 mg/kg body weight per dose. Further optionally, the EFNA modulators of the invention may be administered in an amount in the range of about 0.5 mg/kg body weight to about 20 mg/kg body weight per dose. In certain embodiments the compounds of present invention are provided a dose of at least about 100 µg/kg body weight, at least about 250 µg/kg body weight, at least about 750 µg/kg body weight, at least about 3 mg/kg body weight, at least about 5 mg/kg body weight, at least about 10 mg/kg body weight is administered.

Other dosing regimens may be predicated on Body Surface Area (BSA) calculations as disclosed in U.S. Pat. No. 7,744,877 which is incorporated herein by reference in its entirety. As is well known in the art the BSA is calculated using the patient's height and weight and provides a measure of a subject's size as represented by the surface area of his or her body. In selected embodiments of the invention using the BSA the modulators may be administered in dosages from 10 mg/m$^2$ to 800 mg/m$^2$. In other preferred embodiments the modulators will be administered in dosages from 50 mg/m$^2$ to 500 mg/m$^2$ and even mg/m$^2$, 350 mg/m$^2$, 400 mg/m$^2$ or 450 mg/m$^2$. Of course it will be appreciated that, regardless of how the dosages are calculated, multiple dosages may be administered over a selected time period to provide an absolute dosage that is substantially higher than the individual administrations.

In any event, the EFNA modulators are preferably administered as needed to subjects in need thereof. Determination of the frequency of administration may be made by persons skilled in the art, such as an attending physician based on considerations of the condition being treated, age of the subject being treated, severity of the condition being treated, general state of health of the subject being treated and the like. Generally, an effective dose of the EFNA modulator is administered to a subject one or more times. More particularly, an effective dose of the modulator is administered to the subject once a month, more than once a month, or less than once a month. In certain embodiments, the effective dose of the EFNA modulator may be administered multiple times, including for periods of at least a month, at least six months, or at least a year.

Dosages and regimens may also be determined empirically for the disclosed therapeutic compositions in individuals who have been given one or more administration(s). For example, individuals may be given incremental dosages of a therapeutic composition produced as described herein. To assess efficacy of the selected composition, a marker of the specific disease, disorder or condition can be followed as described previously. In embodiments where the individual has cancer, these include direct measurements of tumor size via palpation or visual observation, indirect measurement of tumor size by x-ray or other imaging techniques; an improvement as assessed by direct tumor biopsy and microscopic examination of the tumor sample; the measurement of an indirect tumor marker (e.g., PSA for prostate cancer) or an antigen identified according to the methods described herein, a decrease in pain or paralysis; improved speech, vision, breathing or other disability associated with the tumor; increased appetite; or an increase in quality of life as measured by accepted tests or prolongation of survival. It will be apparent to one of skill in the art that the dosage will vary depending on the individual, the type of neoplastic condition, the stage of neoplastic condition, whether the neoplastic condition has begun to metastasize to other location in the individual, and the past and concurrent treatments being used.

c. Combination Therapies

Combination therapies contemplated by the invention may be particularly useful in decreasing or inhibiting unwanted neoplastic cell proliferation (e.g. endothelial cells), decreasing the occurrence of cancer, decreasing or preventing the recurrence of cancer, or decreasing or preventing the spread or metastasis of cancer. In such cases the compounds of the instant invention may function as sensitizing or chemosensitizing agent by removing the TPC propping up and perpetuating the tumor mass (e.g. NTG cells) and allow for more effective use of current standard of care debulking or anti-cancer agents. That is, a combination therapy comprising an EFNA modulator and one or more anti-cancer agents may be used to diminish established cancer e.g., decrease the number of cancer cells present and/or decrease tumor burden, or ameliorate at least one manifestation or side effect of cancer. As such, combination therapy refers to the administration of a EFNA modulator and one or more anti-cancer agent that include, but are not limited to, cytotoxic agents, cytostatic agents, chemotherapeutic agents, targeted anti-cancer agents, biological response modifiers, immunotherapeutic agents, cancer vaccines, anti-angiogenic agents, cytokines, hormone therapies, radiation therapy and anti-metastatic agents.

According to the methods of the present invention, there is no requirement for the combined results to be additive of the effects observed when each treatment (e.g., anti-EFNA antibody and anti-cancer agent) is conducted separately. Although at least additive effects are generally desirable, any increased anti-tumor effect above one of the single therapies is beneficial. Furthermore, the invention does not require the combined treatment to exhibit synergistic effects. However, those skilled in the art will appreciate that with certain selected combinations that comprise preferred embodiments, synergism may be observed.

To practice combination therapy according to the invention, an EFNA modulator (e.g., anti-EFNA antibody) in combination with one or more anti-cancer agent may be administered to a subject in need thereof in a manner effective to result in anti-cancer activity within the subject. The EFNA modulator and anti-cancer agent are provided in amounts effective and for periods of time effective to result in their combined presence and their combined actions in the tumor environment as desired. To achieve this goal, the EFNA modulator and anti-cancer agent may be administered to the subject simultaneously, either in a single composition, or as two or more distinct compositions using the same or different administration routes.

Alternatively, the modulator may precede, or follow, the anti-cancer agent treatment by, e.g., intervals ranging from minutes to weeks. In certain embodiments wherein the anti-cancer agent and the antibody are applied separately to the subject, the time period between the time of each delivery is such that the anti-cancer agent and modulator are able to exert a combined effect on the tumor. In a particular embodiment, it is contemplated that both the anti-cancer agent and the EFNA modulator are administered within about 5 minutes to about two weeks of each other.

In yet other embodiments, several days (2, 3, 4, 5, 6 or 7), several weeks (1, 2, 3, 4, 5, 6, 7 or 8) or several months (1, 2, 3, 4, 5, 6, 7 or 8) may lapse between administration of the modulator and the anti-cancer agent. The EFNA modulator and one or more anti-cancer agent (combination therapy) may be administered once, twice or at least the period of time until the condition is treated, palliated or cured. Preferably, the combination therapy is administered multiple times. The combination therapy may be administered from three times daily to once every six months. The administering may be on a schedule such as three times daily, twice daily, once daily, once every two days, once every three days, once weekly, once every two weeks, once every month, once every two months, once every three months, once every six months or may be administered continuously via a minipump. As previously indicated the combination therapy may be administered via an oral, mucosal, buccal, intranasal, inhalable, intravenous, subcutaneous, intramuscular, parenteral, intratumor or topical route. The combination therapy may be administered at a site distant from the site of the tumor. The combination therapy generally will be administered for as long as the tumor is present provided that the combination therapy causes the tumor or cancer to stop growing or to decrease in weight or volume.

In one embodiment an EFNA modulator is administered in combination with one or more anti-cancer agents for a short treatment cycle to a subject in need thereof. The duration of treatment with the antibody may vary according to the particular anti-cancer agent used. The invention also contemplates discontinuous administration or daily doses divided into several partial administrations. An appropriate treatment time for a particular anti-cancer agent will be appreciated by the skilled artisan, and the invention contemplates the continued assessment of optimal treatment schedules for each anti-cancer agent.

The present invention contemplates at least one cycle, preferably more than one cycle during which the combination therapy is administered. An appropriate period of time for one cycle will be appreciated by the skilled artisan, as will the total number of cycles, and the interval between cycles. The invention contemplates the continued assessment of optimal treatment schedules for each modulator and anti-cancer agent. Moreover, the invention also provides for more than one administration of either the anti-EFNA antibody or the anti-cancer agent. The modulator and anti-cancer agent may be administered interchangeably, on alternate days or weeks; or a sequence of antibody treatment may be given, followed by one or more treatments of anti-cancer agent therapy. In any event, as will be understood by those of ordinary skill in the art, the appropriate doses of chemotherapeutic agents will be generally around those already employed in clinical therapies wherein the chemotherapeutics are administered alone or in combination with other chemotherapeutics.

In another preferred embodiment the EFNA modulators of the instant invention may be used in maintenance therapy to reduce or eliminate the chance of tumor recurrence following the initial presentation of the disease. Preferably the disorder will have been treated and the initial tumor mass eliminated, reduced or otherwise ameliorated so the patient is asymptomatic or in remission. As such time the subject may be administered pharmaceutically effective amounts of the disclosed modulators one or more times even though there is little or no indication of disease using standard diagnostic procedures. In some embodiments the effectors will be administered on a regular schedule over a period of time. For example the EFNA modulators could be administered weekly, every two weeks, monthly, every six weeks, every two months, every three months every six months or annually. Given the teachings herein, one skilled in the art could readily determine favorable dosages and dosing regimens to reduce the potential of disease recurrence. Moreover such treatments could be continued for a period of weeks, months, years or even indefinitely depending on the patient response and clinical and diagnostic parameters.

In yet another preferred embodiment the effectors of the present invention may be used to prophylactically to prevent or reduce the possibility of tumor metastasis following a debulking procedure. As used in the instant disclosure a debulking procedure is defined broadly and shall mean any procedure, technique or method that eliminates, reduces, treats or ameliorates a tumor or tumor proliferation. Exemplary debulking procedures include, but are not limited to, surgery, radiation treatments (i.e., beam radiation), chemotherapy or ablation. At appropriate times readily determined by one skilled in the art in view of the instant disclosure the EFNA modulators may be administered as suggested by clinical and diagnostic or theragnostic procedures to reduce tumor metastasis. The modulators may be administered one or more times at pharmaceutically effective dosages as determined using standard techniques. Preferably the dosing regimen will be accompanied by appropriate diagnostic or monitoring techniques that allow it to be modified as necessary.

d. Anti-Cancer Agents

As used herein the term anti-cancer agent means any agent that can be used to treat a cell proliferative disorder such as cancer, including cytotoxic agents, cytostatic agents, anti-angiogenic agents, debulking agents, chemotherapeutic agents, radiotherapy and radiotherapeutic agents, targeted anti-cancer agents, biological response modifiers, antibodies, and immunotherapeutic agents. It will be appreciated that, in selected embodiments as discussed above, anti-cancer agents may comprise conjugates and may be associated with modulators prior to administration.

The term cytotoxic agent means a substance that decreases or inhibits the function of cells and/or causes destruction of cells, i.e., the substance is toxic to the cells. Typically, the substance is a naturally occurring molecule derived from a living organism. Examples of cytotoxic agents include, but are not limited to, small molecule toxins or enzymatically active toxins of bacteria (e.g., Diptheria toxin, *Pseudomonas* endotoxin and exotoxin, Staphylococcal enterotoxin A), fungal (e.g., α-sarcin, restrictocin), plants (e.g., abrin, ricin, modeccin, viscumin, pokeweed anti-viral protein, saporin, gelonin, momoridin, trichosanthin, barley toxin, *Aleurites fordii* proteins, dianthin proteins, *Phytolacca mericana* proteins (PAPI, PAPII, and PAP-S), *Momordica charantia* inhibitor, curcin, crotin, *saponaria officinalis* inhibitor, gelonin, mitegellin, restrictocin, phenomycin, neomycin, and the tricothecenes) or animals, e.g., cytotoxic RNases, such as extracellular pancreatic RNases; DNase I, including fragments and/or variants thereof.

A chemotherapeutic agent means a chemical compound that non-specifically decreases or inhibits the growth, proliferation, and/or survival of cancer cells (e.g., cytotoxic or cytostatic agents). Such chemical agents are often directed to intracellular processes necessary for cell growth or division, and are thus particularly effective against cancerous cells, which generally grow and divide rapidly. For example, vincristine depolymerizes microtubules, and thus inhibits cells from entering mitosis. In general, chemotherapeutic agents can include any chemical agent that inhibits, or is designed to inhibit, a cancerous cell or a cell likely to become cancerous or generate tumorigenic progeny (e.g., TIC). Such agents are often administered, and are often most effective, in combination, e.g., in the formulation CHOP.

Examples of anti-cancer agents that may be used in combination with (or conjugated to) the modulators of the present invention include, but are not limited to, alkylating agents, alkyl sulfonates, aziridines, ethylenimines and methylamelamines, acetogenins, a camptothecin, bryostatin, callystatin, CC-1065, cryptophycins, dolastatin, duocarmycin, eleutherobin, pancratistatin, a sarcodictyin, spongistatin, nitrogen mustards, antibiotics, enediyne antibiotics, dynemicin, bisphosphonates, an esperamicin, chromoprotein enediyne antiobiotic chromophores, aclacinomysins, actinomycin, authramycin, azaserine, bleomycins, cactinomycin, carabicin, carminomycin, carzinophilin, chromomycinis, dactinomycin, daunorubicin, detorubicin, 6-diazo-5-oxo-L-norleucine, ADRIAMYCIN® doxorubicin, epirubicin, esorubicin, idarubicin, marcellomycin, mitomycins, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites, folic acid analogues, purine analogs, androgens, anti-adrenals, folic acid replenisher such as frolinic acid, aceglatone, aldophosphamide glycoside, aminolevulinic acid, eniluracil, amsacrine, bestrabucil, bisantrene, edatraxate, defofamine, demecolcine, diaziquone, elfornithine, elliptinium acetate, an epothilone, etoglucid, gallium nitrate, hydroxyurea, lentinan, lonidainine, maytansinoids, mitoguazone, mitoxantrone, mopidanmol, nitraerine, pentostatin, phenamet, pirarubicin, losoxantrone, podophyllinic acid, 2-ethylhydrazide, procarbazine, PSK® polysaccharide complex (JHS Natural Products, Eugene, Oreg.), razoxane; rhizoxin; sizofiran; spirogermanium; tenuazonic acid; triaziquone; 2,2',2''-trichlorotriethylamine; trichothecenes (especially T-2 toxin, verracurin A, roridin A and anguidine); urethan; vindesine; dacarbazine; mannomustine; mitobronitol; mitolactol; pipobroman; gacytosine; arabinoside ("Ara-C"); cyclophosphamide; thiotepa; taxoids, chloranbucil; GEMZAR® gemcitabine; 6-thioguanine; mercaptopurine; methotrexate; platinum analogs, vinblastine; platinum; etoposide (VP-16); ifosfamide; mitoxantrone; vincristine; NAVELBINE® vinorelbine; novantrone; teniposide; edatrexate; daunomycin; aminopterin; xeloda; ibandronate; irinotecan (Camptosar, CPT-11), topoisomerase inhibitor RFS 2000; difluorometlhylornithine (DMFO); retinoids; capecitabine; combretastatin; leucovorin (LV); oxaliplatin; inhibitors of PKC-alpha, Raf, H-Ras, EGFR and VEGF-A that reduce cell proliferation and pharmaceutically acceptable salts, acids or derivatives of any of the above. Also included in this definition are anti-hormonal agents that act to regulate or inhibit hormone action on tumors such as anti-estrogens and selective estrogen receptor modulators (SERMs), aromatase inhibitors that inhibit the enzyme aromatase, which regulates estrogen production in the adrenal glands, and anti-androgens; as well as troxacitabine (a 1,3-dioxolane nucleoside cytosine analog); antisense oligonucleotides; ribozymes such as a VEGF expression inhibitor and a HER2 expression inhibitor; vaccines, PROLEUKIN® rIL-2; LURTOTECAN® topoisomerase 1 inhibitor; ABARELIX® rmRH; Vinorelbine and Esperamicins and pharmaceutically acceptable salts, acids or derivatives of any of the above. Other embodiments comprise the use of antibodies approved for cancer therapy including, but not limited to, rituximab, trastuzumab, gemtuzumab ozogamcin, alemtuzumab, ibritumomab tiuxetan, tositumomab, bevacizumab, cetuximab, patitumumab, ofatumumab, ipilimumab and brentuximab vedotin. Those skilled in the art will be able to readily identify additional anti-cancer agents that are compatible with the teachings herein.

e. Radiotherapy

The present invention also provides for the combination of EFNA modulators with radiotherapy (i.e., any mechanism for inducing DNA damage locally within tumor cells such as gamma.-irradiation, X-rays, UV-irradiation, microwaves, electronic emissions and the like). Combination therapy using the directed delivery of radioisotopes to tumor cells is also contemplated, and may be used in connection with a targeted anti-cancer agent or other targeting means. Typically, radiation therapy is administered in pulses over a period of time from about 1 to about 2 weeks. The radiation therapy may be administered to subjects having head and neck cancer for about 6 to 7 weeks. Optionally, the radiation therapy may be administered as a single dose or as multiple, sequential doses.

f. Neoplastic Conditions

Whether administered alone or in combination with an anti-cancer agent or radiotherapy, the EFNA modulators of the instant invention are particularly useful for generally treating neoplastic conditions in patients or subjects which may include benign or malignant tumors (e.g., renal, liver, kidney, bladder, breast, gastric, ovarian, colorectal, prostate, pancreatic, lung, thyroid, hepatic carcinomas; sarcomas; glioblastomas; and various head and neck tumors); leukemias and lymphoid malignancies; other disorders such as neuronal, glial, astrocytal, hypothalamic and other glandular, macrophagal, epithelial, stromal and blastocoelic disorders; and inflammatory, angiogenic, immunologic disorders and disorders caused by pathogens. Particularly preferred targets for treatment with therapeutic compositions and methods of the present invention are neoplastic conditions comprising solid tumors. In other preferred embodiments the modulators of the present invention may be used for the diagnosis, prevention or treatment of hematologic malignancies. Preferably the subject or patient to be treated will be human although, as used herein, the terms are expressly held to comprise any mammalian species.

More specifically, neoplastic conditions subject to treatment in accordance with the instant invention may be selected from the group including, but not limited to, adrenal gland tumors, AIDS-associated cancers, alveolar soft part sarcoma, astrocytic tumors, bladder cancer (squamous cell carcinoma and transitional cell carcinoma), bone cancer (adamantinoma, aneurismal bone cysts, osteochondroma, osteosarcoma), brain and spinal cord cancers, metastatic brain tumors, breast cancer, carotid body tumors, cervical cancer, chondrosarcoma, chordoma, chromophobe renal cell carcinoma, clear cell carcinoma, colon cancer, colorectal cancer, cutaneous benign fibrous histiocytomas, desmoplastic small round cell tumors, ependymomas, Ewing's tumors, extraskeletal myxoid chondrosarcoma, fibrogenesis imperfecta ossium, fibrous dysplasia of the bone, gallbladder and bile duct cancers, gestational trophoblastic disease, germ cell tumors, head and neck cancers, islet cell tumors, Kaposi's Sarcoma, kidney cancer (nephroblastoma, papillary renal cell carcinoma), leukemias, lipoma/benign lipomatous tumors, liposarcoma/malignant lipomatous tumors, liver cancer (hepatoblastoma, hepatocellular carcinoma), lymphomas, lung cancers (small cell carcinoma, adenocarcinoma, squamous cell carcinoma, large cell carcinoma etc.), medulloblastoma, melanoma, meningiomas, multiple endocrine neoplasia, multiple myeloma, myelodysplastic syndrome, neuroblastoma, neuroendocrine tumors, ovarian cancer, pancreatic cancers, papillary thyroid carcinomas, parathyroid tumors, pediatric cancers, peripheral nerve sheath tumors, phaeochromocytoma, pituitary tumors, prostate cancer, posterious unveal melanoma, rare hematologic disorders, renal metastatic cancer, rhabdoid tumor, rhabdomysarcoma, sarcomas, skin cancer, soft-tissue sarcomas, squamous cell cancer, stomach cancer, synovial sarcoma, testicular cancer, thymic carcinoma, thymoma, thyroid metastatic cancer, and uterine cancers (carcinoma of the cervix, endometrial carcinoma, and leiomyoma). In certain preferred embodiments, the cancerous cells are selected from the group of solid tumors including but not limited to breast cancer, non-small cell lung cancer (NSCLC), small cell lung cancer, pancreatic cancer, colon cancer, prostate cancer, sarcomas, renal metastatic cancer, thyroid metastatic cancer, and clear cell carcinoma.

With regard to hematologic malignancies it will be further be appreciated that the compounds and methods of the present invention may be particularly effective in treating a variety of B-cell lymphomas, including low grade/NHL follicular cell lymphoma (FCC), mantle cell lymphoma (MCL), diffuse large cell lymphoma (DLCL), small lymphocytic (SL) NHL, intermediate grade/follicular NHL, intermediate grade diffuse NHL, high grade immunoblastic NHL, high grade lymphoblastic NHL, high grade small non-cleaved cell NHL, bulky disease NHL, Waldenstrom's Macroglobulinemia, lymphoplasmacytoid lymphoma (LPL), mantle cell lymphoma (MCL), follicular lymphoma (FL), diffuse large cell lymphoma (DLCL), Burkitt's lymphoma (BL), AIDS-related lymphomas, monocytic B cell lymphoma, angioimmunoblastic lymphoadenopathy, small lymphocytic, follicular, diffuse large cell, diffuse small cleaved cell, large cell immunoblastic lymphoblastoma, small, non-cleaved, Burkitt's and non-Burkitt's, follicular, predominantly large cell; follicular, predominantly small cleaved cell; and follicular, mixed small cleaved and large cell lymphomas. See, Gaidono et al., "Lymphomas", IN CANCER: PRINCIPLES & PRACTICE OF ONCOLOGY, Vol. 2: 2131-2145 (DeVita et al., eds., 5.sup.th ed. 1997). It should be clear to those of skill in the art that these lymphomas will often have different names due to changing systems of classification, and that patients having lymphomas classified under different names may also benefit from the combined therapeutic regimens of the present invention.

In yet other preferred embodiments the EFNA modulators may be used to effectively treat certain myeloid and hematologic malignancies including leukemias such as chronic lymphocytic leukemia (CLL or B-CLL). CLL is predominantly a disease of the elderly that starts to increase in incidence after fifty years of age and reaches a peak by late sixties. It generally involves the proliferation of neoplastic peripheral blood lymphocytes. Clinical finding of CLL involves lymphocytosis, lymphadenopathy, splenomegaly, anemia and thrombocytopenia. A characteristic feature of CLL is monoclonal B cell proliferation and accumulation of B-lymphocytes arrested at an intermediate state of differentiation where such B cells express surface IgM (sIgM) or both sIgM and sIgD, and a single light chain at densities lower than that on the normal B cells. However, as discussed above and shown in the Examples appended hereto, selected EFNA expression (e.g., EFNA) is upregulated on B-CLL cells thereby providing an attractive target for the disclosed modulators.

The present invention also provides for a preventative or prophylactic treatment of subjects who present with benign or precancerous tumors. It is not believed that any particular type of tumor or neoplastic disorder should be excluded from treatment using the present invention. However, the type of tumor cells may be relevant to the use of the invention in combination with secondary therapeutic agents, particularly chemotherapeutic agents and targeted anti-cancer agents.

Still other preferred embodiments of the instant invention comprise the use of EFNA modulators to treat subjects suffering from solid tumors. In such subjects many of these solid tumors comprise tissue exhibiting various genetic mutations that may render them particularly susceptible to treatment with the disclosed effectors. For example, KRAS, APC and CTNNB1 and CDH1 mutations are relatively common in patients with colorectal cancer. Moreover, patients suffering from tumors with these mutations are usually the most refractory to current therapies; especially those patients with KRAS mutations. KRAS activating mutations, which typically result in single amino acid substitutions, are also implicated in other difficult to treat malignancies, including lung adenocarcinoma, mucinous adenoma, and ductal carcinoma of the pancreas.

Currently, the most reliable prediction of whether colorectal cancer patients will respond to EGFR- or VEGF-inhibiting drugs, for example, is to test for certain KRAS "activating" mutations. KRAS is mutated in 35-45% of colorectal cancers, and patients whose tumors express mutated KRAS do not respond well to these drugs. For example, KRAS mutations are predictive of a lack of response to panitumumab and cetuximab therapy in colorectal cancer (Lievre et al. *Cancer Res* 66:3992-5; Karapetis et al. *NEJM* 359:1757-1765). Approximately 85% of patients with colorectal cancer have mutations in the APC gene (Markowitz & Bertagnolli. *NEJM* 361:2449-60), and more than 800 APC mutations have been characterized in patients with familial adenomatous polyposis and colorectal cancer. A majority of these mutations result in a truncated APC protein with reduced functional ability to mediate the destruction of beta-catenin. Mutations in the beta-catenin gene, CTNNB1, can also result in increased stabilization of the protein, resulting in nuclear import and subsequent activation of several oncogenic transcriptional programs, which is also the mechanism of oncogenesis resulting from failure of mutated APC to appropriately mediate beta-catenin destruction, which is required to keep normal cell proliferation and differentiation programs in check.

Loss of CDH1 (E-cadherin) expression is yet another common occurrence in colorectal cancer, often observed in more advanced stages of the disease. E-cadherin is the central member of adherin junctions that connect and organize cells in epithelial layers. Normally E-cadherin physically sequesters beta-catenin (CTNNB 1) at the plasma membrane; loss of E-cadherin expression in colorectal cancer results in localization of beta-catenin to the nucleus and transcriptional activation of the beta-catenin/WNT pathway. Aberrant beta-catenin/WNT signaling is central to oncogenesis and nuclear beta-catenin has been implicated in cancer stemness (Schmalhofer et al., 2009 PMID 19153669). E-cadherin is required for the expression and function of EphA2 a known binding partner for EFNA ligands in epithelia cells (Dodge Zantek et al., 1999 PMID 10511313; Orsulic S and Kemler R, 2000 PMID 10769210). Using modulators that bind to EFNA ligands and agonize with or antagonize Eph receptor binding may modify, interrupt or revert pro-oncogenic processes. Alternatively, EFNA modulators may preferentially bind to tumor cells with aberrant Eph/ephrin interactions based on the binding preferences of the EFNA modulators. Hence patients with cancers carrying the above mentioned genetic traits may benefits from treatment with aforementioned EFNA modulators.

XIV. Articles of Manufacture

Pharmaceutical packs and kits comprising one or more containers, comprising one or more doses of an EFNA modulator are also provided. In certain embodiments, a unit dosage is provided wherein the unit dosage contains a predetermined amount of a composition comprising, for example, an anti-EFNA antibody, with or without one or more additional agents. For other embodiments, such a unit dosage is supplied in single-use prefilled syringe for injection. In still other embodiments, the composition contained in the unit dosage may comprise saline, sucrose, or the like; a buffer, such as phosphate, or the like; and/or be formulated within a stable and effective pH range. Alternatively, in certain embodiments, the composition may be provided as a lyophilized powder that may be reconstituted upon addition of an appropriate liquid, for example, sterile water. In certain preferred embodiments, the composition comprises one or more substances that inhibit protein aggregation, including, but not limited to, sucrose and arginine. Any label on, or associated with, the container(s) indicates that the enclosed composition is used for diagnosing or treating the disease condition of choice.

The present invention also provides kits for producing single-dose or multi-dose administration units of an EFNA modulator and, optionally, one or more anti-cancer agents. The kit comprises a container and a label or package insert on or associated with the container. Suitable containers include, for example, bottles, vials, syringes, etc. The containers may be formed from a variety of materials such as glass or plastic. The container holds a composition that is effective for treating the condition and may have a sterile access port (for example the container may be an intravenous solution bag or a vial having a stopper pierceable by a hypodermic injection needle). Such kits will generally contain in a suitable container a pharmaceutically acceptable formulation of the EFNA modulator and, optionally, one or more anti-cancer agents in the same or different containers. The kits may also contain other pharmaceutically acceptable formulations, either for diagnosis or combined therapy. For example, in addition to the EFNA modulator of the invention such kits may contain any one or more of a range of anti-cancer agents such as chemotherapeutic or radiotherapeutic drugs; anti-angiogenic agents; anti-metastatic agents; targeted anti-cancer agents; cytotoxic agents; and/or other anti-cancer agents. Such kits may also provide appropriate reagents to conjugate the EFNA modulator with an anti-cancer agent or diagnostic agent (e.g., see U.S. Pat. No. 7,422,739 which is incorporated herein by reference in its entirety).

More specifically the kits may have a single container that contains the EFNA modulator, with or without additional components, or they may have distinct containers for each desired agent. Where combined therapeutics are provided for conjugation, a single solution may be pre-mixed, either in a molar equivalent combination, or with one component in excess of the other. Alternatively, the EFNA modulator and any optional anti-cancer agent of the kit may be maintained separately within distinct containers prior to administration to a patient. The kits may also comprise a second/third container means for containing a sterile, pharmaceutically acceptable buffer or other diluent such as bacteriostatic water for injection (BWFI), phosphate-buffered saline (PBS), Ringer's solution and dextrose solution.

When the components of the kit are provided in one or more liquid solutions, the liquid solution is preferably an aqueous solution, with a sterile aqueous solution being particularly preferred. However, the components of the kit may be provided as dried powder(s). When reagents or components are provided as a dry powder, the powder can be reconstituted by the addition of a suitable solvent. It is envisioned that the solvent may also be provided in another container.

As indicated briefly above the kits may also contain a means by which to administer the antibody and any optional components to an animal or patient, e.g., one or more needles or syringes, or even an eye dropper, pipette, or other such like apparatus, from which the formulation may be injected or introduced into the animal or applied to a diseased area of the body. The kits of the present invention will also typically include a means for containing the vials, or such like, and other component in close confinement for commercial sale, such as, e.g., injection or blow-molded plastic containers into which the desired vials and other apparatus are placed and retained. Any label or package insert indicates that the EFNA modulator composition is used for treating cancer, for example colorectal cancer.

XV. Research Reagents

Other preferred embodiments of the invention also exploit the properties of the disclosed modulators as an instrument useful for identifying, isolating, sectioning or enriching populations or subpopulations of tumor initiating cells through methods such as fluorescent activated cell sorting (FACS), magnetic activated cell sorting (MACS) or laser mediated sectioning. Those skilled in the art will appreciate that the modulators may be used in several compatible techniques for the characterization and manipulation of TIC including cancer stem cells (e.g., see U.S. Ser. Nos. 12/686, 359, 12/669,136 and 12/757,649 each of which is incorporated herein by reference in its entirety).

XVI. Miscellaneous

Unless otherwise defined herein, scientific and technical terms used in connection with the present invention shall have the meanings that are commonly understood by those of ordinary skill in the art. Further, unless otherwise required by context, singular terms shall include pluralities and plural terms shall include the singular. More specifically, as used in this specification and the appended claims, the singular forms "a," "an" and "the" include plural referents unless the context clearly dictates otherwise. Thus, for example, reference to "a protein" includes a plurality of proteins; reference to "a cell" includes mixtures of cells, and the like. In addition, ranges provided in the specification and appended claims include both end points and all points between the end points. Therefore, a range of 2.0 to 3.0 includes 2.0, 3.0, and all points between 2.0 and 3.0.

Generally, nomenclature used in connection with, and techniques of, cell and tissue culture, molecular biology, immunology, microbiology, genetics and protein and nucleic acid chemistry and hybridization described herein are those well known and commonly used in the art. The methods and techniques of the present invention are generally performed according to conventional methods well known in the art and as described in various general and more specific references that are cited and discussed throughout the present specification unless otherwise indicated. See, e.g., Sambrook J. & Russell D. Molecular Cloning: A Laboratory Manual, 3rd ed., Cold Spring Harbor Laboratory Press, Cold Spring Harbor, N.Y. (2000); Ausubel et al., Short Protocols in Molecular Biology: A Compendium of Methods from Current Protocols in Molecular Biology, Wiley, John & Sons, Inc. (2002); Harlow and Lane Using Antibodies: A Laboratory Manual, Cold Spring Harbor Laboratory Press, Cold Spring Harbor, N.Y. (1998); and Coligan et al., Short Protocols in Protein Science, Wiley, John & Sons, Inc. (2003). Enzymatic reactions and purification techniques are performed according to manufacturer's specifications, as commonly accomplished in the art or as described herein. The nomenclature used in connection with, and the laboratory procedures and techniques of, analytical chemistry, synthetic organic chemistry, and medicinal and pharmaceutical chemistry described herein are those well known and commonly used in the art.

All references or documents disclosed or cited within this specification are, without limitation, incorporated herein by reference in their entirety. Moreover, any section headings used herein are for organizational purposes only and are not to be construed as limiting the subject matter described.

EXAMPLES

The present invention, thus generally described above, will be understood more readily by reference to the following examples, which are provided by way of illustration and are not intended to be limiting of the instant invention. The examples are not intended to represent that the experiments below are all or the only experiments performed. Unless indicated otherwise, parts are parts by weight, molecular weight is weight average molecular weight, temperature is in degrees Centigrade, and pressure is at or near atmospheric.

Example 1

Enrichment of Tumor Initiating Cell Populations

To characterize the cellular heterogeneity of solid tumors as they exist in cancer patients, elucidate the identity of tumor perpetuating cells (TPC; i.e. cancer stem cells: CSC) using particular phenotypic markers and identify clinically relevant therapeutic targets, a large non-traditional xenograft (NTX) tumor bank was developed and maintained using art recognized techniques. The NTX tumor bank, comprising a large number of discrete tumor cell lines, was propagated in immunocompromised mice through multiple passages of heterogeneous tumor cells originally obtained from numerous cancer patients afflicted by a variety of solid tumor malignancies. The continued availability of a large number of discrete early passage NTX tumor cell lines having well defined lineages greatly facilitate the identification and isolation of TPC as they allow for the reproducible and repeated characterization of cells purified from the cell lines. More particularly, isolated or purified TPC are most accurately defined retrospectively according to their ability to generate phenotypically and morphologically heterogeneous tumors in mice that recapitulate the patient tumor sample from which the cells originated. Thus, the ability to use small populations of isolated cells to generate fully heterogeneous tumors in mice is strongly indicative of the fact that the isolated cells comprise TPC. In such work the use of minimally passaged NTX cell lines greatly simplifies in vivo experimentation and provides readily verifiable results. Moreover, early passage NTX tumors also respond to therapeutic agents such as irinotecan (i.e. Camptosar®), which provides clinically relevant insights into underlying mechanisms driving tumor growth, resistance to current therapies and tumor recurrence.

As the NTX tumor cell lines were established the constituent tumor cell phenotypes were analyzed using flow cytometry to identify discrete markers that might be used to characterize, isolate, purify or enrich tumor initiating cells (TIC) and separate or analyze TPC and TProg cells within such populations. In this regard the inventors employed a proprietary proteomic based platform (i.e. PhenoPrint™ Array) that provided for the rapid characterization of cells based on protein expression and the concomitant identification of potentially useful markers. The PhenoPrint Array is a proprietary proteomic platform comprising hundreds of discrete binding molecules, many obtained from commercial sources, arrayed in 96 well plates wherein each well contains a distinct antibody in the phycoerythrin fluorescent channel and multiple additional antibodies in different fluorochromes arrayed in every well across the plate. This allows for the determination of expression levels of the antigen of interest in a subpopulation of selected tumor cells through rapid inclusion of relevant cells or elimination of non-relevant cells via non-phycoerythrin channels. When the PhenoPrint Array was used in combination with tissue dissociation, transplantation and stem cell techniques well known in the art (Al-Hajj et al., 2004, Dalerba et al., 2007 and Dylla et al., 2008, all supra, each of which is incorporated herein by reference in its entirety), it was possible to effectively identify relevant markers and subsequently isolate and transplant specific human tumor cell subpopulations with great efficiency.

Accordingly, upon establishing various NTX tumor cell lines as is commonly done for human tumors in severely immune compromised mice, the tumors were resected from mice upon reaching 800-2,000 $mm^3$ and the cells were dissociated into single cell suspensions using art-recognized enzymatic digestion techniques (See for example U.S.P.N. 2007/0292414 which is incorporated herein). Data obtained from these suspensions using the PhenoPrint Array provided both absolute (per cell) and relative (vs. other cells in the population) surface protein expression on a cell-by-cell basis, leading to more complex characterization and stratification of cell populations. More specifically, use of the PhenoPrint Array allowed for the rapid identification of proteins or markers that prospectively distinguished TIC or TPC from NTG bulk tumor cells and tumor stroma and, when isolated from NTX tumor models, provided for the relatively rapid characterization of tumor cell subpopulations expressing differing levels of specific cell surface proteins. In particular, proteins with heterogeneous expression across the tumor cell population allow for the isolation and transplantation of distinct, and highly purified, tumor cell subpopulations expressing either high and low levels of a particular protein or marker into immune-compromised mice, thereby facilitating the assessment of whether TPC were enriched in one subpopulation or another.

The term enriching is used synonymously with isolating cells and means that the yield (fraction) of cells of one type is increased over the fraction of other types of cells as compared to the starting or initial cell population. Preferably, enriching refers to increasing the percentage by about 10%, by about 20%, by about 30%, by about 40%, by about 50% or greater than 50% of one type of cell in a population of cells as compared to the starting population of cells.

As used herein a marker, in the context of a cell or tissue, means any characteristic in the form of a chemical or biological entity that is identifiably associated with, or specifically found in or on a particular cell, cell population or tissue including those identified in or on a tissue or cell population affected by a disease or disorder. As manifested, market's may be morphological, functional or biochemical in nature. In preferred embodiments the marker is a cell surface antigen that is differentially or preferentially expressed by specific cell types (e.g., TPC) or by cells under certain conditions (e.g., during specific points of the cell life cycle or cells in a particular niche). Preferably, such markers are proteins, and more preferably, possess an epitope for antibodies, aptamers or other binding molecules as known in the art. However, a marker may consist of any molecule found on the surface or within a cell including, but not limited to, proteins (peptides and polypeptides), lipids, polysaccharides, nucleic acids and steroids. Examples of morphological marker characteristics or traits include, but are not limited to, shape, size, and nuclear to cytoplasmic ratio. Examples of functional marker characteristics or traits include, but are not limited to, the ability to adhere to particular substrates, ability to incorporate or exclude particular dyes, for example but not limited to exclusions of lipophilic dyes, ability to migrate under particular conditions and the ability to differentiate along particular lineages. Markers can also be a protein expressed from a reporter gene, for example a reporter gene expressed by the cell as a result of introduction of the nucleic acid sequence encoding the reporter gene into the cell and its transcription resulting in the production of the reporter protein that can be used as a marker. Such reporter genes that can be used as markers are, for example but not limited to fluorescent proteins enzymes, chromomeric proteins, resistance genes and the like.

In a related sense the term marker phenotype in the context of a tissue, cell or cell population (e.g., a stable TPC phenotype) means any marker or combination of markers that may be used to characterize, identify, separate, isolate or enrich a particular cell or cell population (e.g., by FACS). In specific embodiments, the marker phenotype is a cell surface phenotype that may be determined by detecting or identifying the expression of a combination of cell surface markers.

Those skilled in the art will recognize that numerous markers (or their absence) have been associated with various populations of cancer stem cells and used to isolate or characterize tumor cell subpopulations. In this respect exemplary cancer stem cell markers comprise OCT4, Nanog, STAT3, EPCAM, CD24, CD34, NB84, TrkA, GD2, CD 133, CD20, CD56, CD29, B7H3, CD46, transferrin receptor, JAM3, carboxypeptidase M, ADAM9, oncostatin M, Lgr5, Lgr6, CD324, CD325, nestin, Sox1, Bmi-1, eed, easyh1, easyh2, mf2, yy1, smarcA3, smarckA5, smarcD3, smarcE1, mllt3, FZD1, FZD2, FZD3, FZD4, FZD6, FZD7, FZD8, FZD9, FZD10, WNT2, WNT2B, WNT3, WNT5A, WNT10B, WNT16, AXIN1, BCL9, MYC, (TCF4) SLC7A8, IL1RAP, TEM8, TMPRSS4, MUC16, GPRC5B, SLC6A14, SLC4A11, PPAP2C, CAV1, CAV2, PTPN3, EPHA1, EPHA2, SLC1A1, CX3CL1, ADORA2A, MPZL1, FLJ10052, C4.4A, EDG3, RARRES1, TMEPAI, PTS, CEACAM6, NID2, STEAP, ABCA3, CRIM1, IL1R1, OPN3, DAF, MUC1, MCP, CPD, NMA, ADAM9, GJA1, SLC19A2, ABCA1, PCDH7, ADCY9, SLC39A1, NPC1, ENPP1, N33, GPNMB, LY6E, CELSR1, LRP3, C20orf52, TMEPAI, FLVCR, PCDHA10, GPR54, TGFBR3, SEMA4B, PCDHB2, ABCG2, CD166, AFP, BMP-4, β-catenin, CD2, CD3, CD9, CD14, CD31, CD38, CD44, CD45, CD74, CD90, CXCR4, decorin, EGFR, CD105, CD64, CD16, CD16a, CD16b, GLI1, GLI2, CD49b, and CD49f. See, for example, Schulenburg et al., 2010, PMID: 20185329, U.S. Pat. No. 7,632,678 and U.S.P.Ns. 2007/0292414, 2008/0175870, 2010/0275280, 2010/0162416 and 2011/0020221 each of which is incorporated herein by reference. It will be appreciated that a number of these markers were included in the PhenoPrint Array described above.

Similarly, non-limiting examples of cell surface phenotypes associated with cancer stem cells of certain tumor types include CD44$^{hi}$CD24$^{low}$, ALDH$^+$, CD133$^+$, CD123$^+$, CD34$^+$CD38$^-$, CD44$^+$CD24$^-$, CD46$^{hi}$CD324$^+$CD66c$^-$, CD133$^+$CD34$^+$CD10$^-$CD19$^-$, CD138$^-$CD34$^-$CD19$^+$, CD133RC2$^+$, CD44$^+$α$_2$β$_1$$^{hi}$CD133$^+$, CD44$^+$CD24$^+$ESA$^+$, CD271$^+$, ABCB5$^+$ as well as other cancer stem cell surface phenotypes that are known in the art. See, for example, Schulenburg et al., 2010, supra, Visvader et al., 2008, PMID: 18784658 and U.S.P.N. 2008/0138313, each of which is incorporated herein in its entirety by reference. Those skilled in the art will appreciate that marker phenotypes such as those exemplified immediately above may be used in conjunction with standard flow cytometric analysis and cell sorting techniques to characterize, isolate, purify or enrich TIC and/or TPC cells or cell populations for further analysis. Of interest with regard to the instant invention CD46, CD324 and, optionally, CD66c are either highly or heterogeneously expressed on the surface of many human colorectal ("CR"), breast ("BR"), non-small cell lung (NSCLC), small cell lung (SCLC), pancreatic ("PA"), melanoma ("Mel"), ovarian ("OV"), and head and neck cancer ("HN") tumor cells, regardless of whether the tumor specimens being analyzed were primary patient tumor specimens or patient-derived NTX tumors.

Cells with negative expression (i.e."−") are herein defined as those cells expressing less than, or equal to, the 95$^{th}$ percentile of expression observed with an isotype control antibody in the channel of fluorescence in the presence of the complete antibody staining cocktail labeling for other proteins of interest in additional channels of fluorescence emission. Those skilled in the art will appreciate that this procedure for defining negative events is referred to as "fluorescence minus one", or "FMO", staining. Cells with expression greater than the 95$^{th}$ percentile of expression observed with an isotype control antibody using the FMO staining procedure described above are herein defined as "positive" (i.e."+"). As defined herein there are various populations of cells broadly defined as "positive." First, cells with low expression (i.e. "lo") are generally defined as those cells with observed expression above the 95$^{th}$ percentile determined using FMO staining with an isotype control antibody and within one standard deviation of the 95$^{th}$ percentile of expression observed with an isotype control antibody using the FMO staining procedure described above. Cells with "high" expression (i.e. "hi") may be defined as those cells with observed expression above the 95$^{th}$ percentile determined using FMO staining with an isotype control antibody and greater than one standard deviation above the 95$^{th}$ percentile of expression observed with an isotype control antibody using the FMO staining procedure described above. In other embodiments the 99$^{th}$ percentile may preferably be used as a demarcation point between negative and positive FMO staining and in particularly preferred embodiments the percentile may be greater than 99%.

Using techniques such as those described above to quickly identify and rank colorectal tumor antigens based on expression intensity and heterogeneity across several NTX tumors from colorectal cancer patients, candidate TPC antigens were further assessed by comparison of tumor versus normal adjacent tissue and then selected based, at least in part, on the up- or down-regulation of the particular antigen in malignant cells. Moreover, systematic analysis of a variety of cell surface markers for their ability to enrich for the ability to transplant fully heterogeneous tumors into mice (i.e. tumorigenic ability), and subsequent combination of these markers substantially improved the resolution of the method and improved the ability to tailor fluorescence activated cell sorting (FACS) techniques to identify and characterize distinct, highly enriched tumor cell subpopulations that exclusively contained all tumor generating ability upon transplantation (i.e. tumor initiating cells). To reiterate, the term tumor initiating cell (TIC) or tumorigenic (TG) cell encompasses both Tumor Perpetuating Cells (TPC; i.e. cancer stem cells) and highly proliferative Tumor Progenitor cells (TProg), which together generally comprise a unique subpopulation (i.e. 0.1-25%) of a bulk tumor or mass; the characteristics of which are defined above. The majority of tumor cells characterized in this fashion are devoid of this tumor forming ability, and can thus be characterized as non-tumorigenic (NTG). Surprisingly, it was observed that most distinct markers identified using the proprietary PhenoPrint Array did not demonstrate an ability to enrich tumor initiating cell populations in colorectal tumors using standard FACS protocols, but that distinct marker combinations could be used to identify two subpopulations of tumor initiating cells: TPC and TProg. Those skilled in the art will recognize that the defining difference between TPC and TProg, though both are tumor initiating in primary transplants, is the ability of TPC to perpetually fuel tumor growth upon serial transplantation at low cell numbers. Furthermore, the marker/proteins used in combination to enrich for both TPC and TProg were unknown to be associated with cells containing such activity in any tissue or neoplasm prior to discovery by current inventors though others have defined cell surface markers or enzymatic activity that can similarly be used to enrich for tumorigenic cells (Dylla et al 2008, supra). As set forth below, specific tumor cell sub-populations isolated using cell surface marker combinations alluded to above were then analyzed using whole transcriptome next generation sequencing to identify and characterize differentially expressed genes.

Example 2

Isolation and Analysis of RNA Samples From Enriched Tumor Initiating Cell Populations Several established colorectal NTX cell lines (SCRX-CR4, CR11, CR33, PA3, PA6 & PA14) generated and passaged as described in Example 1 were used to initiate tumors in immune compromised mice. For mice bearing SCRX-CR4, PA3 or PA6 tumors, once the mean tumor burden reached ~300 mm$^3$ the mice were randomized and treated with 15 mg/kg irinotecan, 25 mg/kg Gemcitabine, or vehicle control (PBS) twice weekly for a period of at least twenty days prior to euthanization. Tumors arising from all six NTX lines, including those from mice undergoing chemotherapeutic treatment were removed and TPC, TProg and NTG cells, respectively, were isolated from freshly resected colorectal NTX tumors and, similarly, TG and NTG cells were isolated from pancreatic NTX tumors, generally using the technique set out in Example 1. More particularly, cell populations were isolated by FACS and immediately pelleted and lysed in Qiagen RLTplus RNA lysis buffer (Qiagen, Inc.). The lysates were then stored at −80° C. until used. Upon thawing, total RNA was extracted using the Qiagen RNeasy isolation kit (Qiagen, Inc.) following vendor's instructions and quantified on the Nanodrop (Thermo Scientific) and a Bioanalyzer 2100 (Agilent Technologies) again using the vendor's protocols and recommended instrument settings. The resulting total RNA preparation was suitable for genetic sequencing and analysis.

Total RNA samples obtained from the respective cell populations isolated as described above from vehicle or chemotherapeutic agent-treated mice were prepared for whole transcriptome sequencing using an Applied Biosystems SOLiD 3.0 (Sequencing by Oligo Ligation/Detection) next generation sequencing platform (Life Technologies), starting with 5 ng of total RNA per sample. The data generated by the SOLiD platform mapped to 34,609 genes from the human genome and was able to detect ephrin-A ligands, including EFNA4, and provided verifiable measurements of ENFA levels in most samples.

Generally the SOLiD3 next generation sequencing platform enables parallel sequencing of clonally-amplified RNA/DNA fragments linked to beads. Sequencing by ligation with dye-labeled oligonucleotides is then used to generate 50 base reads of each fragment that exists in the sample with a total of greater than 50 million reads generating a much more accurate representation of the mRNA transcript level expression of proteins in the genome. The SOLiD3 platform is able to capture not only expression, but SNPs, known and unknown alternative splicing events, and potentially new exon discoveries based solely on the read coverage (reads mapped uniquely to genomic locations). Thus, use of this next generation platform allowed the determination of differences in transcript level expression as well as differences or preferences for specific splice variants of those expressed mRNA transcripts. Moreover, analysis with the SOLiD3 platform using a modified whole transcriptome protocol from Applied Biosystems only required approximately 5 ng of starting material pre-amplification. This is significant as extraction of total RNA from sorted cell populations where the TPC subset of cells is, for example, vastly smaller in number than the NTG or bulk tumors and thus results in very small quantities of usable starting material.

Figures 3A, 3B:
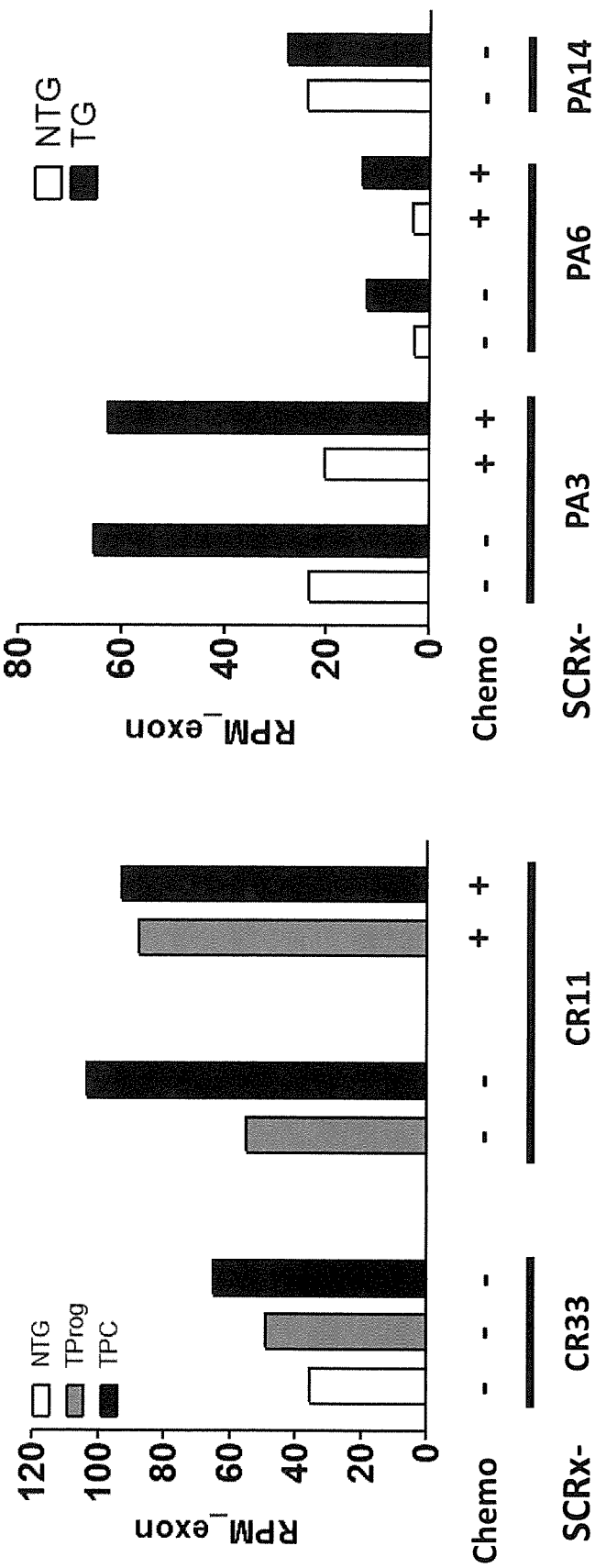
FIGS. 3A and 3B are graphical representations depicting the gene expression levels of human ephrin-A4 ligand in colorectal tumor samples (FIG. 3A) and pancreatic tumor samples (FIG. 3B) as measured using whole transcriptome sequencing of highly enriched tumor progenitor cell (TProg) and tumor perpetuating cell (TPC) and non-tumorigenic cell (NTG) populations or tumorigenic (TG) and non-tumorigenic cell (NTG) populations.

Duplicate runs of sequencing data from the SOLiD3 platform were normalized and transformed and fold ratios calculated as is standard industry practice. As seen in FIG. 2, levels of EFNA1, EFNA3 and EFNA4 from a tumor were measured as well as levels of Eph receptors EPHA1, EPHA2 and EPHA10. An analysis of the data showed that EFNA4 was up-regulated at the transcript level by 1.9-3 fold in the SCRx-CR4 NTX tumor TPC over the NTG population, and 1.2-1.4 fold in TPC over the TProg population, irrespective of whether cells were obtained from mice being treated with (FIG. 2A) vehicle or (FIG. 2B) 15 mg/kg irinotecan. It will further be appreciated that EFNA1 was also elevated in TPC versus TProg and NTG cells, respectively, although to a lesser extent than EFNA4. Furthermore, when additional colorectal (SCRx-CR11 & CR33) and pancreatic (SCRx-PA3, PA6 & PA14) tumor samples were analyzed by SOLiD3 whole-transcriptome sequencing, EFNA4 gene expression was similarly elevated in TPC versus TProg and NTG cells in colorectal cancer (FIG. 3A) and in the TIC (or TG) subpopulation of cells from pancreatic tumors (FIG. 3B), defined using a panel of unique cell surface markers discovered as illustrated above (TPC and TProg cell subsets, which constitute the TIC population in pancreatic tumors have not yet been defined).

It was also observed that the expression of EPHA2 receptor, with which both EFNA4 and EFNA1 ligands interact, inversely reflects that of both EFNA4 and EFNA1 during the progression of differentiation from TPC to NTG cells. This converse expression pattern of the EFNA1/EFNA4 ligands and EPHA2 receptor suggests that crosstalk between these ligand/receptor pairs might play a role in cell fate decisions during colorectal cancer stem cell differentiation and that neutralizing these interactions might negatively impact tumor growth. Specifically, by blocking EphA2 interactions with EFNA1 and/or EFNA4 using neutralizing antibodies against the later pair of ephrin-A ligands, TPC might be sensitized to chemotherapeutic agents, for example, or forced to differentiate. Moreover, by targeting TPC using EFNA1 and/or EFNA4-internalizing antibodies, TPC might be killed directly by the naked modulator or through the use of a toxin or antibody drug conjugate.

The observations detailed above show that EFNA1 and/or EFNA4 expression is generally elevated in TPC populations and suggests that these membrane-tethered ligands may play an important role in tumorigenesis and tumor maintenance, thus constituting excellent targets for novel therapeutic approaches.

Example 3

Real-Time PCR Analysis of Ephrin-A Ligands in Enriched Tumor Initiating Cell Populations To validate the differential ephrin-A ligand expression observed by whole transcriptome sequencing in TPC populations versus TProg and NTG cells in colorectal cancer, and TG versus NTG cells in pancreatic cancer, TaqMan® quantitative real-time PCR was used to measure gene expression levels in respective cell populations isolated from various NTX lines as set forth above. It will be appreciated that such real-time PCR analysis allows for a more direct and rapid measurement of gene expression levels for discrete targets using primers and probe sets specific to a particular gene of interest. TaqMan® real-time quantitative PCR was performed on an Applied Biosystems 7900HT Machine (Life Technologies), which was used to measure EFNA4 gene expression in multiple patient-derived NTX line cell populations and corresponding controls. Moreover, the analysis was conducted as specified in the instructions supplied with the TaqMan System and using commercially available EFNA4 primer/probe sets (Life Technologies).

Figure 4:
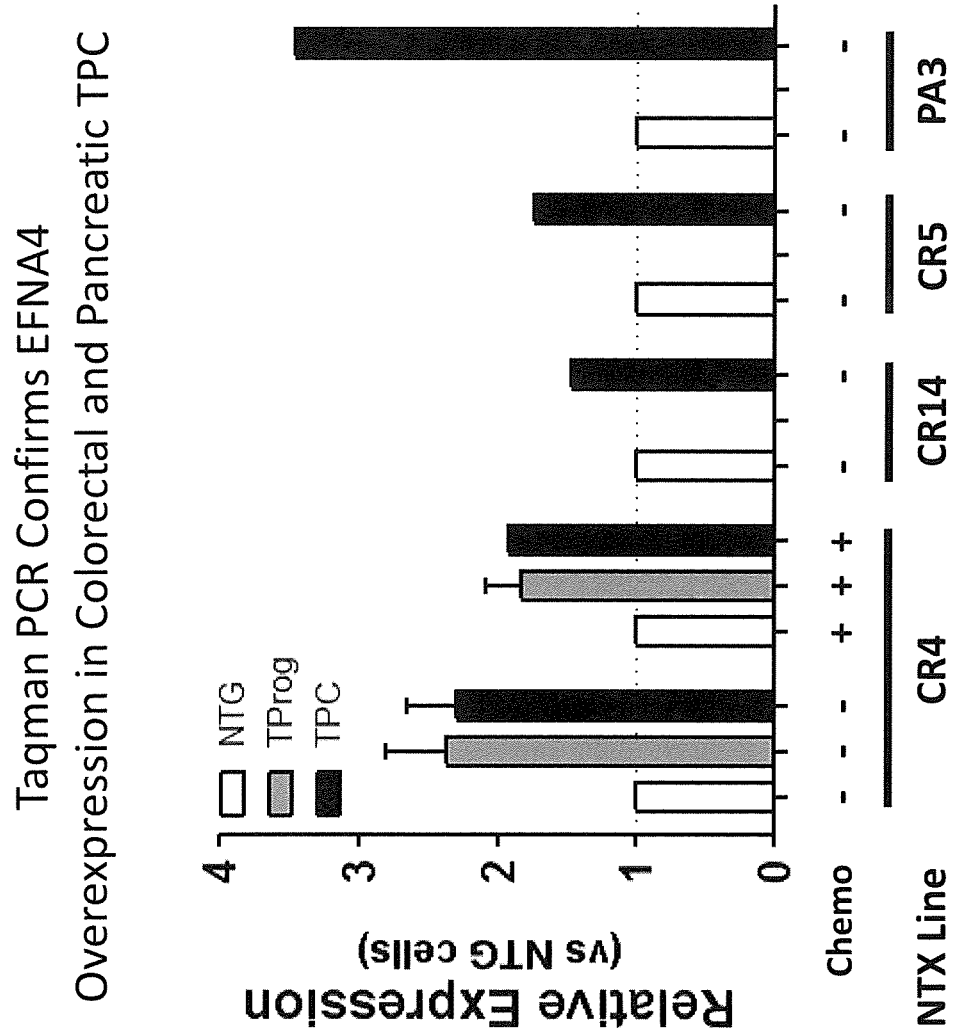
FIG. 4 is a graphical representation showing the relative gene expression levels of human EFNA4 in highly enriched tumor progenitor cell (TProg) and tumor perpetuating cell (TPC) populations obtained from mice bearing one of four different non-traditional xenograft (NTX) colorectal or pancreatic tumor cell lines, and normalized against non-tumorigenic (NTG) enriched cell populations as measured using quantitative RT-PCR.

As seen in FIG. 4, quantitative real-time PCR interrogation of gene expression in NTG, TProg and TPC populations isolated from 3 distinct colorectal NTX tumor lines (SCRx-CR4, CR5 & CR14) showed that EFNA4 gene expression is elevated more than 1.4-fold in the TIC subpopulations (TPC and/or TProg) versus NTG cells. EFNA4 was also elevated approximately 1.8-fold in TIC populations in mice undergoing treatment with irinotecan, and in the TG cell population of pancreatic tumors (e.g. SCRx-PA3). The observation of elevated EFNA4 expression in NTX TIC cell preparations as compared with NTG cell controls from both colorectal and pancreatic patient-derived NTX tumors using the more widely accepted methodology of real-time quantitative PCR confirms the more sensitive SOLiD3 whole transcriptome sequencing data of the previous Example, and supports the observed association between EFNA4 and cells underlying tumorigenesis, resistance to therapy and recurrence.

Example 4

Expression of Ephrin-A Ligands in Unfractionated Colorectal Tumor Specimens

In light of the fact that ephrin-A ligand gene expression was found to be elevated in TPC populations from colorectal tumors when compared with TProg and NTG cells from the same tumors, experiments were conducted to determine whether elevated ephrin-A ligand (i.e., EFNA4) expression was also detectable in unfractionated colorectal tumor samples versus normal adjacent tissue (NAT). Similarly, measurements were also made to determine how the expression of ephrin-A ligands in tumors compares with levels in normal tissue samples. Custom TumorScan qPCR (Origene Technologies) 384-well arrays containing 110 colorectal patient tumor specimens, normal adjacent tissue, and 48 normal tissues were designed and fabricated using art known techniques. Using the procedures detailed in Example 3 and the same EFNA4 specific primer/probe sets, TaqMan real-time quantitative PCR was performed in the wells of the custom plates.

Figures 5A, 5B:
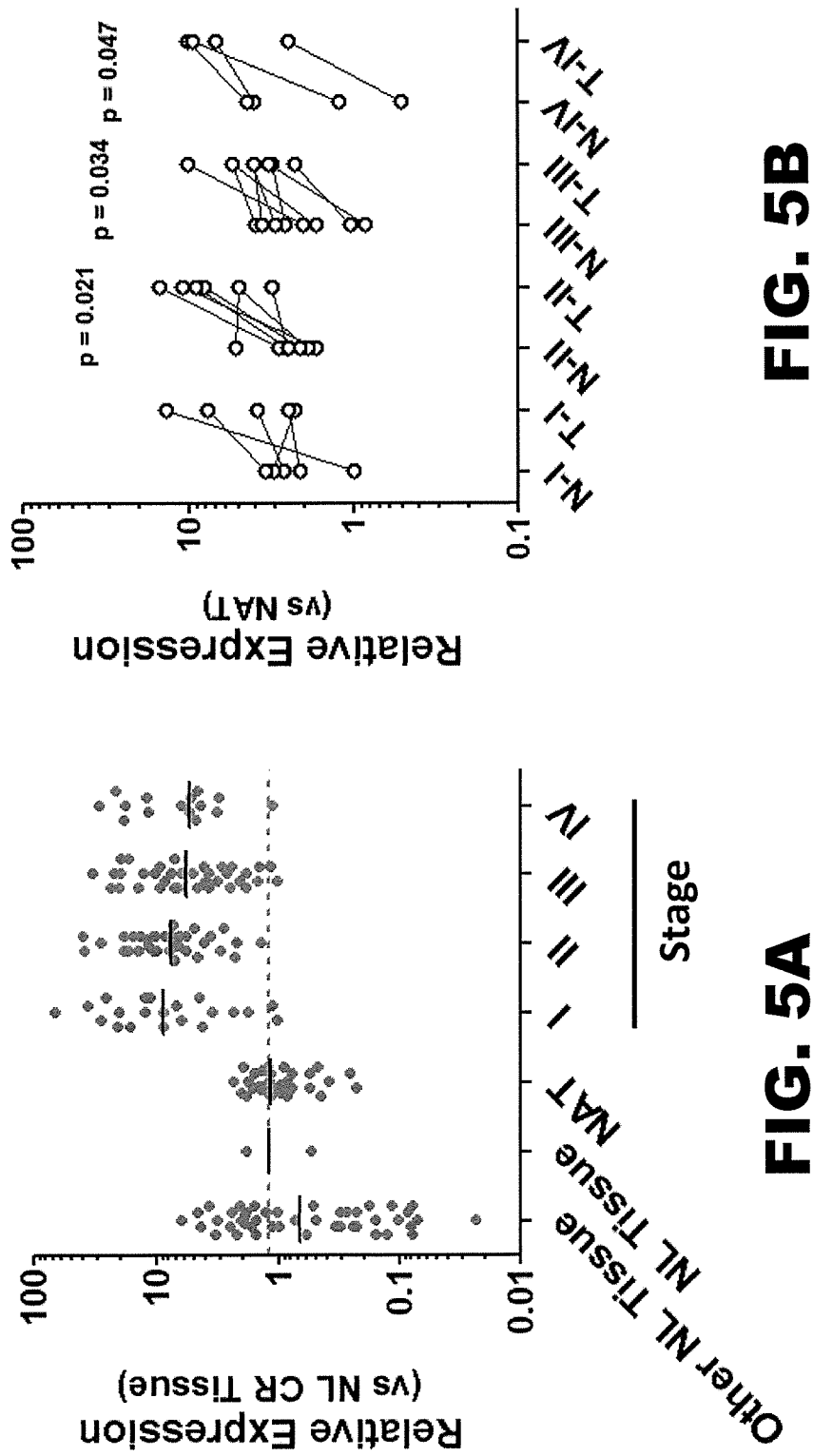
FIGS. 5A and 5B are graphical representations showing the relative gene expression levels of human EFNA4 as measured using RT-PCR in whole colorectal tumor specimens from patients with Stage I-IV disease, as normalized against the mean of expression in normal colon and rectum tissue (FIG. 5A) or matched with normal adjacent tissue (FIG. 5B)

FIGS. 5A and 5B show the results of the expression data in a graphical format normalized against the mean expression in normal colon and rectum tissue. More specifically, FIG. 5A summarizes data generated using 168 tissue specimens, obtained from 110 colorectal cancer patients, (35 tissue specimens of which are normal (NL) adjacent tissue from colorectal cancer patients) and 48 normal tissues from other locations (Other NL). In the plot, data from each tissue specimen/patient is represented by a dot, with the geometric mean value of each population demarcated on the X-axis represented as a line. Similarly, FIG. 5B contains data from 24 matched colorectal patient specimens obtained from tumor (T) or normal adjacent tissue (N) at various stages of the disease (I-IV). Here the plotted data is presented on a sample by sample basis with linkage between the respective tumor and normal adjacent tissue from individual patients. Expression of EFNA4 is clearly higher in the majority of matched tumor versus normal adjacent tissue, with the differential expression in Stages 2, 3 and 4 reaching statistical significance ($n \geq 4$, $P \leq 0.047$). Both FIGS. 5A and 5B indicate that, in all four stages presented, the expressed level of the EFNA4 gene is elevated in a majority of colorectal tumors and in matched tumor specimens versus normal adjacent tissue. Moreover, the mean EFNA4 gene expression in any Stage of colorectal cancer appears at least equal to, if not greater than, the highest levels of EFNA4 gene expression in any normal tissue interrogated in these experiments (FIG. 5A). These results demonstrate that EFNA4 expression is increased in colorectal cancer and when coupled with the above observations that EFNA4 expression is greatest in colorectal TPC and pancreatic TIC, suggests that therapeutic targeting of tumorigenic cells expressing EFNA4 may provide great therapeutic benefit to cancer patients.

Example 5

Differential Expression of Ephrin-A Ligand in Exemplary Tumor Samples

To further assess ephrin-A ligand gene expression in additional colorectal cancer patient tumor samples and tumor specimens from patients diagnosed with 1 of 17 other different solid tumor types, Taqman qRT-PCR was performed using TissueScan™ qPCR (Origene Technologies) 384-well arrays, which were custom fabricated as described in Example 4. The results of the measurements are presented in FIG. 6 and show that gene expression of EFNA4 is significantly elevated or repressed in a number of tumor samples.

In this regard, FIGS. 6A and 6B show the relative and absolute gene expression levels, respectively, of human EFNA4 in whole tumor specimens (grey dots) or matched normal adjacent tissue (NAT; white dots) from patients with one of eighteen different solid tumor types. In FIG. 6A, data is normalized against mean gene expression in NAT for each tumor type analyzed. In FIG. 6B, the absolute expression of EFNA4 was assessed in various tissues/tumors, with the data being plotted as the number of cycles (Ct) needed to reach exponential amplification by quantitative real-time PCR. Specimens not amplified were assigned a Ct value of 45, which represents the last cycle of amplification in the experimental protocol. Each dot represents an individual tissue specimen, with the mean value represented as a black line.

Using the custom Array, it was observed that the majority of patients diagnosed with colorectal cancer and most patients diagnosed with endometrial, esophageal, liver, lung, prostate, bladder and uterine cancer had significantly more EFNA4 gene expression in their tumors versus NAT, suggesting that EFNA4 might play a role in tumorigenesis and/or tumor progression in these tumors. In contrast, expression of EFNA4 appeared significantly repressed in tumors from patients with adrenal and pancreatic cancer. What was also clear from the these studies is that EFNA4 gene expression was generally low to moderate in most NAT samples; with the highest expression being observed in the adrenal gland, breast, cervix and ovaries. Again, these data suggest that differential EFNA4 expression (high or low) is indicative, and potentially dispositive, as to tumorigenesis or perpetuation in patients presenting selected hyperproliferative disorders.

EFNA4 expression was also assessed using proprietary non-traditional xenografts (NTX) as discussed above and quantified in relation to normal tissue expression. Quantitative real-time PCR was performed on commercial normal tissue RNA samples (breast, colon, esophagus, heart, kidney, liver, lung, ovary, pancreas, skeletal muscle, small intestine) and on NTX tumors from breast cancer (BR), colorectal cancer (CR), kidney cancer (KDY), liver cancer (LIV), melanoma (MEL), non-small cell lung cancer (NSCLC), ovarian cancer (OV), pancreatic cancer (PA), and small cell lung cancer (SCLC). The results, shown in FIG. 6C demonstrate elevated expression of EFNA4 in the breast, colon, and liver NTX lines relative to expression in normal tissues. Conversely, FIG. 6D documents expression of the related family member EFNA1 in many of the same normal and NTX lines and shows little differential expression between normal and tumor tissues. Despite this expression profile EFNA modulators of the instant invention that react with EFNA1 (including those that react with other EFNA) may effectively be used to eliminate tumorigenic cells as evidenced in the subsequent Examples.

In any event, to confirm that the elevated mRNA expression detected by quantitative real-time PCR also translates to elevated protein levels of EFNA4, Western blots were run. Cell lysates of NTX and cell lines (293 naive and 293 EFNA4 over-expressing cells) were produced using a total protein extraction kit (Bio Chain Institute # K3011010) following the provided protocol, to match the commercially available normal tissue lysates (Novus Biologicals). Protein concentration of the lysates was determined using a BCA protein assay (Pierce/Thermo Fisher #23225). Equal amounts of cell lysates were run on NuPAGE Novex 4-12% Bis-Tris gels (Life Technologies) in MES Buffer under reducing conditions. A commercially available antibody against human EFNA4 (R&D Systems—AF369) was used to detect EFNA4 protein expression. In the top panel of FIG. 6E, 293 cells engineered to over-express EFNA4 show high expression compared to naive 293 cells. Additionally, in the top panel several breast, colon and non-small cell lung cancer NTX showed relatively high expression of EFNA4. Under similar conditions the Western blot in the bottom panel of FIG. 6E shows that normal tissues express low or undetectable levels of EFNA4 when compared with the high EFNA4 expression in the NTX cell line CR11. An anti-GAPDH control antibody is used to demonstrate equal loading of cell lysates in both panels.

Example 6

Generation of Anti-EFNA Antibodies Using EFNA Immunogens

EFNA modulators in the form of murine antibodies were produced in accordance with the teachings herein through inoculation with hEFNA4-ECD-Fc, hEFNA4-ECD-His, hEFNA1-ECD-His, whole cell BALB/c 3T3 cells over expressing EFNA4 or the plasma preps prepared as set forth herein (ECD—extracellular domain). Immunogens were all prepared using commercially available starting materials (e.g., Recombinant Human ephrin-A4 Fc Chimera, CF R&D systems #369-EA-200) and/or techniques well known to those skilled in the art.

More particularly murine antibodies were generated by immunizing 9 female mice (3 each: Balb/c, CD-1, FVB) with various preparations of EFNA4 or EFNA1 antigen. Immunogens included Fc constructs or His tagged human EFNA4 or EFNA1, membrane fractions extracted from $10^7$ over expressing EFNA4 293 cells or whole 3T3 cells over expressing human EFNA4 on the surface. Mice were immunized via footpad route for all injections. 10 µg of EFNA4 or EFNA1 immunogen or $1\times10^6$ cells or cell equivalents emulsified with an equal volume of TITERMAX™ or alum adjuvant were used for immunization. After immunization mice were euthanized, and draining lymph nodes (popliteal and inguinal, if enlarged) were dissected out and used as a source for antibody producing cells. Lymphocytes were released by mechanical disruption of the lymph nodes using a tissue grinder.

One of two fusion protocols was used. In the first electrofusion with a Genetronic device was performed followed by plating and screening of the polyclonal hybridomas with a subsequent subcloning to generate monoclonal hybridomas. In the second ectrofusion with a BTX instrument was performed followed by growth of the hybridoma library in bulk and single cell deposition of the hybridomas with a subsequent screen of the clones.

Genetronic device fusion protocol: The fusion was performed by mixing a single cell suspension of B cells with non-secreting P3x63Ag8.653 myeloma cells purchased from (ATCC CRL-1580; Kearney et al, J. Immunol. 123:1548-1550 (1979)) at a ratio of 1:1. The cell mixture was gently pelleted by centrifugation at 800 g. After complete removal of the supernatant, the cells were treated with 2-4 mL of Pronase solution for no more than 2 minutes. Electrofusion was performed using a fusion generator, model ECM2001 (Genetronic, Inc.).

Cells were plated at $2\times10^4$/well in flat bottom microtiter plates, followed by two weeks incubation in selective HAT medium (Sigma, CRL P-7185). Individual wells were then screened by ELISA and FACS for anti-human EFNA4 monoclonal IgG antibodies.

ELISA microtiter plates were coated with purified recombinant EFNA4 His fusion proteins from transfected 293 cells at 100 ng/well in carbonate buffer. Plates incubated at 4° C. overnight than blocked with 200 µl/well of 3% BSA in PBS/Tween (0.05%). Supernatant from hybridoma plates were added to each well and incubated for 1-2 hours at ambient temperature. The plates were washed with PBS/Tween and than incubated with Goat anti mouse IgG, Fc Fragment Specific conjugated with horseradish proxidase (HRP) Jackson ImmunoResearch) for one hour at room temperature. After washing, the plates were developed with TMB substrate (Thermo Scientific 34028) and analyzed by spectrophotometer at OD 450.

EFNA4 secreted hybridoma from positive wells were, rescreened and subcloned by limited dilution or single cell FACS sorting.

Sub cloning was performed on selected antigen-positive wells using limited dilution plating. Plates were visually inspected for the presence of single colony growth and supernatants from single colony wells then screened by antigen-specific ELISAs described above and FACS confirmation as described below. The resulting clonal populations were expanded and cryopreserved in freezing medium (90% FBS, 10% DMSO) and stored in liquid nitrogen. This fusion from mice immunized with EFNA4 yielded 159 murine monoclonal antibodies reactive for EFNA4 using the ELISA protocol described above.

BTX instrument fusion protocol: A single cell suspension of B cells were fused with non-secreting P3x63Ag8.653 myeloma cells at a ratio of 1:1 by electrofusion. Electrofusion was performed using the Hybrimune System, model 47-0300, (BTX Harvard Apparatus). Fused cells were resuspended in hybridoma selection medium supplemented with Azaserine (Sigma #A9666) (DMEM (Cellgro cat#15-017-CM) medium containing, 15% Fetal Clone I serum (Hyclone), 10% BM Condimed (Roche Applied Sciences), 1 mM sodium pyruvate, 4 mM L-glutamine, 100 IU Penicillin-Streptomycin, 50 µM 2-mercaptoethanol, and 100 µM hypoxanthine) and then plated in four T225 flasks at 90 ml selection medium per flask. The flasks are then placed in a humidified 37° C. incubator containing 5% $CO_2$ and 95% air for 6-7 days.

At 6-7 days of growth the library is plated at 1 cell per well in 48 Falcon 96 well U-bottom plates using the Aria I cell sorter. Briefly culture medium containing 15% Fetal Clone I serum (Hyclone), 10% BM-Condimed (Roche Applied Sciences), 1 mM sodium pyruvate, 4 mM L-glutamine, 100 IU Penecillin-Streptamycin, 50 µM 2-mercaptoethanol, and 100 µM hypoxanthine is plated at 200 ul per well in 48 Falcon 96 well U-bottom plates. Viable hybridomas are placed at 1 cell per well using the Aria I cell sorter and cultured for 10-11 days and the supernatants are assayed for antibodies reactive by FACS or ELISA for EFNA4 or EFNA1.

Growth positive hybridomas wells secreting mouse immunoglobulins were screened for murine EFNA4 specificity using an ELISA assay similar to that described above. Briefly, 96 well plates (VWR, 610744) were coated with 1 µg/mL murine EFNA4-His in sodium carbonate buffer overnight at 4° C. The plates were washed and blocked with 2% FCS-PBS for one hour at 37° C. and used immediately or kept at 4° C. Undiluted hybridoma supernatants were incubated on the plates for one hour at RT. The plates are washed and probed with HRP labeled goat anti-mouse IgG diluted 1:10,000 in 1% BSA-PBS for one hour at RT. The plates are then incubated with substrate solution as described above and read at OD 450.

Growth positive hybridomas wells secreting mouse immunoglobulins were also screened for human EFNA1 specificity using a FACS assay as follows. Briefly $1 \times 10^5$ per well Jurkat cells expressing human EFNA1 were incubated for 30 minutes with 25-100 ul hybridoma supernatant. Cells were washed PBS/2% FCS twice and then incubated with 50 ul per sample DyeLight 649 labeled goat-anti-mouse IgG, Fc fragment specific secondary diluted 1:200 in PBS/2% FCS. After a 15 minute incubation cells were washed 2 times with PBS/2% FCS and re-suspended in PBS/2% FCS with DAPI and analyzed by FACS Canto II (BD Biosciences) under standard conditions and using the HTS attachment. The resulting EFNA1 specific clonal hybridomas were expanded and cryopreserved in CS-10 freezing medium (Biolife Solutions) and stored in liquid nitrogen. This fusion from mice immunized with EFNA1 yielded 1 hybridoma reactive with EFNA4 as determined using FACS analysis. Moreover, FACS analysis confirmed that purified antibody from most or all of these hybridomas bind EFNA4 or EFNA1 in a concentration-dependent manner.

Example 7

Sequencing and Humanization of Ephrin-A Ligand Modulators

7(a) Sequencing:

Based on the foregoing, a number of exemplary distinct monoclonal antibodies that bind immobilized human EFNA4 or EFNA1 with apparently high affinity were selected. As shown in a tabular fashion in FIG. 7A sequence analysis of the DNA encoding mAbs from Example 6 confirmed that many had a unique VDJ rearrangements and displayed novel complementarity determining regions. Note that the complementarity determining regions set forth in FIG. 7A (SEQ ID NOS: 8-59 and 70-95) were derived from VBASE2 analysis.

For initiation of sequencing TRIZOL reagent was purchased from Invitrogen (Life Technologies). One step RT PCR kit and QIAquick PCR Purification Kit were purchased from Qiagen, Inc. with RNasin were from Promega. Custom oligonucleotides were purchased from Integrated DNA Technologies.

Hybridoma cells were lysed in TRIZOL reagent for RNA preparation. Between $10^4$ µL and $10^5$ cells were resuspended in 1 ml TRIZOL. Tubes were shaken vigorously after addition of 200 µl of chloroform. Samples were centrifuged at 4° C. for 10 minutes. The aqueous phase was transferred to a fresh microfuge tube and an equal volume of isopropanol was added. Tubes were shaken vigorously and allowed to incubate at room temperature for 10 minutes. Samples were then centrifuged at 4° C. for 10 minutes. The pellets were washed once with 1 ml of 70% ethanol and dried briefly at room temperature. The RNA pellets were resuspended with 40 µL of DEPC-treated water. The quality of the RNA preparations was determined by fractionating 3 µL in a 1% agarose gel. The RNA was stored in a −80° C. freezer until used.

The variable DNA sequences of the hybridoma amplified with consensus primer sets specific for murine immunoglobulin heavy chains and kappa light chains were obtained using a mix of variable domain primers. One step RT-PCR kit was used to amplify the VH and VK gene segments from each RNA sample. The Qiagen One-Step RT-PCR Kit provides a blend of Sensiscript and Omniscript Reverse Transcriptases, HotStarTaq DNA Polymerase, Qiagen OneStep RT-PCR Buffer, a dNTP mix, and Q-Solution, a novel additive that enables efficient amplification of "difficult" (e.g., GC-rich) templates.

Reaction mixtures were prepared that included 3 µL of RNA, 0.5 of 100 µM of either heavy chain or kappa light chain primers 5 µL of 5×RT-PCR buffer, 1 µL dNTPs, 1 µL of enzyme mix containing reverse transcriptase and DNA polymerase, and 0.4 µL of ribonuclease inhibitor RNasin (1 unit). The reaction mixture contains all of the reagents required for both reverse transcription and PCR. The thermal cycler program was RT step 50° C. for 30 minutes 95° C. for 15 minutes followed by 30 cycles of (95° C. for 30 seconds, 48° C. for 30 seconds, 72° C. for 1.0 minutes). There was then a final incubation at 72° C. for 10 minutes.

To prepare the PCR products for direct DNA sequencing, they were purified using the QIAquick™ PCR Purification Kit according to the manufacturer's protocol. The DNA was eluted from the spin column using 50 µL of sterile water and then sequenced directly from both strands. PCR fragments were sequenced directly and DNA sequences were analyzed using VBASE2 (Retter et al., Nucleic Acid Res. 33; 671-674, 2005).

As briefly alluded to above the genetic arrangements and derived CDRs from VBASE2 analysis) of several exemplary anti-hEFNA4/hEFNA1 antibodies are set forth in a tabular form in FIG. 7A (SEQ ID NOS: 8-59 and 70-95). Further, the nucleic and amino acid sequences of these same exemplary antibody heavy and light chain variable regions are set forth in FIGS. 7B-7N (SEQ ID NOS: 96-147).

7(b) Humanization:

Four of the murine antibodies from Example 6 were humanized using complementarity determining region (CDR) grafting. Human frameworks for heavy and light chains were selected based on sequence and structure similarity with respect to functional human germline genes. In this regard structural similarity was evaluated by comparing the mouse canonical CDR structure to human candidates with the same canonical structures as derived from VBASE2 analysis.

More particularly murine antibodies SC4.5, SC4.15, SC4.22 and SC4.47 were humanized using a computer-aided CDR-grafting method (Abysis Database, UCL Business Plc.) and standard molecular engineering techniques to provide hSC4.5, hSC4.15, hSC4.22 and hSC4.47 modulators (Note: the addition of a subsequent numeral following the clone or antibody designation i.e., SC4.47.3 refers to a particular subclone and is not material for the purposes of the instant disclosure unless otherwise noted or required by context). The human framework regions of the variable regions were selected based on their highest sequence homology to the mouse framework sequence and its canonical structure. For the purposes of the analysis the assignment of amino acids to each of the CDR domains is in accordance with the Kabat et al. numbering. Several humanized antibody variants were made in order to generate the optimal humanized antibody with the humanized antibodies generally retaining the antigen-binding complementarity-determining regions (CDRs) from the mouse hybridoma in association with human framework regions. Humanized SC4.15, SC4.22 and SC4.471 mAbs bind to EFNA4 antigen with similar affinity to their murine counterparts while hSC1.5 bound with a slightly lower affinity as measured using the Biacore system.

Molecular engineering procedures were conducted using art-recognized techniques. To that end total mRNA was extracted from the hybridomas according to the manufacturer's protocol (Trizol® Plus RNA Purification System, Life Technologies). A primer mix comprising thirty-two mouse specific 5' leader sequence primers, designed to target the complete mouse repertoire, was used in combination with 3' mouse Cγ1 primer to amplify and sequence the variable region of the antibody heavy chains. Similarly thirty-two 5' Vk leader sequence primer mix designed to amplify each of the Vk mouse families combined with a single reverse primer specific to the mouse kappa constant region were used to amplify and sequence the kappa light chain. The $V_H$ and $V_L$ transcripts were amplified from 100 ng total RNA using reverse transcriptase polymerase chain reaction (RT-PCR).

A total of eight RT-PCR reactions were run for each hybridoma: four for the V kappa light chain and four for the V gamma heavy chain (γ1). The QIAGEN One Step RT-PCR kit was used for amplification, (Qiagen, Inc.). The extracted PCR products were directly sequenced using specific V region primers. Nucleotide sequences were analyzed using IMGT to identify germline V, D and J gene members with the highest sequence homology. The derived sequences were compared to known germline DNA sequences of the Ig V- and J-regions using V-BASE2 (Retter et al., supra) and by alignment of $V_H$ and $V_L$ genes to the mouse germ line database.

From the nucleotide sequence information, data regarding V, D and J gene segments of the heavy and light chains of SC4.5, SC4.15, SC4.22 and SC4.47 were obtained. Based on the sequence data new primer sets specific to the leader sequence of the Ig $V_H$ and $V_K$ chain of the antibodies were designed for cloning of the recombinant monoclonal antibody. Subsequently the V-(D)-J sequences were aligned with mouse Ig germ line sequences. Heavy chain genes of SC4.5 were identified as IGHV2-6 (V), and JH3. Analysis of the short CDR3 of the E5 monoclonal antibody heavy chain did not identified a specific mouse D gene. The heavy chain genes of SC4.15 were identified as IGHV5-6 (V), DSP2.9(D) and JH3. The heavy chain genes of SC4.22 were identified as VHJ558 (V), D segment was identified as DFL16.1e and JH4 (J). The heavy chain genes of SC4.47 were identified as IGHV1-26 (V), P1inv(D) and JH2 (J). All four light chains were K class. Light chains genes were identified as IGKV6-15, JK2 for SC4.5 mAb, IGKV6-b and JK5 for SC4.15 mAb, IGKV1-110 and JK1 germ line sequence for SC4.22 mAb and IGKV21-7, JK1 germ line sequences for SC4.47 kappa light chain. These results are summarized in TABLE 1 immediately below.

TABLE 2

| Clone | Mouse Isotype | VH | DH | JH | VL | JL |
|---|---|---|---|---|---|---|
| SC4.5 | IgG1/K | IGHV2-6 | none | JH3 | IGKV6-15 | JK2 |
| SC4.15 | IgG1/K | IGHV5-6 | DSP2.9 | JH3 | IGKV6-b | JK5 |
| SC4.22 | IgG2b/K | VHJ558 | DFL16.1e | JH4 | IGKV1-110 | JK1 |
| SC4.47 | IgG1/K | IGHV1-26 | P1inv | JH2 | IGKV21-7 | JK1 |

The obtained heavy and light chain sequences from all four clones were aligned to the functional human variable region sequences and reviewed for homology and canonical structure. The result the heavy and light chain analysis are shown below in TABLES 3 and 4 respectively.

TABLE 3

| Clone | human VH | human DH | Human JH | % Homology to human germ line sequence | % homology to mouse sequence |
|---|---|---|---|---|---|
| SC4.5 | VH3-66 | IGHD2-21 | JH4 | 82 | 75 |
| SC4.15 | VH3-21 | IGHD5-5 | JH4 | 88 | 88 |
| SC4.22 | VH1-18 | IGHD5-24 | JH6 | 87 | 83 |
| SC4.47 | VH1-46 | IGHD3-10 | JH4 | 91 | 76 |

TABLE 4

| Clone | Human VK | Human JK | % Homology to human germ line sequence | % Homology to mouse sequence |
|---|---|---|---|---|
| SC4.5 | L1 | JK2 | 86 | 79 |
| SC4.15 | A27 | JK4 | 89 | 76 |
| SC4.22 | A18b | JK1 | 89 | 91 |
| SC4.47 | L6 | JK4 | 87 | 84 |

As the germ line selection and CDR grafting processes appeared to provide antibodies that generally retained their binding characteristics, there was apparently little need to insert murine residues in most of the constructs. However, in hSC4.15 the heavy chain residue 68 was back mutated from Thr (T) to Lys (K) to improve the antibody characteristics.

The amino acid sequences (along with the associated nucleic acid sequence) of the humanized heavy variable region chains and the humanized kappa light chains for all four antibodies are shown in FIGS. 7O-7R (SEQ ID NOS: 148-163) wherein the CDRs in the amino acid sequences (as defined by Kabat et al., supra) are underlined.

More particularly the nucleic acid sequences and corresponding amino acid sequences of the humanized SC4.5 heavy chain (SEQ ID NOS: 148 and 149), and the humanized light chain (SEQ ID NOS: 150 and 151) are shown in FIG. 7O. Similarly, the nucleic acid sequences and corresponding amino acid sequences of the humanized SC4.15 heavy chain (SEQ ID NOS: 152 and 153), and the humanized light chain (SEQ ID NOS: 154 and 155) are shown in FIG. 7P. Another embodiment of the invention is illustrated in FIG. 7Q wherein the nucleic acid sequences and corresponding amino acid sequences of the humanized SC4.22 heavy chain (SEQ ID NOS: 156 and 157), and the humanized light chain (SEQ ID NOS: 158 and 159) are shown. In yet another embodiment FIG. 7R shows the nucleic acid sequences and corresponding amino acid sequences of the humanized SC4.47 heavy chain (SEQ ID NOS: 160 and 161), and the humanized light chain (SEQ ID NOS: 162 and 163). As demonstrated in the Examples below each of the aforementioned humanized antibodies functions as an effective EFNA modulator in accordance with the teachings herein.

In any event the disclosed modulators were expressed and isolated using art recognized techniques. To that end synthetic humanized variable DNA fragments (Integrated DNA Technologies) of both heavy chains were cloned into human IgG1 expression vector. The variable light chain fragments were cloned into human C-kappa expression vector. Antibodies were expressed by co-transfection of the heavy and the light chain into CHO cells.

More particularly, for antibody production directional cloning of the murine and humanized variable gene PCR products into human immunoglobulin expression vectors was undertaken. All primers used in Ig gene-specific PCRs included restriction sites (AgeI and XhoI for IgH, XmaI and DraIII for IgK, which allowed direct cloning into expression vectors containing the human IgG1, and IGK constant regions, respectively. In brief, PCR products were purified with Qiaquick PCR purification kit (Qiagen, Inc.) followed by digestion with AgeI and XhoI (IgH), XmaI and DraIII (IgK), respectively. Digested PCR products were purified prior to ligation into expression vectors. Ligation reactions were performed in a total volume of 10 µL with 200 U T4-DNA Ligase (New England Biolabs), 7.5 µL of digested and purified gene-specific PCR product and 25 ng linearized vector DNA. Competent E. coli DH10B bacteria (Life Technologies) were transformed via heat shock at 42° C. with 3 µL ligation product and plated onto ampicillin plates (100 µg/mL). The AgeI-EcoRI fragment of the $V_H$ region was than inserted into the same sites of pEE6.4HuIgG1 expression vector while the synthetic XmaI-DraIII $V_K$ insert was cloned into the XmaI-DraIII sites of the respective pEE12.4Hu-Kappa expression vector.

Cells producing humanized antibodies were generated by transfection of HEK 293 cells with the appropriate plasmids using 293fectin. In this respect plasmid DNA was purified with QIAprep Spin columns (Qiagen). Human embryonic kidney (HEK) 293T (ATCC No CRL-11268) cells were cultured in 150 mm plates (Falcon, Becton Dickinson) under standard conditions in Dulbecco's Modified Eagle's Medium (DMEM) supplemented with 10% heat inactivated FCS, 100 µg/mL streptomycin, 100 U/mL penicillin G (all from Life Technologies).

For transient transfections cells were grown to 80% confluency. Equal amounts of IgH and corresponding IgL chain vector DNA (12.5 µg of each vector DNA) was added to 1.5 mL Opti-MEM mixed with 50 µL HEK 293 transfection reagent in 1.5 mL opti-MEM. The mix was incubated for 30 min at room temperature and distributed evenly to the culture plate. Supernatants were harvested three days after transfection, replaced by 20 mL of fresh DMEM supplemented with 10% FBS and harvested again at day 6 after transfection. Culture supernatants were cleared from cell debris by centrifugation at 800×g for 10 min and stored at 4° C. Recombinant chimeric and humanized antibodies were purified with Protein G beads (GE Healthcare).

Example 8

Characteristics of EFNA Modulators

8(a) General Modulator Characteristics

Various methods were used to analyze the binding characteristics of selected ephrin-A4 modulators generated as set forth above. Specifically, a number of EFNA4 antibodies were characterized as to affinity, kinetics, binning, and cross-reactivity with regard to cynomolgus and mouse homologs (generated internally) by ForteBIO®. Western reactivity was also measured and epitopes were determined for two antibodies (SC4.22 and SC4.91) that bind under reducing conditions. In addition, the antibodies were tested for their ability to neutralize (i.e. block receptor ligand interaction), internalize and were benchmarked for their relative $EC_{50}$ of killing by in vitro cytotoxicity assay using the procedures set forth in these Examples (e.g., see Examples 12 and 16). The results of this characterization are set forth in tabular form in FIG. 8A.

With regard to the data, affinity was measured in three ways to ensure accuracy. First, binding signal was measured for a fixed amount of antibody probed against serial dilutions of antigen in an ELISA to determine relative modulator activity (data shown for cyno binding only). Second, the affinities and kinetic constants $k_{on}$ and $k_{off}$ of the selected modulators were then measured using bio-layer interferometry analysis on a ForteBIO RED (ForteBIO, Inc.) with a standard antigen concentration series. Finally, the affinity of selected modulators was measured by surface plasmon resonance (Biacore System, GE Healthcare). Based on a standard antigen concentration series and using a 1:1 Langmuir binding model, the $K_d$ of the antibody binding to antigen and the kinetic constants $k_{on}$ and $k_{off}$ were determined. In general, the selected modulators exhibited relatively high affinities in the nanomolar range.

As to antibody binning, ForteBIO was used per manufacturer's instructions to identify antibodies, which bound to the same or different bins. Briefly, an antibody (Ab 1) was captured onto an anti-mouse capture chip, a high concentration of nonbinding antibody was then used to block the chip and a baseline was collected. Monomeric, recombinant ephrin-A4-His was then captured by the specific antibody (Ab1) and the tip was dipped into a well with either the same antibody (Ab1) as a control or into a well with a different antibody (Ab2). If additional binding was observed with a new antibody, then Ab1 and Ab2 were determined to be in a different bin. If no further binding occurred, similar to the control Ab1, then Ab2 was determined to be in the same bin. This process can be expanded to screen large libraries of unique antibodies using a full row of antibodies representing unique bins in a 96-well plate. This experiment showed the screened antibodies bound to at least three different bins or epitopes on the EFNA4 protein.

In order to determine whether the epitope recognized by the ephrin-A4 modulator comprises contiguous amino acids or is formed by noncontiguous amino acids juxtaposed by secondary structure of the antigen, Western blots were run under reducing and non-reducing conditions. More particularly, using standard electrophoresis techniques well known in the art, ephrin-A4 antigen in both states was exposed to the selected modulator. As shown in FIG. 8A most ephrin-A4 modulators substantially reacted only with antigen where disulphide bonds were intact (NR), while two modulators reacted with both non-reduced and reduced antigen (NR/R). For these antibodies, a Pepspot (JPT) membrane was used to determine the limits of the antibody recognition by peptide. SC4.22 and SC4.91 were found to recognize the sequence QRFTPFSLGFE (SEQ ID NO: 164) and RLLRGDAVVE (SEQ ID NO: 165), respectively. Retesting of these peptides ability to bind the peptides of interest by ELISA confirmed that the antibodies were indeed specific to these epitopes.

Finally, cross-reactivity with regard to cynomolgus ephrin-A4 homologs were evaluated in ForteBIO using a concentration series with recombinantly expressed, monomeric ephrin-A4 antigens. As shown in FIG. 8A selected modulators were reactive with the homologs. In particular, SC4.5, SC4.15, SC4.91 and SC4.105 were cross-reactive with mouse ephrin- A4, while all antibodies cross-reacted with the highly similar cynomolgus ephrin-A4. ND in the table indicates that the data was not determined.

8(b) Humanized Modulator Characteristics

Using techniques set forth above in this Example the humanized constructs hSC4.15, hSC4.22 and hSC4.47 were analyzed to determine their binding characteristics. Moreover, humanized antibody binding was directly compared with the parent murine antibody for both antibodies to identify any subtle changes in rate constants brought about by the humanization process.

More specifically, the affinity of murine SC4.47 was measured by a Biacore using surface plasmon resonance (SPR) to provide the results set forth in FIG. 8B. Based on a concentration series of 25, 12.5, and 6.25 nM (generating the curves from top to bottom in the FIGS. 8B and 8C) and using a 1:1 Langmuir binding model, the $K_d$ of the antibody binding to antigen was estimated to be 1.1 nM. Similar experiments then run with the humanized construct showed equivalent results (FIG. 8C) indicating that the humanization process had not adversely impacted the affinity. In this regard the measurements indicated that the humanized construct had a $K_d$ of $<1 \times 10^{-10}$, which was substantially identical to the parent murine antibody.

Along with the other techniques set out in this Example, these measurements showed that all humanized ephrin-A4 effectors from Example 7 possess desirable qualities. As set out in FIG. 8D, SC4.15 strongly cross-reacts with murine ephrin-A4 homolog thereby facilitating toxicology studies. The reactivity of all antibodies for the cynomolgus antigen by ELISA could not be distinguished from human EFNA and so is expected to be very similar.

Example 9

Ephrin-A Ligand Modulators Demonstrate Cell Surface Binding

Supernatants from hybridomas producing antibodies raised against hEFNA4-Fc as set forth above were screened for cell surface binding as measured in a flow cytometric assay. To demonstrate the binding properties of the antibodies two cell lines, JurkatE6 cells and Z138 cells each of which are known to express high levels of surface ephrin-A4, were employed. More specifically six million Jurkat E6 cells, stained with the cell labeling dye CFSE (for simple identification), and four million unlabeled Z138 cells, incubated with 20 μg/ml Fc blocking reagent (Trueblock, Biolegend, Inc.) were mixed to a final concentration of 1 million cells/mL. 50 μL of this cell mixture was added to 50 μL of antibody-containing supernatant in each well and incubated for 60 minutes at 4° C. The cells were washed once with PBS containing 2% FBS, 2 mM EDTA and 0.05% sodium azide (wash buffer) and then stained for 60 minutes at 4° C. in the dark with a Fc-region specific F(ab)2 fragment of Goat-anti-mouse IgG polyclonal antibody conjugated to DyLight649 (Jackson Immuno Research). Cells were washed twice with wash buffer, and counterstained with 2 μg/ml DAPI. Negative control samples were a Mouse IgG1 isotype antibody (10 μg/ml, Biolegend, Inc.) and supernatant from a hybridoma (H13.2) known to not secrete mouse IgG. Positive control samples were prepared using 10 μg/ml of a purified antibody (SC4.76.2 aka E76.2) identified before by ELISA to be EFNA4 specific (left side of FIG. 9). Samples were collected on a FACS Canto II (BD Biosciences) under standard conditions and using the HTS attachment. Eighty four (84) clones of one hundred fourteen (114) were judged to display significant cell surface binding as demonstrated by flow cytometry through the staining of both cell lines significantly above negative control samples. In this regard FIG. 9 shows the relative binding capacity of fifty exemplary hybridoma supernatants.

Example 10

Selected EFNA4 Modulators Neutralize Ephrin-A4 Ligand Binding

Supernatants from hybridomas producing antibodies known to bind to ENFA4 expressing cells (Example 9) were tested for their ability to block the binding of soluble hEFNA4-Fc to bind its receptors (EphAs) on the surface of HEK293Td cells. Initially, as seen in FIG. 10A HEK293Td cells are shown to bind hEFNA4-Fc in a dose-dependent manner when compared to a negative control antibody. To demonstrate neutralization of this binding 60 μl of anti-EFNA4 hybridoma supernatants were incubated with 200 ng/ml hEFNA4-Fc diluted in wash buffer for 2 hours at 4° C. The mixture was then added to fifty thousand HEK293Td cells and incubated for 1 hour at 4° C. Cells were washed once in wash buffer and then stained for 45 minutes at 4° C. in the dark with Fc-region specific F(ab)2 fragment of goat-anti-mouse IgG polyclonal antibody conjugated to DyLight649 (Jackson Immuno Research). Cells were then washed twice with wash buffer, and counterstained with 2 μg/ml DAPI. Negative control samples were unstained cells, cells stained with supernatants from a non-IgG producing hybridoma (H13.2) and cells stained with a human IgG Fcγ1 fragment. Positive control samples were hEFNA4-Fc stained cells in absence of hybridoma supernatants and hEFNA4-Fc stained samples in presence of non-IgG producing hybridoma supernatant (left side of FIG. 10B). Samples were measured on a FACS Canto II as previously discussed. As evidenced by FIG. 10B sixty two (62) clones of eighty three (83) tested demonstrated some ability to neutralize hEFNA4-Fc binding to its cell surface receptors when measured using flow cytometry.

Example 11

EFNA Modulators Block Cell Surface EFNA Binding in a Concentration Dependent Manner To further measure the ability of the ephrin-A ligand modulators of the instant invention to neutralize EFNA activity, anti-EFNA4 antibodies from selected hybridomas were purified and used as sterile reagents in PBS buffer. Initially a full dose response curve of human and murine EFNA4-Fc (Recombinant Murine ephrin-A4 Fc Chimera, CF R&D Systems) alone was set up in parallel to demonstrate dose-limited binding of EFNA4-Fc to HEK293Td cells (FIG. 11A). Once this control had been established, serial dilutions of anti-EFNA4 antibodies obtained from three exemplary hybridomas (i.e. SC4.15.3, SC4.47.3 and SC4.76.2) were incubated with limiting concentrations (0.1 μg/ml and 1.0 μg/ml) of hEFNA4-Fc and mEFNA4-Fc respectively in wash buffer for 1 hr at 4° C. The resulting reagent mixtures were then transferred to fifty thousand HEK293Td cells and incubated for 1 hour at 4° C. Cells were washed once in wash buffer and then stained for 45 minutes at 4° C. in the dark with a Fc-region specific F(ab)2 fragment of goat-anti-mouse IgG polyclonal antibody conjugated to DyLight649 (Jackson Immuno Research). Cells were washed twice with wash buffer, and counterstained with 2 μg/ml DAPI. Negative control samples were unstained cells and cells stained with a human IgG Fcγ1 fragment. Samples were collected on a FACS Canto II as previously alluded to above. FIG. 11B shows the activity of mAb SC4.15.3 which partially inhibits human and mouse EFNA4-Fc binding to cells at relatively high concentrations. FIG. 11C illustrates the activity of mAb SC4.47.3 which almost completely blocks the ability of hEFNA4-Fc to bind to cells but not the ability of mEFNA4-Fc. Similarly, FIG. 11D demonstrates the ability of ephrin-A ligand modulator mAb SC4.76.2 to substantially inhibit the ability of hEFNA4-Fc to bind to cells while not dramatically impacting the ability of mEFNA4-Fc to bind to the cells. These results are strongly indicative of the capacity of selected modulators of the instant invention to inhibit the binding of ephrin-A ligands to cell surface receptors and thus inhibit any associated tumorigenic activity.

Example 12

EFNA Modulators Block Binding of EFNA to EphA Receptors in a Concentration Dependent Manner As discussed above EphA2 is a known binding partner for EFNA4. To exploit this known relationship the extracellular domain of EphA2 was fused to the Fc portion of a human IgG using standard techniques, transiently expressed in HEK293Td cells and purified from the supernatant of the culture using Protein A affinity chromatography. As seen in FIG. 12A the EphA2-Fc homodimer binds in a dose dependent to fashion to Jurkat cells (known to express EFNA) while the Fc portion of human IgG alone does not show any binding. This binding of EphA2-Fc to Jurkat cells can be inhibited using the ephrin-A modulators of the instant invention and, in particular, through the use of monoclonal antibodies to ephrin-A4. To this end fifty thousand Jurkat cells per well were incubated with 10 µg/ml of four selected anti-ENFA4 antibodies (i.e. SC4.22, SC4.31.3, SC4.47.3 and SC4.73, all prepared as described above) in wash buffer for 1 hr at 4° C. Mouse IgG and no antibody (data not shown) serve as negative controls. After washing, serial dilutions of EphA2-Fc were added to the cells in wash buffer for 1 hr at 4° C. to provide the results graphically represented in FIG. 12B. A review of FIG. 12B shows that modulators SC4.31.3 and SC4.47.3 substantially inhibit the binding of EphA2-Fc to EFNA4 whereas modulators SC4.22 and SC4.73 exhibit relatively less inhibition. To further illustrate the ability of the disclosed modulators to inhibit interactions with the receptor, Jurkat cells were first incubated with serial dilutions of antibodies, followed by incubation with 10 µg/ml EphA2-Fc. The cells were then washed twice with wash buffer, counterstained with 2 µg/ml DAPI, and analyzed on a FACS Canto II (BD Biosciences) under standard conditions using the HTS attachment to provide the data represented in FIG. 12C. As with FIG. 12B, FIG. 12C demonstrates that modulator mAb SC4.47.3 is a relatively potent inhibitor and efficiently blocks the binding of EphA2-Fc to EFNA4 expressed on Jurkat cells. By way of comparison the other modulators show somewhat less activity with SC4.31.3 providing a moderate amount of inhibition at higher concentrations.

To extend these findings, interactions between additional EFNA4 modulators and EphA receptors were explored. Experiments were carried out similar the one described above except that HEK293T cells overexpressing EFNA4 by means of retroviral transduction (referred to as HEK293T.hEFNA4 cells) (FIG. 12D) or HEK293T cells overexpressing EFNA1 by means of retroviral transduction (FIG. 12E) were used. In addition, the assay was carried out at a single EphAx-Fc concentration (10 µg/ml). The data show that SC4.2, SC4.31, and SC4.47 are able to block binding of all tested EphA receptor binding partners to ephrin-A4 ligand (i.e., EphA2, EphA3, EphA4, EphA6, EphA7, EphA8 and EphA10. In addition it was established that EFNA4 modulator SC9.65, which was generated in an immunization campaign against EFNA1, (as per Example 6) has the ability to interfere with the binding of EphA1, EphA2, EphA4 and EphA7 to ephrin-A1 ligand. These data, when combined with the results of the other Examples herein, suggest that this modulator ability to antagonize the binding of various receptors may be significant in providing the observed therapeutic effects of the instant invention.

Example 13

Modulators to Human Ephrin-A Cross-React with the Mouse Ortholog

In light of the fact that the extracellular domains of human and mouse ephrin-A4 ligand share 80% sequence identity on the protein level, the disclosed modulators to human EFNA4 were tested to see if they associated with the mouse homolog. More specifically, an antibody sandwich ELISA was used to determine the level of cross-reactivity of hEFNA4 specific monoclonal antibodies with its mouse homolog. A high protein binding 96-well assay plate was coated with 0.5 µg/ml of a donkey-anti-human IgG polyclonal antibody specific for the Fc portion of the IgG molecule. The protein coating of the plate occurred in 100 µl volume per well using a 50 mM Sodium Carbonate buffer (pH9.6) during a 16 hour incubation at 4° C. Human and mouse EFNA4 molecules fused to the Fcγµ1 potion of a human IgG molecule (EFNA4-Fc) were serially diluted in PBS buffer containing 2% (w/v) bovine serum albumin (PBSA). After washing the coated plate in PBS buffer containing 0.05% Tween20 (PBST), 100 µl per well diluted mouse or human EFNA4-Fc in PBSA was added to wells for the duration 3 hours at ambient temperature. The plate was then washed again with PBST and 100 µl/well PBSA containing 10% spent hybridoma supernatant or 1 µg/ml purified monoclonal antibody (as positive control) was added to the plate for the duration of 1 hour at ambient temperature. After washing the plate with PBST, 100 µl per well of PBSA containing a 1:5000 dilution of goat anti-mouse IgG polyclonal antibody, specific for the Fc portion of Mouse IgG and conjugated to horseradish peroxidase (Jackson Immuno Research), was added to the plate for 30 minutes at ambient temperature. After washing the plate extensively with PBST, 100 µl per well TMB substrate (Thermo Fisher) was added to the wells for 15 minutes. The enzymatic reaction was stopped by adding 100 µl/well 2M sulfuric acid. The absorbance of this colorimetric assay was measured at 450 nm using a Victor plate reader (Perkin Elmer). Data are presented as mean absorbance reading plus standard deviation using two replicates. FIG. 13A shows an exemplary monoclonal antibody SC4.31.3 that recognizes hEFNA4 but not mEFNA4. Conversely FIG. 13B shows the binding of exemplary monoclonal antibody SC4.91.4 which recognizes both human and mouse EFNA4.

To confirm these results the assay was run using the humanized ephrin-A4 modulator hSC4.15. More particularly titrated amounts of human and mouse ephrin-A4-His were coated on high protein binding 96-well plates in PBS at 4° C. for 16 hours. After blocking the plates for 2 hr at ambient temperature in PBSA, 0.5 µg/ml of hSC4.15 modulator was added for 2 hours in PBSA. The ELISA was developed as described above using a donkey-anti human IgG polyclonal antibody conjugated to horseradish peroxidase (Jackson Immuno Research). FIG. 13C shows that the hSC4.15 modulator recognizes both human and mouse ephrin-A4 ligand equally well indicating that the disclosed humanized modulators are entirely compatible with the teachings herein.

Example 14

Ephrin-A Ligand Expression in Exemplary Tumor Samples, Tumor Cell Subpopulations and Hematopoietic Cells After documenting elevated gene expression levels and generating antibodies against EFNA4 in the previous Examples, evidence was sought for corresponding EFNA4 protein expression is selected cell populations. In this respect, reverse phase cancer protein lysate arrays (ProteoScan Arrays; OriGene Technologies) comprising 4 dilutions of 432 tissue lysates from 11 tumor types, or their respective normal adjacent tissue, were provided along with controls consisting of HEK 293 cells without or with TP53-overexpression driven by an exogenous promoter. EFNA4 protein expression in the lysates on this array were detected using a mouse monoclonal EFNA4 antibody of the instant invention that recognizes EFNA4 protein by Western Blot (e.g. clone E47.3 aka SC4.47.3). Colorimetric detection reagents and protocols were provided by the manufacturer of the ProteoScan Arrays, spots on the fabricated array were converted to a digital image using a flatbed scanner using BZScan2 Java Software (IN-SERM-TAGC) to quantify spot intensity.

Selected results of such assays are shown in FIG. 14, and indicate that expression of the EFNA4 protein is upregulated in colorectal tumor samples. More specifically, FIG. 14A shows that EFNA4 protein expression appears significantly elevated in a subset of colorectal tumor specimens; especially in patients with Stage IV disease when compared to normal adjacent tissue or tumor tissue from specimens obtained from earlier stages of disease. Data was generated as described above and represented as average pixel intensity per spot (spot intensity). The horizontal black bar in each sample represents the mean for specimens in each respective category.

After confirming that EFNA4 protein was upregulated in certain colorectal whole tumor cell lysates tests were conducted to establish that the same target was expressed on tumor initiating cells. More specifically, to determine whether EFNA4 protein expression could be detected on the cell surface of tumor initiating cells, tumors were disassociated as described above for flow cytometric analysis. After the tumor sample (e.g. colorectal cell line CR33 as per Example 2) was disassociated to a single cell suspension, they were incubated at 37° C. for 24 hours to facilitate antigen re-expression (due to the enzymatic sensitivity of the EFNA4 antigen to collagenase/hyaluronidase), and then stained with a phycoerythrin (PE)-conjugated monoclonal antibody able to recognize EFNA4. The cells were then analyzed as in previous examples with a FACS Canto II (BD Biosciences) under standard conditions using the HTS attachment. In conducting such experiments it was observed that EFNA4 expression was noticeably higher on the TIC cell subpopulation (as defined by co-staining of the cells with antibodies recognizing TIC-defining cell surface markers; e.g. $46^+$, $324^+$, $66^-$) than on NTG cells. A representative result from an experiment using SCRx-CR33 colorectal NTX tumor cells and EFNA4 modulator SC4.47.3 shows that the expression of EFNA4 was more than 2-fold higher on TIC than on NTG cells (FIG. 14B).

Figure 14D:
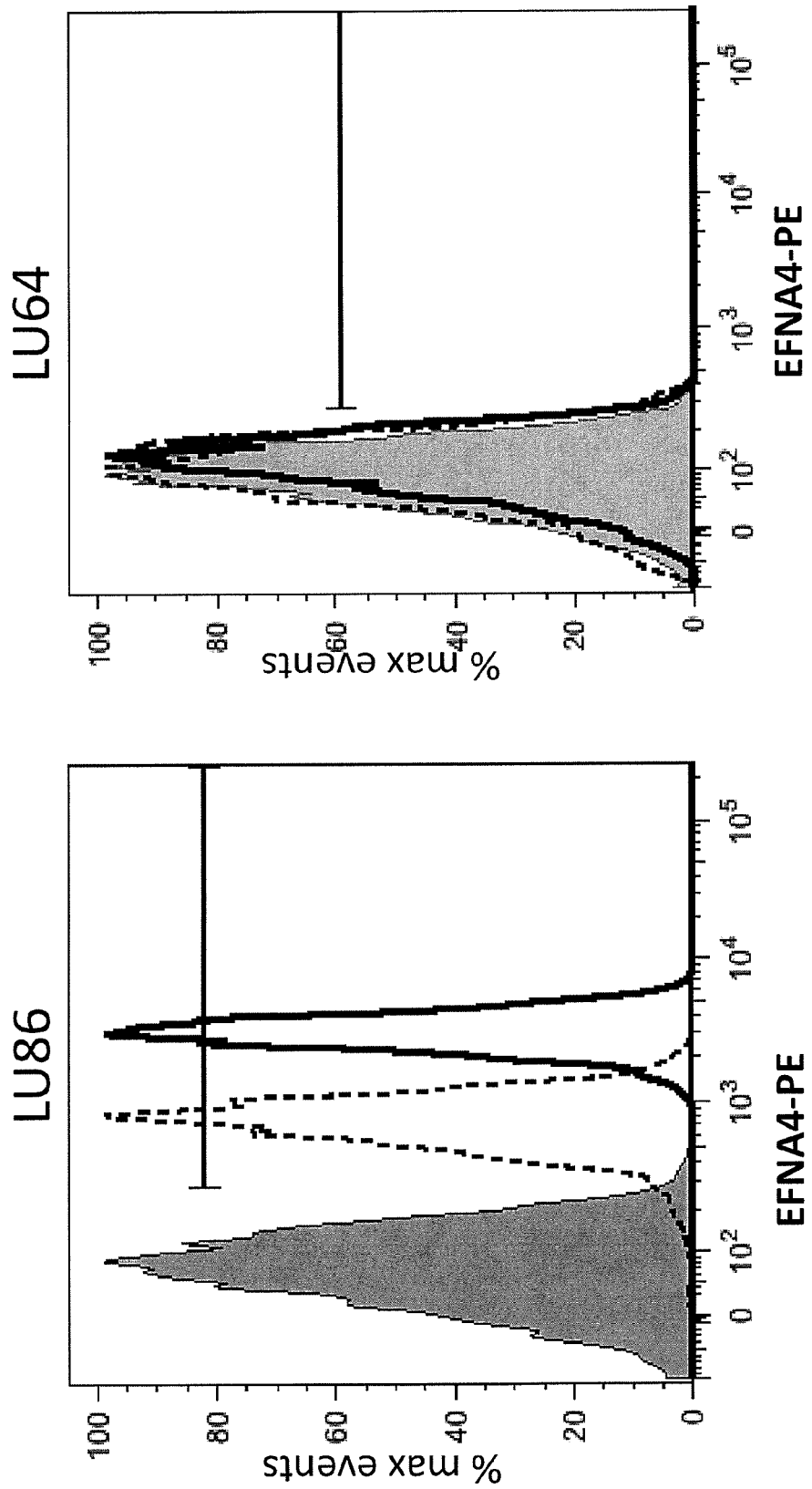

To further confirm that EFNA4 is relatively highly expressed on TIC cells, LU86 and LU64 cells were cultured in vitro for 10 days and expression was measured by flow cytometry using a PE conjugated SC4.47 antibody as set forth herein. Resulting colonies were harvested and stained as described above. As illustrated in FIG. 14D the TIC population of LU86 cells (solid black line) express EFNA4 well above isotype control (shaded gray) and the NTG population (dashed black line) from the same tumor line. Additionally, LU86 cells cultured in vivo can be killed with EFNA4 antibodies (as shown in Example 16 below). Conversely LU64 cells were found not express elevated levels of EFNA4 (FIG. 14D) and subsequently were not killed with anti-EFNA antibodies.

While it is believed that EFNA4 protein expression has not been assessed in solid tumor specimens prior to the instant disclosure, it has been reported that the protein is expressed at relatively low levels on B-cells and elevated on B-cells from Chronic Lymphocytic Leukemia (CLL) patients. In order to confirm the expression of EFNA4 proteins on normal peripheral blood mononuclear cells (PBMC) assays were run as previously described in this Example to provide the data set forth in FIG. 14C. A review of the plots presented in FIG. 14C shows that when EFNA4 expression was gauged on PBMC from a normal donor, only $CD19^+$ B-cells were weakly positive, confirming reports in the literature as to where EFNA4 is expressed.

These data support the observations in above examples that EFNA4 overexpression is associated with TIC and/or TPC in colorectal cancer, and may be involved in proliferation and/or survival. The data further shows that EFNA4 is not expressed on the majority of normal PBMC, and that expression on normal B-cells is minimal. In view of the forgoing Examples showing: a) EFNA4 gene expression is associated with the TPC cell subpopulation in colorectal cancer and the tumorigenic cell subpopulation in pancreatic tumors; b) that EFNA4 protein expression is higher on the TIC cell subpopulation; c) EFNA4 protein expression is elevated in whole tumor specimens from late stage colorectal cancer; and d) the general observation is that TIC are more frequent in late stage tumors, it appears that EFNA4 is associated with those cells underlying tumor growth, resistance to therapy and tumor recurrence, advocating that EFNA4 may play in integral role in supporting TPC and/or TIC in the above mentioned tumors.

Example 15

Ephrin-A Ligand Modulators Are Internalized By K562 Cells

Given the expression profile of ephrin-A ligands established in the previous Examples, assays were conducted to see if the modulators of the instant invention were internalized upon binding to the cell surface antigen. In this respect supernatant from hybridomas producing antibodies raised against EFNA4-Fc in Example were screened for their ability to internalize in K562 cells, which express EFNA4 at low levels on the cell surface. K562 cells at a starting concentration of $10^6$/ml (single cells suspension) were blocked with Human TruStain (BioLegend, Inc.) for 10 minutes at room temperature, and then diluted to $5 \times 10^4$ cells per well. Duplicate samples were then stained for 30 minutes on ice with anti-EFNA antibody containing supernatant for a final volume of 50 µl. Cells were then washed with FACS staining medium (FSM; 2% fetal bovine serum/Hank's buffered saline solution/25 mM HEPES [pH7.4]) to remove unbound antibody. This was followed by a second stain with donkey anti-mouse Alexa647 (Life Technologies) for 30 minutes on ice. Samples were washed again to remove unbound antibody and then re-suspended in internalization medium (2% fetal bovine serum/Iscove's Modified Dulbecco's Medium). To allow internalization, samples were incubated in 5% CO2 @ 37° C. (or 4° C. for the Control) for an hour. Internalization was stopped by transferring samples to ice and adding excess ice cold FSM. To remove any antibody that did not internalize and remained on the cell surface, samples were treated with low pH phosphate buffered saline (PBS [pH2.0]) for 10 minutes on ice. Following this "acid strip" procedure, samples were washed extensively with FSM, re-suspended in 150 μl of FSM containing 2 μg/ml of DAPI, and analyzed by flow cytometry (again using a FACS Canto II (BD Biosciences) under standard conditions using the HTS attachment). Any signal detected beyond background results from antibody internalization: a process that protects the fluorescent conjugate from removal from the cell surface during the acid strip process. All incubations were performed in FSM unless stated otherwise.

Screening of 159 EFNA4 antibody-containing hybridoma supernatant clones using the acid strip protocol described above showed many supernatants display a positive shift in fluorescence vs. the IgG negative control antibodies (data not shown). The exemplary SC4.5, SC4.22 and SC4.73 clones, for instance, demonstrated internalization in as far as supernatants from these clones was able to internalize and protect the Alexa647 secondary antibody from acid stripping (FIG. 15A). Compared to the IgG controls, approximately 15% of the EFNA4 antibody-containing supernatants induced internalization to varying degrees, with the top nineteen (19) demonstrating a Delta Mean Fluorescent Intensity (MFI at 37° C. vs. 4° C.) above 150 (FIG. 15B). This data demonstrates that a subset of modulators generated against human EFNA4 ECD bind the antigen as it is presented on cells and is able to internalize. Such results underscore the potential therapeutic value of ephrin-A ligands as targets for the modulators of the instant invention with or without cytotoxic payloads.

The assay was repeated using selected purified EFNA4 modulators at a concentration of 10 μg/ml and HEK293T (FIG. 15C) and HEK293T.hEFNA4 (FIG. 15D) cells as target cells. Parental HEK293T express a low level of ephrin-A4 ligand on their cell surface. Following the protocol described above, the data demonstrate that all tested ephrin-A4 modulators are internalized upon binding to ephrin-A4 ligand expressed on the surface of cells. Recorded mean fluorescence intensities (MFI) for each sample were compared against a standard bead (Becton Dickenson Spherotech 8-color rainbow beads) containing eight different known amounts of encapsulated fluorophore (data not shown). This permitted the transformation of MFI values into linear values and calculation of relative receptor number per cell.

Example 16

EFNA4 Modulators as Targeting Moieties

Targeting of a cytotoxic drug stably linked to an antibody represent an empowered antibody approach that might have great therapeutic benefit for patients with solid tumors. To determine whether the EFNA4-specific antibodies described above were able to mediate the delivery of a cytotoxic agent to live cells, an in vitro cell killing assay was performed wherein streptavidin conjugated to the ribosome-inactivating protein Saporin (Advanced Targeting Systems) was bound to biotinylated EFNA4 antibodies, and the ability of these Saporin complexes to internalize and kill cells was measured 72 hours later by measuring cell viability.

Specifically, $10^5$ Z138 cells per well were plated in wells of a 96-well plate. The anti-EFNA4 antibodies described above were purified from supernatants, biotinylated and then diluted to 20 μg/mL. The Z138 cell line (ATCC CRL-3001) was derived from a patient with mantle cell lymphoma and expresses modest amounts of EFNA4. An aliquot of each antibody, respectively, was mixed 1:1 with streptavidin-ZAP (Advanced Targeting Systems), vortexed for 5 seconds, and then incubated at room temperature for 1 hour. Two additional serial 10-fold dilutions of the antibody-Saporin complexes were then made 50 μL of each mixture, respectively, was added to Z138 cell containing wells. The cell/antibody-saporin mixture was then incubated at 37° C./5% $CO_2$ for 24 hours. Following this incubation, cells were spun down in the round-bottom 96-well plates, supernatant was removed, and 100 μL of fresh culture medium was added to each well. The cells were then incubated for an additional 72 hours and then viable cell numbers were enumerated using CellTiter-Glo (Promega Corp.) per the manufacturer's protocol.

Using this protocol several antibodies that were able to internalize as described in the previous Example were also able to mediate cell killing in vitro (data not shown) whereas a biotinylated isotype control antibody was not able to kill cells. That is, several of these internalizing modulators were able to mediate Saporin toxin internalization that resulted in cell death. FIG. 16A illustrates this cell killing capacity for the exemplary internalizing modulator SC4.5.3 where the downward slope of the curve represents cell death in a concentration dependent manner as compared to the control. These data clearly demonstrate the effectiveness of the disclosed modulators when acting as vectors for the selective internalization of cytotoxic payloads in tumorigenic cells expressing ephrin-A ligands.

To corroborate the these results and determine whether EFNA4 effectors can mediate toxin internalization and cell killing of primary human tumor cells, mouse lineage-depleted NTX cells (i.e. human tumor cells propagated as low-passage xenografts in immunocompromised mice) were plated and subsequently exposed to anti-EFNA4 antibodies and Fab-ZAP.

Specifically, NTX tumors representing lung and skin tumor specimens were dissociated into a single cell suspension and plated on BD Primaria™ plates (BD Biosciences) in growth factor supplemented serum free media as is known in the art. After 3-5 days of culture at 37° C./5% $CO_2$/5% $O_2$, cells were contacted with a control (IgG1 or IgG2b) or a murine EFNA4 modulator (SC4.5, SC4.22, SC4.47, or SC4.91 at 1 nM;), and Fab-ZAP (at 40 nM). Modulator-mediated saporin cytotoxicity was then assessed by quantifying the remaining number of cells using CellTiter Glo 5-7 days later. As seen in FIG. 16B exposure to the EFNA4 antibodies resulted in reduced LU86 cell numbers, whereas the IgG2b and IgG1 isotype control antibody did not impact the number of live cells after treatment. In FIG. 16C exposure to SC4.5, SC4.47, SC4.91 antibodies resulted in reduced SK19 cell numbers whereas isotype controls and SC4.22 were ineffective. Not only does this data demonstrate that exemplary antibodies described herein are specific to EFNA4, are able to bind EFNA4 antigen on the cell surface and facilitate the delivery of a cytotoxic payload resulting in cell death, but the above data also demonstrated that multiple anti-EFNA4 antibodies can mediate killing of multiple NTX tumor cells.

In a variation of the aforementioned killing assay, delivery of a cytotoxic payload via EFNA modulators was demonstrated for additional antibodies and in additional cells. 2000 cells/well of the following cell types were plated into 96 well tissue culture plates in their respective culture media one day before the addition of antibodies and toxin: HEK293T cells (FIG. 16C), HEK293T.hEFNA4 cells (FIG. 16D). Purified ('naked') mouse monoclonal antibodies at various concentrations and a fixed concentration of 10 nM Anti-Mouse IgG Fab fragment covalently linked to Saporin (Advanced Targeting Systems, #IT-48) were added to the cultures for 72 hr. Viable cell numbers were enumerated as described above. Raw luminescence counts using cultures containing cells with the Saporin Fab fragment were set as 100% reference values and all other counts calculated accordingly (referred to as "Normalized RLU").

Using this assay, we are able to demonstrate that all tested EFNA antibodies but not isotype control antibodies are able to kill target cells. This assay further demonstrates that internalization occurs solely because of binding of the EFNA4 antibody to the cell surface without the need for additional cross-linking. Finally, the data demonstrate that only cells that express a sufficient number of EFNA on their surface are killed by EFNA modulators. Parental HEK293T cells express a low number of EFNA on their cell surface while HEK293T.hEFNA4 cells express this ligand strongly (see FIGS. 15C and 15D from the previous Example). Table 5 below lists half-maximal effective concentration (commonly referred to as "EC50") for all tested antibody/target cell combination. In addition to the aforementioned cell lines PC3 cells (ATCC CRL-1435), a cell line derived from a human adenocarcinoma, was used as a target cell.

TABLE 5

EFNA Modulators Deliver a Cytotoxic Payload

| EC50 (pM) | HEK293T | HEK293T.hEFNA4 | PC3 | Z138 |
|---|---|---|---|---|
| Isotype | No killing | No killing | No killing | No killing |
| SC4.2.1 | No killing | 10.1 | N.T. | N.T. |
| SC4.5.1 | No killing | 15.0 | N.T. | 4.6 |
| hSC4.15 | N.T. | 13.7 | 5.4 | N.T |
| SC4.22.1 | No killing | 28.6 | 5.4 | 18.7 |
| SC4.31.3 | No killing | 14.2 | N.T. | 33.8 |
| SC4.47.3 | 201 | 23.2 | 2.5 | 9.6 |
| SC4.91.4 | No killing | 7.8 | N.T. | 15.8 |
| SC4.105.4 | No killing | 17.3 | N.T. | 65.2 |
| SC9.65 | No killing | 28.9 | N.T. | N.T. |

(N.T. = not tested)

In another variation of the in vitro killing assay, humanized EFNA modulators were tested for their ability to internalize and deliver a cytotoxic payload. The assay was carried out just as described above, except that only 500 cells/well were plated and Anti-Human IgG Fab fragment covalently linked to saporin (Advanced Targeting Systems, #IT-51) was added to the cultures. FIG. 16E illustrates that humanized (Hz in FIG. 16E) EFNA modulators described in Example 7 are able to bind to ephrin-A4 ligand expressed on the surface of target cells and induce internalization of EFNA together with bound antibody and cytotoxic payload.

In yet another variation of the in vitro killing assay, humanized EFNA modulator hSC4.15 shown to bind to mouse and human EFNA equally well (see FIG. 13C) was tested for its ability to internalize and deliver a cytotoxic payload to HEK293T cells overexpressing human or mouse EFNA. To ensure direct comparability, lentivirally transduced cells were stained with hSC4.15 and sorted by FACS for moderate expression of either human or mouse ephrin-A4 (data not shown). The killing assay was carried out just as described above. FIG. 16F illustrates that humanized SC4.15 modulator kills cells expressing mouse or human EFNA equally well.

Example 17

EFNA Modulators Detect Secreted Ephrin-A Ligand

As discussed in some detail above EFNA4 can exist as GPI-linked molecule associated with cell membranes or as secreted truncated ligands or isoforms. Detection of these secreted compounds in biological material, such as bodily fluids or cell culture media, may be useful for diagnostic purposes or as an aid in patient management (utility as biomarker). For example it has been suggested that that secreted EFNA4 may be found at elevated concentrations in B cell chronic lymphocytic leukemia (B-CLL) patients (Alonso-C L M et al., 2009, Leukemia Research 33: 395-406). In order to demonstrate such preferred aspects of the instant invention, disclosed modulators were used recognize non-overlapping epitopes of purified EFNA4 and generally detect and quantify secreted EFNA ligands in selected tumorigenic samples. With regard to this latter feature of the instant invention EFNA modulators were used to detect and quantify secreted ephrin-A ligand in human serum (data not shown) and human plasma obtained from B-CLL patients and from sera of mice bearing human tumor xenotransplants (e.g. as described in Example 1 above). In each case the modulators were able to effectively measure ligand levels as described immediately below.

To detect soluble human EFNA4, antibody SC4.91 was absorbed to a high-protein binding microtiter plate, (Greiner BioOne Microlon plates), at 5 µg/ml in 50 mM sodium carbonate buffer (pH9.6) during an overnight incubation at 4° C. After washing the plate in phosphate buffered saline (PBS) containing 0.05% (v/v) Tween20 (PBST), the plate was blocked in PBS containing 2% (w/v) bovine serum albumin (PBSA) for 2 hours at ambient temperature. Purified ephrin-A4-His, expressed transiently in CHO-S cells and purified using sequentially Nickel NTA resin and gel filtration, was serially diluted in PBSA and added for 2 hours to the plate. After washing with PBST, biotinylated antibody SC4.47 was added at 1 µg/ml in PBSA for 1 hour to the plate. The plate was then washed with PBST and then Streptavidin-horseradish peroxidase conjugate (e.g. Jackson Immuno Research) was added at a 1:5000 dilution into PBSA for 30 minutes. The treated plate was then washed again in PBST and TMB substrate solution (e.g. Thermo Fisher) was added for 30 minutes. The color reaction was stopped by adding an equal volume of 2M sulfuric acid after which the plate was read using an absorbance reading of 450 nm in a standard plate reader. Results of the experiments are shown in FIGS. 17A-C.

Using the techniques described immediately above the concentration of soluble hephrin-A4-His was plotted against absorbance values to provide the curves shown in FIG. 17A. More specifically, the primary curve shows results of absorbance measurements at soluble EFNA4 concentrations from 0-40 pg/ml while the inset shows the same curve at concentrations from 0-1,000 pg/ml. Those skilled in the art will appreciate that the standard curves shown in FIG. 17A may be used to provide an extremely sensitive assay for the measurement of EFNA4 concentrations in biological samples.

Taking advantage of the aforementioned measurements and using non-linear regression (Prism 5, Graphpad Software), the concentration of ephrin-A4 in unknown samples was calculated. In this regard plasma samples of four healthy adults, four patients diagnosed with B cell chronic lymphocytic leukemia (B-CLL) and four patients diagnosed with multiple myeloma (MM) were analyzed for their secreted ephrin-A4 concentration. The data obtained suggest that the hEFNA4 analyte be significantly higher in CLL patients than in healthy adults or other selected B-cell derived tumors (FIG. 17B). Moreover, as previously indicted and shown in FIG. 17C, secreted hENFA4 is also detectable in mice harboring human colorectal cancer xenotransplants. Specifically in FIG. 17C each point is representative of secreted hEFNA4 levels in sera obtained from a different mouse. Conversely, serum levels of secreted hEFNA4 in non-xenotransplanted mice were essentially undetectable (data not shown). Even more surprisingly, when plotting tumor volume against the concentration of hEFNA4 in the serum samples, a significant correlation was observed suggesting that the secreted analyte might be particularly useful to monitor tumor growth of certain human solid tumors in vivo. More generally, these results are strongly indicative as to the applicability of the instant invention in both therapeutic and diagnostic settings.

Using the above described method, plasma samples from 23 normal human donors obtained from a blood bank were used to determine the concentration range of this analyte in healthy adults. As shown in FIG. 17D, a mean concentration of 332 pg/ml EFNA4 (6.2 pg/ml standard deviation) was found. This indicates that EFNA is secreted or shed at very low and tightly regulated concentration and makes EFNA an ideal biomarker or diagnostic marker to monitor disease progression or diagnose EFNA associated disorders.

To explore this possibility further, commercially obtained serum samples from 17 patients with colorectal cancer and 10 samples from patients with non-small cell lung cancer were compared to 12 samples from healthy adults were tested for the EFNA4 concentration using the above described method. As shown in FIG. 17E, both patients with colorectal cancer and non-small cell lung cancer had significantly elevated circulating EFNA4 levels in their blood. Using an unpaired t test, the comparison between healthy adults and colorectal cancer patients reached a p-value of 0.0002 and between healthy adults and non-small cell lung cancer patients of 0.01. The data demonstrate that secreted or shed EFNA4 is elevated in patients with solid tumors and illustrates the value of using the disclosed modulators in analytical testing or clinical diagnostics.

Example 18

EFNA4 Modulators Can Target Cells that Express Related EFNA Ligands

Ligand specificity of EFNA4 modulators was tested against related EFNA ligands to evaluate the degree of cross-reactivity. As an example, SC4.2.1 and SC9.65 were tested in the in vitro killing assay using HEK293T cells overexpressing EFNA4 (FIG. 17A), EFNA3 (FIG. 17B) and EFNA1 (FIG. 17C). Note that the modulator SC9.65 was generated by immunizing mice with EFNA1 immunogen (as per Example 6). The killing assay was carried out just as described in Example 16. FIG. 17 demonstrates that SC4.2.1 is able to kill EFNA3 in addition to EFNA4 expressing cells, and SC9.65 is able to kill EFNA1 and EFNA4 expressing cells. These data illustrate that selected modulators generated against a specific EFNA family member can bind other family members sufficiently well to bind, induce internalization and deliver a cytotoxic payload to ligand expressing cells. This discovery is somewhat unexpected given the low degree of homology between EFNA family members (approximately 34-45% amino acid sequence identity between human EFNA1, 2, 3 and 4) and exemplifies that, as described herein, pan-EFNA modulators can be generated for diagnostic or therapeutic purposes.

Example 19

EFNA Ligands Interact Selectively with Multiple EphA Receptors

As discussed above ephrin-A ligands are known to bind to numerous EphA receptors. To explore which EphA receptors have the potential to interact with EFNA4, a flow cytometric binding assay similar to the one described in Example 9 was developed. More particularly soluble EphA receptors expressed as human IgG1 Fc fusion constructs were added to fifty thousand HEK293T cells per well (FIG. 19A) or HEK293T cells overexpressing EFNA4 (FIG. 19B) by means of retroviral transduction (referred to as HEK293T.hEFNA4 cells) for 1 hour in staining buffer at 4° C. After washing, a secondary anti-human IgG polyclonal antibody conjugated to Dylight 649 (Jackson Immuno Research) was added for one hour. After washing twice, samples were resuspended in staining buffer containing 2 µg/ml DAPI and analyzed on a FACS Canto II (BD Biosciences) under standard conditions using the HTS attachment. FIGS. 19A and 19B demonstrate that EphA2, EphA3, EphA4, EphA6, EphA7 and EphA10 but not EphA1 bind to ephrin-A4 ligand. This again points to the advantages and potential multifaceted points of action inherent in modulators of the instant invention.

Example 20

EFNA4 Binds to EphB2 but not EphB3 and EphB4 Receptors

Extending the finding shown in Example 20, the ability of ephrin-A4 ligand to bind to EphB receptors was explored. EFNA4 was initially identified as CSC associated target as demonstrated above in Examples 2-4. In the tissue hierarchy of the normal mouse colon crypts, EphB2 and EphB3 receptors are highly expressed by cells residing at colon crypt base and not by cells located at top of the crypt indicating that EphB expression and forward or reverse signaling through EphB receptors is important in tissue organization and individual cell fate decisions (Batlle et al.; 2002 PMID: 12408869). More recently, EphB2 expression by colorectal cancer cells has been linked to tumor initiation and long-term proliferative capabilities suggesting that EphB2 may serve as phenotypic marker for cancer stem cells of the colon (Merlos-Suarez et al., 2011 PMID: 21419747). Hence the ability of ephrin-A4 ligand to bind to any of the differentially expressed EphB receptors might be of biological importance of colorectal cancer stem cells.

Using art-recognized techniques soluble EphB receptors expressed as human IgG1 Fc fusion constructs as well as EphA1-Fc (which does not bind EFNA4) and EphA2-Fc (which does bind EFANA4 ligand strongly) were added to fifty thousand HEK293T cells per well (FIG. 20A) or HEK293T.hEFNA4 cells (FIG. 20B) by for 1 hour in staining buffer at 4° C. After washing, a secondary anti-human IgG polyclonal antibody conjugated to Dylight 649 (Jackson Immuno Research) was added for one hour. After washing twice, samples were resuspended in staining buffer containing 2 µg/ml DAPI and analyzed on a FACS Canto II (BD Biosciences) under standard conditions using the HTS attachment. FIGS. 20A and 20B demonstrate that EphB2 but not EphB3 and EphB4 bind to EFNA4 ligand again emphasizing the potential diversity of therapeutic pathways that may be advantageously impacted by the disclosed modulators.

Those skilled in the art will further appreciate that the present invention may be embodied in other specific forms without departing from the spirit or central attributes thereof. In that the foregoing description of the present invention discloses only exemplary embodiments thereof, it is to be understood that other variations are contemplated as being within the scope of the present invention. Accordingly, the present invention is not limited to the particular embodiments that have been described in detail herein. Rather, reference should be made to the appended claims as indicative of the scope and content of the invention.

The invention claimed is:

1. A chimeric, CDR-grafted, humanized antibody, or fragment thereof, that comprises the same antigen-binding site as, and competes for binding to human EFNA4 with, an antibody comprising a heavy chain variable region set forth as SEQ ID NO: 113 and a light chain variable region set forth as SEQ ID NO: 115.

2. The antibody of claim 1, which is a neutralizing antibody.

3. The antibody of claim 1, which is an internalizing antibody.

4. The antibody of claim 1, which is a depleting antibody.

5. The antibody of claim 1 comprising at least one heavy chain variable region and at least one light chain variable region, wherein the at least one heavy chain variable region comprises three CDRs set forth as SEQ ID NOs: 12, 25, and 38.

6. The antibody of claim 1 comprising at least one heavy chain variable region and at least one light chain variable region, wherein the at least one light chain variable region comprises three CDRs set forth as SEQ ID NOs: 51, 74, and 87.

7. The antibody of claim 1 comprising:
   (a) a heavy chain variable region comprising three CDRs set forth as SEQ ID NOs: 12, 25, and 38; and
   (b) a light chain variable region comprising three CDRs set forth as SEQ ID NOs: 51, 74, and 87.

8. The antibody of claim 7 comprising a heavy chain variable region having an amino acid sequence that is at least 60% identical to SEQ ID NO: 157 and a light chain variable having an amino acid sequence that is at least 60% identical to SEQ ID NO: 159.

9. The antibody of claim 8 comprising a heavy chain variable region set forth as SEQ ID NO: 157 and a light chain variable region set forth as SEQ ID NO: 159.

10. The antibody of claim 1 comprising a heavy chain variable region set forth as SEQ ID NO: 113 or 157.

11. The antibody of claim 1 comprising a light chain variable region set forth as SEQ ID NO: 115 or 159.

12. The antibody of claim 1 comprising a heavy chain variable region set forth as SEQ ID NO: 113 or 157, and a light chain variable region set forth as SEQ ID NO: 115 or 159.

13. The antibody of claim 1, which is conjugated, linked or otherwise associated with a cytotoxic agent.

14. The antibody of claim 9, which is conjugated, linked or otherwise associated with a cytotoxic agent.

15. A pharmaceutical composition comprising the antibody of claim 1.

16. A pharmaceutical composition comprising the antibody of claim 9.

17. The antibody of claim 1, comprising at least one heavy chain variable region and at least one light chain variable region, wherein the at least one heavy chain variable region comprises three CDRs set forth as residues 31-35 of SEQ ID NO: 113 for CDR-H1, residues 50-65 of SEQ ID NO: 113 for CDR-H2, and residues 95-102 of SEQ ID NO: 113 for CDR-H3, wherein the residues are numbered according to Kabat.

18. The antibody of claim 1, comprising at least one heavy chain variable region and at least one light chain variable region, wherein the at least one light chain variable region comprises three CDRs set forth as residues 24-34 of SEQ ID NO: 115 for CDR-L1, residues 50-56 of SEQ ID NO: 115 for CDR-L2, and residues 89-97 of SEQ ID NO: 115 for CDR-L3, wherein the residues are numbered according to Kabat.

19. The antibody of claim 1, comprising at least one heavy chain variable region and at least one light chain variable region, wherein the at least one heavy chain variable region comprises three CDRs set forth as residues 31-35 of SEQ ID NO: 113 for CDR-H1, residues 50-65 of SEQ ID NO: 113 for CDR-H2, and residues 95-102 of SEQ ID NO: 113 for CDR-H3, and wherein the at least one light chain variable region comprises three CDRs set forth as residues 24-34 of SEQ ID NO: 115 for CDR-L1, residues 50-56 of SEQ ID NO: 115 for CDR-L2, and residues 89-97 of SEQ ID NO: 115 for CDR-L3, wherein the residues are numbered according to Kabat.

20. The antibody of claim 1, comprising at least one heavy chain variable region and at least one light chain variable region, wherein the at least one heavy chain variable region comprises three CDRs set forth as residues 26-32 of SEQ ID NO: 113 for CDR-H1, residues 53-55 of SEQ ID NO: 113 for CDR-H2, and residues 96-101 of SEQ ID NO: 113 for CDR-H3, wherein the residues are numbered according to Chothia.

21. The antibody of claim 1, comprising at least one heavy chain variable region and at least one light chain variable region, wherein the at least one light chain variable region comprises three CDRs set forth as residues 26-32 of SEQ ID NO: 115 for CDR-L1, residues 50-52 of SEQ ID NO: 115 for CDR-L2, and residues 91-96 of SEQ ID NO: 115 for CDR-L3, wherein the residues are numbered according to Chothia.

22. The antibody of claim 1, comprising at least one heavy chain variable region and at least one light chain variable region, wherein the at least one heavy chain variable region comprises three CDRs set forth as residues 26-32 of SEQ ID NO: 113 for CDR-H1, residues 53-55 of SEQ ID NO: 113 for CDR-H2, and residues 96-101 of SEQ ID NO: 113 for CDR-H3, and wherein the at least one light chain variable region comprises three CDRs set forth as residues 26-32 of SEQ ID NO: 115 for CDR-L1, residues 50-52 of SEQ ID NO: 115 for CDR-L2, and residues 91-96 of SEQ ID NO: 115 for CDR-L3, wherein the residues are numbered according to Chothia.

23. The antibody of claim 1, comprising at least one heavy chain variable region and at least one light chain variable region, wherein the at least one heavy chain variable region comprises three CDRs set forth as residues 30-35 of SEQ ID NO: 113 for CDR-H1, residues 47-58 of SEQ ID NO: 113 for CDR-H2, and residues 93-101 of SEQ ID NO: 113 for CDR-H3, wherein the residues are numbered according to MacCallum.

24. The antibody of claim 1, comprising at least one heavy chain variable region and at least one light chain variable region, wherein the at least one light chain variable region comprises three CDRs set forth as residues 30-36 of SEQ ID NO: 115 for CDR-L1, residues 46-55 of SEQ ID NO: 115 for CDR-L2, and residues 89-96 of SEQ ID NO: 115 for CDR-L3, wherein the residues are numbered according to MacCallum.

25. The antibody of claim 1, comprising at least one heavy chain variable region and at least one light chain variable region, wherein the at least one heavy chain variable region comprises three CDRs set forth as residues 30-35 of SEQ ID NO: 113 for CDR-H1, residues 47-58 of SEQ ID NO: 113 for CDR-H2, and residues 93-101 of SEQ ID NO: 113 for CDR-H3, and wherein the at least one light chain variable region comprises three CDRs set forth as residues 30-36 of SEQ ID NO: 115 for CDR-L1, residues 46-55 of SEQ ID NO: 115 for CDR-L2, and residues 89-96 of SEQ ID NO: 115 for CDR-L3, wherein the residues are numbered according to MacCallum.

26. The antibody of claim 1, comprising at least one heavy chain variable region and at least one light chain variable region, wherein the at least one heavy chain variable region comprises three CDRs of a heavy chain variable region set forth as SEQ ID NO: 113.

27. The antibody of claim 1, comprising at least one heavy chain variable region and at least one light chain variable region, wherein the at least one light chain variable region comprises three CDRs of a light chain variable region set forth as SEQ ID NO: 115.

28. The antibody of claim 1, comprising at least one heavy chain variable region and at least one light chain variable region, wherein the at least one heavy chain variable region comprises three CDRs of a heavy chain variable region set forth as SEQ ID NO: 113 and wherein the at least one light chain variable region comprises three CDRs of a light chain variable region set forth as SEQ ID NO: 115.

29. The antibody of claim 28, wherein each respective CDR is defined according to the CDR definition of Kabat, Chothia, or MacCallum.

30. An antibody conjugate comprising the antibody of claim 1, which antibody is conjugated, linked or otherwise associated with a cytotoxic agent.

31. An antibody conjugate comprising the antibody of claim 9, which antibody is conjugated, linked or otherwise associated with a cytotoxic agent.

32. A pharmaceutical composition comprising the antibody conjugate of claim 30.

33. A pharmaceutical composition comprising the antibody conjugate of claim 31.

34. A chimeric, CDR-grafted, humanized antibody, or fragment thereof, comprising at least one heavy chain variable region and at least one light chain variable region, wherein the at least one heavy chain variable region comprises three CDRs set forth as residues 31-35 of SEQ ID NO: 113 for CDR-H1, residues 50-65 of SEQ ID NO: 113 for CDR-H2, and residues 95-102 of SEQ ID NO: 113 for CDR-H3, and wherein the at least one light chain variable region comprises three CDRs set forth as residues 24-34 of SEQ ID NO: 115 for CDR-L1, residues 50-56 of SEQ ID NO: 115 for CDR-L2, and residues 89-97 of SEQ ID NO: 115 for CDR-L3, wherein the residues are numbered according to Kabat.

35. The antibody of claim 34, comprising a heavy chain variable region set forth as SEQ ID NO: 157 and a light chain variable region set forth as SEQ ID NO: 159.

36. An antibody conjugate comprising the antibody of claim 34, which antibody is conjugated, linked or otherwise associated with a cytotoxic agent.

* * * * *